US012357345B2

(12) United States Patent
Schoonmaker et al.

(10) Patent No.: US 12,357,345 B2
(45) Date of Patent: Jul. 15, 2025

(54) TRANSCUTANEOUS ANALYTE SENSORS, APPLICATORS THEREFOR, AND ASSOCIATED METHODS

(71) Applicant: DexCom, Inc., San Diego, CA (US)

(72) Inventors: Ryan Everett Schoonmaker, Oceanside, CA (US); Jennifer Blackwell, San Diego, CA (US); Eric Gobrecht, Madison, WI (US); Jason Halac, Solana Beach, CA (US); Randall Scott Koplin, Middleton, WI (US); Justen Deering England, San Francisco, CA (US)

(73) Assignee: DexCom, Inc., San Diego, CA (US)

( * ) Notice: Subject to any disclaimer, the term of this patent is extended or adjusted under 35 U.S.C. 154(b) by 186 days.

(21) Appl. No.: 17/962,308

(22) Filed: Oct. 7, 2022

(65) Prior Publication Data

US 2023/0032816 A1 Feb. 2, 2023

Related U.S. Application Data

(63) Continuation of application No. 16/784,198, filed on Feb. 6, 2020, now abandoned, which is a continuation
(Continued)

(51) Int. Cl.
*A61B 5/145* (2006.01)
*A61B 5/00* (2006.01)
(Continued)

(52) U.S. Cl.
CPC ........ *A61B 17/3468* (2013.01); *A61B 5/0004* (2013.01); *A61B 5/14503* (2013.01);
(Continued)

(58) Field of Classification Search
CPC ........ A61B 17/3468; A61B 2017/0023; A61B 2017/00407; A61B 2017/00862;
(Continued)

(56) References Cited

U.S. PATENT DOCUMENTS

| 65,604 A | 6/1867 | Reynolds |
| 4,757,022 A | 7/1988 | Shults et al. |

(Continued)

FOREIGN PATENT DOCUMENTS

| CN | 103300866 A | 9/2013 |
| CN | 104168826 A | 11/2014 |

(Continued)

OTHER PUBLICATIONS

US 8,027,708 B1, 09/2011, Shults et al. (withdrawn)
(Continued)

*Primary Examiner* — Eric J Messersmith
(74) *Attorney, Agent, or Firm* — Snell & Wilmer LLP

(57) ABSTRACT

The present embodiments relate generally to systems and methods for measuring an analyte in a host. More particularly, the present embodiments provide sensor applicators and methods of use with activation that implant the sensor, withdraw the insertion needle, engage the transmitter with the housing, and disengage the applicator from the housing. Systems and methods according to present principles allow for such steps to occur without significant loss of spring force, and without deleterious effects such as seal slingshotting.

22 Claims, 108 Drawing Sheets

Related U.S. Application Data of application No. 15/298,721, filed on Oct. 20, 2016, now Pat. No. 10,595,900.

(60) Provisional application No. 62/244,520, filed on Oct. 21, 2015.

(51) Int. Cl.
*A61B 17/34* (2006.01)
*A61B 17/00* (2006.01)

(52) U.S. Cl.
CPC ........ *A61B 5/14532* (2013.01); *A61B 5/6833* (2013.01); *A61B 2017/0023* (2013.01); *A61B 2017/00407* (2013.01); *A61B 2017/00862* (2013.01)

(58) Field of Classification Search
CPC .............. A61B 5/0004; A61B 5/14503; A61B 5/14532; A61B 5/6833
See application file for complete search history.

(56) References Cited

U.S. PATENT DOCUMENTS

| | | | |
|---|---|---|---|
| 4,994,167 A | 2/1991 | Shults et al. |
| 5,299,571 A | 4/1994 | Mastrototaro |
| 5,390,671 A | 2/1995 | Lord et al. |
| 5,515,871 A | 5/1996 | Bittner et al. |
| 5,568,806 A | 10/1996 | Cheney, II et al. |
| 5,586,553 A | 12/1996 | Halili et al. |
| 5,680,858 A | 10/1997 | Hansen et al. |
| 5,851,197 A | 12/1998 | Marano et al. |
| 5,954,643 A | 9/1999 | Vanantwerp et al. |
| 5,993,411 A | 11/1999 | Choi |
| 6,001,067 A | 12/1999 | Shults et al. |
| 6,093,172 A | 7/2000 | Funderburk et al. |
| 6,197,001 B1 | 3/2001 | Wilson et al. |
| 6,254,586 B1 | 7/2001 | Mann et al. |
| 6,275,717 B1 | 8/2001 | Gross et al. |
| 6,293,925 B1 | 9/2001 | Safabash et al. |
| 6,424,847 B1 | 7/2002 | Mastrototaro et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,558,321 B1 | 5/2003 | Burd et al. |
| 6,565,509 B1 | 5/2003 | Say et al. |
| 6,579,690 B1 | 6/2003 | Bonnecaze et al. |
| 6,607,509 B2 | 8/2003 | Bobroff et al. |
| 6,695,860 B1 | 2/2004 | Ward et al. |
| 6,702,857 B2 | 3/2004 | Brauker et al. |
| 6,741,877 B1 | 5/2004 | Shults et al. |
| 6,862,465 B2 | 3/2005 | Shults et al. |
| 6,931,327 B2 | 8/2005 | Goode, Jr. et al. |
| 6,936,006 B2 | 8/2005 | Sabra |
| 6,990,366 B2 | 1/2006 | Say et al. |
| 6,991,619 B2 | 1/2006 | Marano-Ford et al. |
| 6,991,620 B2 | 1/2006 | Marano-Ford et al. |
| 6,997,907 B2 | 2/2006 | Safabash et al. |
| 7,003,336 B2 | 2/2006 | Holker et al. |
| 7,022,108 B2 | 4/2006 | Marano-Ford et al. |
| 7,074,307 B2 | 7/2006 | Simpson et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,130,544 B2 | 10/2006 | Kasahara et al. |
| 7,134,999 B2 | 11/2006 | Brauker et al. |
| 7,136,689 B2 | 11/2006 | Shults et al. |
| 7,192,450 B2 | 3/2007 | Brauker et al. |
| 7,207,974 B2 | 4/2007 | Safabash et al. |
| 7,226,978 B2 | 6/2007 | Tapsak et al. |
| 7,228,162 B2 | 6/2007 | Ward et al. |
| 7,276,029 B2 | 10/2007 | Goode, Jr. et al. |
| 7,310,544 B2 | 12/2007 | Brister et al. |
| 7,318,816 B2 | 1/2008 | Bobroff et al. |
| 7,343,188 B2 | 3/2008 | Sohrab |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,582,059 B2 | 9/2009 | Funderburk et al. |
| 7,583,990 B2 | 9/2009 | Goode, Jr. et al. |
| 7,585,287 B2 | 9/2009 | Bresina et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,660,615 B2 | 2/2010 | Vanantwerp et al. |
| 7,682,338 B2 | 3/2010 | Griffin |
| 7,686,787 B2 | 3/2010 | Moberg et al. |
| 7,697,967 B2 | 4/2010 | Stafford |
| 7,699,807 B2 | 4/2010 | Faust et al. |
| 7,704,229 B2 | 4/2010 | Moberg et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,731,657 B2 | 6/2010 | Stafford |
| 7,736,310 B2 | 6/2010 | Taub |
| 7,736,338 B2 | 6/2010 | Kavazov et al. |
| 7,736,344 B2 | 6/2010 | Moberg et al. |
| 7,740,613 B2 | 6/2010 | Yokoi et al. |
| 7,744,589 B2 | 6/2010 | Mounce et al. |
| 7,761,130 B2 | 7/2010 | Simpson et al. |
| 7,762,793 B2 | 7/2010 | Gray et al. |
| 7,771,352 B2 | 8/2010 | Shults et al. |
| 7,771,393 B2 | 8/2010 | Liniger et al. |
| 7,774,145 B2 | 8/2010 | Brauker et al. |
| 7,775,975 B2 | 8/2010 | Brister et al. |
| 7,778,680 B2 | 8/2010 | Goode, Jr. et al. |
| 7,783,333 B2 | 8/2010 | Brister et al. |
| 7,785,293 B2 | 8/2010 | Gray et al. |
| 7,789,857 B2 | 9/2010 | Moberg et al. |
| 7,792,562 B2 | 9/2010 | Shults et al. |
| 7,797,028 B2 | 9/2010 | Goode, Jr. et al. |
| 7,815,607 B2 | 10/2010 | Rutti et al. |
| 7,826,981 B2 | 11/2010 | Goode, Jr. et al. |
| 7,828,728 B2 | 11/2010 | Boock et al. |
| 7,831,287 B2 | 11/2010 | Brister et al. |
| 7,835,777 B2 | 11/2010 | Shults et al. |
| 7,846,132 B2 | 12/2010 | Gravesen et al. |
| 7,850,652 B2 | 12/2010 | Liniger et al. |
| 7,857,760 B2 | 12/2010 | Brister et al. |
| 7,860,545 B2 | 12/2010 | Shults et al. |
| 7,875,293 B2 | 1/2011 | Shults et al. |
| 7,881,763 B2 | 2/2011 | Brauker et al. |
| 7,885,697 B2 | 2/2011 | Brister et al. |
| 7,896,809 B2 | 3/2011 | Simpson et al. |
| 7,899,511 B2 | 3/2011 | Shults et al. |
| 7,901,354 B2 | 3/2011 | Shults et al. |
| 7,905,833 B2 | 3/2011 | Brister et al. |
| 7,914,450 B2 | 3/2011 | Goode, Jr. et al. |
| 7,917,186 B2 | 3/2011 | Kamath et al. |
| 7,920,906 B2 | 4/2011 | Goode, Jr. et al. |
| 7,925,321 B2 | 4/2011 | Goode, Jr. et al. |
| 7,927,274 B2 | 4/2011 | Rasdal et al. |
| 7,933,639 B2 | 4/2011 | Goode et al. |
| 7,935,057 B2 | 5/2011 | Goode, Jr. et al. |
| 7,946,984 B2 | 5/2011 | Brister et al. |
| 7,949,381 B2 | 5/2011 | Brister et al. |
| 7,955,261 B2 | 6/2011 | Goode et al. |
| 7,959,569 B2 | 6/2011 | Goode et al. |
| 7,970,448 B2 | 6/2011 | Shults et al. |

(56) References Cited

U.S. PATENT DOCUMENTS

| | | |
|---|---|---|
| 7,974,672 B2 | 7/2011 | Shults et al. |
| 7,976,492 B2 | 7/2011 | Brauker et al. |
| 7,979,104 B2 | 7/2011 | Kamath et al. |
| 7,986,986 B2 | 7/2011 | Goode et al. |
| 7,998,071 B2 | 8/2011 | Goode, Jr. et al. |
| 8,000,901 B2 | 8/2011 | Brauker et al. |
| 8,005,524 B2 | 8/2011 | Brauker et al. |
| 8,005,525 B2 | 8/2011 | Goode, Jr. et al. |
| 8,010,174 B2 | 8/2011 | Goode, Jr. et al. |
| 8,029,441 B2 | 10/2011 | Mazza et al. |
| 8,029,442 B2 | 10/2011 | Funderburk et al. |
| 8,050,731 B2 | 11/2011 | Tapsak et al. |
| 8,052,601 B2 | 11/2011 | Goode, Jr. et al. |
| 8,053,018 B2 | 11/2011 | Tapsak et al. |
| 8,060,173 B2 | 11/2011 | Goode, Jr. et al. |
| 8,060,174 B2 | 11/2011 | Simpson et al. |
| 8,064,977 B2 | 11/2011 | Boock et al. |
| 8,073,519 B2 | 12/2011 | Goode, Jr. et al. |
| 8,073,520 B2 | 12/2011 | Kamath et al. |
| 8,118,877 B2 | 2/2012 | Brauker et al. |
| 8,128,562 B2 | 3/2012 | Goode, Jr. et al. |
| 8,133,178 B2 | 3/2012 | Brauker et al. |
| 8,150,488 B2 | 4/2012 | Goode, Jr. et al. |
| 8,155,723 B2 | 4/2012 | Shults et al. |
| 8,160,669 B2 | 4/2012 | Brauker et al. |
| 8,160,671 B2 | 4/2012 | Kamath et al. |
| 8,167,801 B2 | 5/2012 | Goode, Jr. et al. |
| 8,170,803 B2 | 5/2012 | Kamath et al. |
| 8,195,265 B2 | 6/2012 | Goode, Jr. et al. |
| 8,206,297 B2 | 6/2012 | Kamath et al. |
| 8,216,139 B2 | 7/2012 | Brauker et al. |
| 8,229,534 B2 | 7/2012 | Brister et al. |
| 8,229,535 B2 | 7/2012 | Mensinger et al. |
| 8,229,536 B2 | 7/2012 | Goode, Jr. et al. |
| 8,231,531 B2 | 7/2012 | Brister et al. |
| 8,233,958 B2 | 7/2012 | Brauker et al. |
| 8,233,959 B2 | 7/2012 | Kamath et al. |
| 8,249,684 B2 | 8/2012 | Kamath et al. |
| 8,251,906 B2 | 8/2012 | Brauker et al. |
| 8,255,030 B2 | 8/2012 | Petisce et al. |
| 8,255,032 B2 | 8/2012 | Petisce et al. |
| 8,255,033 B2 | 8/2012 | Petisce et al. |
| 8,257,259 B2 | 9/2012 | Brauker et al. |
| 8,260,393 B2 | 9/2012 | Kamath et al. |
| 8,265,725 B2 | 9/2012 | Brauker et al. |
| 8,275,437 B2 | 9/2012 | Brauker et al. |
| 8,275,438 B2 | 9/2012 | Simpson et al. |
| 8,277,713 B2 | 10/2012 | Petisce et al. |
| 8,280,475 B2 | 10/2012 | Brister et al. |
| 8,282,549 B2 | 10/2012 | Brauker et al. |
| 8,282,550 B2 | 10/2012 | Rasdal et al. |
| 8,285,354 B2 | 10/2012 | Goode et al. |
| 8,287,453 B2 | 10/2012 | Li et al. |
| 8,290,559 B2 | 10/2012 | Shariati et al. |
| 8,290,560 B2 | 10/2012 | Kamath et al. |
| 8,290,561 B2 | 10/2012 | Brauker et al. |
| 8,290,562 B2 | 10/2012 | Goode, Jr. et al. |
| 8,292,810 B2 | 10/2012 | Goode, Jr. et al. |
| 8,298,142 B2 | 10/2012 | Simpson et al. |
| 8,311,749 B2 | 11/2012 | Brauker et al. |
| 8,313,434 B2 | 11/2012 | Brister et al. |
| 8,321,149 B2 | 11/2012 | Brauker et al. |
| 8,332,008 B2 | 12/2012 | Goode et al. |
| 8,346,338 B2 | 1/2013 | Goode, Jr. et al. |
| 8,364,229 B2 | 1/2013 | Simpson et al. |
| 8,369,919 B2 | 2/2013 | Kamath et al. |
| 8,374,667 B2 | 2/2013 | Brauker et al. |
| 8,386,004 B2 | 2/2013 | Kamath et al. |
| 8,394,021 B2 | 3/2013 | Goode et al. |
| 8,527,025 B1 | 9/2013 | Shults et al. |
| 8,764,657 B2 | 7/2014 | Curry et al. |
| 9,119,528 B2 | 9/2015 | Cobelli et al. |
| 9,119,529 B2 | 9/2015 | Hampapuram et al. |
| 9,186,098 B2 | 11/2015 | Lee et al. |
| 9,245,167 B2 | 1/2016 | Carver et al. |
| 9,265,453 B2 | 2/2016 | Curry et al. |
| 9,402,544 B2 | 8/2016 | Yee et al. |
| 10,278,732 B2 | 5/2019 | Schoonmaker et al. |
| 10,595,900 B2 | 3/2020 | Schoonmaker et al. |
| 2002/0013615 A1 | 1/2002 | Haim et al. |
| 2003/0032874 A1 | 2/2003 | Rhodes et al. |
| 2003/0100040 A1 | 5/2003 | Bonnecaze et al. |
| 2004/0133164 A1 | 7/2004 | Funderburk et al. |
| 2005/0033132 A1 | 2/2005 | Shults et al. |
| 2005/0043598 A1 | 2/2005 | Goode, Jr. et al. |
| 2005/0051427 A1 | 3/2005 | Brauker et al. |
| 2005/0056552 A1 | 3/2005 | Simpson et al. |
| 2005/0090607 A1 | 4/2005 | Tapsak et al. |
| 2005/0154271 A1 | 7/2005 | Rasdal et al. |
| 2005/0176136 A1 | 8/2005 | Burd et al. |
| 2005/0182451 A1 | 8/2005 | Griffin et al. |
| 2005/0192557 A1 | 9/2005 | Brauker et al. |
| 2005/0203360 A1 | 9/2005 | Brauker et al. |
| 2005/0245799 A1 | 11/2005 | Brauker et al. |
| 2006/0015020 A1 | 1/2006 | Neale et al. |
| 2006/0016700 A1 | 1/2006 | Brister et al. |
| 2006/0020188 A1 | 1/2006 | Kamath et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036140 A1 | 2/2006 | Brister et al. |
| 2006/0036143 A1 | 2/2006 | Brister et al. |
| 2006/0040402 A1 | 2/2006 | Brauker et al. |
| 2006/0068208 A1 | 3/2006 | Tapsak et al. |
| 2006/0142651 A1 | 6/2006 | Brister et al. |
| 2006/0155180 A1 | 7/2006 | Brister et al. |
| 2006/0198864 A1 | 9/2006 | Shults et al. |
| 2006/0200020 A1 | 9/2006 | Brister et al. |
| 2006/0200022 A1 | 9/2006 | Brauker et al. |
| 2006/0200970 A1 | 9/2006 | Brister et al. |
| 2006/0204536 A1 | 9/2006 | Shults et al. |
| 2006/0222566 A1 | 10/2006 | Brauker et al. |
| 2006/0224108 A1 | 10/2006 | Brauker et al. |
| 2006/0235285 A1 | 10/2006 | Brister et al. |
| 2006/0249381 A1 | 11/2006 | Petisce et al. |
| 2006/0252027 A1 | 11/2006 | Petisce et al. |
| 2006/0253012 A1 | 11/2006 | Petisce et al. |
| 2006/0257995 A1 | 11/2006 | Simpson et al. |
| 2006/0258761 A1 | 11/2006 | Boock et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2007/0016381 A1 | 1/2007 | Kamath et al. |
| 2007/0027370 A1 | 2/2007 | Brauker et al. |
| 2007/0027381 A1 | 2/2007 | Stafford |
| 2007/0032706 A1 | 2/2007 | Kamath et al. |
| 2007/0032718 A1 | 2/2007 | Shults et al. |
| 2007/0045902 A1 | 3/2007 | Brauker et al. |
| 2007/0059196 A1 | 3/2007 | Brister et al. |
| 2007/0060801 A1 | 3/2007 | Neinast |
| 2007/0066873 A1 | 3/2007 | Kamath et al. |
| 2007/0173709 A1 | 7/2007 | Petisce et al. |
| 2007/0173710 A1 | 7/2007 | Petisce et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0232879 A1 | 10/2007 | Brister et al. |
| 2008/0033254 A1 | 2/2008 | Kamath et al. |
| 2008/0033268 A1 | 2/2008 | Stafford |
| 2008/0045824 A1 | 2/2008 | Tapsak et al. |
| 2008/0083617 A1 | 4/2008 | Simpson et al. |
| 2008/0086044 A1 | 4/2008 | Brister et al. |
| 2008/0108942 A1 | 5/2008 | Brister et al. |
| 2008/0114280 A1* | 5/2008 | Stafford ............... A61B 5/1468 604/19 |
| 2008/0119703 A1 | 5/2008 | Brister et al. |
| 2008/0119704 A1 | 5/2008 | Brister et al. |
| 2008/0119706 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194938 A1 | 8/2008 | Brister et al. |

(56) References Cited

U.S. PATENT DOCUMENTS

| | | |
|---|---|---|
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0214915 A1 | 9/2008 | Brister et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287765 A1 | 11/2008 | Rasdal et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0319414 A1 * | 12/2008 | Yodfat ............... A61B 5/6849 604/157 |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0045055 A1 | 2/2009 | Rhodes et al. |
| 2009/0054812 A1 | 2/2009 | Mace |
| 2009/0062633 A1 | 3/2009 | Brauker et al. |
| 2009/0062635 A1 | 3/2009 | Brauker et al. |
| 2009/0076360 A1 | 3/2009 | Brister et al. |
| 2009/0099436 A1 | 4/2009 | Brister et al. |
| 2009/0105569 A1 | 4/2009 | Stafford |
| 2009/0124877 A1 | 5/2009 | Goode, Jr. et al. |
| 2009/0124879 A1 | 5/2009 | Brister et al. |
| 2009/0124964 A1 | 5/2009 | Leach et al. |
| 2009/0131769 A1 | 5/2009 | Leach et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0163790 A1 | 6/2009 | Brister et al. |
| 2009/0178459 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0216103 A1 | 8/2009 | Brister et al. |
| 2009/0240120 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299301 A1 | 12/2009 | Gottlieb et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0030484 A1 | 2/2010 | Brauker et al. |
| 2010/0036215 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0113897 A1 | 5/2010 | Brenneman et al. |
| 2010/0121169 A1 | 5/2010 | Petisce et al. |
| 2010/0161269 A1 | 6/2010 | Kamath et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168657 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185075 A1 | 7/2010 | Brister et al. |
| 2010/0191082 A1 | 7/2010 | Brister et al. |
| 2010/0198035 A1 | 8/2010 | Kamath et al. |
| 2010/0198036 A1 | 8/2010 | Kamath et al. |
| 2010/0212583 A1 | 8/2010 | Brister et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0261987 A1 | 10/2010 | Kamath et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324403 A1 | 12/2010 | Brister et al. |
| 2010/0331644 A1 | 12/2010 | Neale et al. |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046467 A1 | 2/2011 | Simpson et al. |
| 2011/0077490 A1 | 3/2011 | Simpson et al. |
| 2011/0082484 A1 | 4/2011 | Saravia et al. |
| 2011/0118579 A1 | 5/2011 | Goode, Jr. et al. |
| 2011/0124992 A1 | 5/2011 | Brauker et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0144465 A1 | 6/2011 | Shults et al. |
| 2011/0178378 A1 | 7/2011 | Brister et al. |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |

(56) References Cited

U.S. PATENT DOCUMENTS

| | | |
|---|---|---|
| 2011/0263958 A1 | 10/2011 | Brauker et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0290645 A1 | 12/2011 | Brister et al. |
| 2011/0313543 A1 | 12/2011 | Brauker et al. |
| 2011/0320130 A1 | 12/2011 | Valdes et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0059231 A1 | 3/2012 | Frey et al. |
| 2012/0078071 A1 | 3/2012 | Bohm et al. |
| 2012/0095406 A1 | 4/2012 | Gyrn et al. |
| 2012/0108934 A1 | 5/2012 | Valdes et al. |
| 2012/0130214 A1 | 5/2012 | Brister et al. |
| 2012/0157922 A1 | 6/2012 | Shekalim et al. |
| 2012/0172691 A1 | 7/2012 | Brauker et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0203467 A1 | 8/2012 | Kamath et al. |
| 2012/0209098 A1 | 8/2012 | Goode, Jr. et al. |
| 2012/0215086 A1 | 8/2012 | Kamath et al. |
| 2012/0215087 A1 | 8/2012 | Cobelli et al. |
| 2012/0215201 A1 | 8/2012 | Brauker et al. |
| 2012/0215461 A1 | 8/2012 | Goode, Jr. et al. |
| 2012/0215462 A1 | 8/2012 | Goode, Jr. et al. |
| 2012/0215496 A1 | 8/2012 | Kamath et al. |
| 2012/0220979 A1 | 8/2012 | Brauker et al. |
| 2012/0226121 A1 | 9/2012 | Kamath et al. |
| 2012/0228134 A1 | 9/2012 | Simpson et al. |
| 2012/0238852 A1 | 9/2012 | Brauker et al. |
| 2012/0245448 A1 | 9/2012 | Shariati et al. |
| 2012/0245855 A1 | 9/2012 | Kamath et al. |
| 2012/0255875 A1 | 10/2012 | Vicente et al. |
| 2012/0258748 A1 | 10/2012 | San Vicente et al. |
| 2012/0259191 A1 | 10/2012 | Shariati et al. |
| 2012/0260323 A1 | 10/2012 | San Vicente et al. |
| 2012/0262298 A1 | 10/2012 | Bohm et al. |
| 2012/0265035 A1 | 10/2012 | Bohm et al. |
| 2012/0265036 A1 | 10/2012 | Estes et al. |
| 2012/0265037 A1 | 10/2012 | Bohm et al. |
| 2012/0277562 A1 | 11/2012 | Brister et al. |
| 2012/0277566 A1 | 11/2012 | Kamath et al. |
| 2012/0283541 A1 | 11/2012 | Kamath et al. |
| 2012/0283543 A1 | 11/2012 | Brauker et al. |
| 2012/0296311 A1 | 11/2012 | Brauker et al. |
| 2012/0302854 A1 | 11/2012 | Kamath et al. |
| 2012/0302855 A1 | 11/2012 | Kamath et al. |
| 2012/0303043 A1 | 11/2012 | Donnay |
| 2012/0323100 A1 | 12/2012 | Kamath et al. |
| 2013/0012798 A1 | 1/2013 | Brister et al. |
| 2013/0030273 A1 | 1/2013 | Tapsak et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0053665 A1 | 2/2013 | Hughes et al. |
| 2013/0053666 A1 | 2/2013 | Hughes et al. |
| 2013/0060112 A1 | 3/2013 | Pryor et al. |
| 2013/0076531 A1 | 3/2013 | San Vicente et al. |
| 2013/0076532 A1 | 3/2013 | San Vicente et al. |
| 2013/0078912 A1 | 3/2013 | San Vicente et al. |
| 2013/0131478 A1 | 5/2013 | Simpson et al. |
| 2013/0150692 A1 | 6/2013 | Kamath et al. |
| 2013/0245412 A1 | 9/2013 | Rong et al. |
| 2013/0247813 A1* | 9/2013 | Pegg ................ B63B 29/02 114/343 |
| 2013/0267811 A1 | 10/2013 | Pryor et al. |
| 2013/0267813 A1 | 10/2013 | Pryor et al. |
| 2013/0321425 A1 | 12/2013 | Greene et al. |
| 2013/0325504 A1 | 12/2013 | Greene et al. |
| 2014/0005505 A1 | 1/2014 | Peyser et al. |
| 2014/0005508 A1 | 1/2014 | Estes et al. |
| 2014/0031655 A1 | 1/2014 | Stafford |
| 2014/0088389 A1 | 3/2014 | Simpson et al. |
| 2014/0094671 A1 | 4/2014 | Boock et al. |
| 2014/0107450 A1 | 4/2014 | Simpson et al. |
| 2014/0129151 A1 | 5/2014 | Bhavaraju et al. |
| 2014/0182350 A1 | 7/2014 | Bhavaraju et al. |
| 2014/0188402 A1 | 7/2014 | Garcia et al. |
| 2015/0025338 A1 | 1/2015 | Lee et al. |
| 2015/0025345 A1 | 1/2015 | Funderburk et al. |
| 2016/0345876 A1 | 12/2016 | Fritz et al. |
| 2017/0112531 A1 | 4/2017 | Schoonmaker et al. |
| 2017/0112532 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2020/0170671 A1 | 6/2020 | Schoonmaker et al. |

FOREIGN PATENT DOCUMENTS

| | | |
|---|---|---|
| CN | 104394757 A | 3/2015 |
| CN | 104582570 A | 4/2015 |
| CN | 104887242 A | 9/2015 |
| JP | 2010538745 A | 12/2010 |
| WO | WO-2007016399 A2 | 2/2007 |
| WO | WO-2011026130 A1 | 3/2011 |
| WO | WO-2011119898 A1 | 9/2011 |
| WO | WO-2015078636 A1 | 6/2015 |

OTHER PUBLICATIONS

International Preliminary Report on Patentability for Application No. PCT/US2016/057933 mailed on May 3, 2018, 7 pages.
International Search Report and Written Opinion for Application No. PCT/US2016/057933 mailed on Mar. 24, 2017, 9 pages.

* cited by examiner

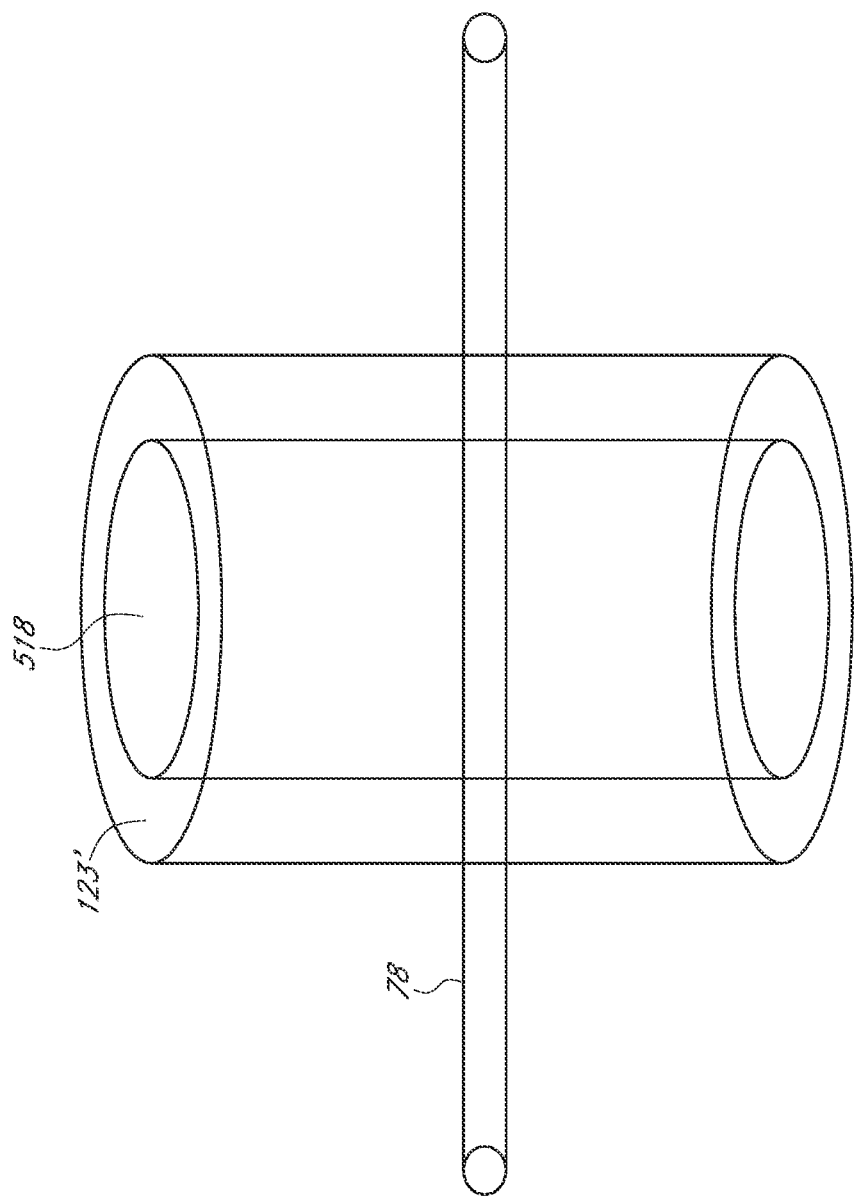

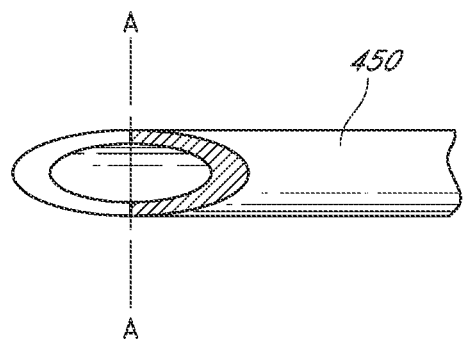
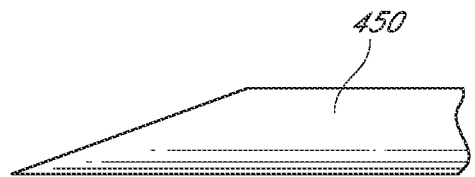
FIG. 99    FIG. 100
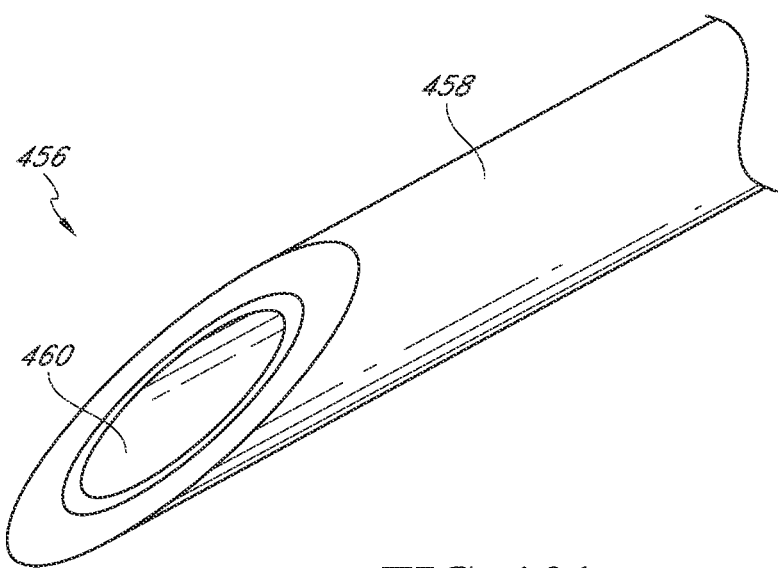
FIG. 101

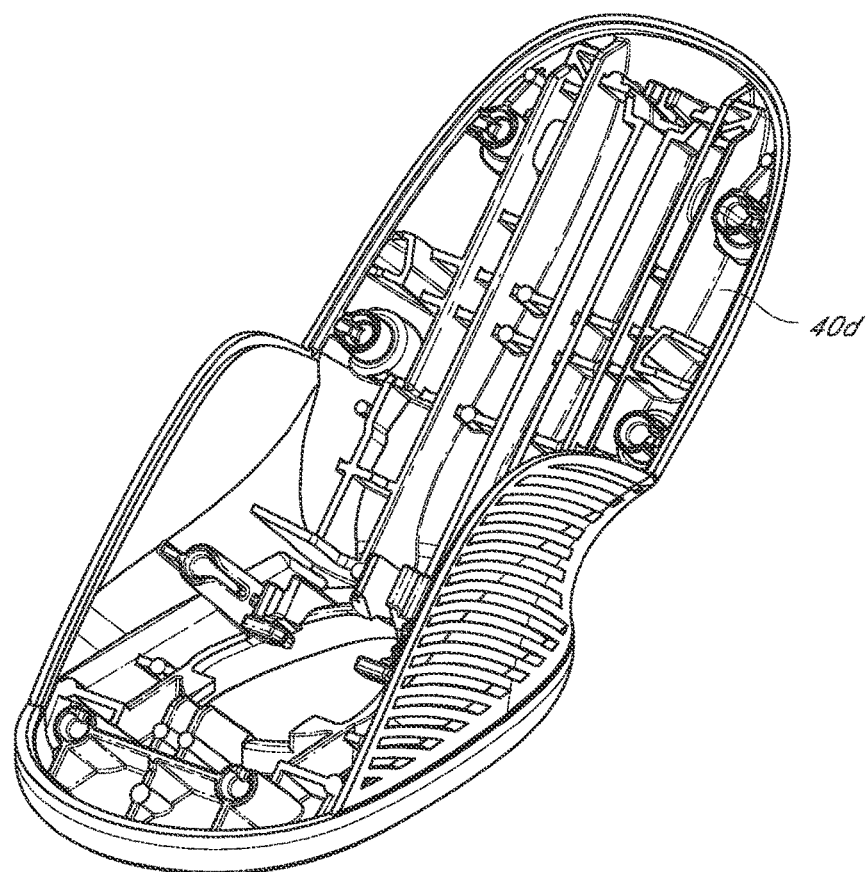
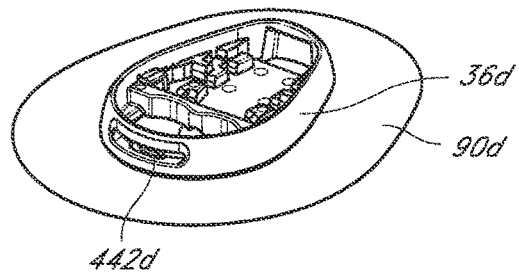
FIG. 105
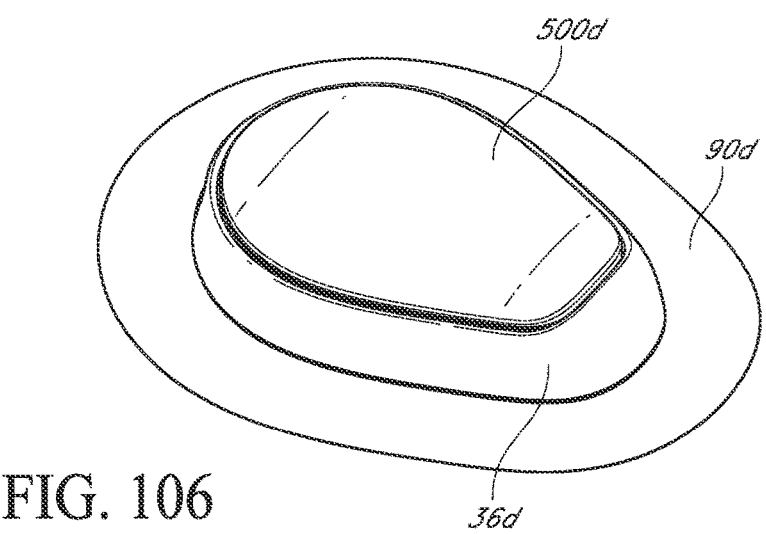
FIG. 106

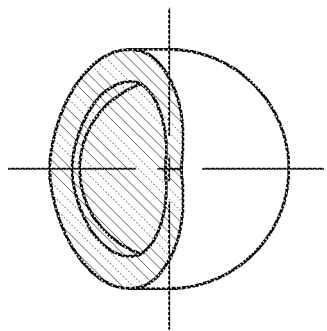
FIG. 119
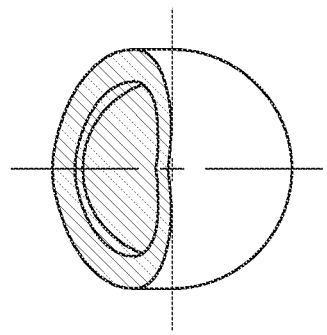
FIG. 120
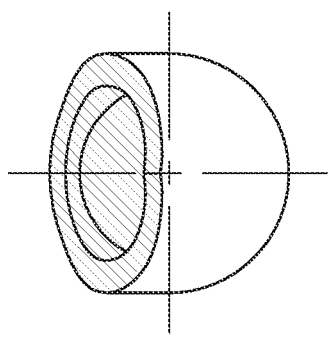
FIG. 122
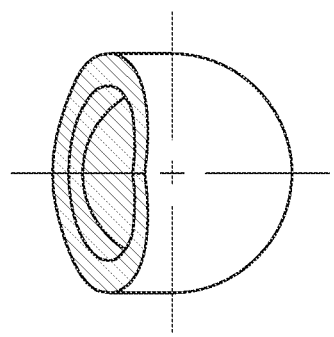
FIG. 123
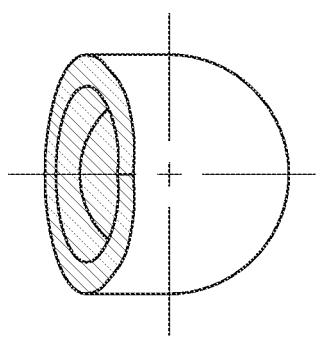
FIG. 118
FIG. 121

TRANSCUTANEOUS ANALYTE SENSORS, APPLICATORS THEREFOR, AND ASSOCIATED METHODS

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 16/784,198, filed Feb. 6, 2020, which is a continuation of U.S. application Ser. No. 15/298,721, filed Oct. 20, 2016, now U.S. Pat. No. 10,595,900, issued Mar. 24, 2020, which claims the benefit of U.S. Provisional Application No. 62/244,520, filed Oct. 21, 2015. The aforementioned application is incorporated by reference herein in its entirety, and is hereby expressly made a part of this specification.

BACKGROUND OF THE INVENTION

Field of the Invention

Systems and methods for measuring an analyte in a host are provided. More particularly, systems and methods are provided for applying a transcutaneous analyte measurement system to a host.

Description of the Related Technology

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

The process of applying the sensor to the person is important for such a system to be effective and user friendly. The application process should result in the sensor assembly being attached to the person in a state where it is capable of sensing glucose level information, communicating the sensed data to the transmitter, and transmitting the glucose level information to the receiver.

Exemplary prior art systems are disclosed in, e.g., US PGP 2014/0088389 and US PGP 2013/0267813, owned by the assignee of the present application and herein incorporated by reference in their entireties. Such systems tended to rely on particular configurations of a spring and a seal. These configurations resulted in certain disadvantages. For example, portions of the movement occurred when the spring was at its lowest force, e.g., at the end of its extension or compression, i.e., at its equilibrium position. In addition, as the spring was maintained in a compressed or extended or otherwise preloaded condition, between the time of manufacture and the time of activation, the same could undergo mechanical fatigue during this time. Such may in addition result in cause mechanical "creep", particularly in plastic components.

Other issues include that certain elements, particularly seals, were subject to "slingshotting" as insertion elements underwent movements caused by the insertion routine such effects resulting in inaccurate sensor wire placement, as the amount of slingshotting is unpredictable. In addition, where a single spring was suggested in prior implementations, the same would generally have to be a large spring to accommodate all the motion required in insertion and retraction, and such a large spring may be expected to deleteriously cause tissue trauma as the needle and sensor were forcefully inserted into a host.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

The present systems and methods relate to systems and methods for measuring an analyte in a host, and for applying a transcutaneous analyte measurement system to a host. The various embodiments of the present systems and methods for applying the analyte measurement system have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

In a first aspect, an applicator is provided for applying an on-skin sensor assembly to skin of a host, the device including: an applicator housing configured to secure a disposable housing, where the disposable housing is configured to receive an electronics unit, and where the electronics unit is configured to generate analyte information based on a signal from a sensor, the sensor including a sensor wire with an electrode contact portion, the electrode contact portion configured for use in powering the sensor and transmitting a signal from the sensor to the electronics unit when the electronics unit is received in the disposable housing; and a sensor insertion drive configured to insert an indwelling portion of the sensor wire into a host and to mount the disposable housing to a portion of the sensor wire and the electrode portion that is not indwelling, the indwelling portion of the sensor wire inserted into skin of a host using a needle configured to provide support and structure to the sensor wire during insertion, the sensor insertion drive configured to perform an insertion step where the needle is inserted into skin of the host to deploy the sensor wire, and a retraction step where the needle is retracted from the skin of the host, thereby leaving the sensor wire deployed in the host, and where the needle insertion step and the needle retraction step are performed so as to provide a predetermined force profile during the needle insertion and retraction steps.

Implementations of the embodiments may include one or more of the following. The predetermined force profile during the needle insertion step may be defined by an equation such that $F=f(x)$, where x is a distance the sensor wire is translated from an initial position. The function $f(x)$ may be defined to be an envelope between $ax2+bx+c$ and $dx2+gx+h$. The function $f(x)$ may be a bimodal curve. The sensor insertion drive may include a crank slider component, a rack and pinion component, or a barrel cam. The applicator may further include a trigger configured to, in response to being activated, cause the insertion component, e.g., a needle and/or cannula, to insert the sensor into the host. A needle may be employed to provide column strength to the sensor, e.g., sensor wire, and a cannula may be employed to provide column strength to the needle. The trigger may be an activatable button configured to be operated by a user, such as one mechanically linked to the insertion component, such that activation of the button forms a portion of the insertion step or the retraction step, or a portion of both.

A spring may be used to perform the insertion step, and activation of the button may perform the retraction step. The spring may be a torsion spring. Activation of the button may perform the insertion step, and a spring may be used to perform the retraction step. Activation of the button may include depressing a plunger. The trigger may be an electromechanical element configured to be activated by a signal received from a transmitter. The transmitter may include a smartphone running an insertion application. The insertion component may further include a cannula to provide additional column strength and isolation to the needle, where the cannula is disposed within and through at least one seal in the housing during the insertion step, and where the cannula is configured to be removed from the seal and housing as part of the retraction step.

The sensor insertion drive may include a primary operating component and a booster component, such that the booster component is configured to insert additional stored energy into the primary operating component to remove the cannula from the seal and housing during the retraction step. The booster component may be a booster spring. The housing may define at least one hole for passage of the sensor wire, and the seal may be configured to substantially isolate the indwelling portion of the sensor wire from the portion of the sensor wire that is not indwelling. The applicator may further include a seal carrier in which the at least one seal is disposed, where the seal is adhered to the seal carrier, including by overmolding or gluing. The seal carrier may include sidewall ribs to reduce seal deformation during cannula removal. The seal carrier may include a spring couple to the seal to reduce seal deformation during cannula removal. The seal may be bonded to the seal carrier to inhibit movement of the seal during removal of the cannula. The seal or the seal carrier or both may define voids configured to reduce friction between the seal or seal carrier and the cannula during removal of the cannula.

At least two pucks may be disposed within the housing to electrically couple areas of the electrode contact portion to respective electrodes on the electronics unit, and the pucks may be configured to reduce friction between the seal or seal carrier and the cannula, the configuration to reduce friction defined by shaved or hollowed out portions of the pucks or by voids within the pucks.

The seal may be a hybrid seal included of silicone and TPE. The seal may be a stack seal, where the stack seal is configured to decouple movement of the sensor wire from movement of the cannula. The seal may be a sandwich seal, and the sandwich seal may include a first seal component and a second seal component, where the cannula is disposed between the first and second seal components. The seal may be a flow seal, where the flow seal defines a channel by a channel wall, the cannula being disposed in the channel, and may further include a lubricant disposed between the channel wall and an exterior of the cannula. The seal may be an O-ring seal.

The applicator may further include a seal support, where the seal support is configured to inhibit movement of the seal during removal of the cannula. The seal support may be a spring. The applicator may further include a sensor wire support, where the sensor wire support is configured to inhibit movement of the sensor wire during removal of the cannula. The sensor wire support may be a spring. The applicator may further include a motor rotationally coupled to the cannula, such that the motor is configured to rotate the cannula prior to and during removal of the cannula. The applicator may further include a cam rotationally coupled to the cannula, such that the cam is configured to rotate the cannula prior to and during removal of the cannula, the cam being coupled to the insertion component and receiving a linear force therefrom. The linear force may be received from a spring. The linear force may be received from user activation of a button. The cam may be configured to rotate the cannula with a cycle time of less than 500 ms.

The insertion component may be configured to retract the cannula prior to retraction of the needle, such that a slingshot effect of the flexible seal causes the seal to strike the needle rather than the sensor wire. During the insertion step, the insertion component may be configured such that the needle is deployed to a first depth and then the sensor wire is deployed to a second depth, where the second depth is deeper than the first depth. The applicator may further include an electronics unit placement spring configured to snap the electronics unit into the housing during the retraction step. The electronics unit placement spring may be configured to draw the electronics unit into the housing. The housing may be configured to secure the electronics unit by a mechanical connection to an electronics unit bay, and the electronics unit and electronics unit bay may be configured such that the electronics unit cannot be removed from the electronics unit bay without destruction of a portion of the electronics unit bay, the destruction also destroying the mechanical connection. The electronics unit may be configured, in response to the trigger being activated and/or the electrical connection of the sensor to the electronics unit, to generate analyte information. The housing may be configured such that the electronics unit cannot be removed from the housing while the housing is adhered to the skin of the host.

A time between sensor insertion into the host and the electronics unit securing to the housing may be less than about 1 second. At least one contact on the electronics unit may be more rigid than the sensor, and the electronics unit may be configured such that, when fully secured to the housing, the at least one contact presses the sensor into an elastomeric seal such that the elastomeric seal is compressed and conforms to the sensor.

The sensor may be configured, after insertion into the host, to be surrounded by an elastomeric seal, and the electronics unit may be configured, in response to the electronics unit being released from a lock, to compress the elastomeric seal to secure the sensor and to form a seal around the sensor.

The device may be configured to disengage from the housing and from the electronics unit in response to the electronics unit being released from a lock. The device may be configured to provide one or more tactile, auditory, or visual indications that the electronics unit has been inserted into the housing to the extent permitted by a lock. The applicator may further include a trigger lock configured to prevent activation of the trigger. The applicator may further include a protective cover configured to cover the electronics unit and the housing after sensor insertion and to secure the electronics unit to the housing.

In a second aspect, a device is provided for applying an on-skin sensor assembly to a host, including: a needle containing a removable sensor, the sensor including a sensor wire with at least two conductive contact points at an ex vivo portion and a sensing portion at an in vivo portion, the needle configured to be inserted into a host to deploy the sensor, including to be inserted into a host to deploy the sensing portion in vivo in the host, and where the needle is configured to be retracted out of the host following deployment; a cannula traversing a seal within a disposable housing, where the needle is configured to be inserted into the host after passing at least partially through the cannula in a first direction when deploying the sensor in the host, and where the needle is configured to at least partially pass through the cannula in a direction opposite the first direction when the needle is being retracted out of the host, and where the cannula is configured to be retracted out of the seal at least partially during the time the needle is being retracted out of the host; where the needle insertion and retraction requires a first portion of a force profile, and where the cannula retraction requires a second portion of a force profile; and further including one or more drive components to provide or enable a force exceeding the force profile during both the first portion and the second portion.

Implementations of the embodiments may include one or more of the following. The one or more of the drive components may convert rotational force to a linear force. The drive component may be a scotch yoke, a crank slider, a barrel cam, or a rack and pinion. The drive component for the first portion of the force profile may be a scotch yoke, a crank slider, a barrel cam, or a rack and pinion, and a drive component for the second portion of the force profile may be a spring. A source of energy for the rotational force may be a torsion spring. The spring may be configured to store energy for the second portion of the force profile by compression or tension. The needle retraction may cause the cannula retraction. The second portion may have a maximum greater than a maximum of the first portion. The first and second portions may be normal curves.

The disposable housing further may include a septum, where the sensor wire passes through the septum, and where the septum provides the sensor wire with a force against removal from the host. The first and second portions together may form a bimodal distribution. The one or more drive components may include a first helical spring configured to perform the first portion of the force profile, and a second helical spring configured to perform a second portion of the force profile. A drive component for the first portion of the force profile may be a scotch yoke coupled to a torsion spring, and a drive component for the second portion of the force profile may be a spring, where the device is configured such that when motion corresponding to the first portion of the force profile is completed, the wheel of the scotch yoke is prevented from rotating any further. The wheel of the scotch yoke may be prevented from rotating any further, neither forwards nor backwards. The applicator may further include a ratchet component, where the wheel of the scotch yoke is prevented from rotating any further due to the ratchet component.

The seal carrier may include one or more elements configured to prevent slingshotting of the seal when the cannula is retracted. The one or more elements may include ribs mounted to the seal carrier and penetrating at least a portion of the seal.

The seal may be a hybrid seal. The hybrid seal may include a first component having a first durometer and a second component having a second durometer, the second durometer higher than the first durometer. The material of the first component may be a thermoplastic elastomer and a material of the second component may be silicone. The seal may define an empty volume at least partially surrounding the cannula before the cannula is retracted, and the seal may be configured such that the empty volume can be at least partially filled with a lubricant such as petroleum jelly.

The seal may be configured to define an injection port for the lubricant, the injection port in pressure communication with the empty volume. The empty volume may be substantially the shape of a rectangular solid. The seal may further define two puck voids, the puck voids substantially cylindrical in shape, and the device further may include two pucks, the pucks essentially cylindrical in shape, each puck occupying one of the puck voids, and the cannula may be situated so as to traverse each puck prior to cannula retraction. The puck voids may be defined by cored-out sections of the pucks.

In a third aspect, a device is provided for depositing a sensor within a disposable housing, the sensor not preconnected to the disposable housing, including: a needle configured to house an implantable sensor configured to be deposited into a host, the sensor constituted by a wire and having a proximal end and a distal end, the sensor held against movement in one direction when disposed in the needle by a push rod; an applicator in which the needle is situated, the applicator including at least one latch; a drive situated within the applicator to insert the needle into the host, and to retract the needle following insertion; where at a distal end of travel of the needle, the push rod engages the latch such that the push rod is maintained in a stationary position during needle retraction, such that the distal end of the sensor is deposited into the host and the proximal end of the sensor is disposed in the disposable housing.

Implementations of the embodiments may include one or more of the following. The applicator may further include a cannula, and the device may be configured such that the needle travels at least partially through the cannula at least during a portion of the insertion and retraction. The cannula may be situated within the disposable housing. The drive may be configured to remove the cannula during the retraction of the needle. The drive may include a torsion spring or a booster spring, for example, e.g., and the booster spring may be configured to perform the retraction. The drive further may include a rack and pinion, a crank slider, a barrel cam, or any other suitable mechanism for converting rotary motion into linear motion. The sensor may be further held against movement in the needle, in two directions, by a definition of a kink in the sensor, where the kink provides a frictional point of contact between an inner wall of the needle and the sensor, e.g., in one implementation one or more wires constituting the sensor.

The device may further include a seal in the disposable housing, such that the proximal end of the sensor is disposed in the seal in the disposable housing upon insertion and retraction. The sensor wire may be a coaxial wire having a first exposed portion and a second exposed portion. The seal may define two voids, and may further include first and second conductive pucks, each puck disposed in a respective void, such that the first conductive puck is in signal communication with the first exposed portion when the sensor wire is inserted in the seal, and such that the second conductive puck is in signal communication with the second exposed portion when the sensor wire is inserted in the seal. The applicator may further include a seal carrier in which the seal is disposed. The applicator may further include a pushrod back spring configured to bias the push rod during movement of the push rod, whereby ambiguity in movement of the pushrod is removed.

In a fourth aspect, a wearable portion of a device for monitoring an analyte is provided, including: a disposable housing in which a seal carrier may be located, the seal carrier configured to support at least one seal and to connect to at least one implantable sensor wire; and a transmitter configured to frictionally or mechanically couple to the disposable housing, the transmitter configured to conductively couple to a proximal portion of the sensor wire; where the disposable housing further includes a frangible portion, such that once the transmitter frictionally or mechanically couples to the disposable housing, the transmitter cannot be removed without removal of the frangible portion. In other words, once the frangible portion is removed, the transmitter can no longer be secured to the disposable housing, and a new disposable housing must be employed.

Implementations of the embodiments may include one or more of the following. The frangible portion may form an exterior perimeter of the seal carrier, and the transmitter may be inserted adjacent the exterior perimeter.

In a fifth aspect, a device is provided for depositing a sensor within a disposable housing, the sensor not preconnected to the disposable housing, including: a needle configured to house an implantable sensor configured to be deposited into a host, the needle passing through a seal, the sensor constituted by a wire and having a proximal end and a distal end, the sensor held against movement in one direction when disposed in the needle by a push rod; an applicator in which the needle is situated; a drive situated within the applicator to insert the needle into the host, and to retract the needle following insertion; and a spring configured to engage the sensor wire at least when the needle is removed, such that, upon removal of the needle and the push rod, the sensor wire is secured against movement caused by movement of the needle through the seal.

A number of advantages may be seen by implementation of arrangements according to present principles. For example, the implementations lead to consistency in insertion, retraction, and speed, leading in turn to a more reproducible sensor environment and in vivo wound response. This in turn may reduce sensor-to-sensor performance variability, including due to the effects of outliers, dip and recover faults, and end-of-life faults. This further enables reduced factory calibration, including more predictable signal trends at start up, as well as reduced pain for the patient.

As one example, a more rapid insertion and retraction step reduces the potential for the user to move while the needle and/or the deployment mechanism are in the body. While the time required for a user to react to pain has been found to be about 0.40 to 1.0 seconds, systems and methods according to present principles may insert and retract the needle within, e.g., 0.25 seconds, so that the needle has exited the skin before a user can begin to react. Systems and methods according to present principles further prevent variability in the needle/sensor angle due to motion of the user. In addition, systems and methods according to present principles reduce the potential for tissue damage and pain due to motion perpendicular to the needle axis, e.g., that could be imparted by motion of the user.

In one aspect, an applicator for applying an on-skin sensor assembly to skin of a host comprises an applicator housing operatively coupled to a disposable housing, the disposable housing being configured to receive an electronics unit, the electronics unit being configured to generate analyte information based on a signal from a sensor. The applicator further comprises an insertion assembly comprising an insertion member, the insertion member being configured to insert the sensor into the skin of the host, a resistance member releasably coupled to the insertion assembly, a first drive assembly containing a first amount of stored energy, the first drive member being configured to drive the insertion member in a distal direction to an inserted position, and a second drive assembly containing a second amount of stored energy. The second drive member is configured to drive the insertion member in a proximal direction, and the second amount of stored energy is sufficient to decouple the resistance member from the insertion assembly. In one embodiment, the first drive assembly is configured to drive the insertion member in the proximal direction after the insertion member reaches the inserted position. In another embodiment, the first drive assembly is configured to activate the second drive assembly after the first drive assembly begins driving the insertion member in the proximal direction. In another embodiment, the first drive assembly is configured to activate the second drive assembly when the first drive assembly reaches a trigger position, the trigger position being proximal of the inserted position. In another embodiment, the second drive assembly is configured to decouple the resistance member from the insertion assembly. In another embodiment, the second amount of stored energy is sufficient to decouple the resistance member from the insertion assembly. In another embodiment, the second amount of stored energy is sufficient to decouple the resistance member from the insertion assembly and drive the insertion member in a proximal direction to a retracted position. In another embodiment, the proximal direction and the distal direction extend along an axis of the insertion member. In another embodiment, the proximal direction and the distal direction extend at an angle to a plane of the disposable housing. In another embodiment, the resistance member is operatively coupled to the disposable housing. In another embodiment, the resistance member is frictionally engaged with the insertion assembly. In another embodiment, the resistance member is slidably coupled with the insertion assembly. In another embodiment, the resistance member comprises an elastomer. In another embodiment, the resistance member comprises a seal. In another embodiment, the applicator further comprises a carrier operatively coupled to the disposable housing, the resistance member being operatively coupled to the carrier. In another embodiment, the carrier is movably coupled to the disposable housing. In another embodiment, the insertion member comprises a needle. In another embodiment, the insertion assembly comprises a cannula. In another embodiment, the insertion member is configured to travel through the cannula as the insertion member moves distally. In another embodiment, the resistance member is releasably coupled to the cannula. In another embodiment, the cannula is fixed relative to the disposable housing as the insertion member moves distally. In another embodiment, the seal comprises a first portion and a second portion, the first portion having a first durometer and the second portion having a second durometer, the second durometer being higher than the first durometer. In another embodiment, the first portion comprises silicone and the second portion comprises TPE. In another embodiment, the cannula is disposed between the first and second seal components. In another embodiment, the resistance member defines a channel configured to receive a fluid or gel. In another embodiment, the applicator further comprises a cam configured to rotate the cannula about an axis of the cannula. In another embodiment, a distal end of the insertion member extends distal of the cannula when the resistance member is decoupled from the insertion assembly. In another embodiment, the resistance member comprises a contact surface configured to engage with the cannula, the contact surface defining one or more voids between the contact surface and the cannula. In another embodiment, the applicator further comprises a plurality of conductive elastomeric contacts disposed within the resistance member, the conductive elastomeric contacts defining one or more voids between the contact surface and the cannula. In another embodiment, at least a portion of the insertion assembly extends through the two conductive elastomeric contacts. In another embodiment, the resistance member comprises a contact surface configured to engage with the cannula, and wherein the conductive elastomeric contacts define one or more voids between the contact surface and the cannula. In another embodiment, the resistance member is coupled directly to the insertion member. In another embodiment, the insertion assembly comprises a support configured to inhibit proximal movement of the sensor, at least after the insertion assembly reaches the inserted position. In another embodiment, the support comprises a pushrod. In another embodiment, the support comprises a spring. In another embodiment, the disposable housing comprises a first portion coupled to a second portion by a frangible member. In another embodiment, the disposable housing comprises a receptacle configured to receive a corresponding key of a compatible electronics unit. In another embodiment, the disposable housing comprises an interference structure configured to prevent installation of an incompatible electronics unit in the disposable housing. In another embodiment, the applicator further comprises a trigger configured to activate the first drive assembly. In another embodiment, the trigger comprises an electromechanical element configured to be activated by a signal received from a transmitter. In another embodiment, the transmitter comprises a smartphone running an insertion application. In another embodiment, the applicator further comprises a safety lock configured to prevent operation of the trigger. In another embodiment, the safety lock comprises a tab coupled to the trigger by at least one frangible member. In another embodiment, the first amount of stored energy exceeds about ¼ lbf and the second amount of stored energy exceeds about ⅛ lbf. In another embodiment, at least one of the first drive assembly and the second drive assembly is configured to convert rotational motion into linear motion. In another embodiment, at least one of the first drive assembly and the second drive assembly includes a scotch yoke, a crank slider, a barrel cam, or a rack and pinion. In another embodiment, at least one of the first drive assembly and the second drive assembly includes a spring. In another embodiment, at least one of the first drive assembly and the second drive assembly includes a torsion spring. In another embodiment, the second amount of stored energy is greater than the first amount of stored energy. In another embodiment, the applicator further comprises a ratchet member configured to prevent backdriving of the first drive assembly. In another embodiment, the sensor comprises a sensor wire. In another embodiment, the resistance member is configured to substantially isolate a first portion of the sensor wire from a second portion of the sensor wire. In another embodiment, the disposable housing defines at least one opening configured to allow passage of the sensor. In another embodiment, the carrier comprises a securement member configured to inhibit proximal movement of the resistance member. In another embodiment, the securement member comprises glue. In another embodiment, the securement member comprises one or more inwardly-extending ribs. In another embodiment, the securement member comprises a spring. In another embodiment, the disposable housing is configured such that the electronics unit, once installed, cannot be removed from the disposable housing while the housing is adhered to the skin of the host. In another embodiment, the disposable housing is configured such that the electronics unit, once installed, cannot be removed from the disposable housing without breaking the frangible member. In another embodiment, the sensor comprises a bend configured to frictionally engage with the insertion member. In another embodiment, the insertion assembly comprises a needle hub, a cannula, and a cannula hub, and wherein engagement of the needle hub with the cannula hub causes the cannula to move in a proximal direction.

In another aspect, an applicator for applying an on-skin sensor assembly to skin of a host comprises an applicator housing operatively coupled to a disposable housing, the disposable housing being configured to receive an electronics unit, and the electronics unit being configured to generate analyte information based on a signal from a sensor. The applicator further comprises an insertion assembly comprising an insertion member, the insertion member being configured to insert the sensor into the skin of the host, a first drive assembly containing a first amount of stored energy, the first drive member being configured to drive the insertion member in a distal direction during a first phase and in a proximal direction during a second phase, and a second drive assembly containing a second amount of stored energy, the second drive member being configured to drive the insertion member in the proximal direction. The first drive assembly is configured to activate the second drive assembly during the second phase. In one embodiment, the drive assembly is self-reversing from the first phase to the second phase. In another embodiment, a distal end of the insertion member extends distal of the cannula during the second phase. In another embodiment, the first drive assembly is configured to drive the insertion member in the proximal direction after the insertion member reaches an inserted position. In another embodiment, the first drive assembly is configured to activate the second drive assembly during the second phase. In another embodiment, the first drive assembly is configured to activate the second drive assembly in response to the first drive assembly reaching a trigger position during the second phase. In another embodiment, the applicator further comprises a resistance member, the resistance member being operatively coupled to the insertion assembly during the first phase, wherein the second drive assembly is configured to decouple the resistance member from the insertion assembly during the second phase. In another embodiment, the second amount of stored energy is sufficient to decouple the resistance member from the insertion assembly. In another embodiment, the insertion assembly comprises a cannula. In another embodiment, the insertion member is configured to travel through the cannula during the first phase. In another embodiment, the resistance member is releasably coupled to the cannula. In another embodiment, the cannula is fixed relative to the disposable housing as the insertion member moves distally. In another embodiment, at least one of the first drive assembly and the second drive assembly is configured to convert rotational motion into linear motion. In another embodiment, at least one of the first drive assembly and the second drive assembly includes a scotch yoke, a crank slider, a barrel cam, or a rack and pinion. In another embodiment, at least one of the first drive assembly and the second drive assembly includes a spring. In another embodiment, at least one of the first drive assembly and the second drive assembly includes a torsion spring. In another embodiment, the second amount of stored energy is greater than the first amount of stored energy. In another embodiment, the applicator further comprising a ratchet member configured to prevent backdriving of the first drive assembly.

In another aspect, a sensor inserter assembly for applying an on-skin device to a skin of a host, the assembly comprises an applicator body, a disposable housing releasably coupled to the applicator body, a sharp configured to place a sensor at least partially into the skin of the host, a resistance member operatively coupled to the disposable housing, a separation member releasably coupled to the resistance member, the separation member being configured to prevent contact of the sharp with the resistance member, a deployment assembly configured to cause the sharp to move from a proximal starting position to a distal insertion position during a first phase and then to a proximal retracted position during a second phase, the deployment assembly being further configured to release the separation member from the resistance member during the second phase, a first stored energy component storing sufficient energy to drive the first phase and at least a first part of the second phase, and a second stored energy component storing sufficient energy to drive at least a second part of the second phase. In one embodiment, the second stored energy component stores sufficient energy to drive the second phase. In another embodiment, the second stored energy component stores more energy than the first stored energy component. In another embodiment, the disposable housing is configured to automatically release from the applicator body after the separation member is released from the resistance member. In another embodiment, the disposable housing is configured to automatically release from the applicator body in response to the separation member being released from the resistance member. In another embodiment, the resistance member is moveable relative to the disposable housing, at least after the separation member is released from the resistance member. In another embodiment, the deployment assembly is self-reversing from the first phase to the second phase. In another embodiment, the deployment assembly is configured to activate the second stored energy component during the second phase. In another embodiment, the separation member is frictionally engaged with the resistance member. In another embodiment, the separation member is slidably coupled to the resistance member. In another embodiment, at least one of the first drive assembly and the second drive assembly is configured to convert rotational motion into linear motion.

In another aspect, a method of applying an on-skin sensor assembly to skin of a host comprises providing an assembly comprising an applicator housing operatively coupled to a disposable housing, an insertion assembly comprising an insertion member, a first drive assembly containing a first amount of stored energy, and a second drive assembly containing a second amount of stored energy. The method further comprises activating a trigger of the assembly, wherein activating the trigger causes the first drive assembly to drive the insertion member in a distal direction during a first phase, wherein a sensor is inserted into the skin of the host, the first drive assembly to drive the insertion member in a proximal direction during a second phase, wherein the first drive assembly activates the second drive assembly, and the second drive assembly to drive the insertion member in the proximal direction during the second phase. In one embodiment, the method further comprises installing an electronics unit in the disposable housing, the electronics unit being configured to generate analyte information based on a signal from the sensor. In another embodiment, the assembly further comprises a resistance member coupled to the insertion assembly. In another embodiment, activating the trigger causes the second drive to decouple the resistance member from the insertion assembly during the second phase. In another embodiment, the second amount of stored energy is sufficient to decouple the resistance member from the insertion assembly. In another embodiment, the resistance member comprises a seal. In another embodiment, the insertion assembly comprises a cannula. In another embodiment, the second amount of stored energy is greater than the first amount of stored energy. In another embodiment, at least one of the first drive assembly and the second drive assembly is configured to convert rotational motion into linear motion. In another embodiment, the first drive assembly activates the second drive assembly in response to the first drive assembly reaching a trigger position during the second phase.

In further aspects and embodiments, the above method features of the various aspects are formulated in terms of a system as in various aspects, having an applicator configured to carry out the method features. Any of the features of an embodiment of any of the aspects, including but not limited to any embodiments of any of the first through fifth aspects referred to above, is applicable to all other aspects and embodiments identified herein, including but not limited to any embodiments of any of the first through fifth aspects referred to above. Moreover, any of the features of an embodiment of the various aspects, including but not limited to any embodiments of any of the first through fifth aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through fifth aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through fifth aspects referred to above.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIG. 50 illustrates a cored-out puck configured in accordance with an embodiment.

FIG. 99 illustrates a top plan view of a needle configured in accordance with an embodiment.

FIG. 100 illustrates a side view of the needle of FIG. 99.

FIG. 101 illustrates a perspective view of a multi-lumen needle, configured in accordance with an embodiment.

FIG. 105 illustrates an exploded perspective view of a lower housing and a disposable housing of an applicator system configured in accordance with another embodiment.

FIG. 106 illustrates a top perspective view of the disposable housing of FIG. 105, having a transmitter installed therein, in accordance with another embodiment.

FIG. 117 is a cross-sectional side view of the needle of FIG. 116;

FIG. 118 shows a schematic view of a needle configured in accordance with another embodiment;

FIG. 119 shows a schematic view of a needle configured in accordance with another embodiment;

FIG. 120 shows a schematic view of a needle configured in accordance with another embodiment;

FIG. 121 shows a schematic view of a needle configured in accordance with another embodiment;

FIG. 122 shows a schematic view of a needle configured in accordance with another embodiment;

FIG. 123 shows a schematic view of a needle configured in accordance with another embodiment;

FIG. 124 shows a schematic view of a needle configured in accordance with another embodiment;

FIG. 125 shows a schematic view of a needle configured in accordance with another embodiment;

FIG. 126 shows a schematic view of a needle configured in accordance with another embodiment;

FIG. 127 shows a schematic view of a conventional needle;

FIG. 128 shows another needle configured in accordance with an embodiment;

Figure 129:
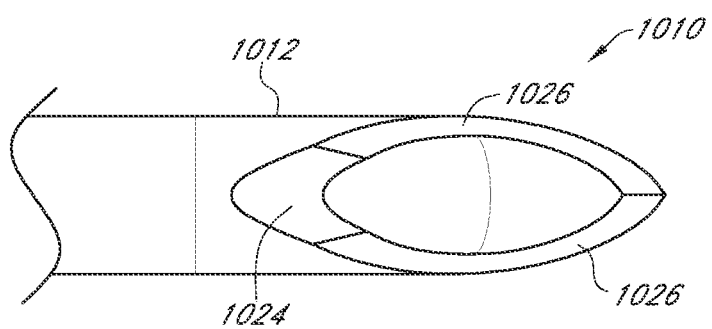
Figure 130:
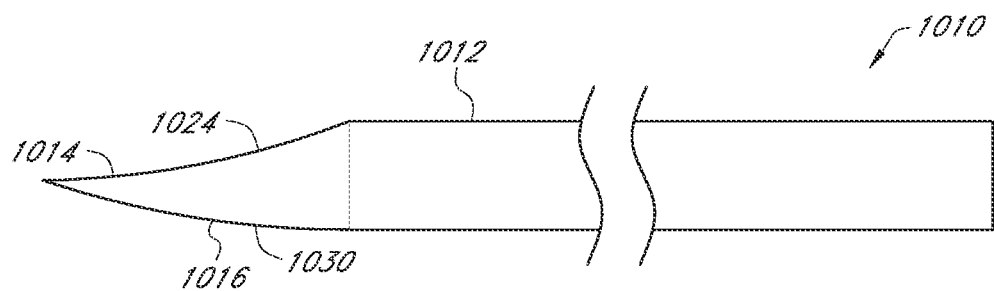
Figure 131:
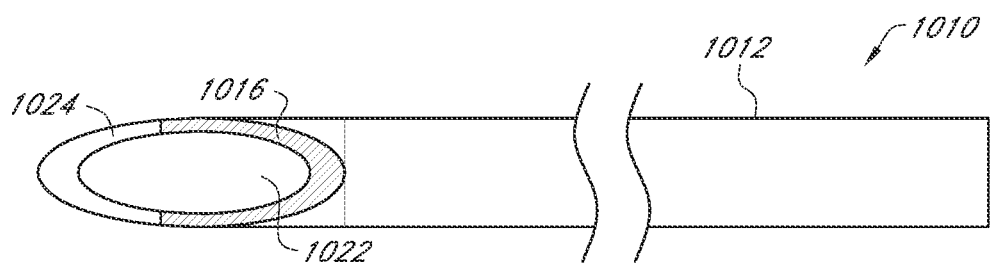
Figure 132:
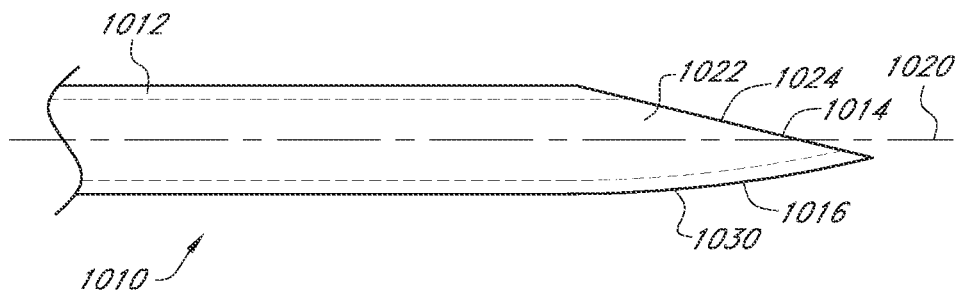
Figure 133:
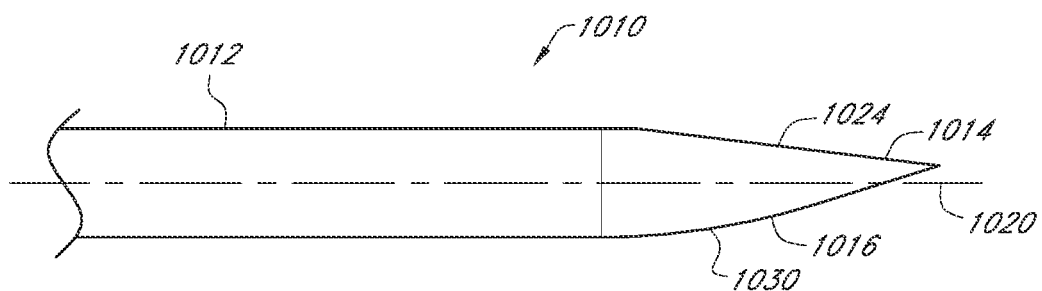
Figure 134:
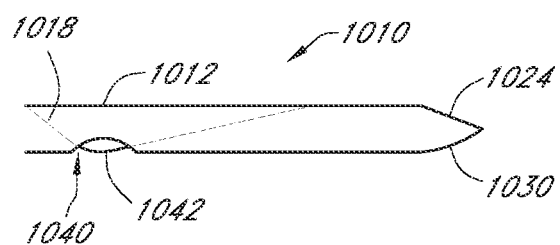

FIG. 129 shows another needle configured in accordance with an embodiment;

FIG. 130 shows a side view of a single bevel needle configured in accordance with an embodiment;

FIG. 131 shows a top view of the needle of FIG. 130;

FIG. 132 shows a side view of another embodiment of a single bevel needle with a 13 degree bend angle;

FIG. 133 shows a side view of another embodiment of a single bevel needle with a 17 degree bend angle;

FIG. 134 shows a side view of another embodiment of a needle including a proximal slot to receive a kink of a sensor.

DETAILED DESCRIPTION OF CERTAIN INVENTIVE EMBODIMENTS

The following description and examples illustrate some example embodiments of the disclosed invention in detail. Those of skill in the art will recognize that there are numerous variations and modifications of this invention that are encompassed by its scope. Accordingly, the description of a certain example embodiment should not be deemed to limit the scope of the present invention.

Sensor System and Applicator

Figure 1:
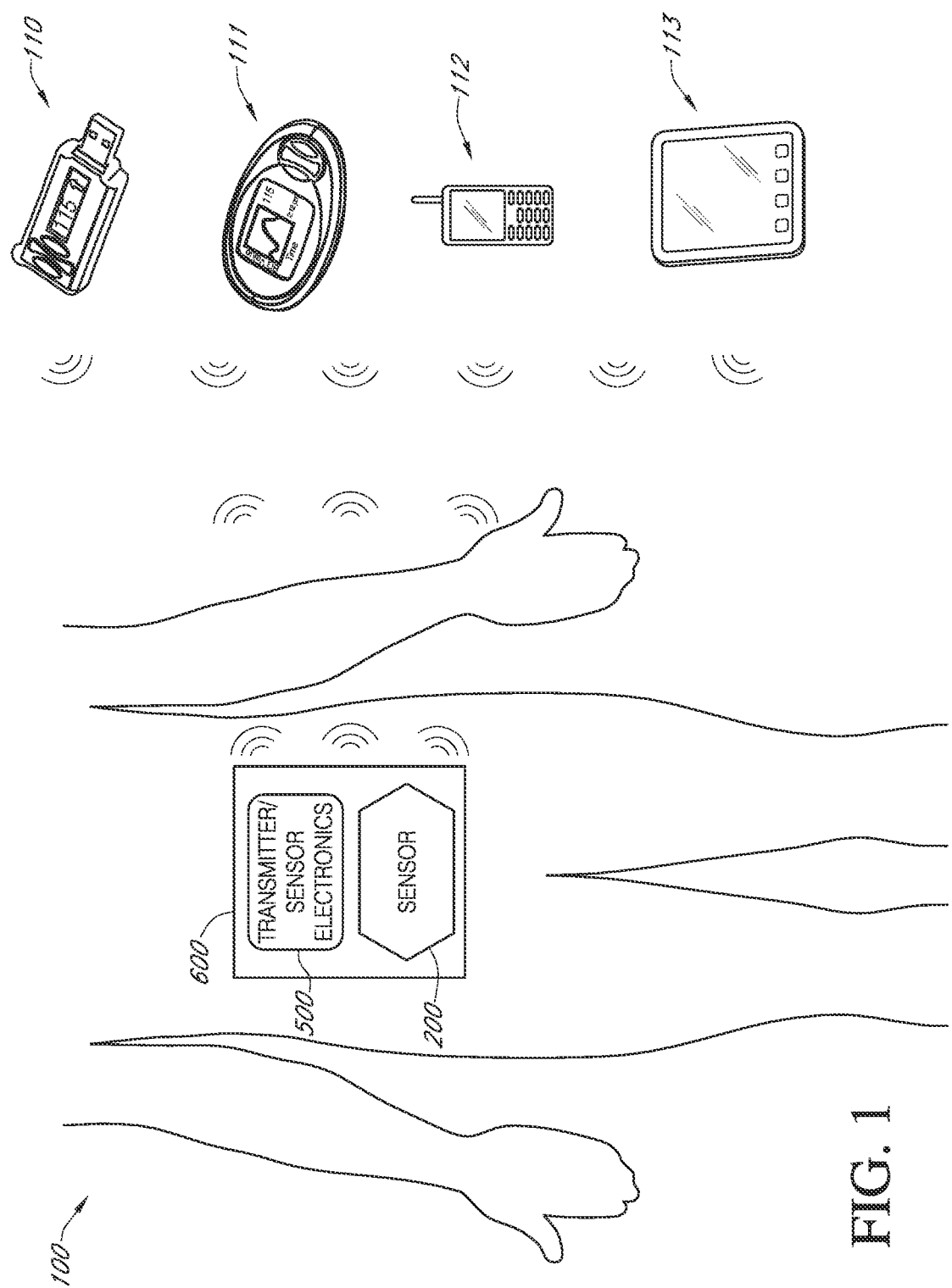
FIG. 1 is a schematic view of a continuous analyte sensor system attached to a host and communicating with other devices.

FIG. 1 is a schematic of a continuous analyte sensor system 100 attached to a host and communicating with a number of other example devices 110-113. A transcutaneous analyte sensor system comprising an on-skin sensor assembly 600 is shown which is fastened to the skin of a host via a disposable housing (not shown). The system includes a transcutaneous analyte sensor 200 and an electronics unit (referred to interchangeably as "sensor electronics" or "transmitter") 500 for wirelessly transmitting analyte information to a receiver. During use, a sensing portion of the sensor 200 is under the host's skin and a contact portion of the sensor 200 is electrically connected to the electronics unit 500. The electronics unit 500 is engaged with a housing which is attached to an adhesive patch fastened to the skin of the host.

The on-skin sensor assembly 600 may be attached to the host with use of an applicator adapted to provide convenient and secure application. Such an applicator may also be used for inserting the sensor 200 through the host's skin. Once the sensor 200 has been inserted, the applicator detaches from the sensor assembly.

In general, the continuous analyte sensor system 100 includes any sensor configuration that provides an output signal indicative of a concentration of an analyte. The output signal including (e.g., sensor data, such as a raw data stream, filtered data, smoothed data, and/or otherwise transformed sensor data) is sent to receiver which may be e.g., a smart phone, smart watch, dedicated device and the like. In one embodiment, the analyte sensor system 100 includes a transcutaneous glucose sensor, such as is described in US Patent Publication No. US-2011-0027127-A1, the contents of which are hereby incorporated by reference in its entirety. In some embodiments, the sensor system 100 includes a continuous glucose sensor and comprises a transcutaneous sensor such as described in U.S. Pat. No. 6,565,509 to Say et al., for example. In another embodiment, the sensor system 100 includes a continuous glucose sensor and comprises a subcutaneous sensor such as described with reference to U.S. Pat. No. 6,579,690 to Bonnecaze et al. or U.S. Pat. No. 6,484,046 to Say et al., for example. In another embodiment, the sensor system 100 includes a continuous glucose sensor and comprises a subcutaneous sensor such as described with reference to U.S. Pat. No. 6,512,939 to Colvin et al. In another embodiment, the sensor system 100 includes a continuous glucose sensor and comprises an intravascular sensor such as described with reference to U.S. Pat. No. 6,477,395 to Schulman et al., for example. In another embodiment, the sensor system 100 includes a continuous glucose sensor and comprises an intravascular sensor such as described with reference to U.S. Pat. No. 6,424,847 to Mastrototaro et al. Other signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entireties. The sensor extends through a housing, which maintains the sensor on the skin and provides for electrical connection of the sensor to sensor electronics, provided in the electronics unit.

In still further embodiments, the system 100 can be configured for use in applying a drug delivery device, such an infusion device, to the skin of a patient. In such embodiments, the system can include a catheter instead of, or in addition to, a sensor, the catheter being connected to an infusion pump configured to deliver liquid medicines or other fluids into the patient's body. In embodiments, the catheter can be deployed into the skin in much the same manner as a sensor would be, for example as described herein.

In one embodiment, the sensor is formed from a wire or is in a form of a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments, the smallest dimension of the elongated conductive body is less than about 0.1 inches, less than about 0.075 inches, less than about 0.05 inches, less than about 0.025 inches, less than about 0.01 inches, less than about 0.004 inches, or less than about 0.002 inches. The sensor may have a circular cross-section. In some embodiments, the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, one or two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In certain embodiments, the materials used to form the elongated conductive body (e.g., stainless steel, titanium, tantalum, platinum, platinum-iridium, iridium, certain polymers, and/or the like) can be strong and hard, and therefore are resistant to breakage. For example, in some embodiments, the ultimate tensile strength of the elongated conductive body is from about 80 kPsi to about 500 kPsi. In another example, in some embodiments, the Young's modulus of the elongated conductive body is from about 160 GPa to about 220 GPa. In still another example, in some embodiments, the yield strength of the elongated conductive body is from about 60 kPsi to about 2200 kPsi. In some embodiments, the sensor's small diameter provides (e.g., imparts, enables) flexibility to these materials, and therefore to the sensor as a whole. Thus, the sensor can withstand repeated forces applied to it by surrounding tissue.

In addition to providing structural support, resiliency and flexibility, in some embodiments, the core (or a component thereof) provides electrical conduction for an electrical signal from the working electrode to sensor electronics (not shown). In some embodiments, the core comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as stainless steel, titanium, tantalum, a conductive polymer, and/or the like. The core and the first layer can be of a single (or same) material, e.g., platinum. One skilled in the art appreciates that additional configurations are possible.

In the illustrated embodiments, the electronics unit 500 is releasably attachable to the sensor 200. The electronics unit 500 includes electronic circuitry associated with measuring and processing the continuous analyte sensor data, and is configured to perform algorithms associated with processing and calibration of the sensor data. For example, the electronics unit 500 can provide various aspects of the functionality of a sensor electronics module as described in U.S. Patent Publication No. 2009-0240120-A1 and U.S. Patent Publication No. 2012-0078071-A1 the contents of which are hereby incorporated by reference in their entireties. The electronics unit 500 may include hardware, firmware, and/or software that enable measurement of levels of the analyte via a glucose sensor, such as an analyte sensor 200. For example, the electronics unit 500 can include a potentiostat, a power source for providing power to the sensor 200, other components useful for signal processing and data storage, and preferably a telemetry module for one- or two-way data communication between the electronics unit 500 and one or more receivers, repeaters, and/or display devices, such as devices 110-113. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The electronics unit 500 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, and the like. Examples of systems and methods for processing sensor analyte data are described in more detail herein and in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-A1, U.S. Patent Publication No. 2005-0192557-A1, U.S. Patent Publication No. 2006-0222566-A1, U.S. Patent Publication No. 2007-0203966-A1 and U.S. Patent Publication No. 2007-0208245-A1, the contents of which are hereby incorporated by reference in their entireties.

One or more repeaters, receivers and/or display devices, such as key fob repeater 110, medical device receiver 111 (e.g., insulin delivery device and/or dedicated glucose sensor receiver), smart phone 112, portable computer 113, and the like are operatively linked to the electronics unit, which receive data from the electronics unit 500, which is also referred to as the transmitter and/or sensor electronics body herein, and in some embodiments transmit data to the electronics unit 500. For example, the sensor data can be transmitted from the sensor electronics unit 500 to one or more of key fob repeater 110, medical device receiver 111, smart phone 112, portable computer 113, and the like. In one embodiment, a display device includes an input module with a quartz crystal operably connected to an RF transceiver (not shown) that together function to transmit, receive and synchronize data streams from the electronics unit 500. However, the input module can be configured in any manner that is capable of receiving data from the electronics unit 500. Once received, the input module sends the data stream to a processor that processes the data stream, such as described in more detail below. The processor is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. The processor includes hardware that performs the processing described herein, for example read-only memory (ROM) provides permanent or semi-permanent storage of data, storing data such as sensor ID (sensor identity), receiver ID (receiver identity), and programming to process data streams (for example, programming for performing estimation and other algorithms described elsewhere herein) and random access memory (RAM) stores the system's cache memory and is helpful in data processing. An output module, which may be integral with and/or operatively connected with the processor, includes programming for generating output based on the sensor data received from the electronics unit (and any processing that incurred in the processor).

In some embodiments, analyte values are displayed on a display device. In some embodiments, prompts or messages can be displayed on the display device to convey information to the user, such as reference outlier values, requests for reference analyte values, therapy recommendations, deviation of the measured analyte values from the estimated analyte values, or the like. Additionally, prompts can be displayed to guide the user through calibration or troubleshooting of the calibration.

Additionally, data output from the output module can provide wired or wireless, one- or two-way communication between the receiver and an external device. The external device can be any device that interfaces or communicates with the receiver. In some embodiments, the external device is a computer, and the receiver is able to download current or historical data for retrospective analysis by a physician, for example. In some embodiments, the external device is a modem, and the receiver is able to send alerts, warnings, emergency messages, or the like, via telecommunication lines to another party, such as a doctor or family member. In some embodiments, the external device is an insulin pen, and the receiver is able to communicate therapy recommendations, such as insulin amount and time, to the insulin pen. In some embodiments, the external device is an insulin pump, and the receiver is able to communicate therapy recommendations, such as insulin amount and time to the insulin pump. The external device can include other technology or medical devices, for example pacemakers, implanted analyte sensor patches, other infusion devices, telemetry devices, or the like. The receiver may communicate with the external device, and/or any number of additional devices, via any suitable communication protocol, including radio frequency, Bluetooth, universal serial bus, any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, and/or a proprietary communication protocol.

Certain aspects of applicators systems are described in U.S. Patent Publication No. 2013-0267811-A1 and U.S. Pat. No. 7,497,827; both of which are owned by the assignee of the present application and herein incorporated by reference in their entireties.

In particular, the implementations described in the applications incorporated by reference above depict systems and methods of applying a transcutaneous sensor into a patient and situating sensor wires within a housing to which the transmitter is attached. In some cases a torsion spring provides the force required for the system to perform the steps, and energy is similarly stored in the torsion spring, which is preloaded prior to shipping. However, in other implementations, it may be desirable to add to the force provided by the torsion spring, or to replace the torsion spring altogether with another source of force. One reason for doing so is that in the above implementation the torsion spring is shipped and stored in the preloaded or constrained configuration, and is thus subject to loss of spring force over time. In addition, use of a previously-constrained torsion spring (or any similar single spring) leads to a reduced spring force at the end of the spring movement due to Hooke's Law, $F=-kx$, where x is the distance from the equilibrium position. That is, at the end of the spring movement, x is close to zero, and thus so is the force.

The below described implementations generally discuss sensors constituted by one or more sensor wires. However, it will be understood that the sensors are not limited to such wire shaped or linear arrangements. Rather, the sensors may be implemented as planar sensors, volumetric sensors, point sensors, or in other shapes as will be understood given this description.

Figure 2:
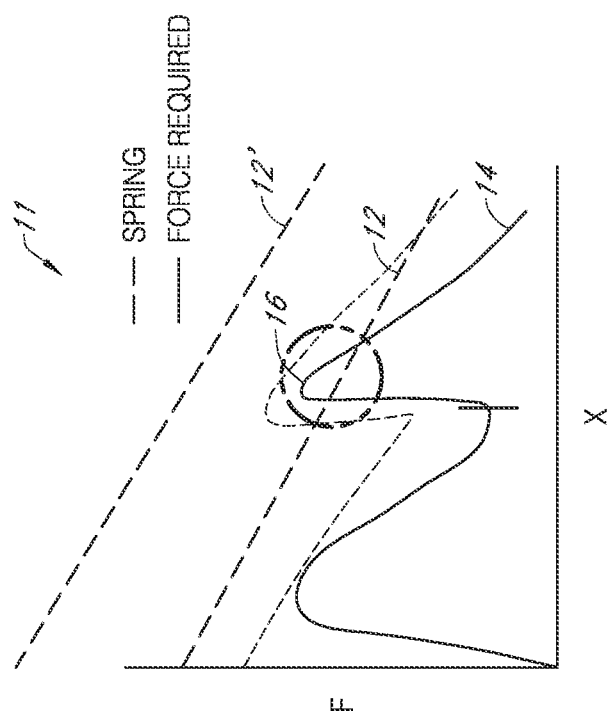
FIG. 2 illustrates a force profile curve for sensor insertion.

For example, and referring to FIG. 2, the line 12 represents the spring force given by Hooke's law above, and curve 14 represents the forces required during performance of the insertion steps above. Where the force required exceeds that available from the spring, e.g., in section 16, the system is unable to provide the necessary force. Larger spring forces may be provided by larger or stiffer spring, e.g., see line 12', but the same are associated with other difficulties, such as tissue damage when such a large force is caused to propel a needle into a host, and are moreover difficult to implement within small housings, as are desired.

Various other types of applicators may thus be employed, and are described below. Such applicators endeavor to tailor the applied force such that the stored force is available and applied as required. Specific examples will be given below with regard to specific applicators. In general it will be desired to have more force available than is required by any given force profile. It is also noted that a typical force profile has a bimodal distribution, e.g., has at least two maxima, as may be seen by the bimodal distribution of FIG. 2. The first maximum, e.g., a first portion of the force profile, is caused by the force required to have the needle entering the skin of the host. Once the skin has been penetrated, the force decreases because the interstitial tissue is easier to pass through. Thus this force is in the direction of propagation, e.g., the insertion direction, of the needle. The next maximum, e.g., a second portion of the force profile, is caused by retraction, and in particular a retraction of the needle and/or cannula, which is a force in the opposite direction from that of the insertion direction. Thus, while for convenience two positive maxima are shown in the figure, i.e., each indicated by positive force values, it will be understood that these maxima pertain to forces acting in opposite directions.

Figure 3:
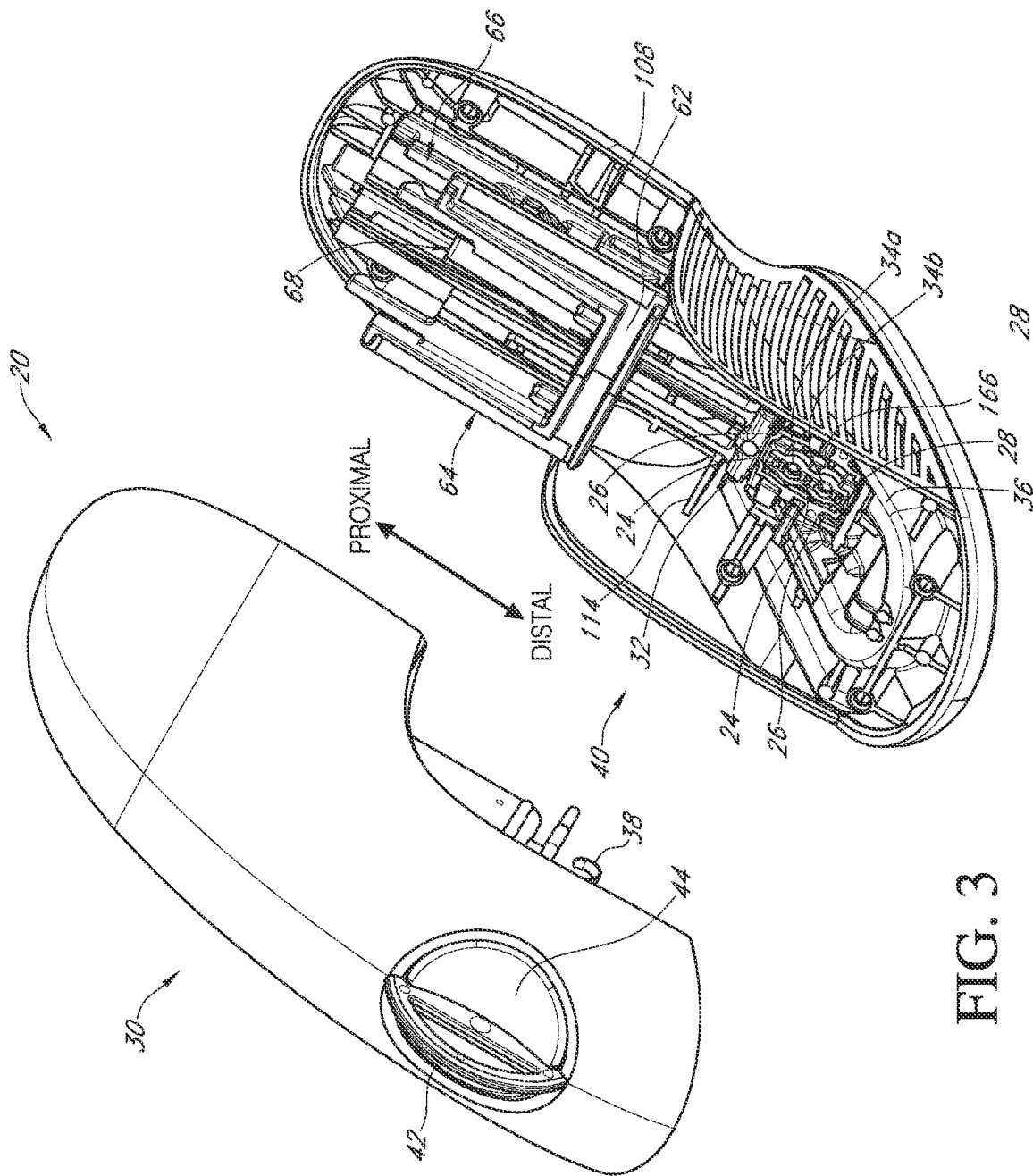
FIG. 3 illustrates a partially exploded view of an applicator configured in accordance with an embodiment.

In one implementation, as shown in FIG. 3, a torsion spring is used for an insertion step, e.g., a first portion of the force profile, while another drive mechanism, which can be different from a torsion spring, is used for a retraction step, e.g., a second portion of the force profile. In an insertion step, a needle and sensor are inserted in a host; in a retraction step, the needle is removed, as well as a cannula, as will be described. In FIG. 3, the drive mechanism is a helical spring, also termed a "booster" spring, preloaded so as to be stored in a compressed state. The preloading provides the energy necessary for the spring to perform expansion and thus cause retraction of the needle and the cannula.

Figure 4:
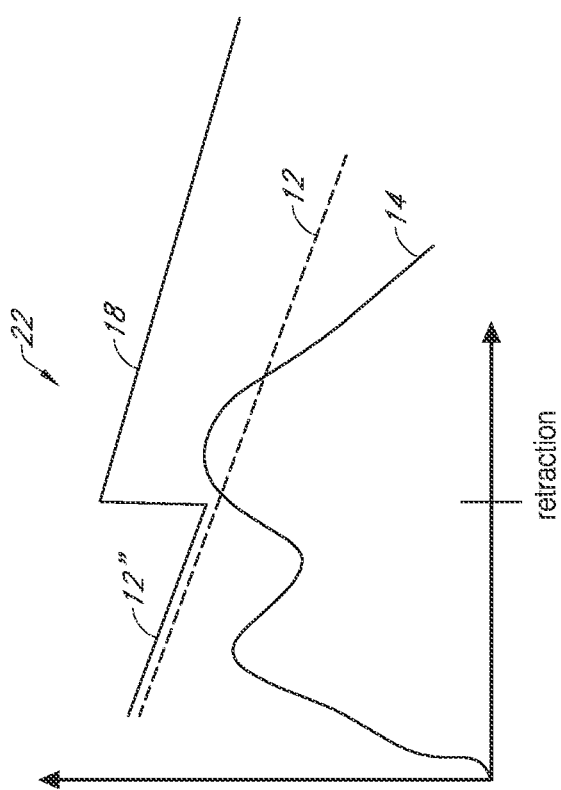
FIG. 4 illustrates another force profile curve for sensor insertion.

A force profile for the device of FIG. 3 is shown by the graph 22 of FIG. 4. In the graph 22, the same bimodal force distribution 14 as in FIG. 2 may still be seen, with the first hump corresponding to needle insertion, with a majority of the force needed for skin penetration, and the second hump corresponding to cannula and needle retraction. In this case, however, at or near the start of the retraction step, the booster spring is activated, leading to the rise in force shown from line 12" to line 18, which rise then exceeds the force required for the cannula and needle retraction. As the booster force is provided by a spring, the force profile (line 18) of the spring follows the form $F=-kx$. In some cases, including in the exemplary device shown in FIG. 3, force from the torsion spring may be arrested, and the retraction force entirely provided by the booster spring. In other implementations, both the torsion spring and the booster spring may be involved in providing retraction forces.

Figure 5:
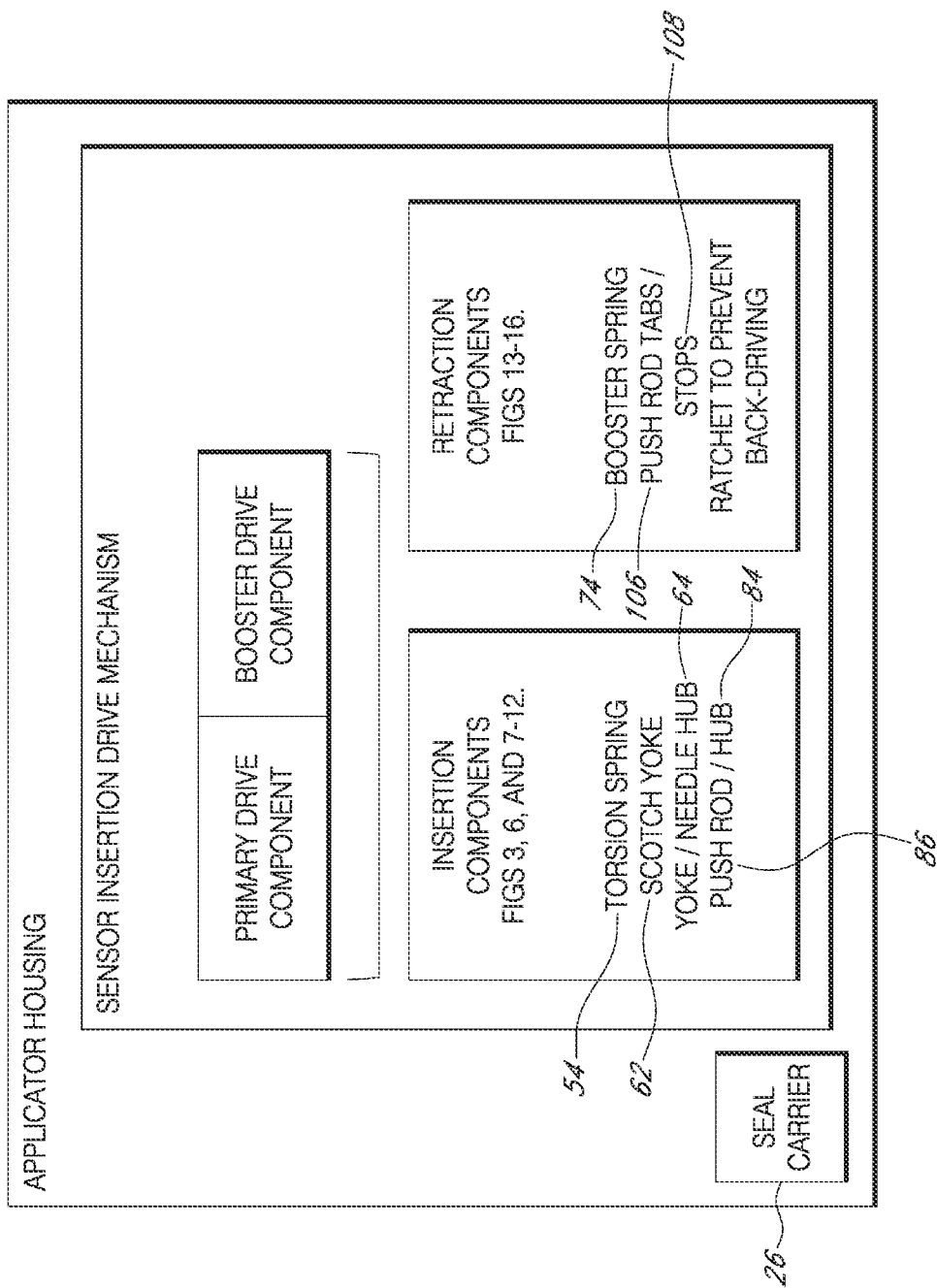
FIG. 5 illustrates a schematic view of components of an applicator in accordance with an embodiment.

The applicator of FIG. 3 will be described in detail below, but initially it is noted that the same includes a number of interoperating components, and these are diagrammed schematically in FIG. 5. In particular, an applicator housing is described generally, but with particular regard to FIGS. 3 and 6. Most of the operations performed by the applicator pertain to a seal carrier 26 and components thereof. The operations generally relate to sensor wire insertion performed by a sensor insertion drive mechanism, which is described in FIGS. 7-16, with variations described in subsequent figures, e.g., FIGS. 20-38. The drive mechanism generally but not always includes a primary drive component, e.g., a torsion spring, and a booster component, e.g., a booster spring. While components often perform multiple functions, the same may be divided very generally into insertion components and retraction components, with the former being detailed in FIGS. 3, 6, and 7-11. Exemplary elements pertaining to insertion are listed in FIG. 5. Elements pertaining generally to retraction are shown in FIGS. 13-16, and exemplary elements therein are also listed in FIG. 5. The above is intended to be a general and nonlimiting description, however. For example, in one implementation, a needle and cannula constitute insertion component that play a key role in insertion of a sensor, but the same are also key components to be retracted once a sensor is inserted.

Referring in more detail now to FIG. 3, the device 20 includes an upper or top applicator housing 30 and a lower or bottom applicator housing 40. The upper housing 30 and the lower housing 40 both form a portion of a disposable device, including all of the components illustrated within and between the upper housing and the lower housing. In use, the upper housing is mounted to the lower housing and the same are shipped as a single unit, with a torsion spring and a booster spring (both in a preloaded state). Other types of drive mechanisms, which may be preloaded or not, are also described below. Here the term "preloaded" or "preload" refers to a drive mechanism that, if activated, performs a desired drive step. For example, a spring that is not in an equilibrium state may be either compressed or expanded, and each of the states may be referred to as "preloaded". A torsion spring may be wound such that, if released, provides a torque on an element about an axis. Such winding is considered here a form of preloading.

The device 20 is intended to perform steps of inserting a sensor, generally embodied by a sensor wire, into a patient, in vivo, the sensor wires extending out of the patient and coupled to an ex vivo disposable housing, the ex vivo disposable housing adhered to the skin of a patient. A transmitter (not shown in FIG. 3) may then be snapped onto the disposable housing. The transmitter has electrical contacts which when snapped onto the disposable housing make contact with respective conductive pucks through which the sensor wires pass, the sensor wires having respective windows in their insulation and thus each sensor wire is electrically coupled to a different puck.

A seal carrier 26 is illustrated in FIG. 3, and on the seal carrier 26 is situated a seal 24. The seal 24 performs various functions, including protecting the sensor wire from moisture, providing a reliable electrical connection, allowing an accurate sensor placement during insertion and retraction steps, and retaining the sensor wire, i.e., providing a secure connection to the sensor wire in order to prevent cases where a disposable housing is removed but a sensor wire stays within the body.

Two holes 34a and 34b are defined within the seal 24, and within the holes are situated the conductive pucks (not shown in FIG. 3). The seal carrier 26, seal 24, and a disposable housing 36 are the elements within FIG. 3 which remain with the patient after use of the applicator (along with sensor/sensor wire, not shown). The seal carrier 26 and the seal 24 rotate about a hinge 28 which also serves to couple the seal carrier 26 to the disposable housing 36 which is removably mounted to a lower surface of the lower housing 40. A detail of the disposable housing 36 and seal carrier 26 may be seen in FIG. 39, which shows the seal 24 and the seal carrier 26 in the same position as in FIG. 3, i.e., situated at an approximately 45° angle to the bottom surface of the lower housing 40. The disposable housing 36, seal carrier 26, and seal 24 are held in this position by a number of features described below. However, once the sensor wire has been installed in the patient and the cannula 78 and cannula hub 32 have been retracted, the seal carrier 26 and seal 24 can rotate about the hinge 28 and rest within the disposable housing 36 (e.g., generally parallel to or within the plane of the disposable housing 36). In some embodiments, the seal carrier 26 can be rotated down manually by the user. Alternatively, in some embodiments, a spring 38 (described in greater detail below) or other biasing member may be employed to cause the seal carrier 26 and the seal 24 to transition from being disposed at an angle to the base of the lower housing 40 to a resting position within (e.g., parallel to or within the plane of) the disposable housing, either simultaneously with the release of the disposable housing from the applicator housing, or before or after release of the disposable housing from the applicator housing.

Figure 6:
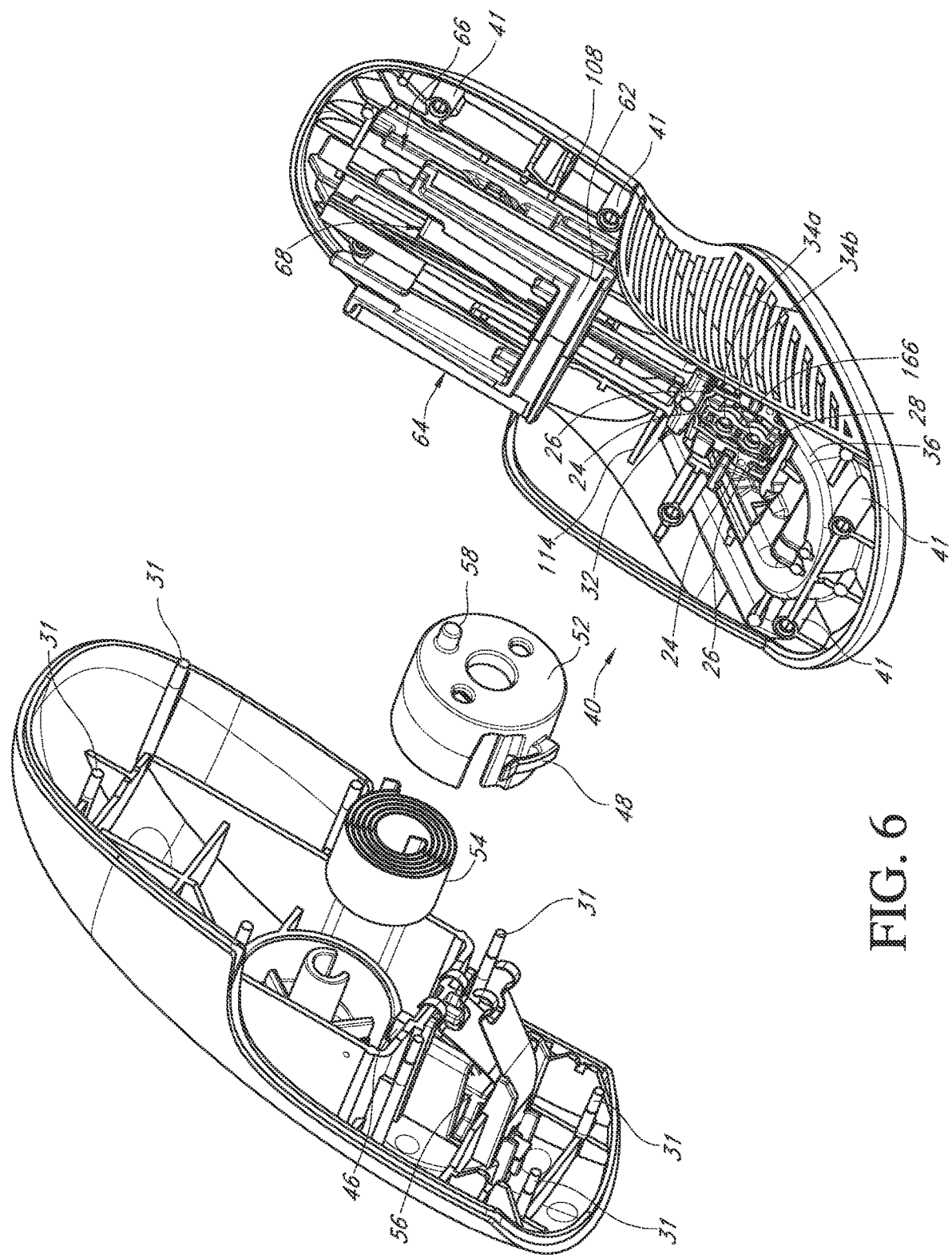
FIG. 6 illustrates another partially exploded view of the applicator configured in accordance with an embodiment of FIG. 3.
Figure 7:
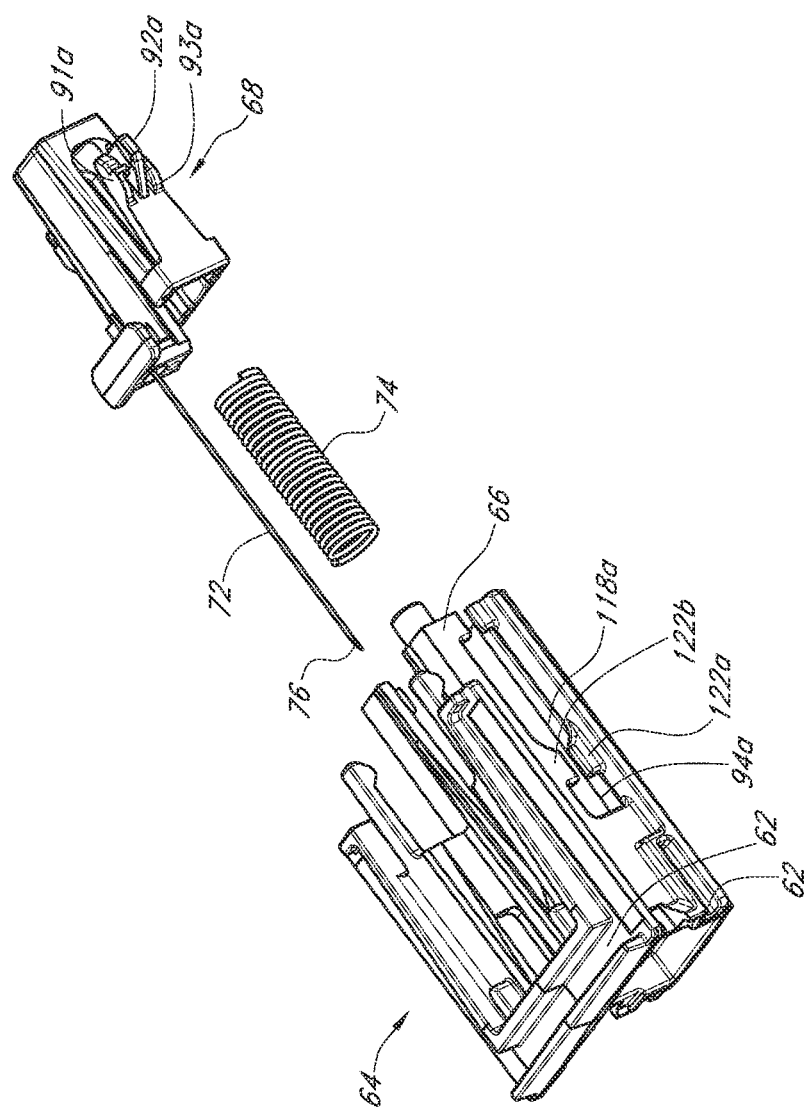
FIG. 7 illustrates an exploded perspective view of the needle hub assembly of the applicator of FIGS. 3 and 6.

Referring now to FIG. 6 along with FIG. 3, an exemplary drive component is described with respect to the pictured components. It will be understood that variations of these components and steps are encompassed within the scope of the current specification.

A user may situate the applicator 20 in a desired location on their skin, and may remove protective tab 42, allowing access to button 44. Depression of the button 44 then starts the process of insertion.

Figure 15:
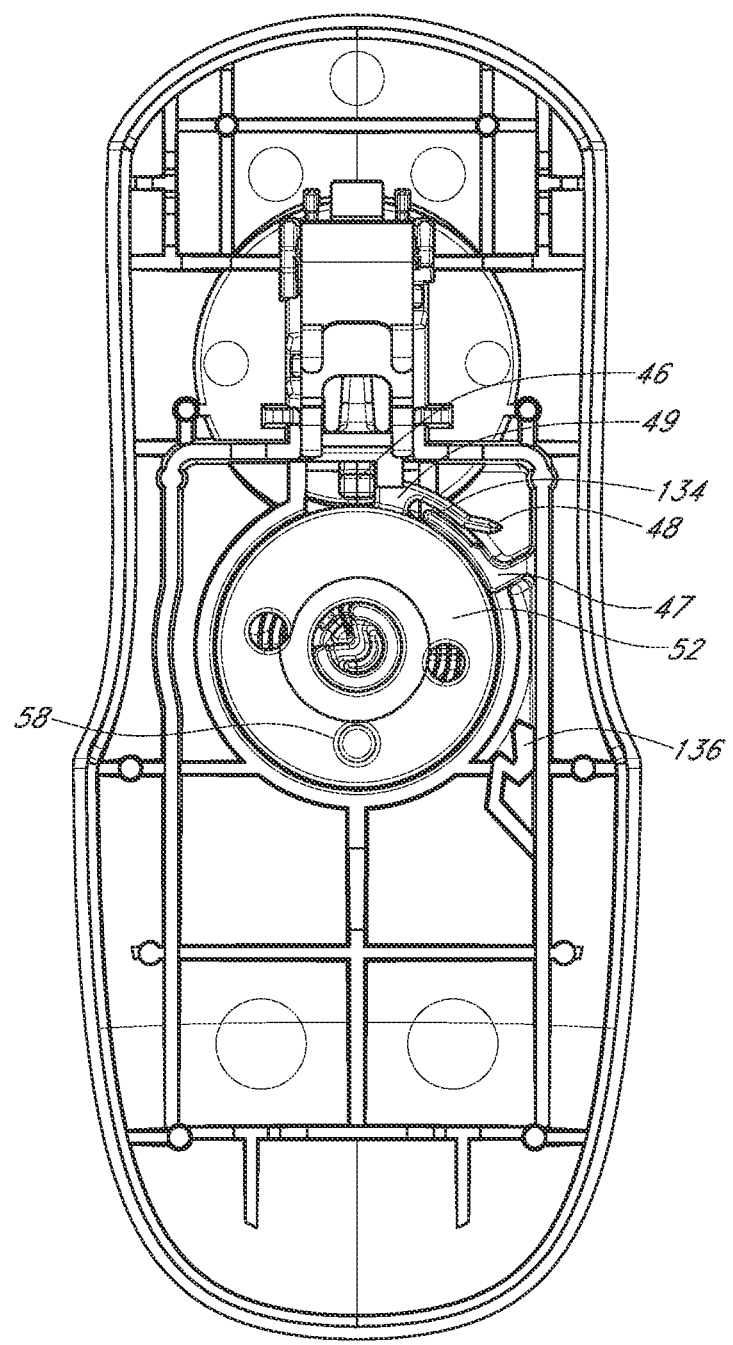
FIG. 15 illustrates a top view of the applicator of FIGS. 3 and 6, with the upper housing removed for purposes of illustration, and with the torsion spring housing in a first configuration.

In particular, depression of the button 44 operates to disengage the trigger tab 46 from a corresponding stop 49 on a torsion spring housing 52. With reference to FIG. 15, the trigger tab 46 becomes disengaged through translation of the button linkage 56 as the button 44 is depressed. The button 44 and/or the button linkage 56 can be biased upward such that, following the disengagement of the trigger tab 46 from the stop 49 and activation of the applicator 20, the button 44 is urged to return to its original position.

In embodiments, the protective tab 42 can function as a safety mechanism or lock, preventing depression of the button 44 (and thus, activation of the system) until after the protective tab 42 is separated and/or removed from the housing 30. In embodiments, the protective tab can include one or more members which extend beyond the perimeter of the button 44, over the surface of the applicator housing 30, so as to prevent depression of the button 44 until after the protective tab (or at least the portions which extend beyond the perimeter of the button 44) is removed. In embodiments, the protective tab can be coupled to the applicator housing 30 by one or more frangible elements which are configured to break when the tab is pressed up, down, sideways, or when the protective tab is twisted or pulled. The frangible element(s) can be configured to break upon application of a force between about 1.0 and 1.8 pounds. In some embodiments, the frangible element(s) can be configured to break upon application of a force between about 1.3 and 1.5 pounds. Depending on the desired user interaction, the protective tab can be configured to be removed via a twisting motion, a sweeping motion, a bending motion, or a pulling motion. In some embodiments, for example as illustrated in FIG. 6, the protective tab 42 can extend straight upward from the applicator housing 30, for example along a median plane of the system (e.g., in a plane perpendicular to the plane of the disposable housing 36).

Figure 97:
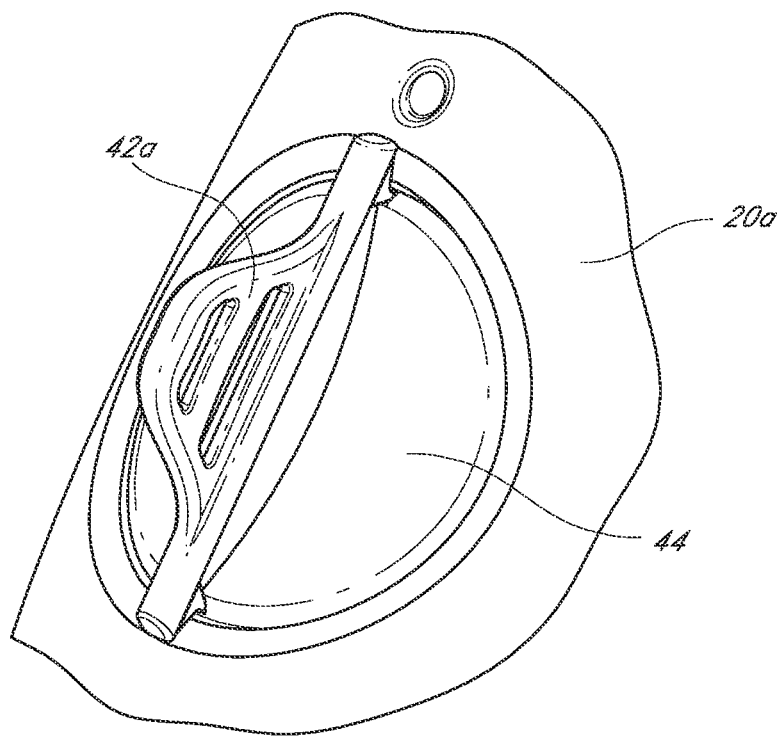
FIG. 97 illustrates a partial perspective view of an applicator system having a protective tab configured in accordance with a further embodiment.
Figure 98:
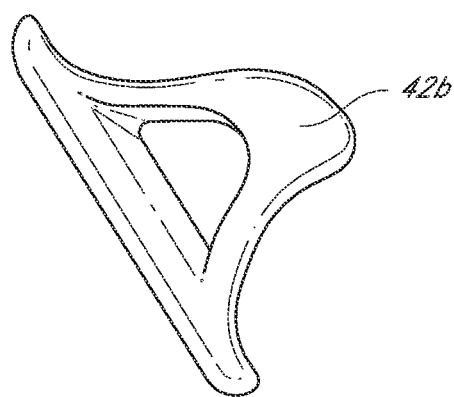
FIG. 98 illustrates another example of a protective tab, in accordance with a still further embodiment.

In some embodiments, the protective tab and/or the button can include one or more visual or tactile features configured to indicate to a user the appropriate method of removal. For example, the protective tab can include arrows, protrusions, ridges, and/or tacky grips to indicate the location and direction in which the user should press on (or pull or twist) the tab to break the frangible member. FIG. 97 illustrates an applicator system 20a configured in accordance with one such embodiment, with a protective tab 42a having ridges 43a, 43b disposed on one side thereof, so as to indicate to the user that the tab 42a should be bent to the left side in order to break the protective tab 42a off of the housing 30. In another example, the protective tab can extend at an angle from the applicator housing, e.g., tilted upward, downward, or to the left or right side, so as to indicate the direction in which the user should press on (or pull or twist) the tab to break the frangible member. FIG. 98 illustrates a protective tab 42b configured in accordance with one such embodiment, in which the protective tab 42 curves to the right as it extends away from the housing, so as to indicate to the user that the tab 42a should be bent to the right side in order to break the protective tab 42b off of the housing.

With reference again to FIG. 6, once the trigger tab 46 disengages from the torsion spring housing stop 49, the torsion spring housing 52 is free to rotate under the force provided by the preloaded torsion spring 54. As the torsion spring housing 52 has a tab 58 which engages with and moves within the yoke 62 of a scotch yoke mechanism, rotational movement of the torsion spring housing 52 is translated into longitudinal motion of various components in the applicator. The yoke 62 of the scotch yoke mechanism is integral with an outer needle hub 66, and the two are referred to here as yoke/needle hub assembly 64. An inner needle hub 68 moves within the outer needle hub 66, and the two are shown in an expanded configuration in FIG. 7, which also shows a needle 72 and a booster spring 74. The sensor wire is deployed through a lumen 76 in the needle 72.

Figure 8:
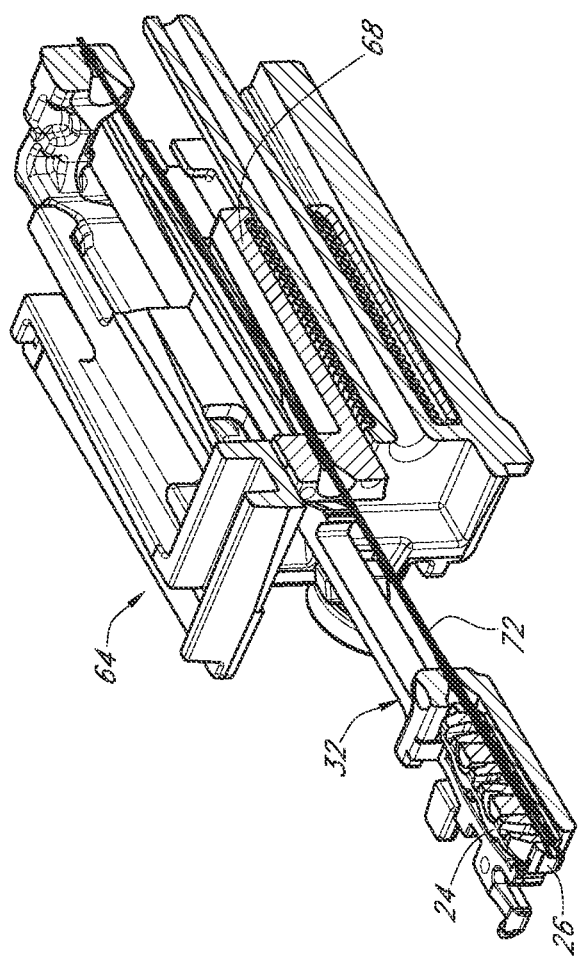
FIG. 8 illustrates a cross-sectional perspective view of the needle hub assembly of the applicator of FIGS. 3 and 6.
Figure 9:
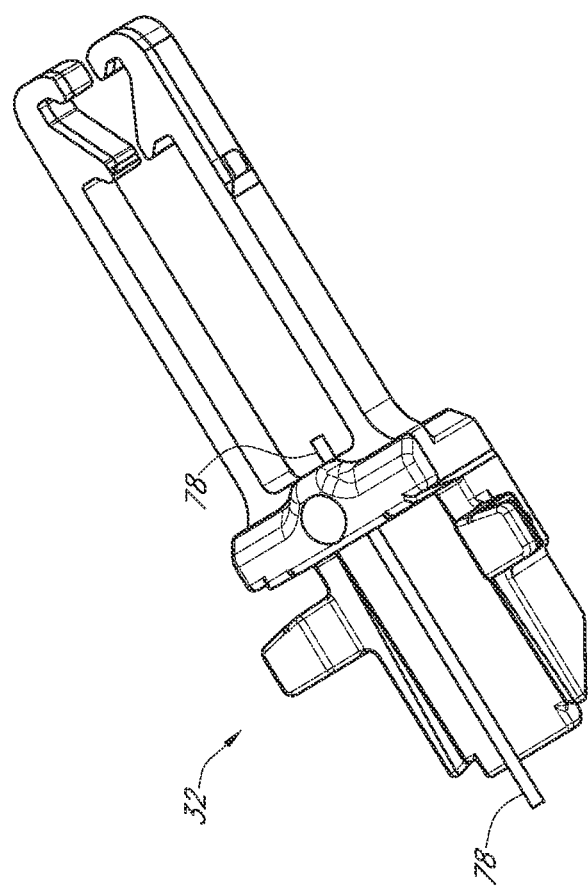
FIG. 9 illustrates a perspective view of the cannula hub of the applicator of FIGS. 3 and 6.
Figure 10:
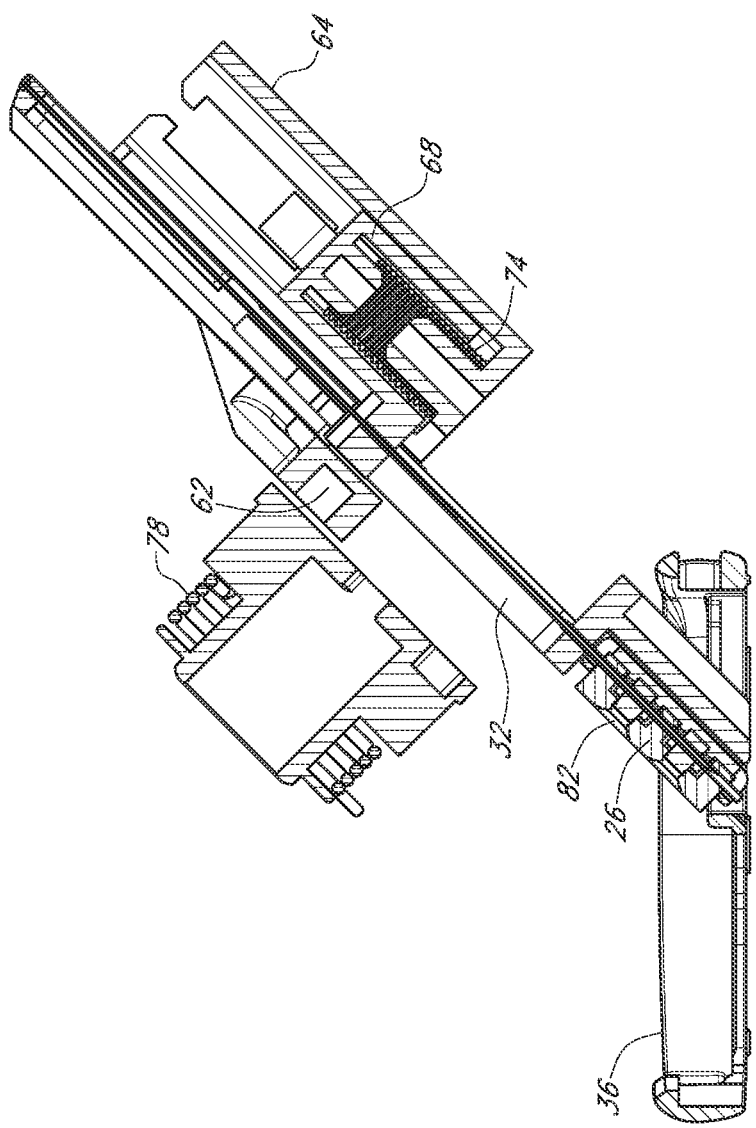
FIG. 10 illustrates a cross-sectional side view of certain components of the applicator of FIGS. 3 and 6.

FIGS. 8 and 9 illustrate the assembly 64 with respect to the inner needle hub 68 and a cannula hub 32 in which a cannula 78 is mounted. The needle 72 passes through the cannula 78 in the deployment of the sensor. The cannula 78 passes through the seal carrier 26, seal 24, and pucks 82 to provide a passage for the needle 72 during sensor insertion. The cannula 78 is removed from the seal carrier, seal, and pucks, as part of the insertion sequence, and in particular is removed by the force of the booster spring 74. FIG. 10 illustrates a side view of the various components described.

The sensor wire may have a kink defined so as to allow a friction fit within the needle. In this way, the sensor wire is held within the needle while still able to be translated through the needle by the force of the push rod. Generally, the kink may be configured so as to hold the wire within the needle, but in the case where the wire is external of the needle, and in the cannula, the kink would not be able to hold the sensor wire within the cannula, or would only be able to hold it to a minimal degree.

Figure 11:
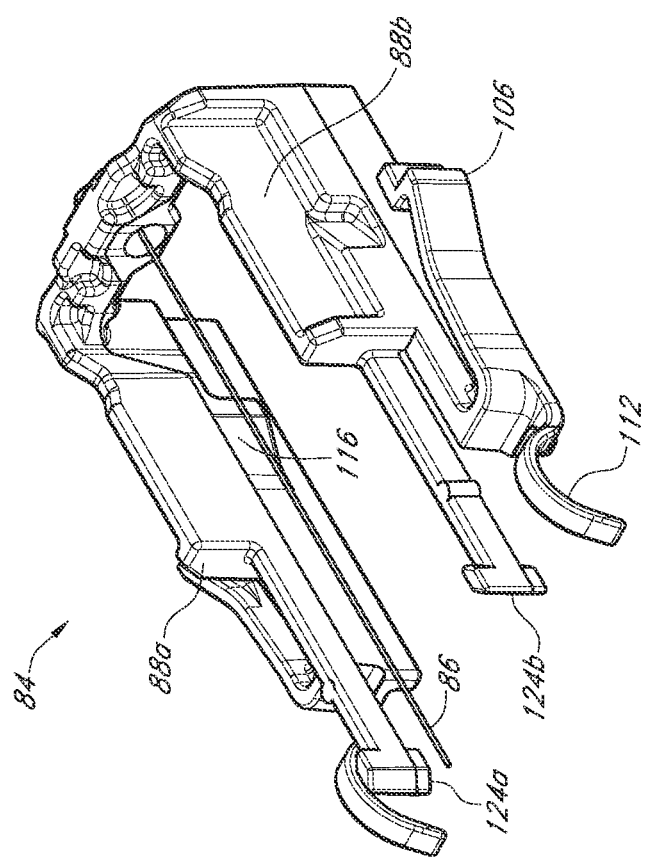
FIG. 11 illustrates a perspective view of the push rod hub of the applicator of FIGS. 3 and 6.
Figure 12:
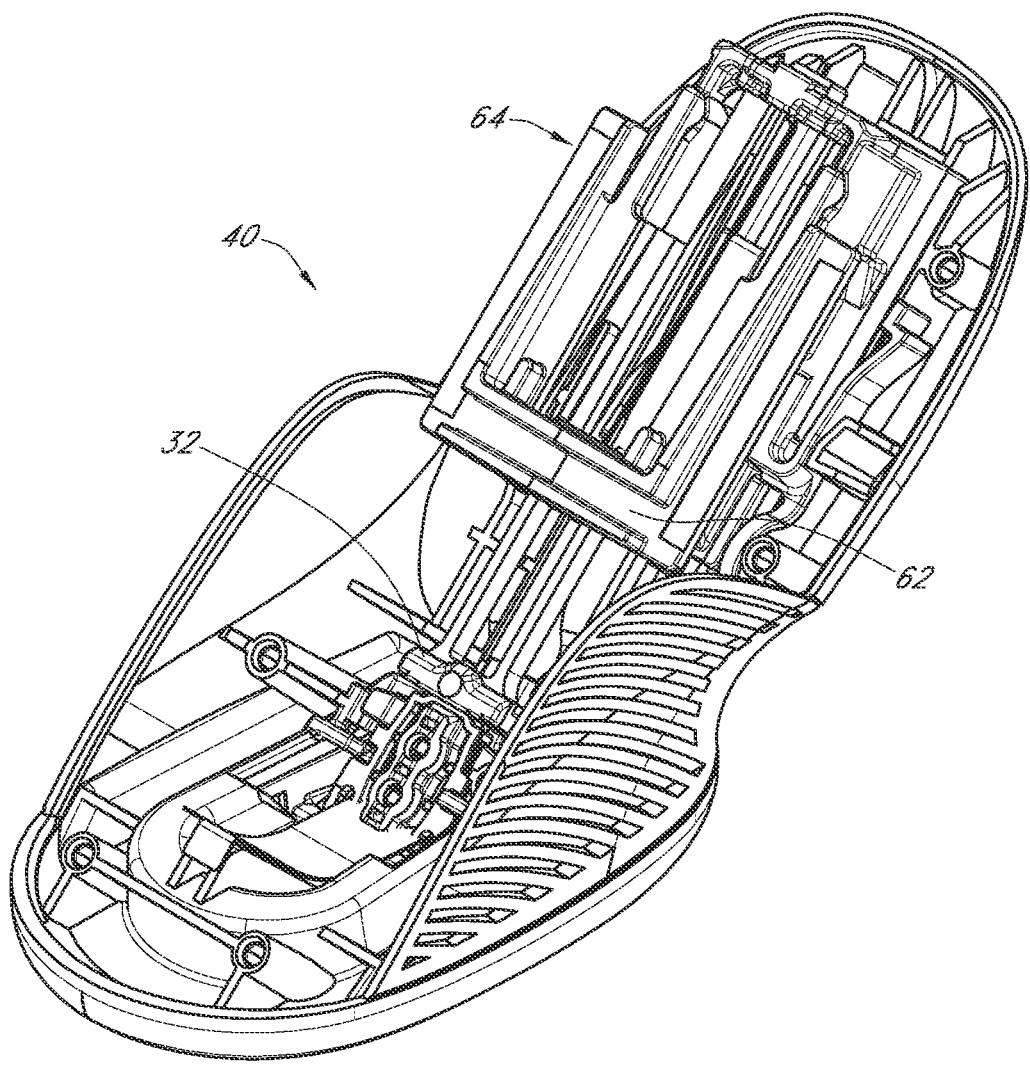
FIG. 12 illustrates a perspective view of the applicator of FIGS. 3 and 6, with the upper housing removed for purposes of illustration.

FIGS. 11 and 12 illustrate a push rod hub 84 in which a push rod 86 is situated. The push rod hub 84 is situated below the yoke 62 and its arms 88a and 88b extend around the assembly 64 and in particular around the outer needle hub 66. In an insertion phase, the push rod hub 84 travels with the yoke/needle hub assembly 64 in the distal direction because the push rod hub has tabs 124a and 124b (see FIG. 11) at distal ends of its arms 88a and 88b that engage slots 126a and 126b on the yoke/needle hub assembly 64 (see FIG. 7).

The push rod 86 is inserted in the needle proximal of the sensor, and after sensor insertion, holds the sensor in place (e.g., in position) while the needle and cannula are retracted. The push rod 86 can hold the sensor in place, e.g., in vivo, as the push rod is caused to be stationary at the distal end of its travel, i.e., the push rod stays in place (e.g., remains fixed or in the same position) while the needle and cannula move proximally around it. The push rod hub 84 is described in greater detail below.

In use the force of the torsion spring causes the yoke/needle hub assembly 64 including the outer needle hub 66, to move downward, i.e., distally, i.e., towards the seal carrier 26. The inner needle hub moves along with the outer needle hub in this downstroke because of the engagement of tab 91a and 93a with slot 94a (and a corresponding tab with a corresponding slot on the opposite side of the assembly 64). By engaging the tab 91a and 93a of the inner needle hub 68 with the locking features of the slot 94a in the outer needle hub 66 (and engaging a corresponding tab with a corresponding slot on the opposite side of the assembly 64) during assembly of the component, the spring 74 becomes compressed and thus preloaded during assembly. When the inner needle hub is caused to disengage from the outer needle hub, as will be described, the force of the spring 74 expanding causes the inner needle hub to move away from the outer needle hub in a proximal direction.

Figure 13:
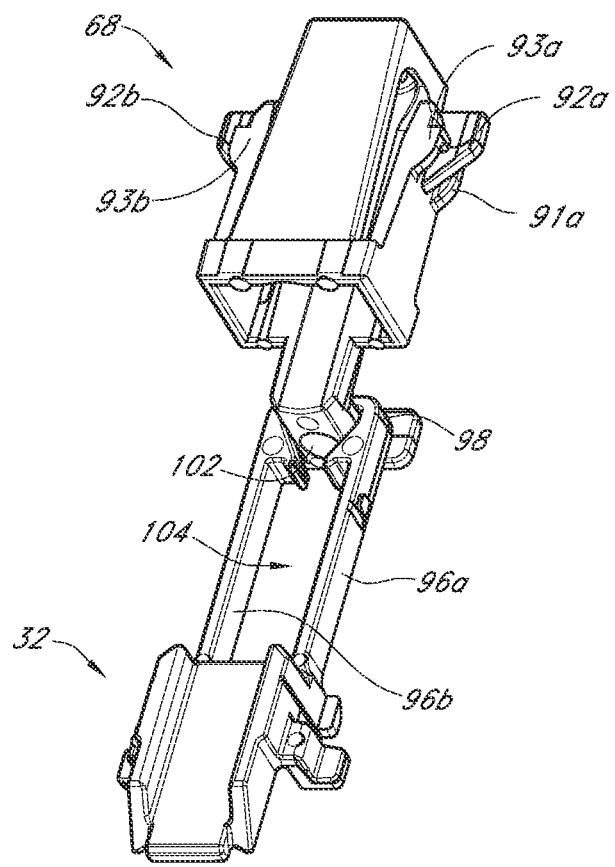
FIG. 13 illustrates a perspective view of the inner needle hub engaged with the cannula hub of the applicator of FIGS. 3 and 6.

Referring to FIG. 13, the cannula hub 32, which is initially stationary with respect to the applicator, has two arms 96a and 96b with a proximal end 98 defining two catches. A distal end 102 of the inner needle hub 68 is shown engaged in the first catch, which may be an initial position of the components prior to button activation. The distal end 102 of the inner needle hub 68 disengages from the first catch and moves into the second catch 104 when the inner needle hub 68 and the cannula hub 32 move towards each other, and more particularly when the inner needle hub 68 moves towards the cannula hub 32, which occurs when the torsion spring and the scotch yoke mechanism force the assembly 64 downward towards the cannula hub 32.

At or near the lowest point of travel of the scotch yoke mechanism, two tabs 106 of the push rod hub 84 (only one is shown in FIG. 11) move past respective stops 108 of the bottom housing 40 (only one is shown in FIG. 6), causing the tabs to initially compress towards the center of the push rod hub, and to flare out when the tabs are distally past the stops, restricting the travel of the push rod hub in a proximal direction. In other words, the push rod and push rod hub are arrested from traveling in the proximal direction, as portions of the remainder of the assembly do, when the scotch yoke mechanism begins its proximal return path, e.g., the retraction phase.

In some embodiments, push rod backspring elements 112 (FIG. 11) are disposed at the distal extremity of the arms of the push rod hub. With the push rod hub 84 in a distal position, the push rod backspring elements 112 are biased against stops 114 of the bottom applicator housing 40 (FIG. 6), such that the push rod hub is substantially arrested from all movement including vibrations. In particular, it is noted that to move the push rod hub into a distal position and lock it in place (e.g., to fix it in a distal position), the tabs 106 (which form hooks that may be deflected) pass stops 108 (also termed catches) on the bottom applicator housing 40. The hooks are deflected inward (e.g., toward the push rod) as they pass the catches during the down or distal travel of deployment. To ensure that the hooks 106 are set in the catches 108 for the retraction phase of deployment, a minimum amount of over travel is required. This over travel results in an ambiguity in push rod location. Since placement accuracy is defined by the push rod, such ambiguity may be deleterious. A deflected member, e.g., the push rod back spring elements 112, are employed which compress during the down travel of the push rod hub at the distal end. When the deployment reverses, the push rod back spring provides a holding force bias for the push rod against the catch. This removes the ambiguity for push rod location, as well as deleterious effects such as vibrations. As the push rod hub and push rod are now fixed at the most distal end of their travel, the sensor is disposed in the host in its deepest and final position.

The torsion spring continues to rotate the wheel, causing the yoke to begin to move in the proximal direction, while the push rod hub remains fixed. The motion of the yoke in the proximal direction, in combination with the arrested push rod hub, activates the booster spring to retract the needle and cannula in the following fashion. In one implementation the amount of rotation remaining in the torsion spring after the pin 58 reaches its lowest point is 5% to 20% of its overall rotation, e.g., 10%.

Figure 14:
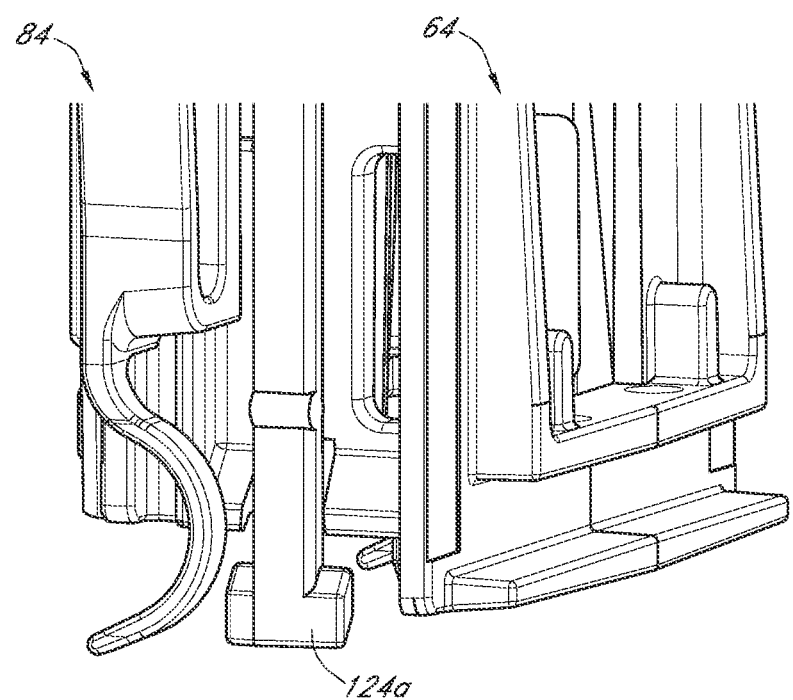
FIG. 14 illustrates a cutaway perspective view of the push rod hub engaged with the needle hub assembly of the applicator of FIGS. 3 and 6.

First, and referring to FIG. 14, the push rod hub 84 disengages from the yoke/needle hub assembly 64 by the tabs 124a and 124b being forced outward by the effect of ramps on the surface of the yoke/needle hub assembly 64 and/or the tabs 124a and 124b themselves, or both. While the needle is being pulled out of the host, the sensor is being deposited into the same, as the push rod is now fixed in a distal position and backstops or holds the sensor in place (e.g., resists proximal movement of the sensor).

Next, two ramps 116 (see FIG. 11, in which only one ramp of the two is visible) are provided on an internal surface of the push rod hub 84. As the push rod hub 84 is stationary once it has reached its lowest (most distal) point of movement, but the outer needle hub (yoke/needle hub assembly 64) is not, as the yoke/needle hub assembly 64 begins to move proximally in the retraction phase, the ramps 116 deflect release tab 92a (as well as corresponding tab on the opposite side of the assembly 64; see FIG. 13), deflecting the release tab 92a and the locking tab 91a, 93a inward toward the needle and disengaging the locking tab 91a and 93a from the slot 94a (and serving the same function on the opposite side of the assembly 64). This action releases the spring and forces the inner needle hub upward in the proximal direction by the force of the booster spring, one end of which being attached to the inner needle hub and the other end attached to the stationary outer needle hub. As shown in FIG. 13, the inner needle hub 68 is coupled to the cannula hub 32, although at this point the distal end 102 is within the second catch 104. Nevertheless, the distal end 102 cannot disengage from the cannula hub 32, and thus the cannula hub is retracted at the same time as the needle. Because the distal end 102 is within the second catch 104, i.e., because two catches are provided, the needle can be configured to be proud of the cannula by, e.g., 0 to 150 mils, e.g., 100 mils, or even negative. Benefits ensue to such systems, as will be described below with respect to seals and seal slingshotting. In some cases the needle need not be proud of the cannula in the retraction phase.

As described above, at this point the scotch yoke mechanism is now beginning to drive in a proximal direction. However, as the initial preloading of the torsion spring caused the distal movement of the yoke, in some cases the force of the booster spring can act to re-load or "back drive" the torsion spring. Accordingly, in such implementations a ratchet mechanism can be employed to arrest movement of the torsion spring. In particular, and referring to FIG. 15, the torsion spring housing 52 is shown in the initial configuration where rotation of the same is locked by the trigger tab 46, and the torsion spring (not shown) is in its fully loaded state. The torsion spring housing 52 has a ratchet pawl 48 which is prohibited from rotating (in the counterclockwise direction as illustrated in FIG. 15) by the trigger tab 46. Once the trigger tab 46 is moved out of the way of the torsion spring housing stop 49 (e.g. by depression of the button 44), the torsion spring housing 52 becomes free to rotate (in the counterclockwise direction as illustrated in FIG. 15) until the ratchet pawl 48 engages within the ratchet teeth 136 and/or the torsion spring housing stop 49 hits the hard stop 47. In the configuration shown in FIG. 15, the pin 58 for the scotch yoke is at its top dead center position, i.e., at its starting position.

Figure 16:
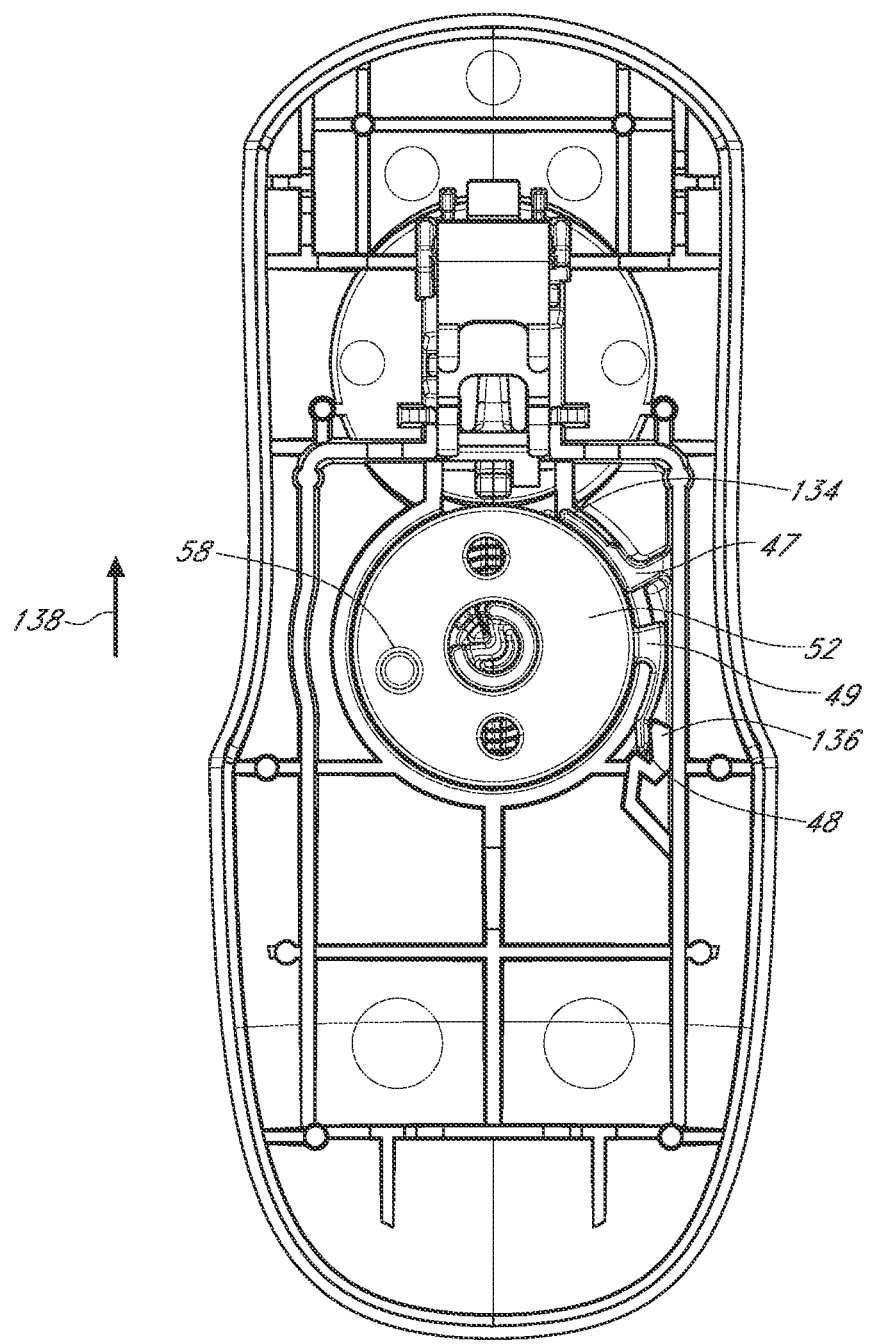
FIG. 16 illustrates another top view of the applicator of FIGS. 3 and 6, with the upper housing removed for purposes of illustration, and with the torsion spring housing in a second configuration.

FIG. 16 shows the configuration as the booster force pushes on the pin 58 in the direction of the arrow 138. As the direction of rotation caused by the torsion spring is counterclockwise, i.e., the booster force is pushing on the pin in a clockwise direction, there is a potential for back driving the torsion spring. Engagement of the ratchet pawl 48 within the ratchet teeth 136 can serve to inhibit or prevent such back driving. In one implementation, the device is configured such that the booster spring is triggered after the ratchet pawl 48 is engaged with the ratchet teeth 136. In this way, any forces on the pin 58 caused by the booster force do not result in back driving of the torsion spring. It is noted that in the position shown in FIG. 16, the needle has almost been extracted out of the host, but the cannula has not yet been retracted.

Engagement of the ratchet pawl 48 is with the ratchet teeth 136 inhibits or prevents clockwise rotation or back driving of the torsion spring housing 52. Similarly, abutment of the stop 49 against the hard stop 47 inhibits or prevents further counterclockwise rotation of the torsion spring housing 52. Motion of the pin 58 is thus also arrested, stopping movement of the scotch yoke mechanism, including the outer needle hub. The needle, however, continues to retract, as the same is driven by the booster spring on the inner needle hub. As described above, movement of the inner needle hub further causes retraction of the cannula hub. In this way the cannula and the needle are fully retracted through the seal by the booster spring. As the cannula hub and cannula are no longer supporting the seal carrier, the same is free to rotate (by the effect of gravity) into the disposable housing. In many cases, it is desirable to include a push spring 38 to assist this motion, the push spring held up by the cannula hub 32 until the same is removed and the seal carrier is ready to drop down into the disposable housing 36, as described in greater detail below. In some embodiments, one or more retention features 166 of the lower housing 40 can be employed to prevent the disposable housing 36 from being released from the housing 40 until after the cannula has been retracted from the seal. In some embodiments, the rotation of the seal carrier can facilitate the release of the retention feature(s) 166, allowing the disposable housing to separate from the device 20. Once the inner needle hub is in a fully retracted position, the sensor has been placed in the body and the applicator can be removed leaving the disposable housing assembly.

Advantages of implementations of the device of FIGS. 3-16 may include one or more of the following. The device has high usability, a smooth sine wave mechanism motion as caused by the scotch yoke, and a capability to tune or control the resulting forces.

Figure 89:
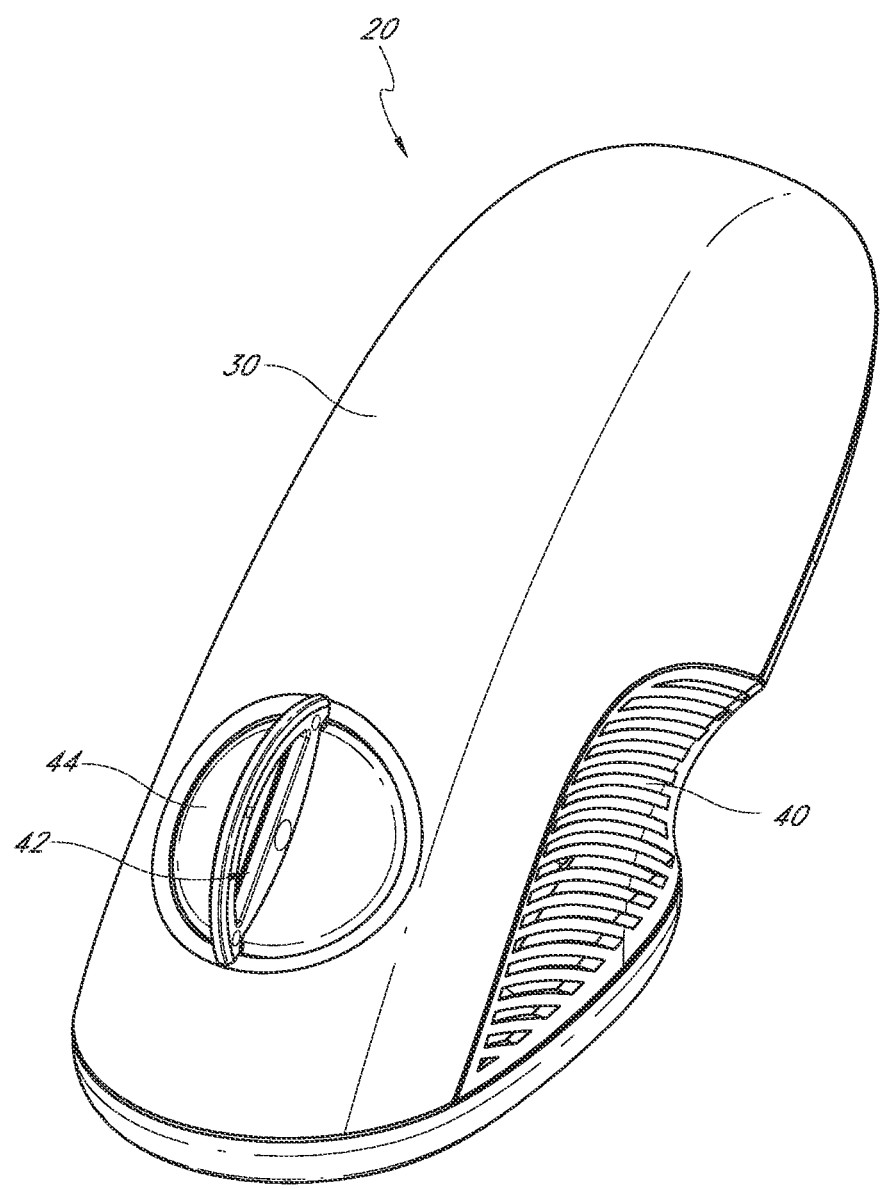
FIG. 89 illustrates a top perspective view of an assembled applicator system, configured in accordance with some embodiments.
Figure 90:
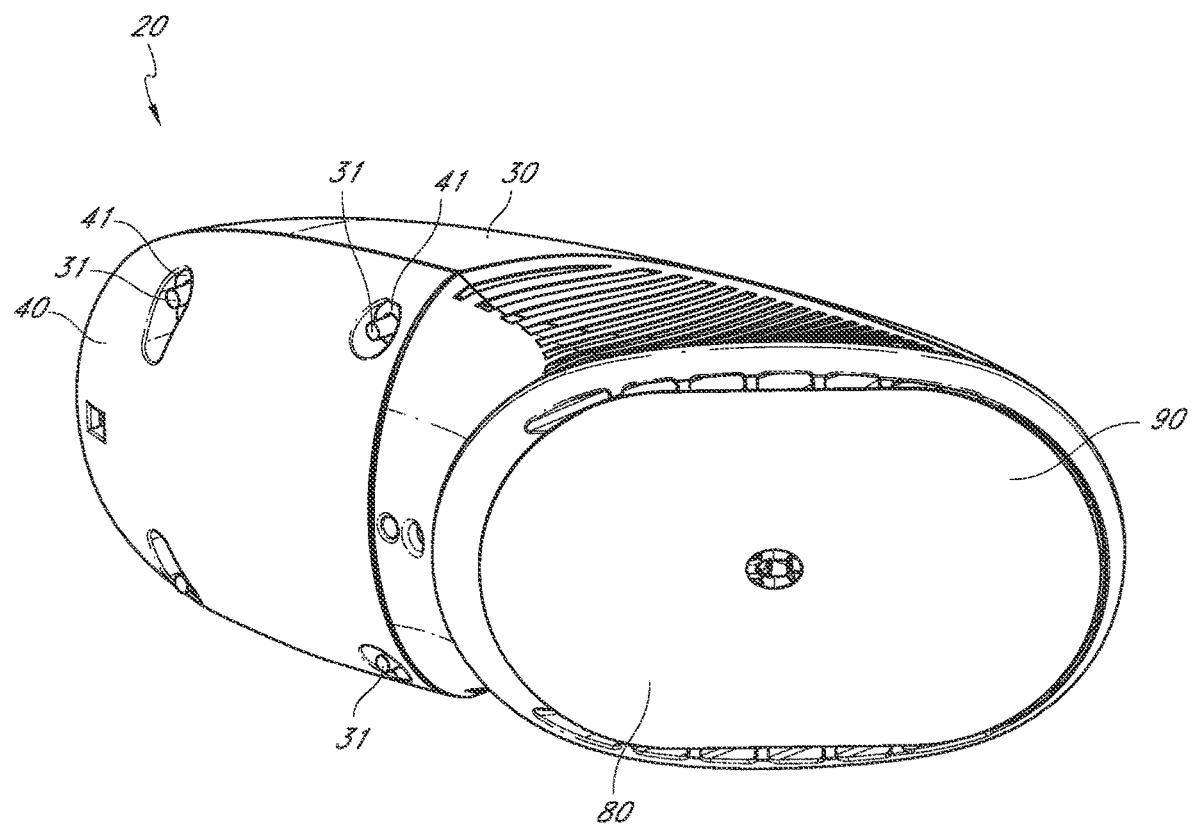
FIG. 90 illustrates a bottom perspective view of the applicator system of FIG. 89.

With reference now to FIG. 89, a top perspective view of the assembled device 20 is illustrated, showing the upper housing 30 coupled to the lower housing 40, with the protective tab 42 intact over the button 44, prior to deployment of the device 20. FIG. 90 shows a bottom perspective view of the assembled device 20 prior to deployment. As can be seen in FIG. 90, the upper housing 30 and the lower housing 40 can be coupled together by mating studs 31 and holes 41. In the embodiment illustrated in FIGS. 89-91, the studs 31 extend from the upper housing 30 and the holes 41 form part of the lower housing 40, but other configurations (e.g., the reverse configuration) are possible. In some embodiments, the upper housing 30 and the lower housing 40 can be coupled together using an interference fit between the studs 31 and the holes 41. In some embodiments, the studs 31 and holes 41 can be staked together, e.g., thermoplastically or heat staked together.

FIG. 90 also illustrates an adhesive patch 90 disposed on a lower (distal, or base) surface of the lower housing 40. The adhesive patch 90 includes a removable liner 80 which covers and protects the adhesive of the adhesive patch 90 until removed by the user prior to deployment. In embodiments, the adhesive can comprise a pressure-sensitive or pressure-activated adhesive. In embodiments, the base of the lower housing 40 can comprise a rigid or semi-rigid surface which can be configured to facilitate activation of the adhesive on the adhesive patch 90, at least in the region of the patch surrounding the disposable housing, as the applicator device 20 is placed or pressed against the skin. In some embodiments, the lower or base surface of the lower housing 40 can be smooth (either flat or slightly contoured) to as to provide uniform activation throughout the extent of the adhesive, at least in the region of the patch surrounding the disposable housing. In other embodiments, the lower or base surface of the lower housing 40 can include one or more dimples, protrusions, ridges, or other relief features to ensure activation of the adhesive in certain regions, e.g. near the outer edge of the patch 90 and/or in the region immediately surrounding the disposable housing. In some embodiments, the lower or base surface of the lower housing 40 can be sized and shaped with a larger footprint than the patch 90 (e.g., such that the base surface of the lower housing 40 extends beyond the adhesive patch 90 in one or more directions, in the plane of the disposable housing 40). Such a configuration can help to prevent undesirable folding or wrinkling of the patch 90.

Figure 91:
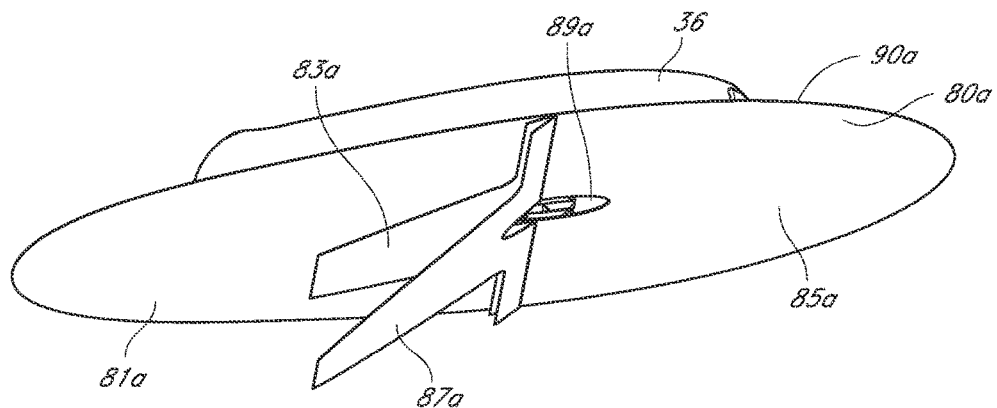
FIG. 91 illustrates a bottom perspective view of a disposable housing on an adhesive patch with a removable liner, in accordance with an embodiment.

With reference now to FIG. 91, a bottom perspective view of one example of an adhesive patch 90*a* is shown, having a disposable housing 36 disposed thereon and having a removable liner 80*a* disposed on its opposing surface. The removable liner 80*a* comprises a first portion 81*a* having a release tab 83*a* which is folded back away from the patch 90*a*, and a second portion 85*a* having a release tab 87*a* which is also folded back away from the patch 90*a*. The release tabs 83*a*, 87*a* are shown separated from one another for purposes of illustration. The liner 80*a* includes an opening 89*a* through which a needle and sensor can pass during the insertion process. In the embodiment illustrated in FIG. 91, the first portion 81*a* can extend across a roughly equal portion of the surface area of the patch 90*a* as the second portion 85*a*, such that the first portion 81*a* and the second portion 85*a* meet at the center of the adhesive patch 90*a*, at or adjacent to the opening 89*a*.

Figure 92:
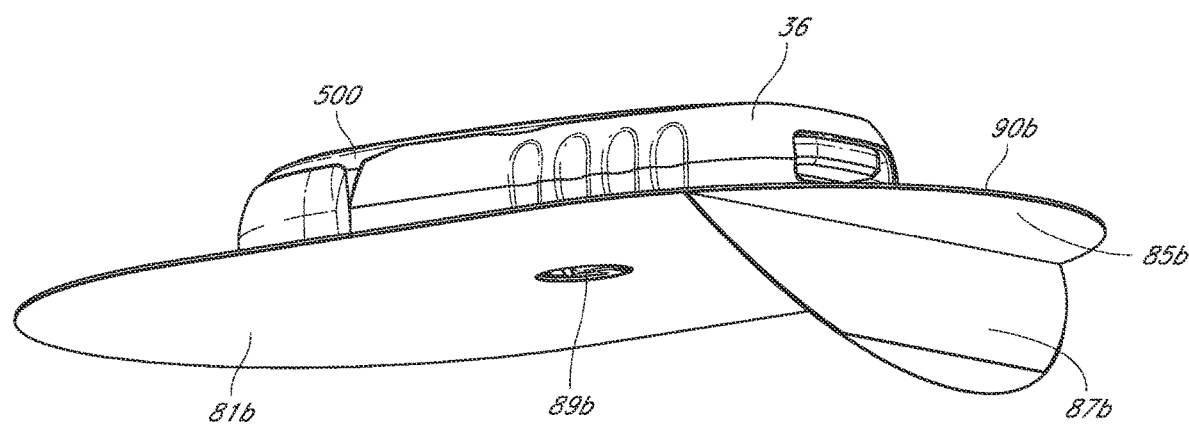
FIG. 92 illustrates a bottom perspective view of a disposable housing on an adhesive patch with a removable liner, in accordance with another embodiment.

With reference now to FIG. 92, a bottom perspective view of another example of an adhesive patch 90*b* is shown, having a disposable housing 36 disposed thereon and having a removable liner 80*b* disposed on its opposing surface. The removable liner 80*b* comprises a first portion 81*b* having a release tab (not visible in FIG. 92, but disposed against the opposing surface of the release tab 87*b*) which is folded back away from the patch 90*b*, and a second portion 85*b* having a release tab 87*b* which is also folded back away from the patch 90*b*. The liner 80*b* includes an opening 89*b* through which a needle and sensor can pass during the insertion process. In the embodiment illustrated in FIG. 92, the first portion 81*b* can extend a larger portion of the surface area of the patch 90*b* than the second portion 85*b*, such that the first portion 81*b* and the second portion 85*b* meet away from the center of the adhesive patch 90*b* and away from the opening 89*b*.

The sensor wire itself may have one or more contact regions, e.g., corresponding to an outer silver layer and an inner platinum layer, separated by a polyurethane layer. It will be understood that the specific constituents of these conductive and insulator layers may vary according to implementation. The conductive regions may be accessed either directly (in the case of contact with the outer silver layer) or via removal of the silver and polyurethane layers to obtain access to the platinum layer.

The wire may include a generally ex vivo portion and a generally in vivo section, both of which being about and approximately ½ inch in length. The ex vivo portion may include electrical contact points, and the in vivo portion may include a sensing portion, which may be at the distal tip of the in vivo portion or may be proximal of the distal tip of the in vivo portion. A transmitter may be employed which has electrical contacts (not shown) which contact first and second pucks. As the wire also contacts the pucks, the wire is in signal communication with the transmitter. To ensure that each puck contacts a separate portion of the wire, the insulated portion of the wire may be disposed between the pucks. In this way, a first contact, e.g., the silver portion, makes contact with the first puck, and a second contact, e.g., the platinum portion, makes contact with the second puck. In one implementation, the diameter of the pucks is about 80 mils, and the distance between the pucks is about 215 mils.

Figure 17:
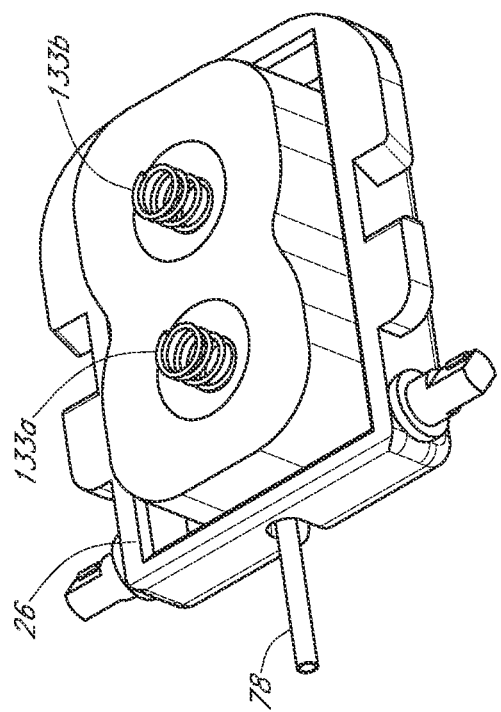
FIG. 17 illustrates one way of coupling a sensor wire to contacts, in accordance with one embodiment.
Figure 18:
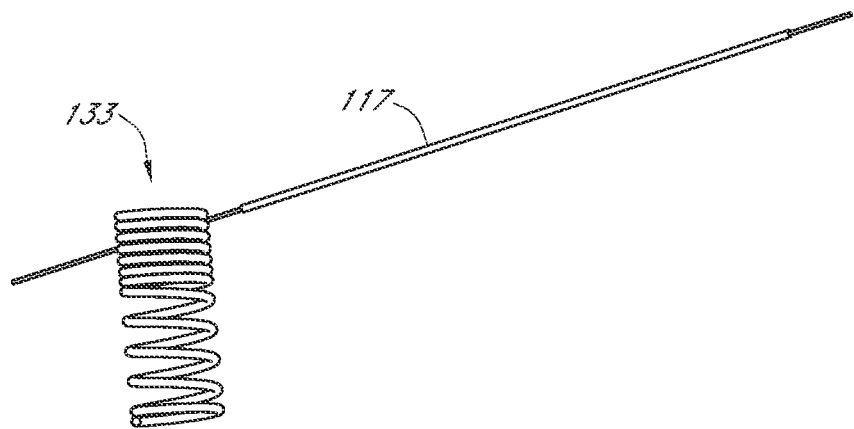
FIG. 18 illustrates a side view of the coupling of a sensor wire with the spring of FIG. 17.
Figure 19:
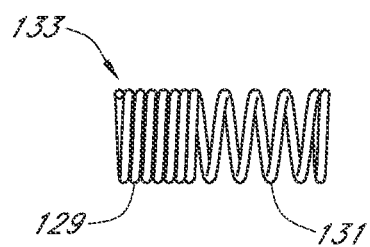
FIG. 19 illustrates another side view of the spring of FIG. 17.

FIGS. 17-19 illustrate another arrangement in which robust connections may be made from a sensor wire to the transmitter. In particular, a seal carrier 26 is illustrated having spring connectors 133a and 133b. Each spring 133 includes a compression section 129 and an extension section 131. The spring 133 is generally metallic, e.g., stainless steel, copper, and so on, and may be plated with a coating, such as gold, nickel, etc. In use within the seal carrier, the springs 133 take the place of the pucks 123 and 125 described above. In the arrangement shown in FIG. 17, the top portion of the spring is the compression section 129 and functions to provide pressure against the transmitter contact for a robust connection. The bottom section 131 is an extension spring and as such is configured to pull the coils together in the relaxed state. The coils in the extension section are held apart during insertion (as well is partially during retraction) by the cannula 78. When the cannula is removed, the coils relax and contract onto the sensor wire 117, holding the same in place with a strong frictional connection, connecting the sensor wire to the spring.

The implementation of FIGS. 17-19 has advantages in the reduction of movement-induced noise in the signal for long-duration sessions, e.g., over 10 days.

In one alternate implementation of an applicator according to present principles, a wearable device, such as is embodied in the disposable housing 36 and transmitter (described below), may be deployed in a host using systems and methods described in the applications incorporated by reference above, and in particular as disclosed in the applications incorporated by reference above. For example, in the applications incorporated by reference, a sensor wire is inserted through the cannula into a host, and the wire is sealed with an elastomeric seal which is compressed by transmitter insertion.

In the above implementation of FIGS. 3-16, a supplemental source of stored energy, i.e., a separate booster spring, was disclosed to provide a supplemental force to ensure that all steps of insertion and retraction could be accomplished effectively, i.e., that the force applied was generally always greater than the required force profile during both of the insertion and retraction steps (see FIG. 2). A main source of force, spring 54, provided a source of energy for an insertion force and even for a portion of a retraction force, particularly with respect to an insertion component such as the needle. A secondary source of force, spring 74, provided a source of energy for a retraction force, particularly for an insertion component such as a cannula. The additional retraction force was in part necessary because the insertion component, e.g., the cannula, was being retracted through a source of resistance, e.g., an elastomeric seal. While a single large or larger spring may also be employed to accomplish the same function, the use of such deleteriously increases the size of the applicator. Thus, to ensure a compact applicator, particularly for usage by children or small adults, the implementation of FIGS. 3-16 provides a more advantageous alternative.

In embodiments employing a booster spring, the booster spring can be fired when the needle is fully inserted, and can be configured to facilitate the retraction of the needle/cannula assembly, leaving the sensor behind and installed in the sensor pod. A considerable amount of force, however, may be released upon firing of the booster spring. This force can result in a large acceleration of the inner needle hub against the cannula hub, possibly creating vibrations or amplifying any existing oscillation in the mechanism. In embodiments, various design parameters of the booster spring can be adjusted to change the acceleration curve of the spring and thereby reduce or avoid any sudden acceleration when it is fired. Embodiments can thus reduce or avoid any vibration imparted to the mechanism by the booster spring during retraction and provide safe and reliable retraction. For example, some embodiments can employ a variable pitch booster spring, a variable diameter (e.g., cone-shaped) booster spring, a variable diameter wire booster spring, or multiple booster springs (e.g., one inside another, or multiple springs in series) to achieve these goals. In addition, different materials and/or material processing techniques can be used to obtain the desired spring constant and thereby achieve these goals.

Figure 29:
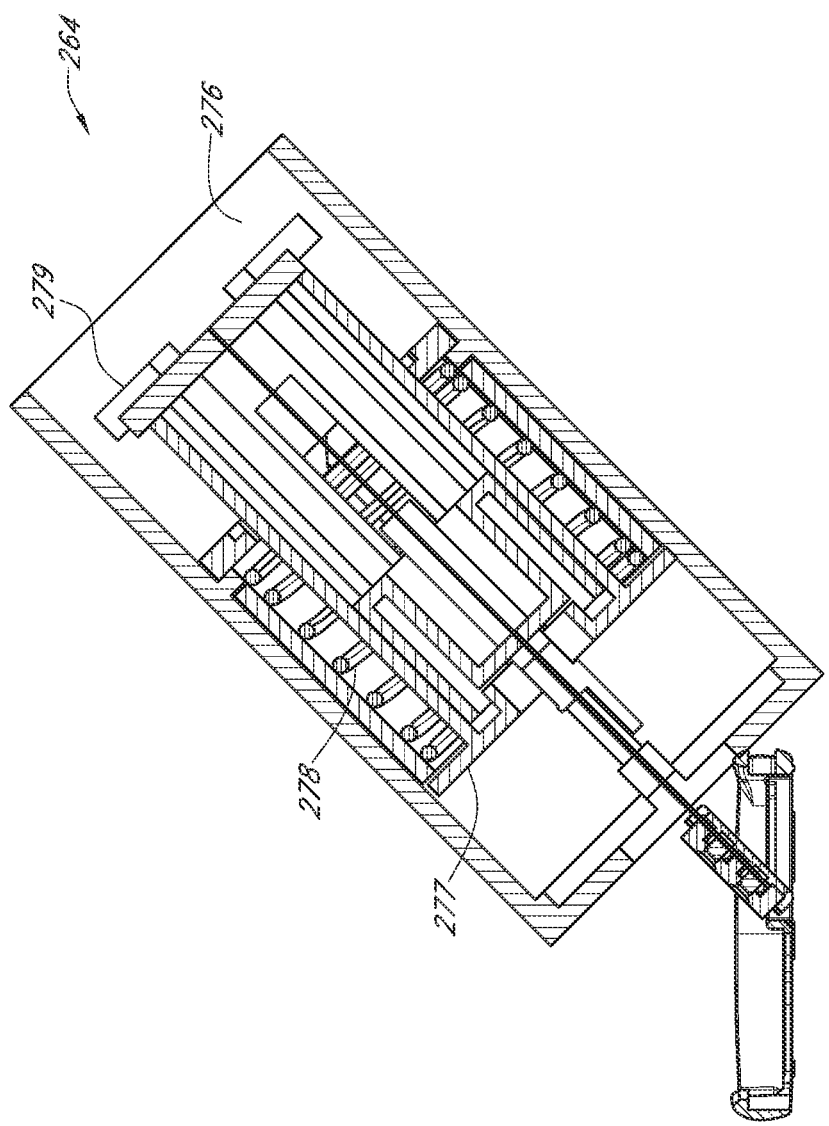
FIG. 29 illustrates a cross-sectional side view of another applicator configured in accordance with an embodiment, with the upper and lower housing removed for purposes of illustration.
Figure 30:
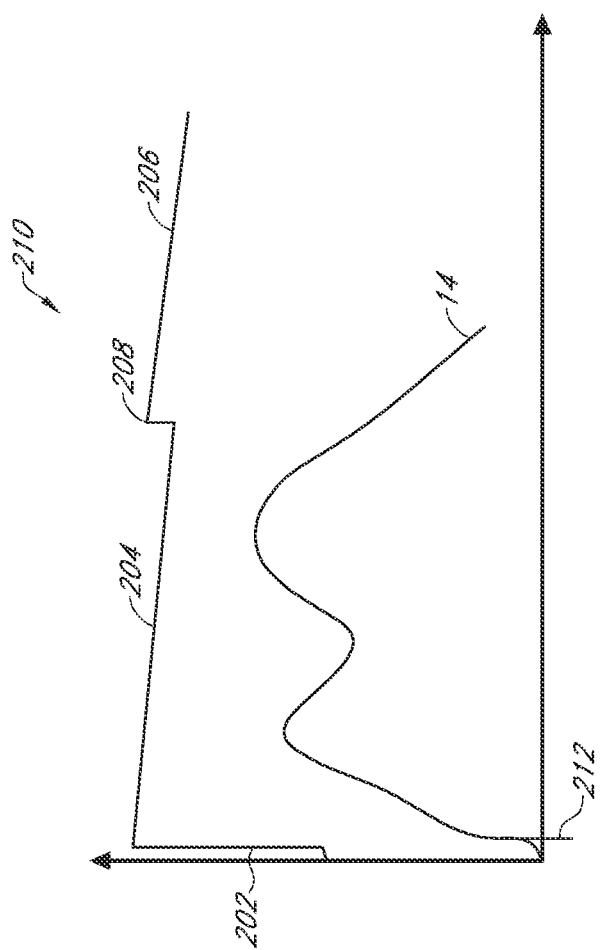
FIG. 30 illustrates a force profile curve for sensor insertion for a manual insertion applicator.
Figure 31:
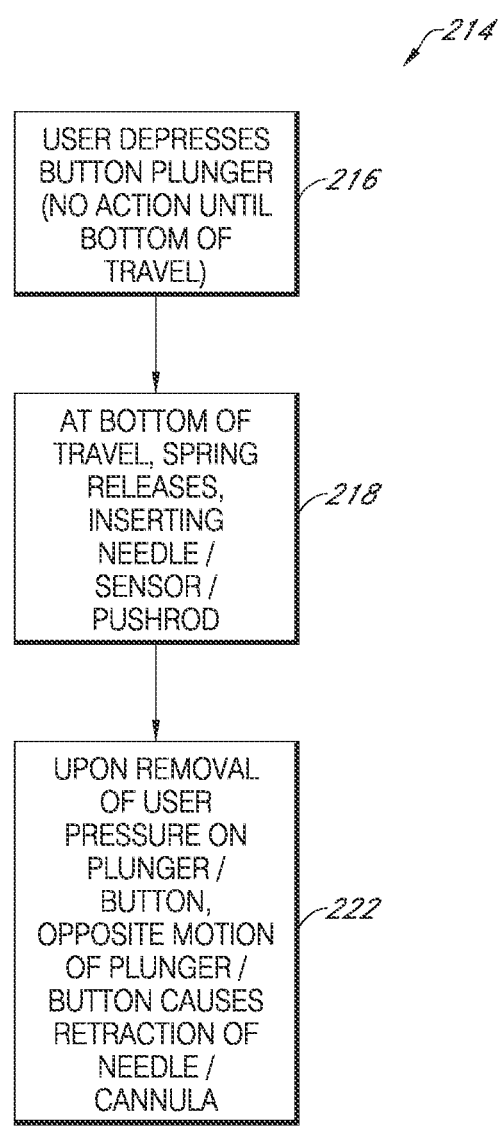
FIG. 31 is a flowchart for steps of sensor insertion in accordance with an embodiment.

Generally, the implementation of FIGS. 3-16 provides an alternative in which additional force is provided by a supplemental source of stored energy, the additional force allowing a more effective insertion and retraction. Other implementations will also be understood that supply additional force in a compact design, and several of these are described below with respect to FIGS. 28 and 34. However, to accomplish the same goal of an effective insertion and retraction, other alternative methodologies may also be employed. These include having a user supply a portion of the force necessary for insertion and retraction, and these are termed manual or semi-manual alternatives, and several of these are described below as well, and in particular with respect to FIGS. 21-24. In yet another alternative methodology, applicator mechanisms may be made more efficient, or may be configured differently, with the added efficiency or different configuration negating the need for an additional force, or otherwise reducing the requirements of the force profile, such as for easing removal of the cannula. Several of these alternatives are also described below, with respect to FIGS. 20, 25-27, 32 and 33. Systems and methods described below address various of these possibilities. In some cases, a combination of techniques may be employed to perform the requisite insertion and retraction steps. For example, FIGS. 29-31 illustrate an implementation in which additional force may be supplied, where the system may be made more efficient, and where user force may be employed.

Figure 20:
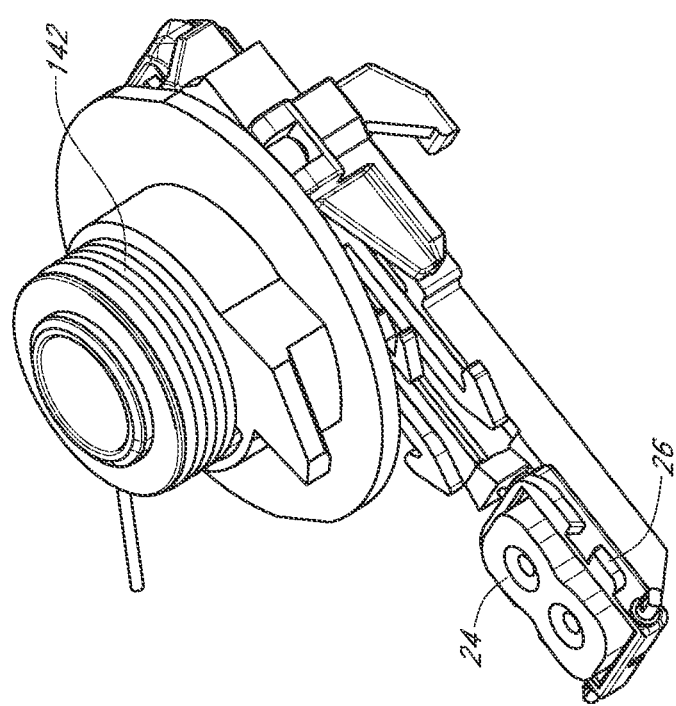
FIG. 20 illustrates a perspective view of another arrangement of a sensor insertion drive in accordance with an embodiment.

As an example of a system configured to obviate any need for an additional force, and referring in particular to FIG. 20, the sensor wire may be pre-inserted through a cannula into a seal. In FIG. 20, for example, the sensor wire is inserted through a cannula that passes through the seal 24 which is situated on the seal carrier 26. In this case there is no need to use the transmitter insertion force to perform the sealing, although the transmitter insertion force may still be employed to stabilize the seal and the sensor wire system. Moreover the systems and methods of, e.g., the application Ser. No. 13/826,372 incorporated by reference above, and in particular the applicator of FIGS. 3A and 3B therein, may be employed to insert wires into the seal systems described here.

One difference between the implementation of FIG. 20 and that of FIGS. 3-16 is that only one spring 142 is included in the implementation of FIG. 20. And in the case of FIG. 20, the one spring is a coiled or helical wire spring, as opposed to the clock spring 54 of FIG. 6. It is noted in this regard that a clock spring or power spring generally provides a flatter torque performance curve in the working range of the spring, and the k factor can be lower than in a coil wire spring. However, any spring can be used that provides a torsional force, including both wire springs and clock springs. Further, any suitable mechanism can be used which is configured to transform rotational force into linear force. The solutions described in this specification improve on many of the devices of the prior art as prior art devices generally do not perform so many actions with just one or two springs, e.g., needle and sensor insertion, needle retraction, cannula retraction, and the like. Advantages of the implementation of FIG. 20 include high usability and a smooth sine wave mechanism motion as caused by the scotch yoke.

Figure 21:
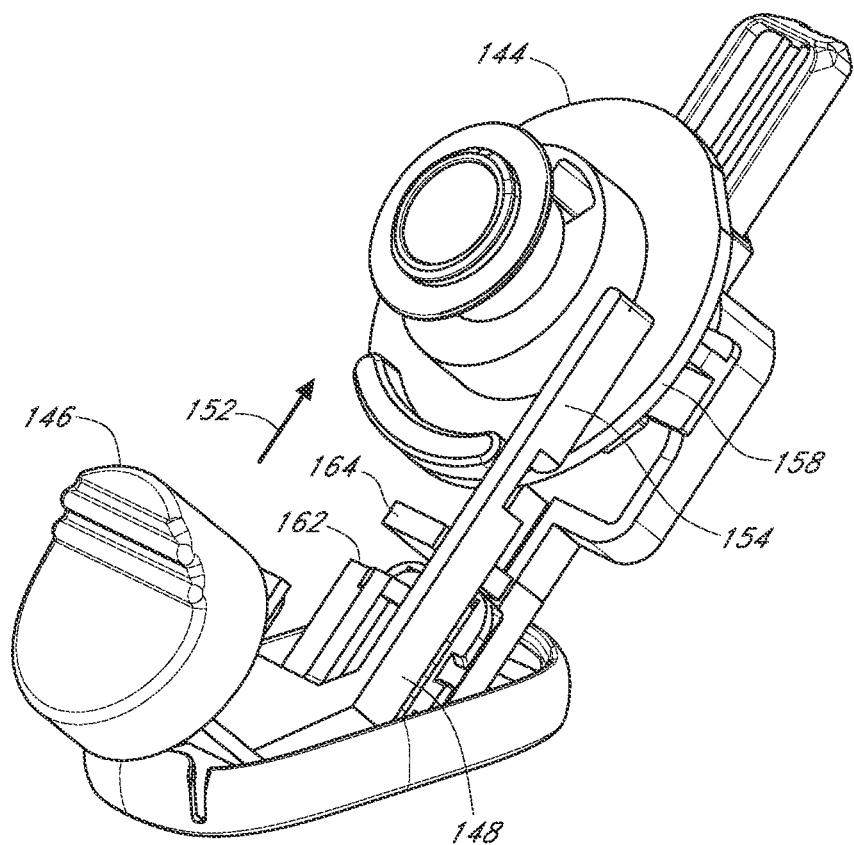
FIG. 21 illustrates a schematic perspective view of another applicator in accordance with an embodiment, with the upper and lower housing removed for purposes of illustration.

As an example of the use of manual or semi-manual or user-supplied force, and referring in particular to FIG. 21, a scotch yoke 144 coupled with a torsion spring may be used for insertion, as in the prior implementation, but a separate manual force may be provided for one or more individual steps. In FIG. 21, for example, the retraction step may be performed manually, instead of with the use of a booster spring. In particular, a button 146 is coupled to a bar 154 which is configured to arrest rotation of the wheel 144 until the button 146 is moved in a proximal direction. For example, movement of the bar may push aside a peg or stop which had previously prohibited rotation of the wheel. Other techniques will also be understood.

Figure 23:
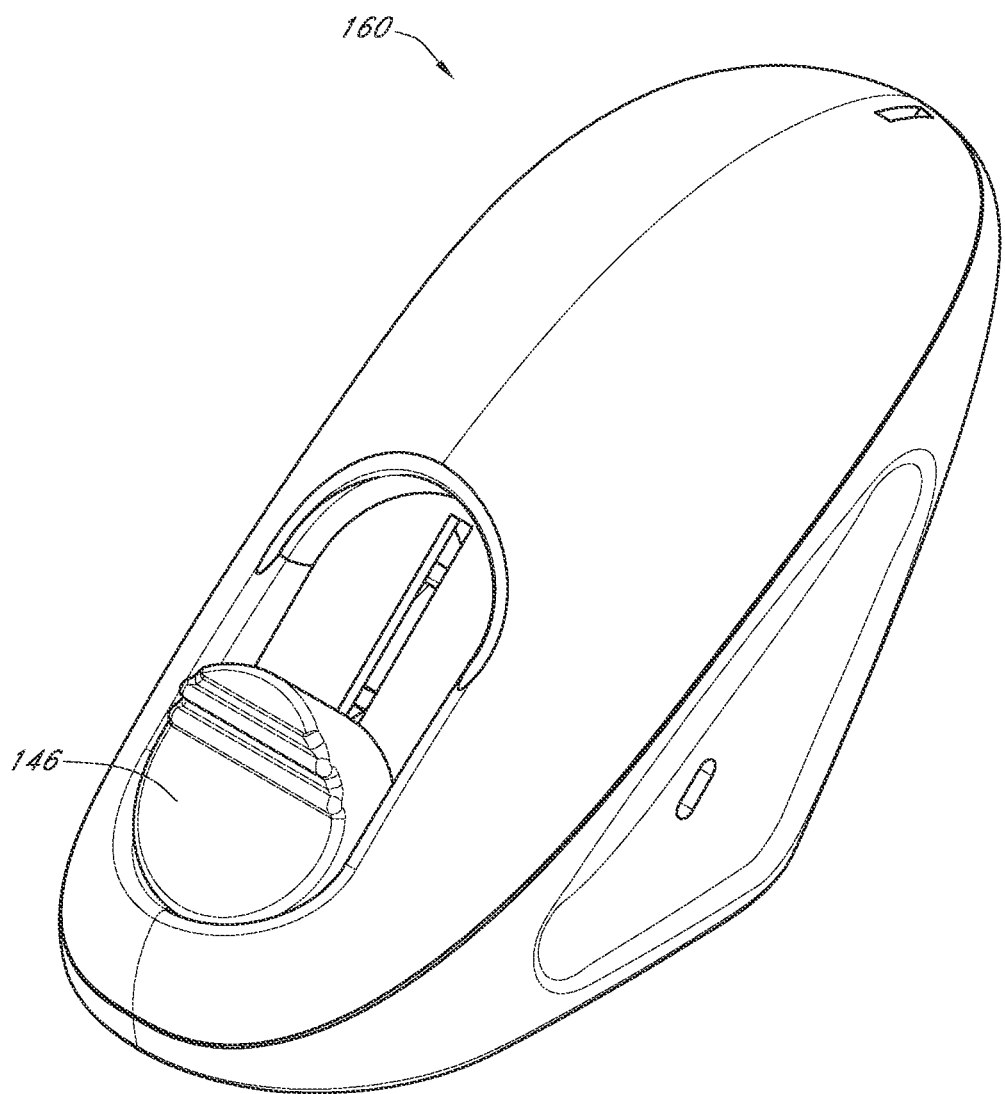
FIG. 23 illustrates another perspective view of the applicator of FIG. 21.
Figure 24A:
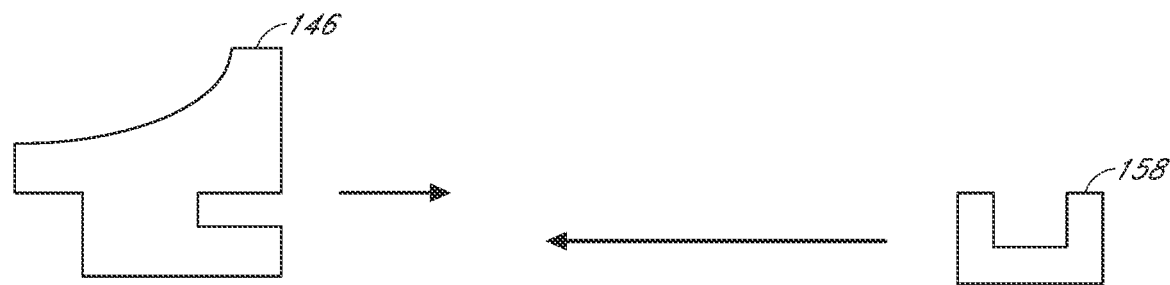
FIGS. 24A, 24B, 24C, and 24D illustrate steps of action of the applicator of FIG. 21.
Figure 24B:
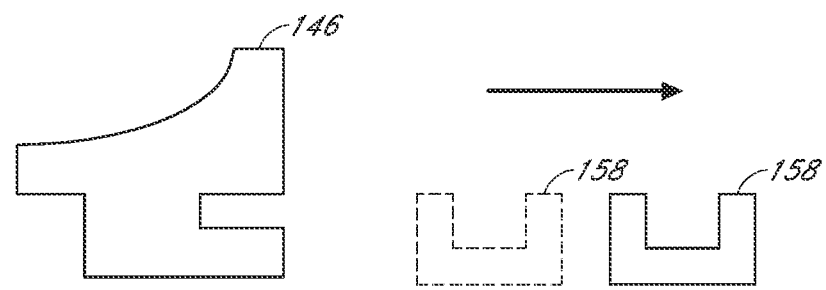
Figure 24C:
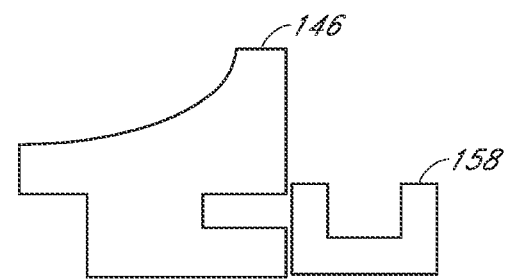
Figure 24D:
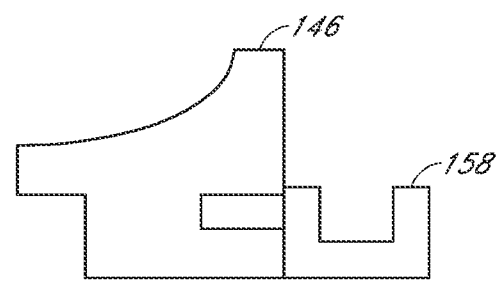

Once the button 146 is moved in a proximal direction, the bar 154 no longer arrests rotation of the wheel 144, and in the same way as described above, the needle and sensor wire may be inserted into the host using the force of a torsion spring (not shown) coaxial with the wheel 144. In particular, a yoke 158 is illustrated which may be driven downward by rotation of the wheel 144, propelling the needle and sensor into the host. This aspect is also illustrated in FIG. 24, in which an initial movement of the button 146 to the right, causing the transition from FIG. 24A to FIG. 24B, also causes the yoke 158 to move towards the button (to the left in the figure). The push rod mechanism as described above or in the applications incorporated by reference may be employed to maintain the sensor in the host during needle retraction. The needle may be retracted by the manual retraction button or by continued rotation of the torsion spring and wheel 144 employing the yoke 158. As shown in FIG. 24B, the lowest point of the yoke is illustrated by the yoke 158 in dotted lines, while the initial retraction of the needle is shown by the yoke in solid lines. To retract the cannula, the button 146 may be moved so as to engage the yoke; by continuing movement to the right, as shown in FIGS. 24C and 24D, the cannula may be removed from the seal and seal carrier. Manual cannula retraction may be particularly useful as it is generally the step requiring the most force. FIG. 23 illustrates an applicator 160 employing manual retraction.

The button 146 may be provided with indentations biased in a way to assist the user in moving the button in the direction indicated by arrow 152 (see FIG. 21), e.g., so as to remove the needle and cannula from the seal system, seal carrier, and housing.

Figure 22:
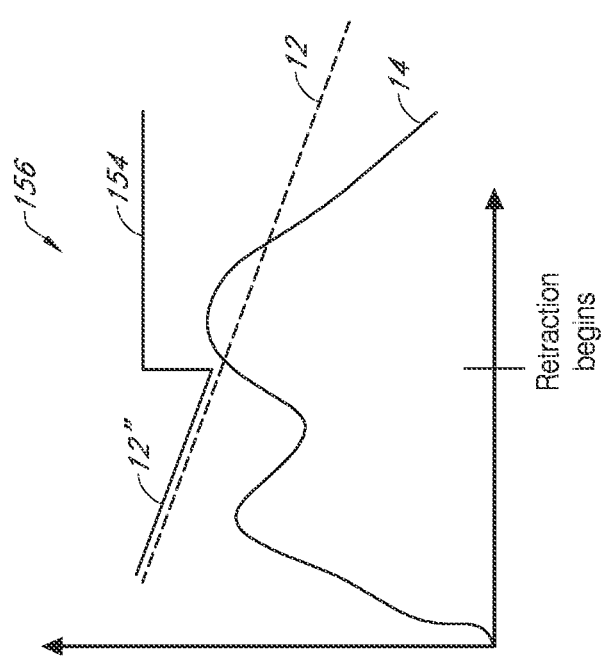
FIG. 22 illustrates a force profile curve for sensor insertion for the applicator of FIG. 21.

FIG. 22 illustrates the resulting force profile. In an initial portion of movement, indicated by the segment 12", the force profile is the same as that of the spring 12 because the same type of spring is causing the movement. In the retraction phase, however, the force available rises to line 154, exceeding that necessary to perform the remainder of the motions called for by the steps. While a constant level of force is indicated by the line 154 in FIG. 22, it will be understood that, being caused by a manual mechanism, the same is essentially arbitrary and is limited only to the force with which a user can bring to bear on the button 146.

Other ways may also be employed of converting rotational energy stored in a torsion spring (and thus resulting in a rotational force) into the more linear translation required in a sensor deposition system. Put another way, one basic requirement of an applicator system is that the same be configured to perform an insertion of a sensor transcutaneously, such that a portion of the sensor is in vivo in the interstitial space in a host (the distal portion) and a portion of the sensor (the proximal portion) is ex vivo. In some cases the sensor may have sufficient column strength and a sharpened end so as to be able to penetrate the skin itself using systems and methods disclosed here or in applications incorporated by reference. In other cases, including in most implementations disclosed here, a needle is used for insertion of the sensor, and the sensor travels with the needle during insertion and is maintained in vivo while the needle retracts, i.e., leaving the sensor in place. In other cases as will be described the needle is used to perform insertion but the sensor wire has sufficient column strength to penetrate even deeper than the needle, through the patient's interstitial area.

Thus a general required motion applicable to most embodiments is that of insertion and retraction, i.e., insertion to insert the needle and sensor assembly, and retraction to remove the needle. In some cases, greater column strength is provided to the needle, and the needle motion itself is significantly eased, by incorporation of a cannula, which is generally a hypotube. For example, and as in FIGS. 3-16, rather than having the needle penetrate a seal, the cannula may be stationary within the seal during insertion, such that the needle can easily move through the cannula to perform the sensor insertion step. However, to effect the seal, the cannula is to be removed, and the same often encounters a significant removal force as the cannula is to be removed from an elastomer seal. To reduce the number of motions required, in many implementations the cannula is removed at the same time as the needle. For example, with respect to the implementation of FIGS. 3-16, the cannula hub latches onto the inner needle hub which is propelled in a proximal direction by the booster spring. In this way the cannula is removed. In all of these implementations, however, a back-and-forth linear motion is required. If energy is stored via a torsional spring, then conversion from rotational force to linear force is also required. In the above implementations a scotch yoke was conveniently used. However, other devices and techniques may also be employed. So long as the back-and-forth motion can be performed, the remainder of the system may be as described above with respect to the applications incorporated by reference above or with respect to the implementations of FIGS. 3-16. For example, in any implementation, on the downward (distal) or initial stroke, a push rod hub may be included to maintain a sensor in place by latching onto a portion of the housing at a distal end of its travel. In the same way, a needle hub may latch onto a cannula hub to allow removal of the cannula where such is included. In embodiments incorporating a cannula hub, the bond force between the cannula hub and the cannula itself can be greater than about 5 pounds, greater than about 10 pounds, or greater than about 20 pounds, to avoid separation of the cannula from the cannula hub as the cannula is retracted from the seal. Extrapolations to other implementations will also be understood.

Figure 25:
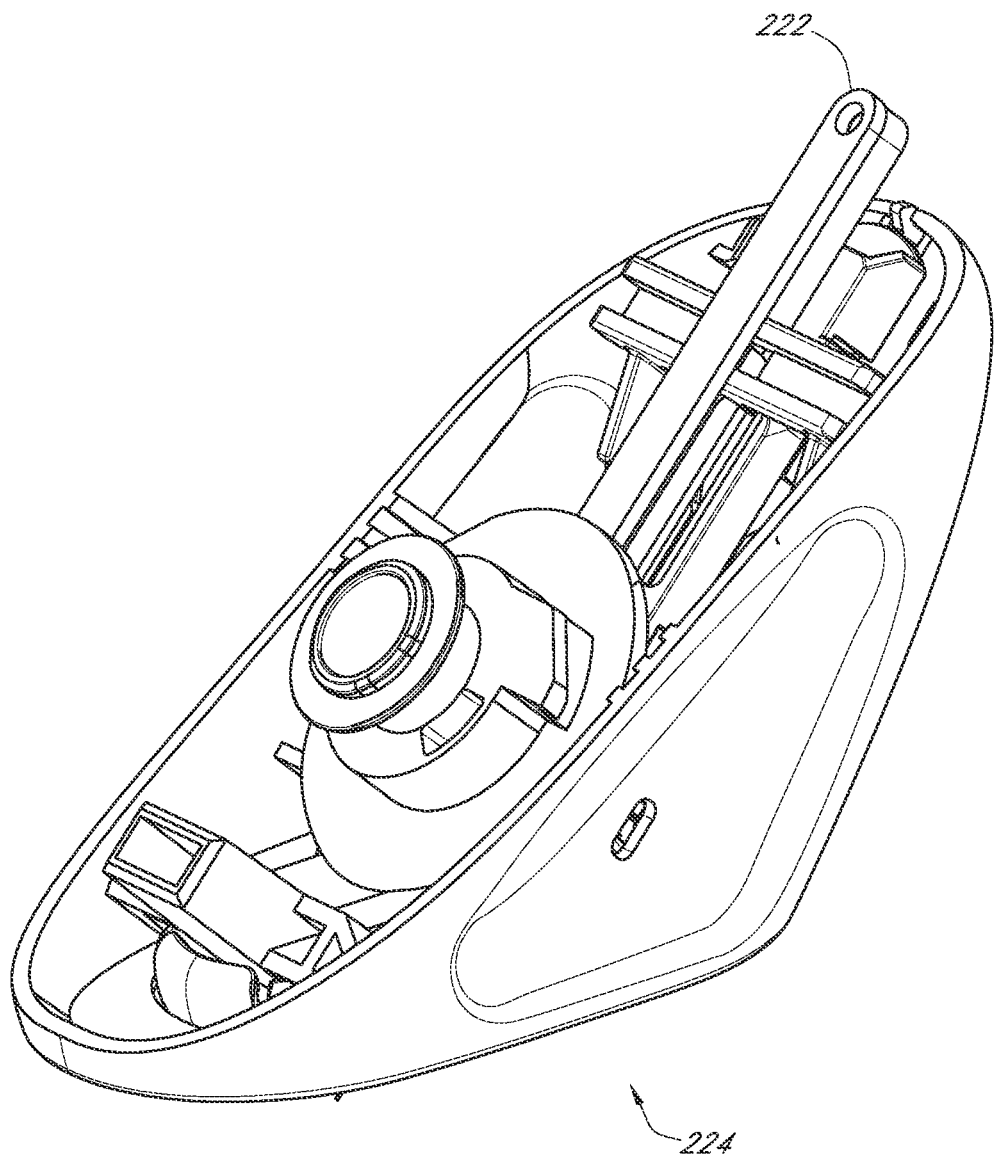
FIG. 25 illustrates a schematic perspective view of another applicator, configured in accordance with an embodiment, with the upper housing removed for purposes of illustration, and with the drive in a first configuration.
Figure 26:
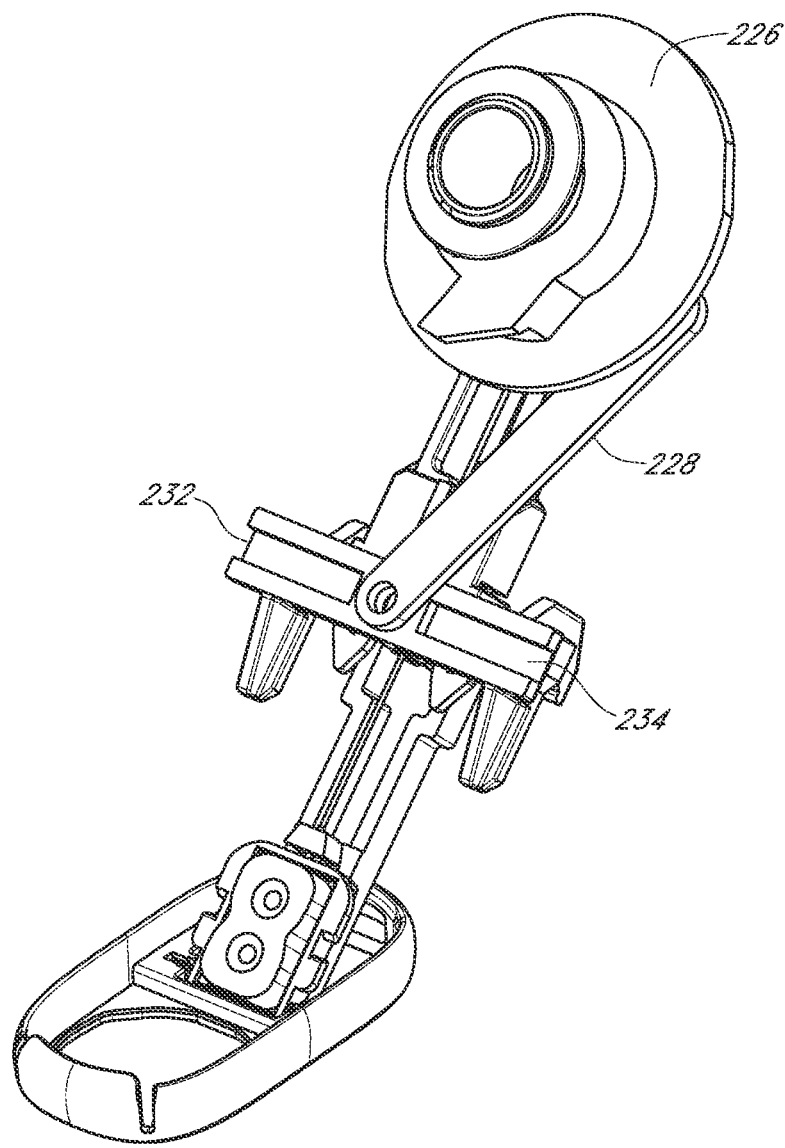
FIG. 26 illustrates another schematic perspective view of the applicator of FIG. 25, with both the upper and lower housing removed for purposes of illustration, and with the drive in a second configuration.

As an example of an implementation in which overall efficiency is increased, thus negating the need for an additional force or driving mechanism or source of stored energy, and referring to FIG. 25, an applicator 224 may include a crank slider mechanism 222 which translates rotational force to linear force in the same way as a crank slider on a sewing machine translates linear motion to rotational motion. In FIG. 25 the crank slider is driven from the bottom. In FIG. 26, the crank slider is driven from the top, and in particular the crank slider 228 is driven by rotation of the wheel 226. The crank slider 228 may be coupled to a point location on the needle/hub assembly 232 or may be coupled within a yoke 234 thereof.

Without wishing to be bound by theory, it is believed that crank slider mechanisms are generally more efficient than scotch yoke mechanisms, and subsequently result in a reduction of energy losses during the deployment cycle. In some implementations, crank slider mechanisms may be employed without a booster spring, because of the reduction of energy losses. As in FIGS. 3-16, a similar button latch system may be employed to arrest rotational movement until such time as a user has activated the button, at which time the crank slider mechanism can be employed to insert and retract the needle and/or cannula in a similar fashion as described above.

Figure 27:
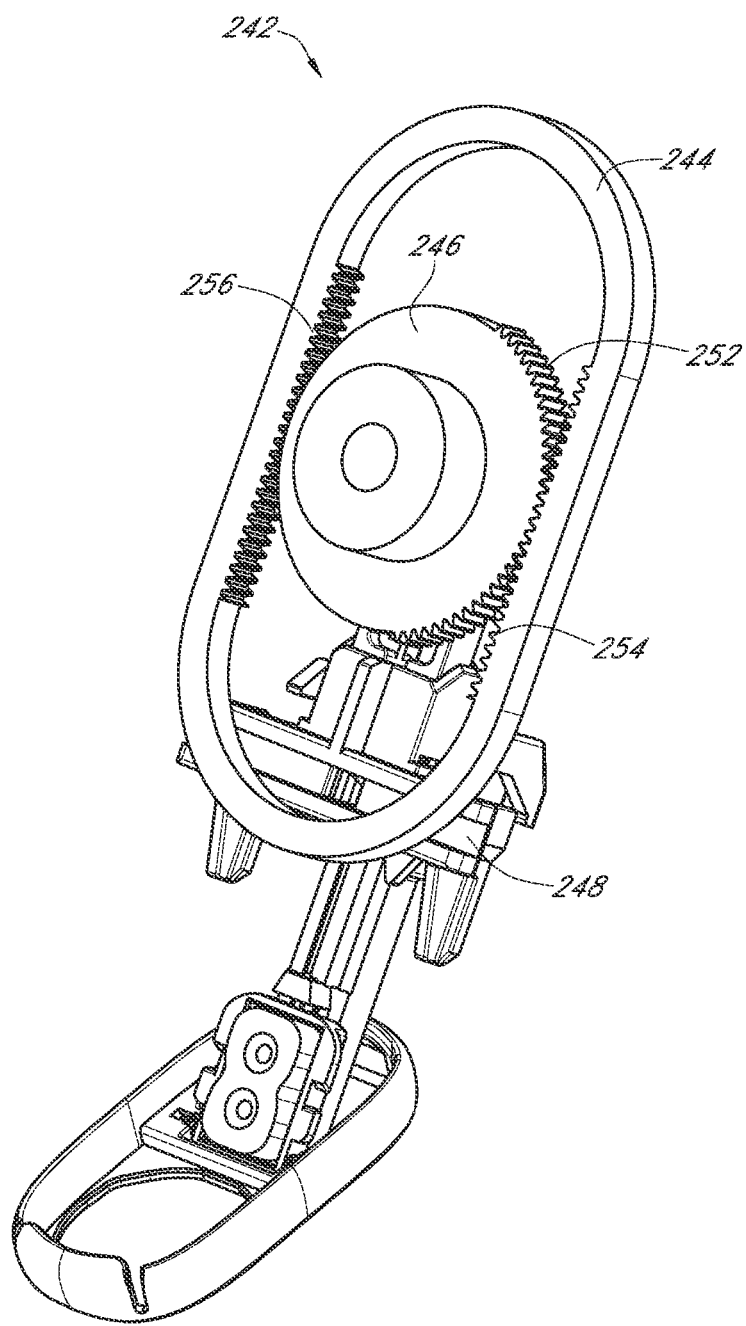
FIG. 27 illustrates a schematic perspective view of another applicator, configured in accordance with an embodiment.

In the same way, and for the same purpose of increasing efficiency of the device, and referring to the device 242 in FIG. 27, a rack and pinion mechanism may be employed to provide the reciprocating or back-and-forth motion. In particular, a rack 244 is coupled to the outer needle hub, indicated by the yoke 248 in the figure. Of course, the attachment for coupling between the rack 244 and the outer needle hub need not be a yoke, but can be any sort of attachment. A pinion 246 is shown, having teeth 252 on only one portion. Rotation of the pinion 246 caused by, e.g., a torsion spring, thus causes movement of the rack 244. As shown, if the pinion 246 were to rotate clockwise under the influence of the torsion spring, the teeth 252 of the pinion 246 would engage teeth 254 on the rack, driving the rack downward. As the pinion 246 continues to rotate, the teeth 252 eventually engage teeth 256 on the rack, driving the rack (and that which it is attached to) upward in a proximal direction, completing the motions required to perform sensor and needle insertion and needle retraction. The remainder of the configuration may be as described above in FIGS. 3-16.

One exemplary benefit to the rack and pinion mechanism is that the same may in some implementations have benefits over the scotch yoke mechanism. For example, scotch yoke mechanisms typically have points in their cycles of low torque and high torque, which can make them susceptible to stalling in places where a large amount of torque is required. A rack and pinion mechanism generally provides a more constant torque and may overall be more efficient in transferring the torsional spring energy to linear motion.

Figure 28:
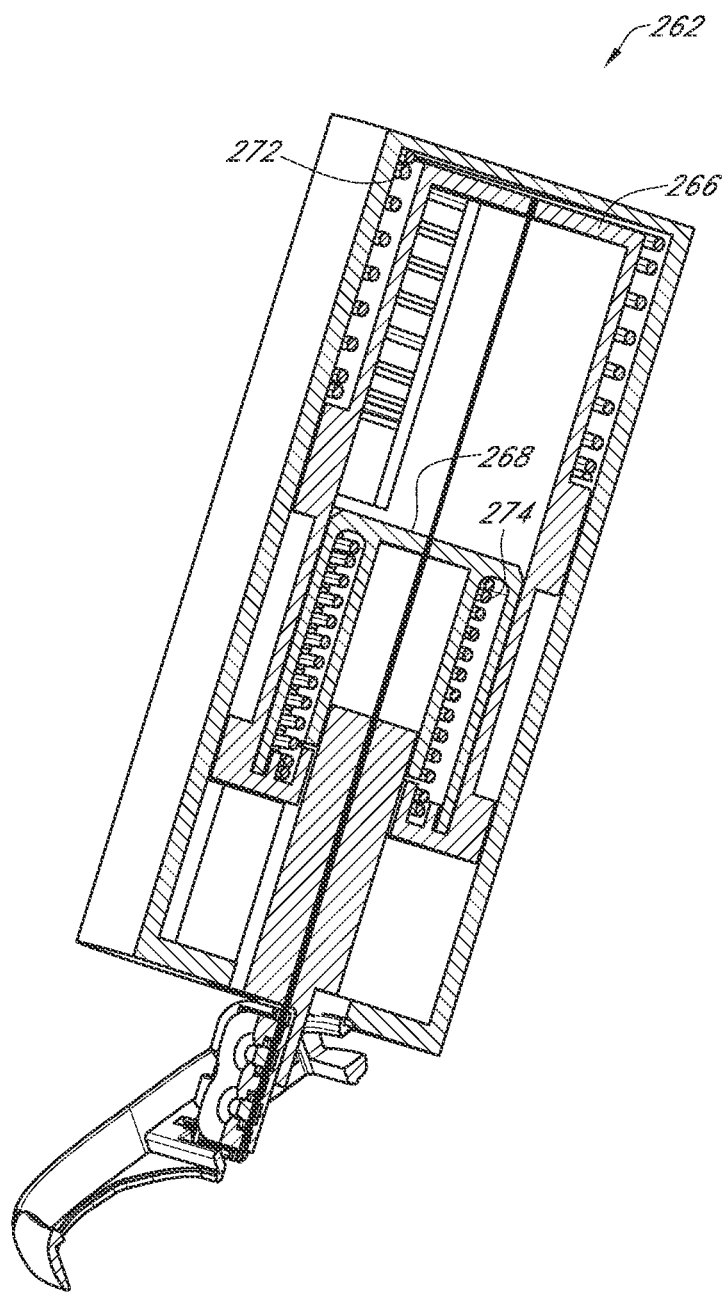
FIG. 28 illustrates a cross-sectional perspective view of another applicator configured in accordance with an embodiment, with the upper and lower housing removed for purposes of illustration.

As another example of an implementation in which additional force is supplied, FIG. 28 illustrates another mechanism which may be employed to perform a reciprocating back and forth motion for purposes of insertion and retraction. In particular, the applicator 262 includes an outer needle hub 266 containing a first compression spring 272, and an inner needle hub 268 containing a second compression spring 274. In one implementation, the spring 272 is maintained until use in a compressed state, and the spring 274 is also maintained until use in a compressed state. The spring 272 may be coupled to the outer needle hub at a proximal point, and the spring 268 may be coupled to the inner needle hub at a distal point.

Activation of the trigger may then cause the release and subsequent extension of the spring 272, driving the needle with sensor into the host. In the same way as described above, with regard to activation of the booster spring e.g., using a push rod hub which latches into a portion of the applicator housing, the spring 274 may be activated, causing retraction of the needle out of the host, while leaving a portion of the sensor within.

FIG. 29 illustrates another implementation 264 of a drive mechanism, this implementation employing just a single compression spring 278 within the applicator 276. In this implementation, the spring 278 provides both a down insertion force (distally, into the body) and an upward retraction force, (proximally, away from the body), and has the manufacturing benefit of eliminating a part as compared to the implementation of FIG. 28. In this case the spring 278 is held in a preloaded fully compressed state. A distal wall 277 holding the spring against expanding in a distal direction is then removed, or moved distally, and the spring thus expands by driving off a proximal wall 279, which holds the spring against expanding in the proximal direction. The spring releases approximately half its stored energy to drive the needle into the body in this insertion step. The spring is now still half loaded with the distal wall in the bottom position. The proximal wall is then released to use the second half of the spring energy to drive the needle (and cannula, if used in a given implementation) in a proximal direction away from the distal wall.

Besides manual retraction, another implementation includes a step of user preload. This implementation may be a variant of the single compression spring. However, for manual insertion, the spring may be placed on the shelf in the half loaded state. The initial input of the force by the user pressing the plunger fully loads the spring. Then the release is identical to the single spring implementation described above with respect to FIG. 29.

One benefit to the implementation of manual insertion is that only a single coaxial spring is required, thus significantly reducing costs. In use, a user would depress the plunger against the resistance of the spring, in the same way as a button on a ballpoint pen is compressed against a spring. No activation of a needle occurs until the bottom of travel is reached by the plunger. When at the bottom of travel, the spring releases, and the needle and push rod are pushed forward under the skin. This position is maintained until the user releases the plunger at which time the plunger retracts, pulling the needle and cannula back and depositing the sensor. As in the other implementations, the push rod may stay in the distal or bottom position, causing the sensor to be deposited into the host. The user may then remove the applicator and install a transmitter.

Advantages to the implementation of user preload insertion include lower-cost and fewer components, as well as the avoidance of partial deployments, as no activation occurs until the user fully depresses the plunger. Another significant advantage to manual insertion is that the spring is not fully preloaded, but rather half-loaded by the user right before activation. In this way, problems with sizing components for sustained loads in plastic components, such as creep, are avoided.

An exemplary force profile is illustrated by the graph 210 in FIG. 30, in which it is seen that only half-force is exerted until the plunger is at the bottom extent of travel, as shown by segment 202, but at that point (point 212) the force increases to a maximum, caused by the spring being compressed to a maximum displacement ($F=-kx_{max}$). The spring then relaxes as it expands, shown by segment 204, and the resulting force decreases linearly. At point 208 the user releases the plunger, causing additional spring force to enter into the system, indicated by the rise of force in graph 210. The force continues to decay, as shown by segment 206, as the spring expands towards equilibrium. The force is then employed to retract the cannula as well as the needle. As may be seen, the available force exceeds that required through all points of the insertion and retraction.

A method of use is illustrated by the flowchart 214 of FIG. 31, in which a first step is that a user depresses a button plunger (step 216). No action occurs until the button reaches its bottom of travel. At the bottom of travel, the spring releases, which inserts the needle, sensor, and push rod (step 218). Upon removal of the user pressure on the plunger, the same begins moving in the opposite direction, causing retraction of the needle, as well as a cannula (step 222), in embodiments where a cannula is included. In some cases the user depression of the plunger may provide the force required to insert the needle and sensor. The sensor deploys as the pushrod inhibits sensor movement during needle retraction.

The implementations of FIGS. 28 and 29, as well as manual insertion, in some cases provide certain benefits over the scotch yoke mechanisms described above. In particular, the torsional spring in the scotch yoke mechanism sometimes cannot provide enough energy to perform all deployment functions. In FIGS. 28 and 29 and manual insertion, the use of compression springs provides a unidirectional assembly process which is convenient for automation. In the implementation of FIG. 28, dedicated springs for "needle in" and "needle/cannula out" functions allow the springs to be custom designed and tuned according to the system requirements. In addition, the same may be associated with certain assembly and manufacturing advantages.

Figure 32:
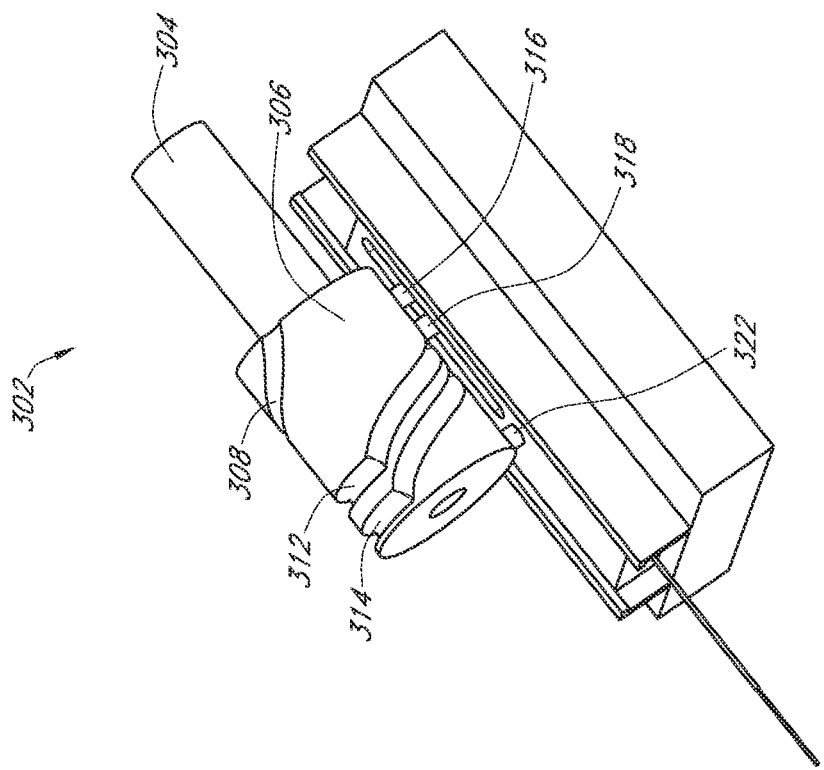
FIG. 32 illustrates a schematic perspective view of a drive mechanism for an applicator, configured in accordance with an embodiment.

FIG. 32 illustrates another implementation of a drive mechanism, this implementation allowing an even wider range of movements and motions of component parts. In particular, the drive mechanism 302 includes a barrel cam 306 having an axle 304 which may be driven by, e.g., a torsion spring or by user motion. The implementation of FIG. 32 may be particularly advantageous in addressing the problem of moving multiple components, which depending on implementation, are required to change direction to perform sensor insertion. A barrel cam may be employed which contains multiple tracks which control the movement of each component independently of each other, and as such may be more reliable and controlled. In this way, the implementation of FIG. 32 may be made particularly efficient.

The barrel cam 306 performs the conversion of rotational force to linear or translational or longitudinal force. The barrel cam 306 includes one or more channels, shown as channels 308, 312, and 314. Parts such as the outer needle hub, inner needle hub, a cannula hub, push rod hub, and the like, are driven by corresponding nubs which a ride within the channels or tracks of the barrel 306. In particular, nub 316 is driven by rotation of the channel 308. Nub 318 is driven by rotation of the channel 312. Nub 322 is driven by rotation of the channel 314. The linear positions of the needle hub, push rod hub, and cannula hub, can be controlled by the shapes of the tracks in the barrel cylinder. In this way, component parts may be inserted and retracted as needed, without the need for hub drop offs. As the cylinder rotates, each of the hubs move linearly independently from one another.

Figure 33:
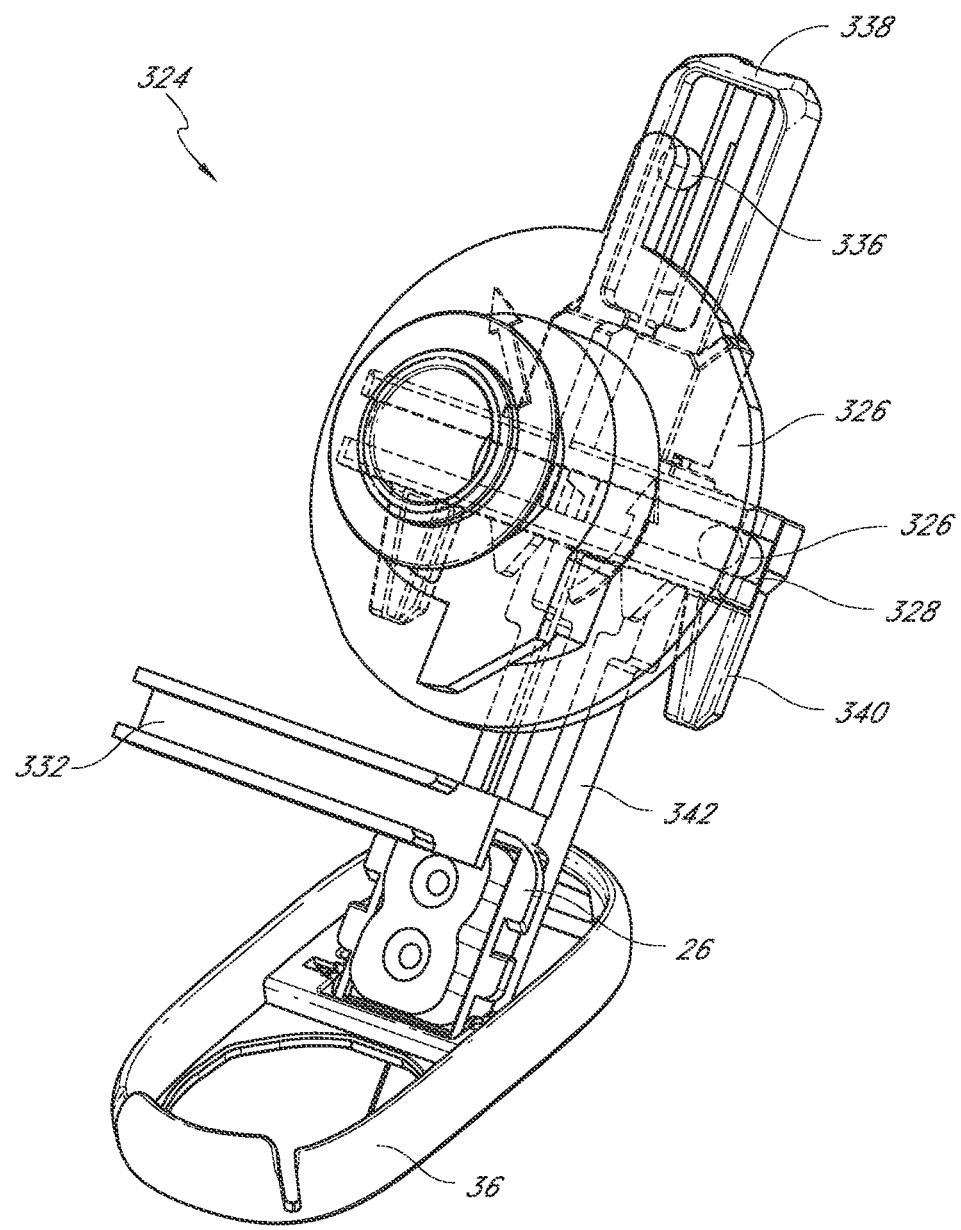
FIG. 33 illustrates a schematic perspective view of another drive mechanism for an applicator, configured in accordance with an embodiment.
Figure 86:
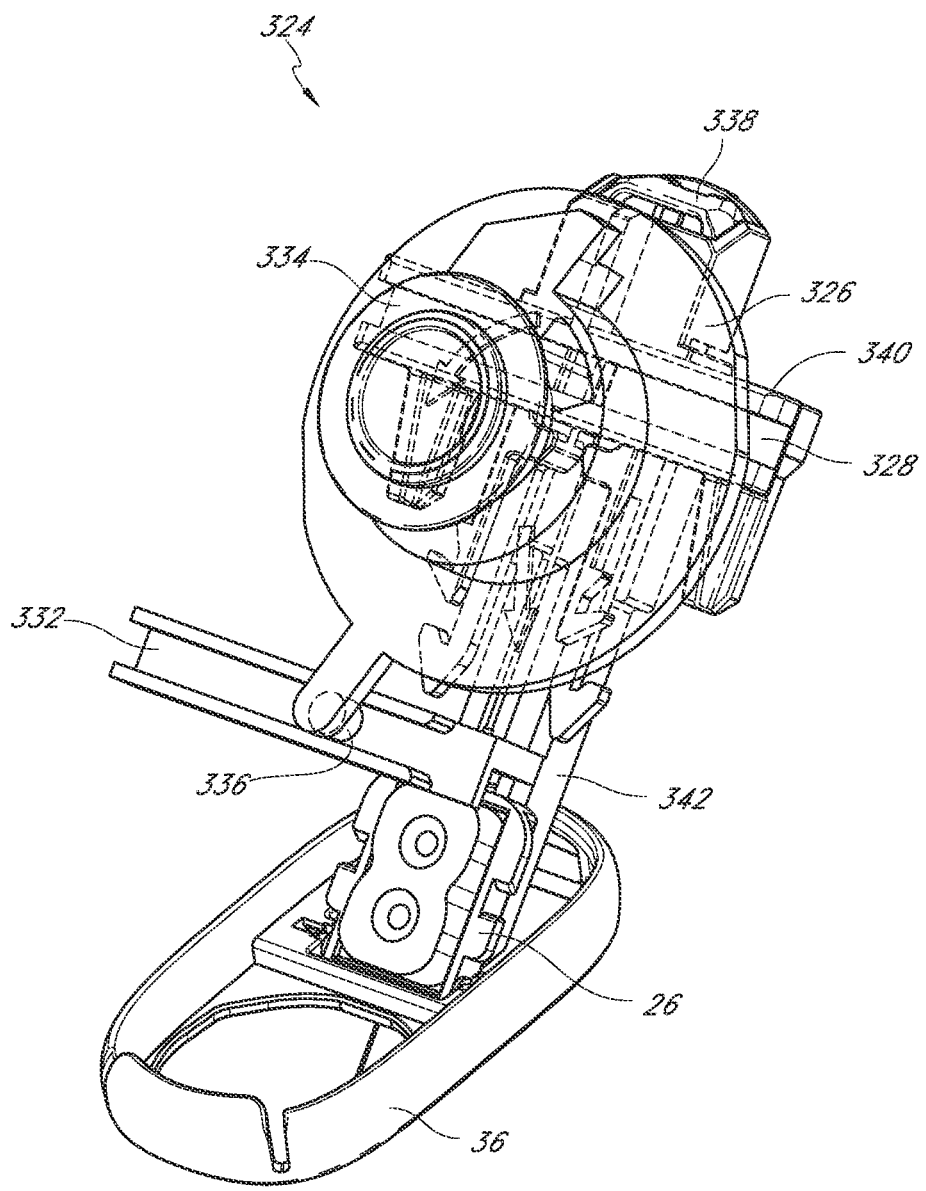
FIG. 86 illustrates a perspective view of the applicator system of FIG. 33, in a second configuration.

FIG. 33 illustrates yet another implementation of a high efficiency drive mechanism, this drive mechanism 324 including a wheel 326 configured to cooperate with a first yoke 328 and a second yoke 332 to facilitate the insertion and retraction processes in a similar way to that described in FIGS. 3-16. The first yoke 328 is operatively coupled to a needle hub 340 and a push rod hub 338, and the second yoke 332 is operatively coupled to a cannula hub 342. The rotation of the wheel 326 may be driven by, e.g., a torsion spring, for example as described herein in connection with FIG. 6. However, in this implementation, the wheel 326 has a first pin 334 extending therefrom which is configured to engage with the first yoke 328 during at least a portion of the rotation of the wheel 326, and a second pin 336 extending therefrom which is configured to engage with the second yoke 332 during at least another portion of the rotation of the wheel 326. In the embodiment illustrated in FIG. 33, the first pin 334 and the second pin 336 are disposed at different radii about the center of the wheel 326. In the configuration illustrated in FIG. 33, the push rod hub 338 is fixed with respect to (e.g., locked to) the first yoke 328 and the needle hub 340, for example as described above in connection with the embodiment illustrated in FIGS. 7 and 11. As the wheel 326 rotates in a clockwise direction, under influence of the torsion spring, the pin 334 pushes the first yoke 328 and the needle hub 340 in a distal direction as it travels within first yoke 328. As illustrated in FIG. 86, as (or after) the first pin 334 begins moving in a distal direction, continued rotation of the wheel 326 causes the second pin 336 to engage with (e.g., enter) the second yoke 332. At this stage the push rod hub 338 is disengaged from the needle hub 340 such that the needle hub 340 can move in a proximal direction as the push rod hub 338 remains in a distal position. As the second pin 336 travels within the second yoke 332, it pulls the second yoke 332 in a proximal direction, away from the seal carrier 26 and disposable housing 36, thus performing retraction steps. In other words, in this implementation, the wheel 326 causes the first yoke 328 to perform insertion and the second yoke 332 to perform retraction. Such a configuration can provide the ability to precisely set different insertion and retraction forces as desired, using a single torsion spring. The mechanical advantage of the cam wheel can thus be tuned to the available spring force.

In the embodiment illustrated in FIGS. 33 and 86, the first pin 334 remains engaged with the first yoke 328 as the second pin 336 engages the second yoke 332 and throughout the insertion and retraction processes. Other configurations are possible, however, in which the first pin disengages from the first yoke before or after the second pin engages with the second yoke. In embodiments, one or both ends of the first yoke 328 can be open, allowing the pin 334 to engage with (e.g., enter) and/or release from (e.g., exit) the first yoke 328 at the desired rotational position(s) of the wheel 326. Similarly, one or both ends of the second yoke 332 can be open, allowing the pin 336 to engage with (e.g., enter) and/or release from (e.g., exit) the second yoke 332 at the desired rotational position(s) of the wheel 326. In the embodiment illustrated in FIGS. 33 and 86, the second pin 336 is disposed at a larger radius of the wheel 326 than the first pin 334, and extends from the underside of a radially-extending arm of the wheel 326. In other embodiments, the second pin can be disposed at the same or smaller radius than the first pin. In still other embodiments, the same pin can be configured to engage with the first yoke and the second yoke during separate portions of the wheel's rotation.

Figure 87:
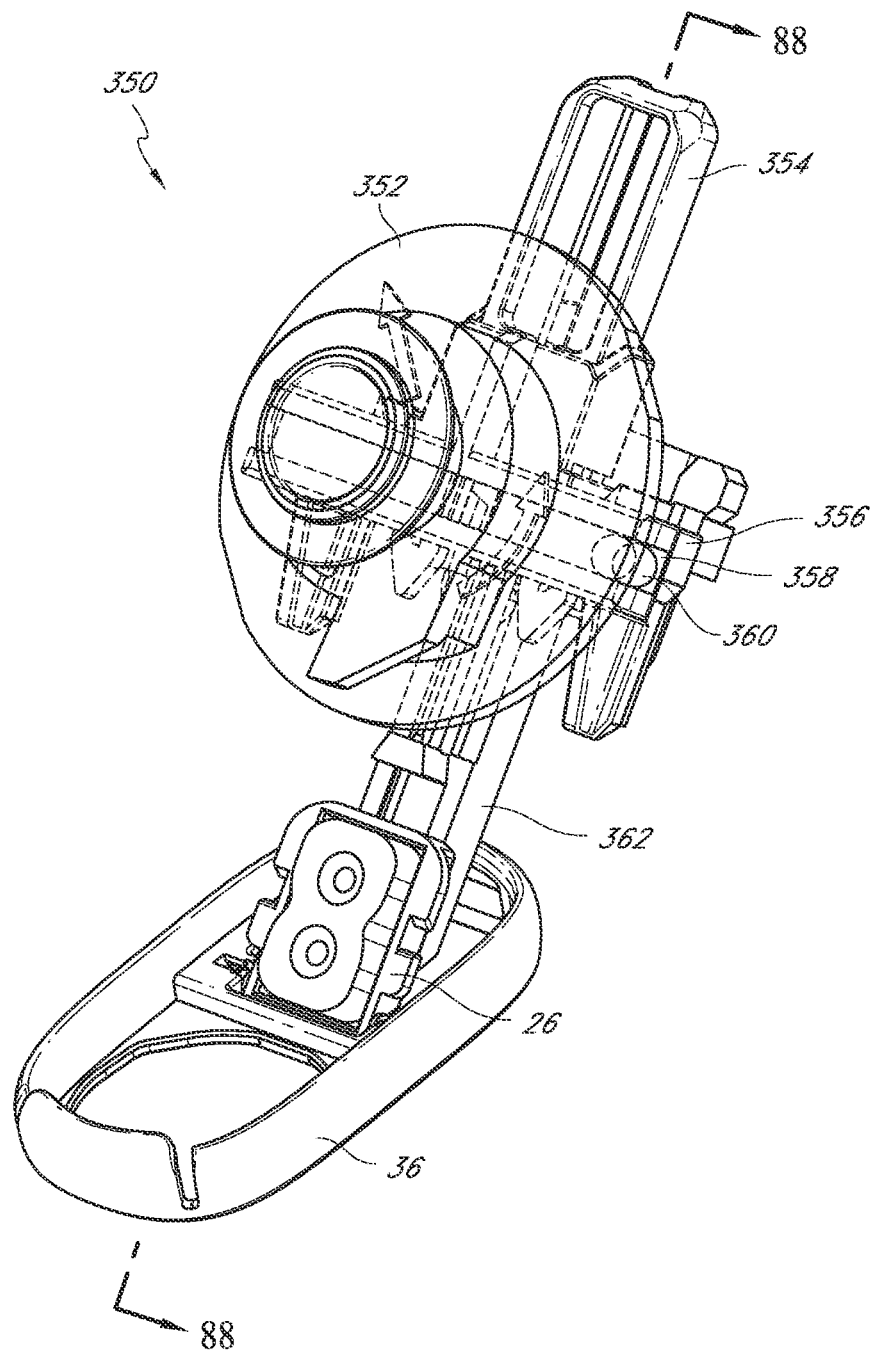
FIG. 87 illustrates a perspective view of an applicator system, configured in accordance with another embodiment.
Figure 88:
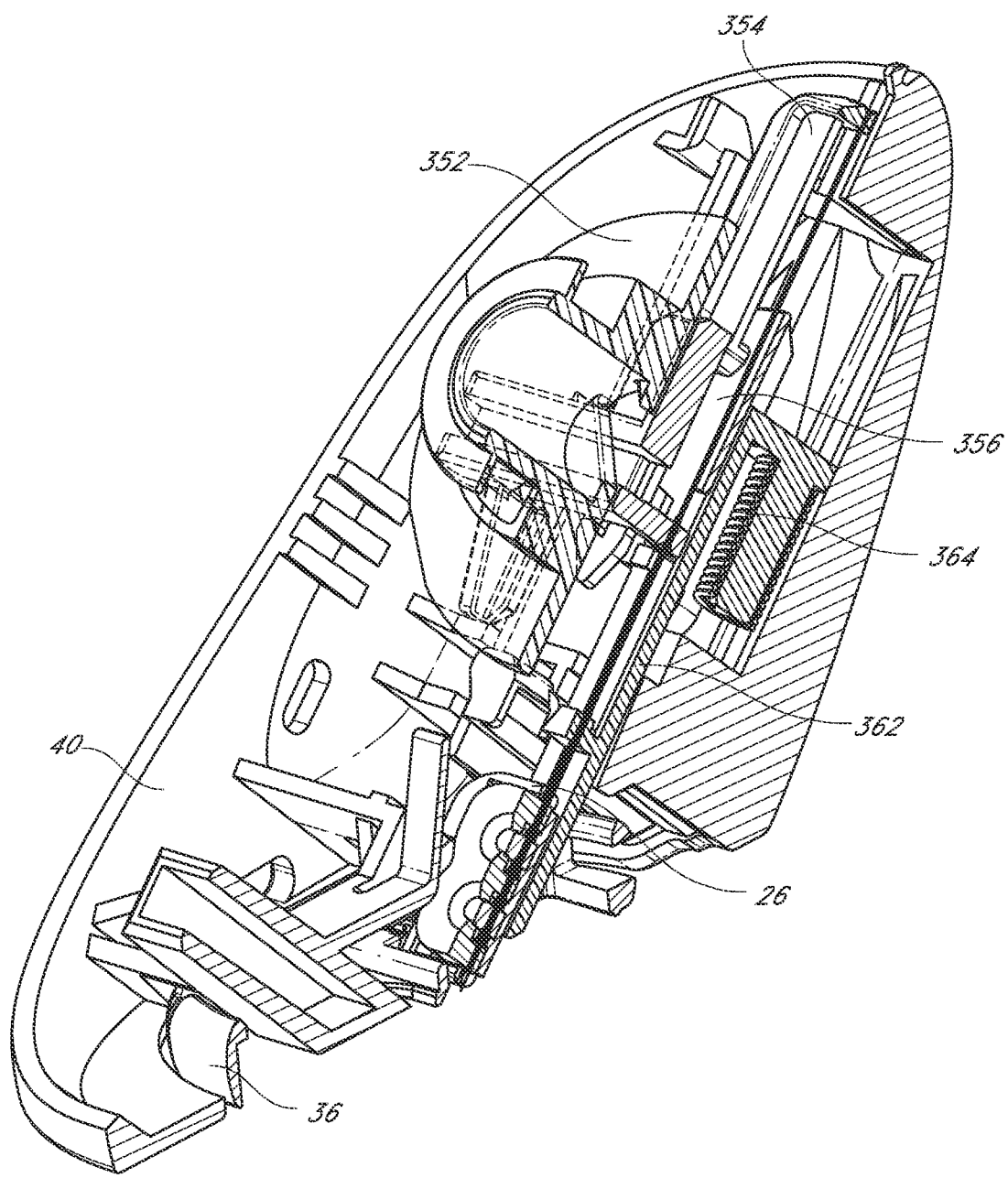
FIG. 88 illustrates a cross-sectional perspective view of the applicator system of FIG. 87, taken along line 88-88 of FIG. 87.

FIGS. 87 and 88 illustrate a drive mechanism 350 according to a further embodiment. The drive mechanism 350 includes a wheel 352 configured to cooperate with a yoke 358 to facilitate the insertion and retraction processes in a similar way to that described in FIGS. 3-16. The yoke 358 is operatively coupled to a needle hub 356 and a push rod hub 354, as well as to a cannula hub 362. The rotation of the wheel 352 may be driven by, e.g., a torsion spring, for example as described herein in connection with FIG. 6. However, in this implementation, as illustrated in FIG. 88, the drive mechanism 350 also includes a booster spring 364 configured to facilitate the cannula retraction process. In the configuration illustrated in FIGS. 87 and 88, the push rod hub 354 is fixed with respect to (e.g., locked to) the needle hub 356, for example in a similar fashion as described above in connection with the embodiment illustrated in FIGS. 7 and 11. As the wheel 352 rotates in a clockwise direction, under influence of the torsion spring, the pin 360 travels within yoke 358 and pushes the needle hub 356 in a distal direction, while the cannula hub 362 remains stationary (e.g., fixed in place or position). After the pin 360 reaches its most distal position, continued rotation of the wheel 352 causes the pin 360 to travel in the opposite direction in the yoke 358 and pull the yoke 358 and the needle hub 356 in a proximal direction. At this stage the push rod hub 354 is disengaged from the needle hub 356 such that the needle hub 356 can move in a proximal direction as the push rod hub 354 remains fixed or locked in a distal position. At the same time or shortly thereafter, a release member is activated which releases the cannula hub 362 from engagement with the base of the lower housing 40, thereby actuating the booster spring 364. As the booster spring 364 expands, it pushes the cannula hub 362 away from the seal carrier 26 and disposable housing 36, thus facilitating the retraction process in conjunction with the torsion spring. Such a configuration can also provide the ability to precisely set different insertion and retraction forces as desired. Variations of booster springs may also be employed, which implementations use similar mechanisms as those shown in FIGS. 3-16. As noted above in some cases the wheel cam can be made larger and the needle may be fully inserted and retracted by the torsion spring. The booster spring may be linked independently to the cannula hub and may fire while the needle is still in motion and being driven by the wheel. The wheel cam may be smaller in this implementation because it does not fully retract the needle from the seal. The booster is fired when the torsion spring has finished its travel. The booster spring is attached to the needle hub and drives the needle (which picks up the cannula and cannula hub) on the way out of the seal.

Figure 93:
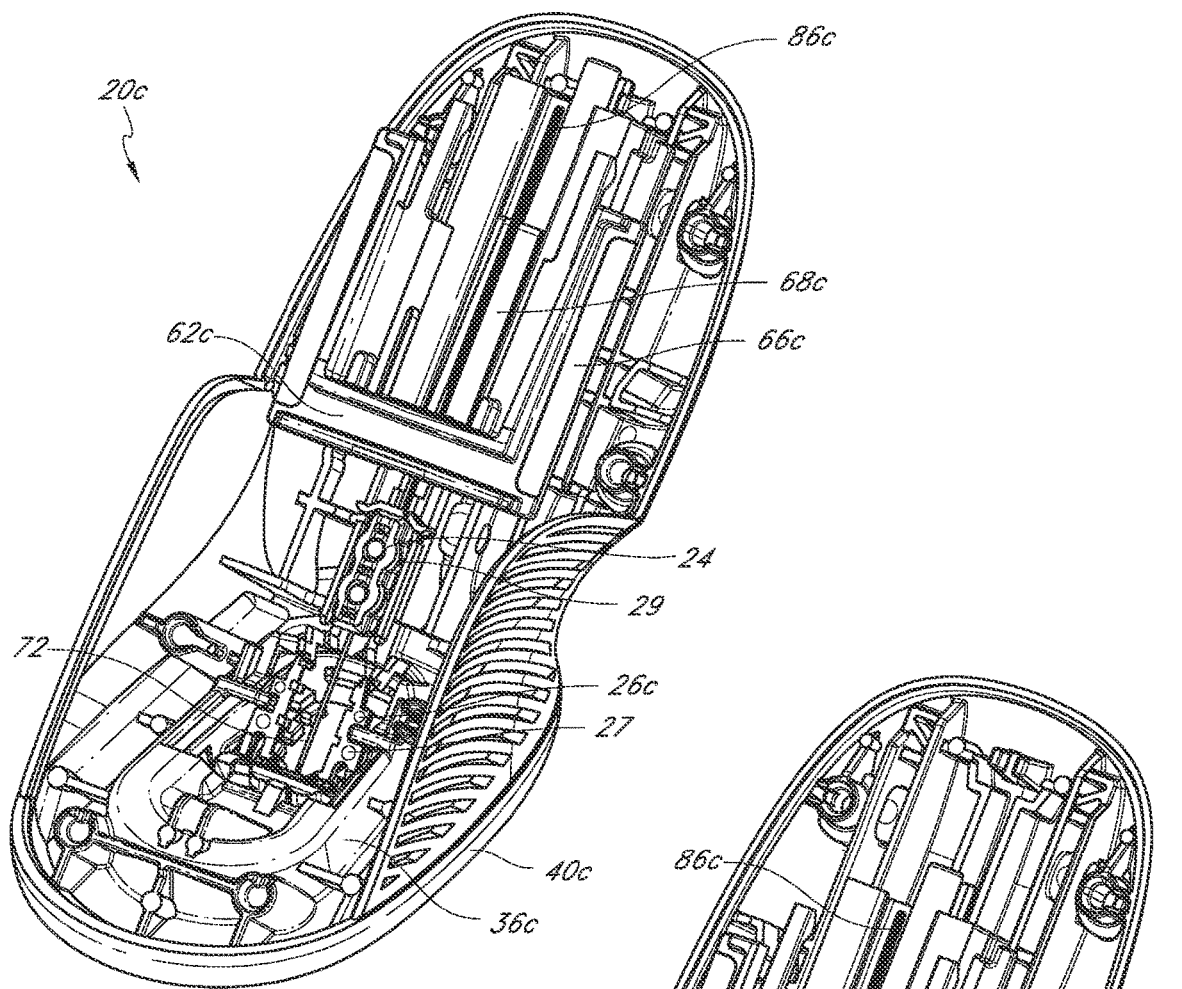
FIG. 93 illustrates a perspective view of an applicator system in accordance with another embodiment, and shown in a first configuration.

Referring now to FIGS. 93-96, an applicator device 20c (with its upper housing and other components removed for purposes of illustration) is illustrated which is configured in accordance with an alternative embodiment. FIG. 93 illustrates the device 20c in a resting state, prior to deployment. The device 20c includes an outer needle hub 66c, an inner needle hub 68c, and a push rod 86c. The device 20c further includes a disposable housing 36c and a seal carrier 26c having a two-part configuration. The seal carrier 26c includes a first portion 27 which is operatively coupled to the disposable housing 36c at a hinge 28, at least prior to deployment of the device 20c. The seal carrier 26c also includes a second portion 29 which is coupled to both the push rod 86c and a needle 72 and which, prior to deployment, is disposed separate from and proximal of the first portion 27. The second portion 29 includes at least one seal 24. The first portion 27 and the second portion 29 are both disposed at the same angle with respect to the plane of the disposable housing 36c.

During the insertion process, the outer needle hub 66c, the inner needle hub 68c, and the push rod 86c move together in a distal direction, along with the second portion 29 of the two-part seal carrier 26c. The second portion 29 slidingly engages with the first portion 27 and ultimately snaps into engagement with the first portion 27. At this stage, the needle 72 and the sensor wire are deployed into the patient's skin.

In configurations with a two part seal carrier negative interactions affecting force required or sensor positioning (e.g. friction or seal recoil) are prevented. This is accomplished by negating relative movement between the sealing member and needle during the insertion phase of the cycle. This also has the additional benefit of lowering component count (e.g. deleting the cannula) and holding a smaller lumen in the seal which may have sealing benefits.

Figure 94:
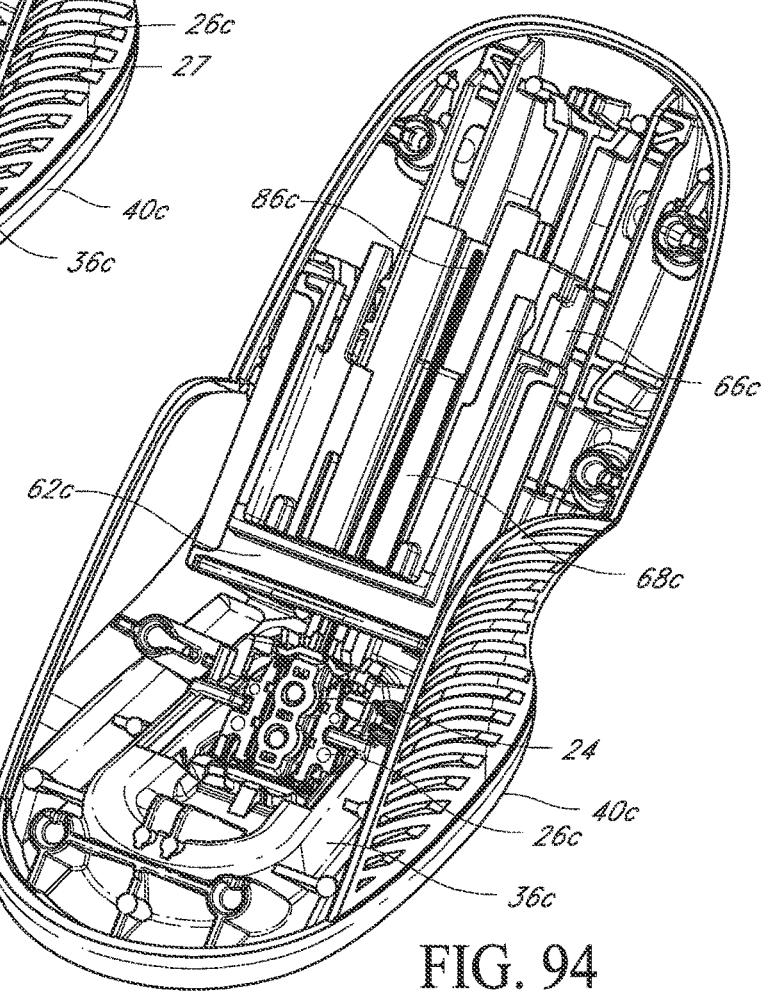
FIG. 94 illustrates a perspective view of the applicator system of FIG. 93, shown in a second configuration.
Figure 95:
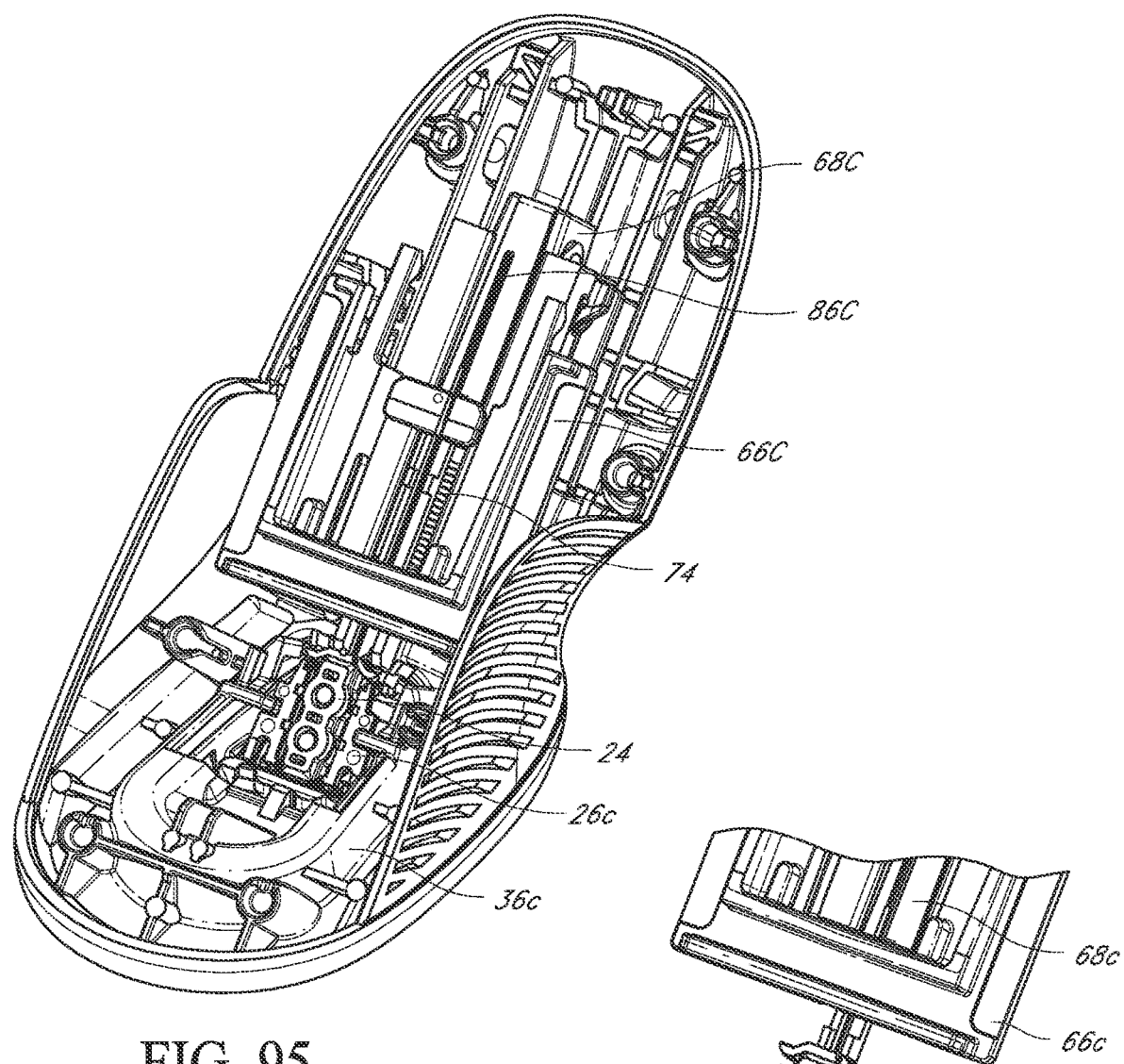
FIG. 95 illustrates a perspective view of the applicator system of FIG. 93, shown in a third configuration.
Figure 96:
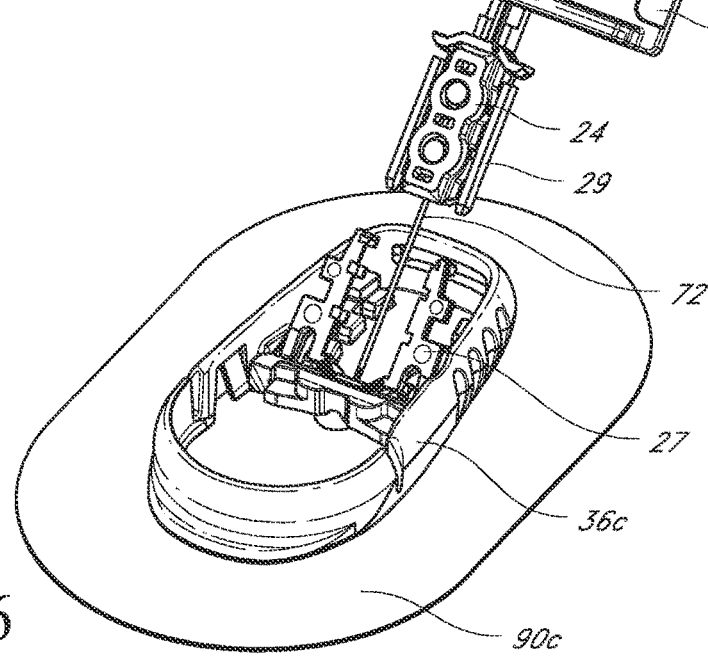
FIG. 96 illustrates a partial perspective view the applicator system of FIG. 93, shown in the first configuration with certain components removed for purposes of illustration.

FIG. 94 illustrates the device 20c just after deployment, with the outer needle hub 66c, the inner needle hub 68c, and the push rod 86c having been driven in a distal direction, for example by a drive mechanism including a torsion spring, a scotch yoke mechanism, a booster spring, and/or any other suitable drive mechanism, for example as described herein. Under the continued influence of the torsion spring (or other drive mechanism), the inner needle hub 68c begins to retract and pull the needle 72 in the distal direction, while the outer needle hub 66c and the push rod 86c remain fixed in a distal position. As illustrated in FIG. 95, a booster spring 74 can be activated at this stage to facilitate the retraction process, in conjunction with the torsion spring. Once the needle 72 is retracted from the seal 24, the seal carrier 26c is rendered free to rotate downward (e.g., under the force of gravity or spring force) into a deployed position, ready to receive a transmitter.

Figure 34:
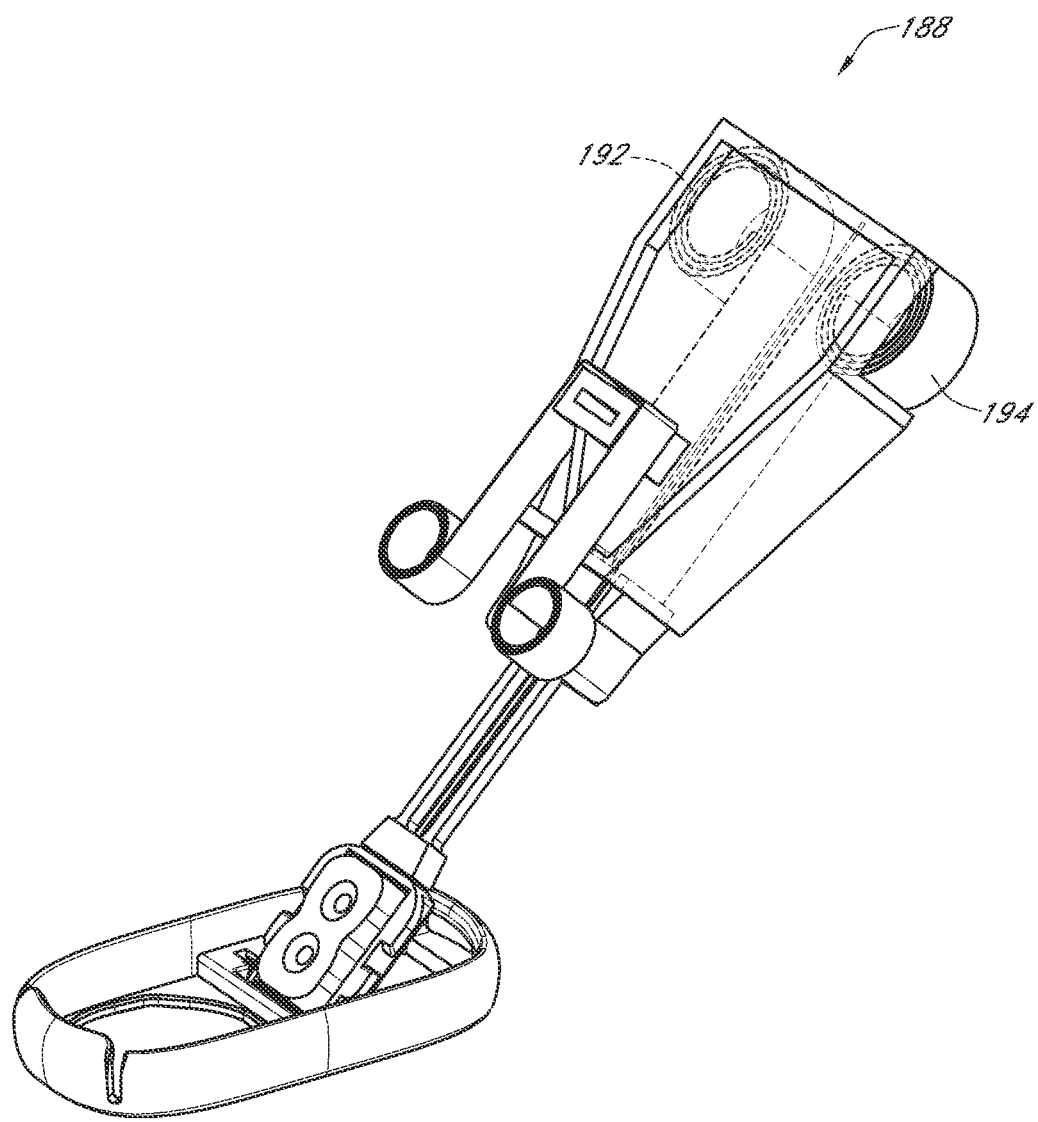
FIG. 34 illustrates a schematic perspective view of another drive mechanism for an applicator, configured in accordance with an embodiment.

FIG. 34 illustrates another implementation according to present principles, in which additional energy is supplied, and in which a dual spring variant is used. In this case, dual constant force springs 192 and 194 are employed instead of compression or tension springs. Use of constant force springs generally provides a different output force curve.

In all of the implementations noted, when the cannula 78 is removed from the seal 24, a deleterious phenomenon termed "slingshotting" may occur, and many of the efforts of systems and methods according to present principles are directed towards reduction or elimination of slingshotting. In particular, when the cannula is removed, the seal, which is generally made of an elastomer, is pulled by the cannula due to friction at the point of contact (actually a cylinder of contact). Thus, a cylindrical portion of the seal, generally in the interior of the seal and adjacent the cannula, is temporarily pulled by the cannula during cannula removal.

As the cannula emerges from the seal, the lack of frictional "pull" of the cannula on the seal causes the seal to rebound in the distal direction. Depending on configuration, the rebounding ("slingshotting") seal may frictionally contact the sensor wire and/or needle and force the same forward, having a deleterious effect on placement of the contact points on the sensor wire vis-a-vis the contact pucks. For example, the slingshotting can result in a change of position of over 100 mils, and to this is compared the diameter of the pucks, which may be, e.g., 80 mils, and the distance between the pucks, which may be, e.g., 215 mils.

Some ways to combat seal slingshotting include modification of the seal to reduce its frictional contact with the cannula. These ways are discussed below. Another way to combat seal slingshotting is to perform an action with the cannula to ease its removal from the seal, or at least to perform an action that causes the seal to slingshot less.

Figure 35:
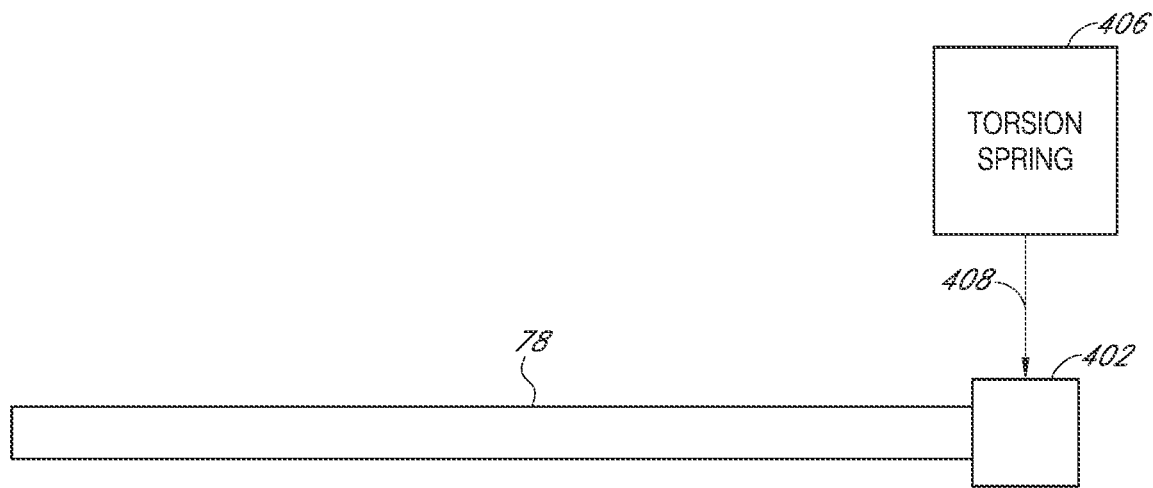
FIG. 35 illustrates one step in a method for deploying a sensor into the skin of a patient, in accordance with an embodiment.
Figure 36:
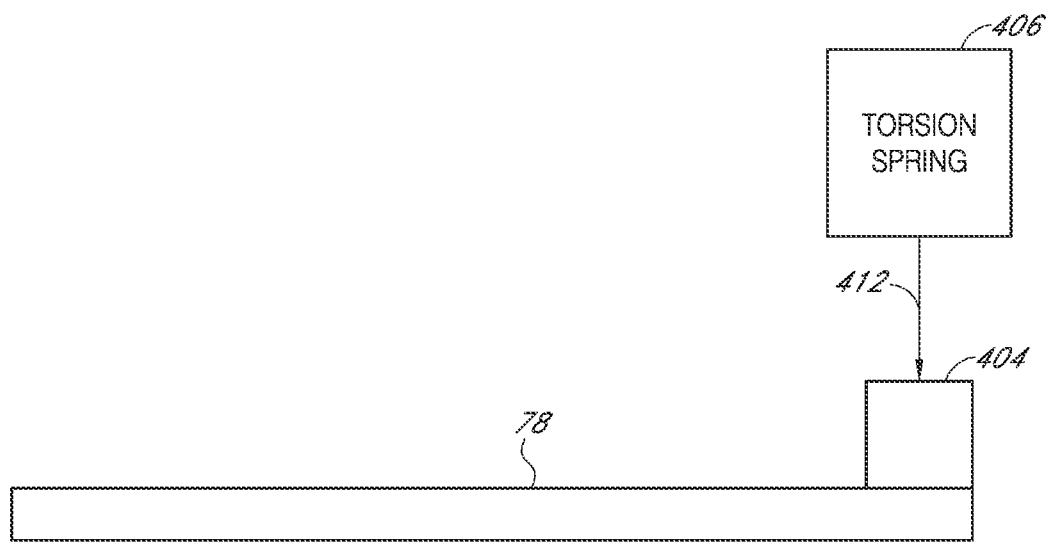
FIG. 36 illustrates another step in a method for deploying a sensor into the skin of a patient, in accordance with an embodiment.

Referring to FIGS. 35 and 36, one such method is to rotate the cannula during removal. In both figures, the cannula 78 is caused to rotate by the torsion spring 406, but it should be noted that the rotational force on the cannula may be caused by a number of different components, including by use of a cam rotationally coupled to the cannula. In FIG. 35, a cannula drive 402 is disposed at an end of the cannula, and the same is shown as being driven by the torsion spring 406 through a linkage 408. In FIG. 36, the cannula 78 is caused to rotate by the cannula drive 404 disposed on a side of the cannula, and the same is driven by a linkage 412 from the torsion spring 406. In one implementation, the cannula is rotated prior to and during removal of the cannula, e.g., with a cycle time of less than 500 ms.

The amount of rotation required may be small, and the same need only rotate during the time immediately before cannula removal up to the time most or all of the cannula is removed. In one implementation, and without wishing to be bound by theory, it is believed that, in the absence of rotation, the static friction and adhesion between the cannula and the seal must be overcome for the seal to not be pulled by the cannula. If the cannula is caused to rotate, the static friction and adhesion has already been overcome, and the only force required is that caused by the kinetic friction. Assuming the normal force is the same, as the kinetic friction is generally less than static friction, the cannula force is much less on the seal during removal. Relative motion between the seal and the cannula about the rotational axis does not cause deformation of the seal elastomer about the longitudinal axis. Therefore slingshotting effects can be minimized by breaking static friction and adhesion in the rotational axis.

It will be understood that the cannula drive may be constituted by a number of devices, including those driven by the same sources of energy performing the insertion and/or retraction, devices specifically dedicated for this purpose, or the like. Such devices may include cams, motors, and so on.

Besides rotating the cannula (or causing the cannula to perform another like motion, e.g., vibrating the cannula) to accomplish the goal of lessening seal slingshotting, another way to specifically reduce the effect of seal slingshotting on the sensor wire is to retract the cannula prior to retraction of the needle. In this way, the seal slingshotting or "snapback" contacts the needle and not the sensor wire itself. The needle shields the sensor wire from the slingshotting effect.

Figure 37:
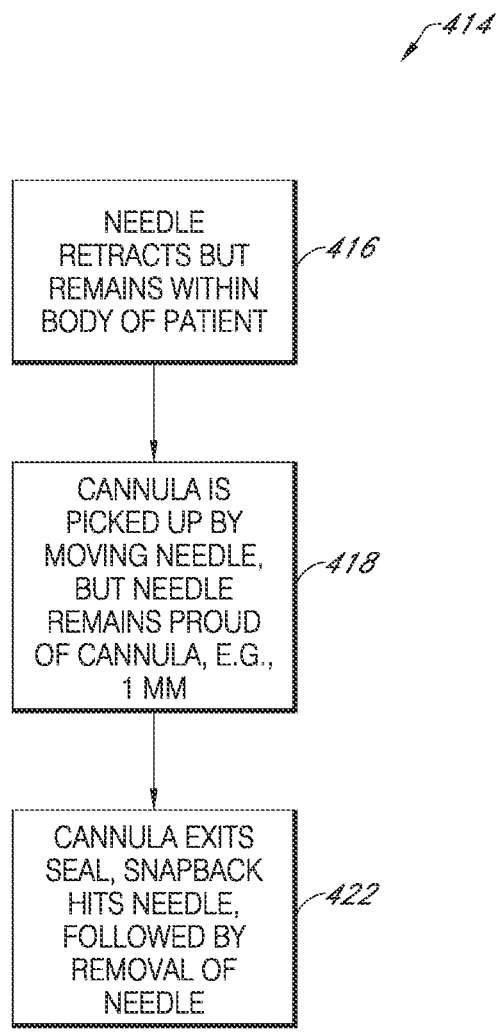
FIG. 37 illustrates a flowchart for steps of sensor insertion according to another embodiment.

Referring to the flowchart 414 of FIG. 37, steps of this implementation of the retraction sequence are shown. A first step is that the needle retracts but remains within the body of the patient (step 416). A next step is that the cannula is picked up by the moving needle in the fashion described above, but the needle remains proud of the cannula by a certain length, e.g., 1 mm (step 418). A final step is that the cannula exits the seal, followed shortly by the needle. This implementation may be similar to that described in FIGS. 3-16, but where the needle is made slightly longer.

The implementation of FIG. 37 may provide several benefits. Without wishing to be bound by theory, it is noted that a kink in the needle (described below with respect to FIG. 38) prevents forward motion during most of the seal recoil during the retraction step. In addition, the seal is allowed to recoil while the sensor wire is still protected by the needle.

Figure 38A:
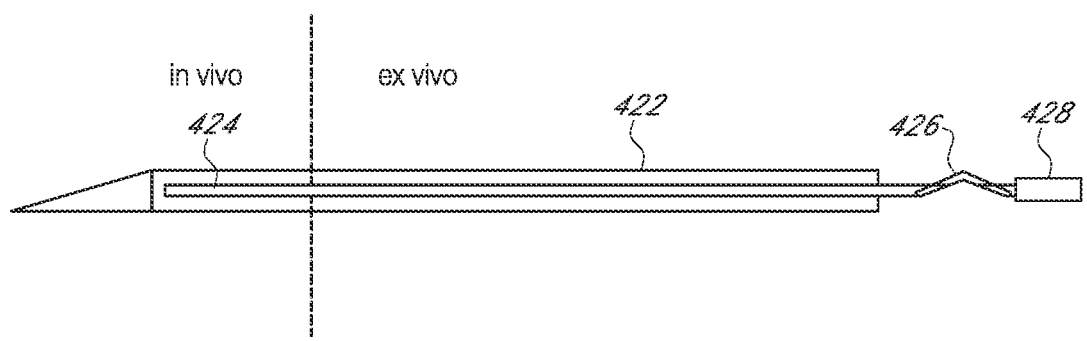
FIGS. 38A-C illustrate steps of needle deployment through a cannula, according to one embodiment.
Figure 38B:
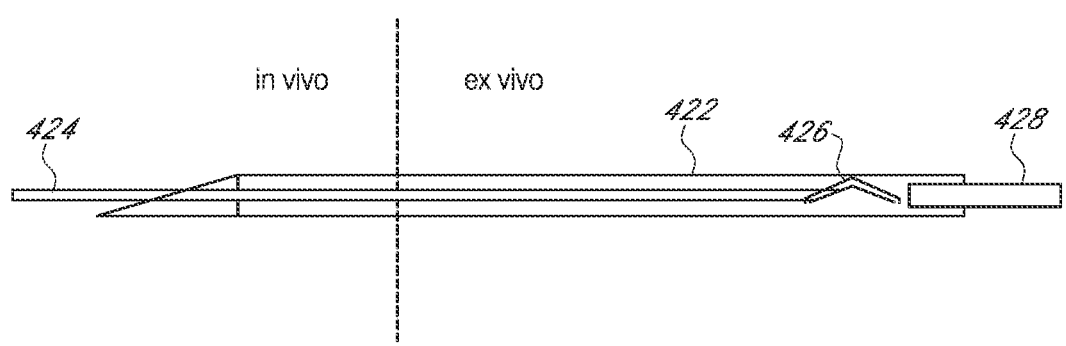
Figure 38C:
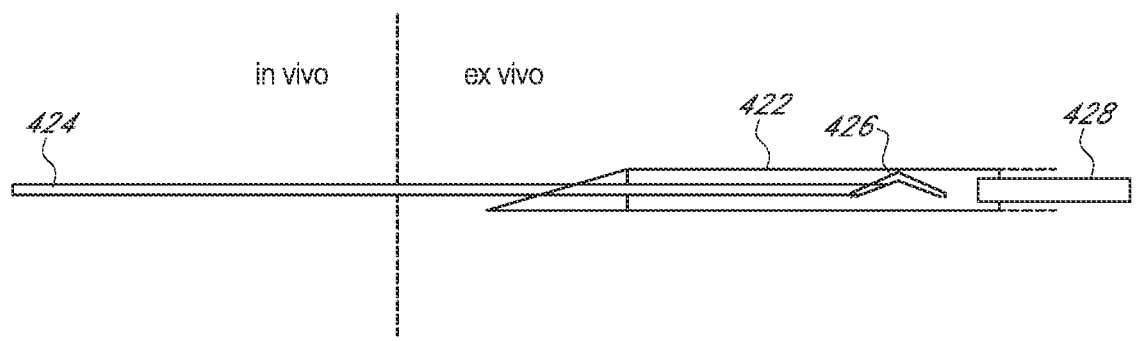

In yet another implementation, and referring to FIG. 38A-C, the length of the needle may be reduced so that the needle does not penetrate as deep as the sensor. Generally the strength of the needle is required to penetrate the skin of the host, but once past the skin, the column strength of even the sensor wire is generally sufficient to allow further penetration into this interstitial area, e.g., at least 2 to 3 mm beyond the needle tip. Referring to FIG. 38A, a needle 422 is shown penetrating the skin of a host. The needle contains within it a sensor wire 424, and in FIG. 38, the kink 426 as well as push rod 428 can also be seen.

In FIG. 38B, the sensor wire 424 has been pushed out to a further distance (more distal) than the needle 422. Retraction of the needle is shown in FIG. 38C, resulting in deposition of the sensor wire 424 into the host.

This implementation may be implemented by modifying the implementation of FIGS. 3-16 by, e.g., lengthening the push rod and/or shortening the needle. Various other mechanisms may be employed to push the sensor to the second depth. Various advantages inure to the implementation of FIG. 38, including that the sensor extends past the location where trauma from the needle is produced, reducing sensor artifacts and other deleterious signal effects, e.g., "first-day noise". In addition, this implementation allows a reduction in the height of the applicator, which is driven at least in part by the length of the needle. In this regard it is noted that the needle is driven approximately 1-6 mm below the skin, which the sensor is driven approximately 4-15 mm.

In embodiments, the needle can be a single-lumen needle with a single bevel at its point, such as the needle 450 illustrated in FIGS. 99 and 100. In some embodiments, the trailing edge or heel of the needle tip (i.e., the portion of the needle tip to the right of line A-A in FIG. 99) can be subjected to special processing during manufacturing, e.g., an extra bead blast at either or both of the inside and outside edges, so as to remove any fine burrs and avoid coring or other trauma to the patient's skin. Embodiments can thus avoid inaccurate glucose readings that might otherwise result from cellular damage to the patient's tissue during sensor deployment.

In some embodiments, the needle can be a multi-lumen needle, such as the needle 456 illustrated in FIG. 101. The needle 456 comprises a metal outer lumen 458 and a polymer inner lumen 460. Embodiments incorporating an inner lumen comprising a compliant material such as a polymer can serve to limit or minimize tissue trauma.

Figure 107:
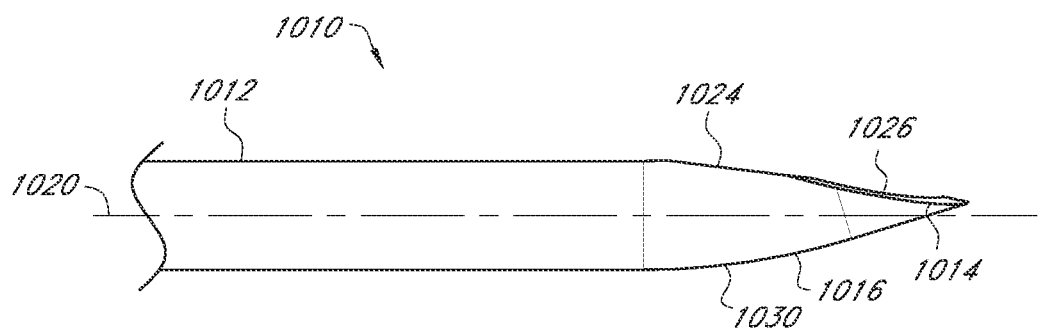
FIG. 107 shows an elevation view of a needle of one embodiment.

In some embodiments, the needle can be a curved, C-shaped, or Tuohy needle. For example, as shown in FIG. 107, a needle 1010 includes a wall structure 1012, a cutting edge 1014 and a blunt contour 1016. The needle 1010 advantageously can be used to deliver a sensor 1018 (such as an analyte sensor, for example, a glucose sensor) through an outer skin layer and into a sensor depth in a less invasive way than when performed by prior art needles. In the needle design, the size of the cutting edge 1014 is balanced against a portion of the distal wall structure 1012 that has blunt contours 1016. Thus, the needle 1010 is capable of cutting the more durable outer skin layer (first phase) and then progressively widening open the cut for further advancement into the subcutaneous layer (second phase) with minimal tissue trauma. When the needle is sufficiently advanced with the sensor therein, the needle and the sensor are then detached, and the needle is retracted leaving the sensor 1018 in a desired position. Early testing has shown a reduction of "dip and recover" incidents (and reduction in average duration of an incident) with glucose sensors delivered using the needles described herein.

The term "needle" as used herein should be construed to cover any delivery device that can contain the sensor 1018 for delivery to the appropriate depth. The "needle" can have any of a variety of shapes with regard to its wall structure 1012. For example, the wall shape can be cylindrical with a circular cross-section or can have a V-shaped, square or rectangular, or even some irregular, cross-section. The wall shape also need not be an extruded shape with the same cross-section along its axis. For example, the wall shape may start as a cylindrical tube with a circular cross-section at a proximal end and then change to a V-shape (in cross section) as it approaches the distal end. The wall shape may also have defined along its length slots or various openings—such as a slot that gives it a C-shape in cross-section. (The open cross-section of the C or V-shapes affords clearance for attachment of wiring, for example.)

Generally, however, the wall structure 1012 defines some inner (relative to some outer surface of the wall) dimension (width or diameter for example) that supports or contains the sensor 1018 for subcutaneous delivery. For example, in a V-shaped cross-section, the inner part of the V near its base has a diameter that is occupied by the sensor lodged between the two inner wall surfaces. Thus, the "dimension" is defined by the position that the sensor occupies (or would occupy) during delivery in or on the needle wall structure 1012. The term "needle" also covers other devices (with different names) that share similar wall structures and functions (e.g., delivery of an implantable device), such as, for example, a tube, channel, cannula, catheter or blunt dilator with a recess or opening for deployment of an implantable device (e.g., a sensor).

The wall structure 1012 of the needle 1010 has, in the embodiment of FIG. 107, a tubular shape defining a central opening 1022 with a central axis 1020. The wall structure 1012 is formed from a tube by bending, machining and polishing as shown generally by FIGS. 109-111. The proximal end of the wall structure 1012 retains its stock tubular shape and has, for example, an outside diameter of 0.018 plus 0.001 or minus 0.0005 inches. Preferably, the inside diameter is an inner dimension sized to contain a cross-section of the sensor 1018 for its delivery. The sensor 1018 has a smaller cross sectional diameter than the diameter of the central opening 1022. The size and shape of the central opening 1022 may vary though according to the size and shape of the sensor 1018 being delivered. As noted above, the needle 1010 may have a wall structure 1012 with a shape that varies axially and in cross-section. For example, the wall structure cross-section could have a rectangular, C-shape or V-shape, as will be discussed in more detail below.

In some embodiments, the outer diameter of the wall structure 1012 at the proximal end, for example, may be about 0.0135 plus 0.001 or minus 0.0002 inches. The outer diameter and thickness of the wall structure 1012 reflects a balance of columnar stiffness and minimization of the wound size for clearance of the needle through the patient's skin. In certain embodiments, the diameter of the wall structure 1012 is minimized, but not to the point where the needle 1010 is susceptible to buckling under the expected axial load from needle insertion.

In one aspect, the wall structure 1012 has a length configured to retain and protect the sensor 1016. In the case of one type of subcutaneously delivered glucose sensor, for example, the wall structure 1012 has a length of about 2.31±0.02 inches.

The strength of the wall structure 1012 (e.g., column strength) is determined in part by its material composition. A range of materials can be used, for example, steel (e.g., stainless steel), ceramics, titanium, tantalum, nickel, nickel-titanium, iridium, silver, palladium, platinum-iridium, iridium, ceramics, composites, and combinations or alloys thereof, and/or the like. Polymers that may be used include, but are not limited to, polycarbonate, polymethacrylic acid, ethylene vinyl acetate, polyesters, fluoropolymers including polytetrafluoroethylene (TEFLON®), polyethylene, polypropylene, high density polyethylene, nylons, polyethylene terephthalate, and polyesters, combinations thereof, and the like. Stiffer materials like stainless steel (SS304 with a full hard temper) can store more deformation energy and have a higher modulus (190-203 GPa Young's modulus) and elastic limit (205-310 MPa) than many other materials and thus have good stiffness and resistance to buckling and permanent (plastic) deformation. This helps to keep the shape of the needle (and its ability to deliver the sensor) through penetration of the skin to the sensor depth. Also, steel has the advantage that it can be machined (formed, filed, ground, etc.) to create a sharper edge than many other materials. Further, steel tends to hold its edge well—the aforementioned modulus and energy storage capability keep the edge sharp through its use.

The insertion force and buckling strength of the needle 1010 has been determined. The needle 1010 is inserted at 45 degrees into 10 N Syndaver at 1 in/min. Peak insertion force was measured using a 10 N load cell. Insertion forces were measured for 8 attempts at an average of 0.22b lbf with a minimum of 0.156 lbf and a maximum of 0.298 lbf and a standard deviation of 0.0505. Insertion forces were also measured for conventional needles and averaged 0.191 lbf with a range of 0.163 lbf and 0.237 lbf and a standard deviation of 0.0239.

Buckling strength was tested by compressing the needle 1010 against a non-pierceable (metal plate) and measuring the axial force required to buckle the needle using the 10 N load cell. The buckling strength of the needle 1010 was (for 8 samples) 2.505 lbf on average with a minimum of 2.185 lbf and a maximum of 2.280 lbf and a standard deviation of 0.2189. For conventional needles, 2.458 lbf on average with a minimum of 2.158 lbf and a maximum of 2.755 lbf was measured.

The ratios of buckling strength as a ratio to insertion force ranged from about 7.3 to 14.6 times the insertion force. Thus, the needle 1010 is capable of withstanding buckling even with presentation of some relatively high percentage of blunt contour for dilation of the skin opening.

The "central axis" is a reference point for an amount and positioning of the cutting edge 1014 and blunt contours relative to the proximal portion of the sensor 1016 (or where the sensor would be if it were within the needle 1010). For example, the central axis of the wall structure 1012 in the implementation of FIG. 107 is defined by the unbent proximal end of the wall structure. Namely, the center, elongate axis of the proximal unbent tube of the wall structure—shown by the intermittently dashed line—is the central axis 1020.

The central axis 1020 is not limited to a linear shape. Generally, the central axis will be defined by a line through a series of points wherein the points are the centroids of a series of cross-sectional slices of the proximal end of the sensor 1018. Thus, as the path of the sensor 1018 bends or curves, the central axis 1020 will follow. (The "centroid" is an average position of all of the points in a shape. For a cylindrical sensor it is the center of the circular cross-section. However, the sensor need not have any particular cross-sectional shape to define a central axis—even an irregular cross-sectional shape has a centroid.) Generally, then, the central axis defines a central location of the composite pathway of the sensor 1018 proximal the edges and blunt contours as a reference point for the positioning of the edges and blunt contours 1014, 1016.

The central opening 1022 is an opening in the center defined by a closed boundary wall structure—such as the one defined by the tubular portion of the needle 1010 wall structure 1012 in FIG. 107. The central opening 1022 is an opening that is configured to receive (through sizing, finishing, etc.) the major dimensions (e.g., diameter or width) of the sensor 1018 to be delivered.

Figure 112:
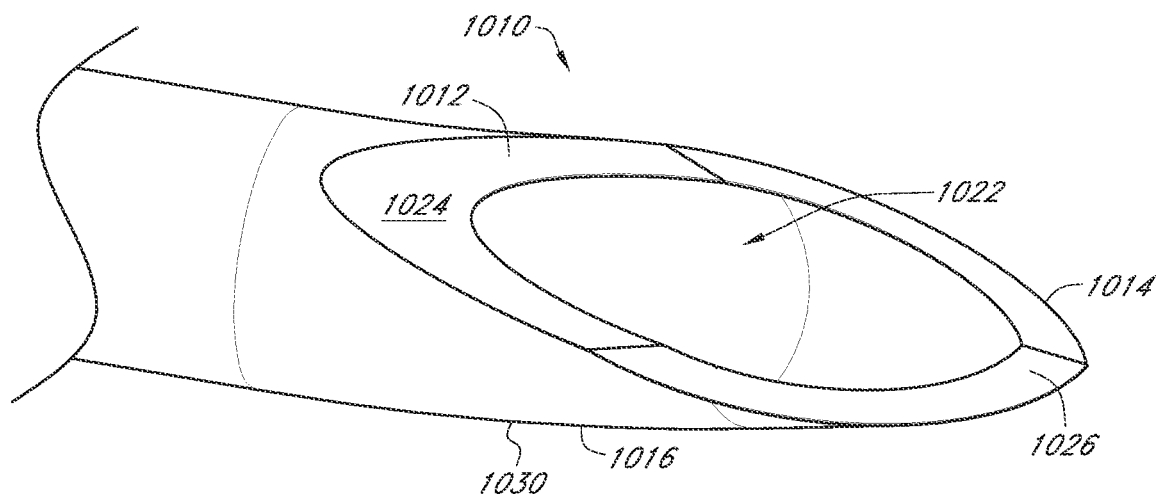
FIG. 112 shows an enlarged perspective view of the bevels of FIG. 111.

Referring back to FIGS. 107, 108 and 112, the distal end of the wall structure 1012 has formed thereon the cutting edge 1014 and blunt contours 1016. The blunt contours 1016 may include a bend 1030 in the wall structure 1012 of the needle 1010. The bend 1030 is formed in the tubing used to create the wall structure 1012, as shown in FIG. 109, prior to application of the bevels and cutting edge 1014. The bend angle can range from about 5 degrees, in increments of one degree, to about 30 degrees for the cutting edge 1014 configurations with primary bevel angles ranging from 3 to 12 degrees and (optionally) secondary bevel angles of 8 to 24 degrees.

The bend may be any of a variety of angles depending on the desired angle of entry of the tip of the cutting edge. Preferably, the bevel angle of the cutting edge 1014 is balanced to the amount of blunt contour 1016 seen by the skin as it is penetrated. The amount of blunt contour and cutting edge "seen" by the skin for example is the projected area occupied by the blunt contour and cutting edge when viewed along the central axis 1020. (This captures a measure of what proportion of the blunt and cutting edges impacts the skin as the needle is advanced along the central axis line.) The blunt surface area is the amount of area occupied by the blunt contours of the needle from this view and the cutting surface area is the amount of surface area positioned opposite the blunt contours starting with the cutting edge, again as viewed along the central axis 1020.

Generally, a design with a greater bend (and a larger blunt contour area seen at the insertion site) is more advantageous for reducing wound size. However, the extent of the bend (and size of the blunt contour seen at the insertion site) is limited by the need for some aspect of the cutting edge 1014 to be positioned to penetrate the skin surface and form a hole large enough for expansion of the hole without further tearing. Thus the bevel angle or other angle of the cutting edge 1014 relative to the central axis balances the amount of bend 1030's angle.

Lubricants or other materials may be added into the lumen of the needle 1010 to facilitate sensor withdrawal. For example, silane, silicone, parylene or other material with a low coefficient of friction may be added to the luminal surface of the needle. Coating the lumen walls with lubricious fluid improves the ease of release of the sensor without damaging the sensor membrane or otherwise inhibiting sensor operation.

The cutting edge 1014 may include several sharpened edges or portions thereof in composite or a single planar facet forming a single sharpened edge. In any case, the cutting edge 1014 in the embodiment of FIGS. 107 and 108 is formed on a set of beveled surfaces.

Figure 108:
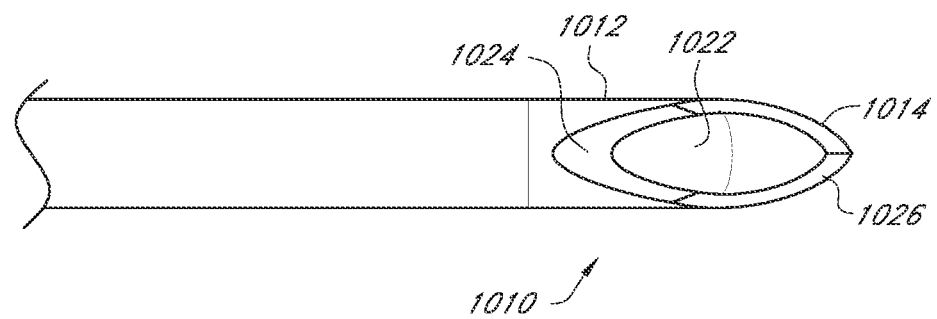
FIG. 108 shows a plan view of beveled surfaces of the needle of FIG. 107.
Figure 109:
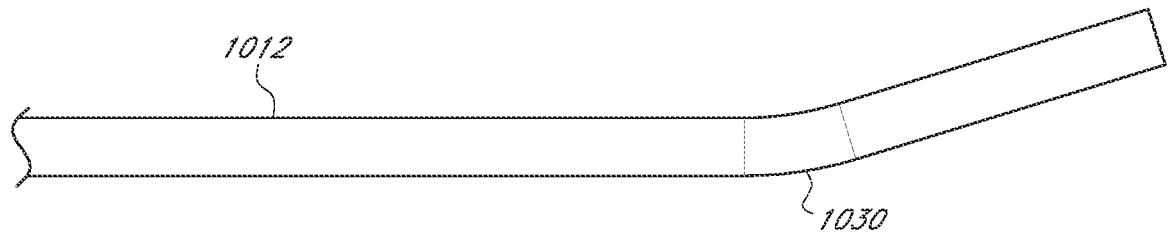
FIG. 109 shows an elevation view of tubing being bent to form a needle of another aspect.

The beveled surfaces may include a primary or proximal bevel 1024 and a pair of secondary or distal bevels 1026, as shown in FIG. 108. The primary bevel, as shown in FIG. 107, may extend at about a 7 degree angle relative to a line paralleling the central axis and extending from the outer surface of the wall structure 1012 on the proximal, unbent end of the wall structure. The primary bevel could be at any of a variety of angles depending upon the desired proportion and orientation of forward facing cutting edge 1014 and blunt contours 1016. For example, the primary bevel 1024 could be within a range of about 3 degrees to about 12 degrees, depending upon the amount of upstream bend in the wall structure 1012.

Figure 110:
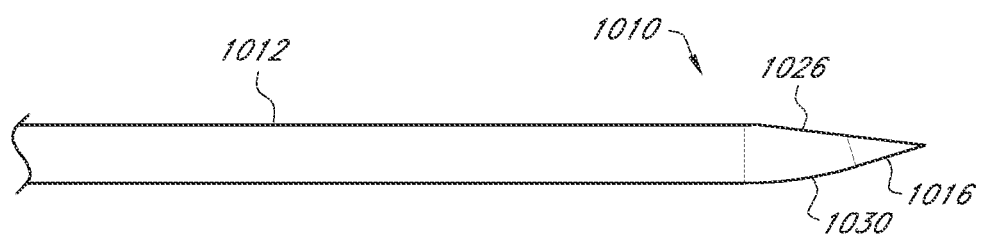
FIG. 110 shows an elevation view of the tubing of FIG. 109 with a primary bevel formed thereon.

In one implementation, the cutting edge 1014 could be defined on a single, primary bevel 1024 having an angle in the angle ranges described above, such as the angle shown in FIG. 110. (FIG. 110 is an intermediate stage in the process of manufacturing the needle 1010 in FIG. 111, but represents where a single-bevel embodiment would stop for sharpening.) The distal edges of this primary bevel 1024 could then be sharpened to form the cutting edge 1014 sized in some desired proportion to polished edges and blunt contours to create the desired two-phase cutting and dilation that reduces invasiveness and dip and recover. (A more detailed description of how the blunt dissection and cutting surfaces are balanced in their proportions is described above and below in more detail.)

Figure 128:
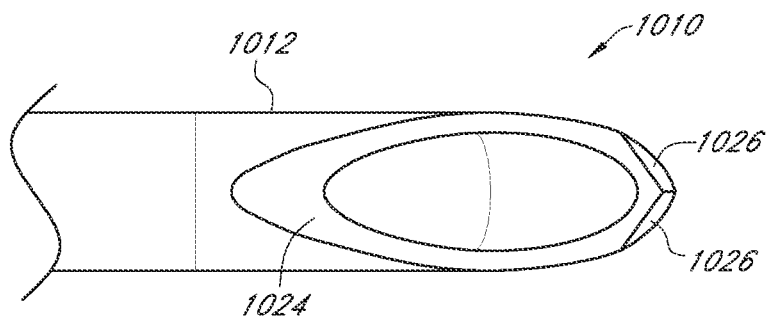

In certain embodiments, such as the one illustrated FIGS. 107, 108, and 111-114, two additional secondary or distal bevels 1026 are formed on the distal tip of the wall structure 1012 on the opposite side of the wall structure from the bend 1030. (FIGS. 109 and 110 show the embodiment of FIG. 5 being formed from stock tubing.) Relative to the same reference point, the bevels 1026 are angled at about 12.4 degrees, as shown in FIG. 107. The two distal bevels 1026 may also define an angle between their proximal edges, as shown in FIGS. 128 and 129. FIG. 128 shows an angle between the proximal bevel edges of 120 degrees. FIG. 129 shows an angle between the proximal bevel edges of 20 degrees.

The secondary bevels 1026 may be varied in their angle from the outer surface line. However, a range of about 8 to 24 degrees balances the proportion of cutting edges 1014 and blunt contours 1016 for wound reduction. In some embodiments, the needle may have a 17 degree bend 30, 7 degree primary bevel 1024 and 16 degree secondary bevel 1026.

In FIG. 108, the distance between the proximal most-tip of the beveled surfaces (along the central axis 1020) to the distal-most tip of the beveled surfaces is 0.05±0.01 inches. The distance between the proximal most point of the secondary bevels 1016 and the distal-most tip of the secondary bevels 1016 is 0.03±0.006 inches.

Although the set of bevels 1024, 1026 form several axially oriented edges on the distal end of the wall structure 1012, not all of those edges are necessarily sharpened. Instead, the cutting edge 1014 is formed only on more distal portions of the secondary bevels 1026. In particular, for example, on FIG. 113 a circle centered on the central axis is shown circumscribed about a bottom edge of the proximal wall structure 1012 and extending over the bevels. In this implementation, only the portion of the bevels within the circle are sharpened. Those bevels outside the circle are rounded.

Figure 113:
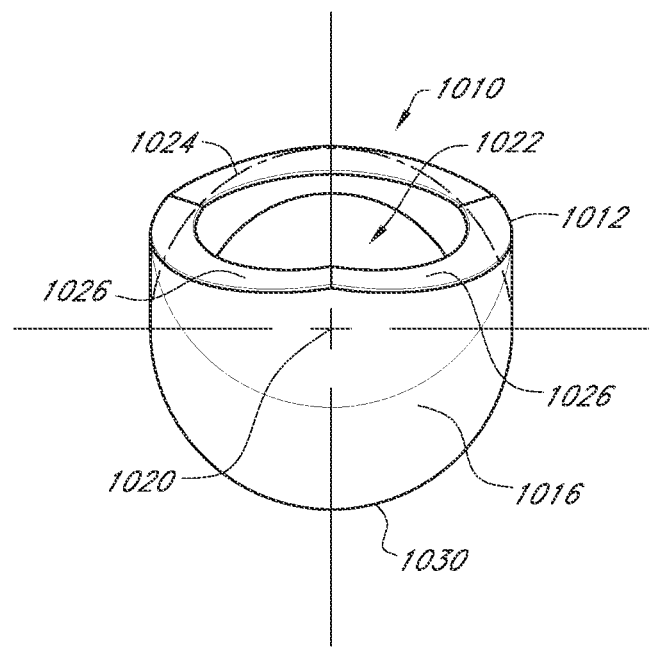
FIG. 113 shows a front elevational view (along a central axis) of the distal end of the bevels of FIG. 111.

In the illustrated embodiment of FIG. 113, the circle has a diameter of 0.018 inches—the same diameter of the tube used to form the wall structure 1012. The sharpened portion of the bevels 1026 extends only to the edge of that circle as it maps onto the secondary bevels 1026. Although having the advantage of matching up with the proximal cross-section of the wall structure 1012, the sharpened portions can be expanded or reduced based on desired wound size, sensor characteristics, patient variation, etc.

The remainder of the edges of the bevels 1024, 1026 may be rounded into smoothed, non-cutting edges having about 2 to 3 thousandths of an inch radius or greater. For example, the heel and other edges of the primary bevel 1024 may be blasted with media to smooth them. Blasting the heel of the bevel (the proximal, inner edge defining the central opening 1022) may smooth it to reduce or eliminate coring, which occurs when the skin is picked up during needle 1010 insertion (also sometimes referred to as "coring").

As shown in FIG. 113, in some embodiments, the needle design 1010 balances the cutting edge 1014 and blunt contours 1016 to promote the two-phase cutting and dilation process of sensor 1018 insertion. Various metrics can be used to define and describe the balance in the needle design between cutting edge 1014 and blunt contour 1015. For example, as shown in FIG. 113, in one embodiment, the cutting edge 1014 only occupies about 60 degrees (33%) of the 180 degrees of the outer peripheral edge of the bevels 1024, 1026. Generally, the smaller the proportion of the edges of the bevels 1024, 1026 that are sharpened to the edges that are unsharpened, the smaller the initial wound before dilation. Variations are possible from 50% of the total edge being sharpened down to 20% in increments of 5%.

Figure 114:
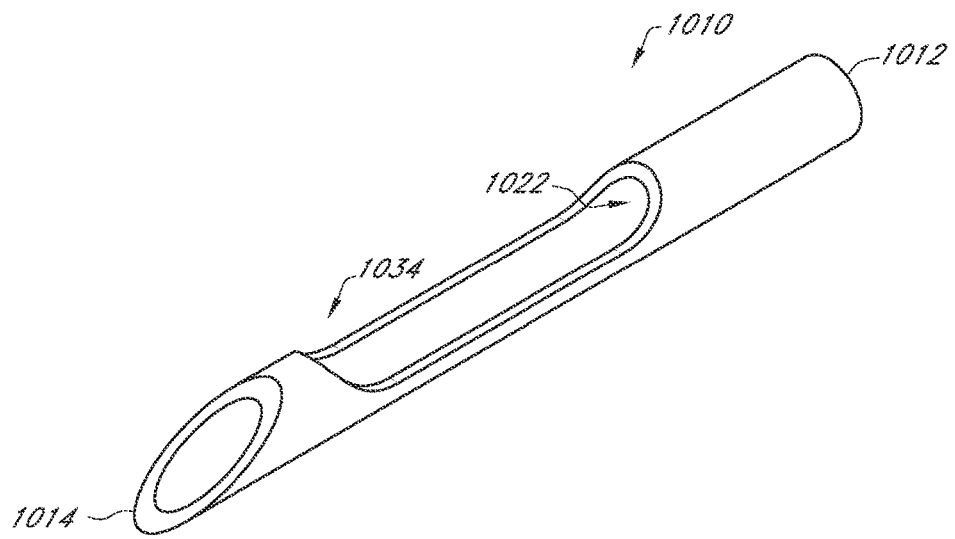
FIG. 114 is a perspective view of a needle of another embodiment wherein the needle has a slot.
Figure 115:
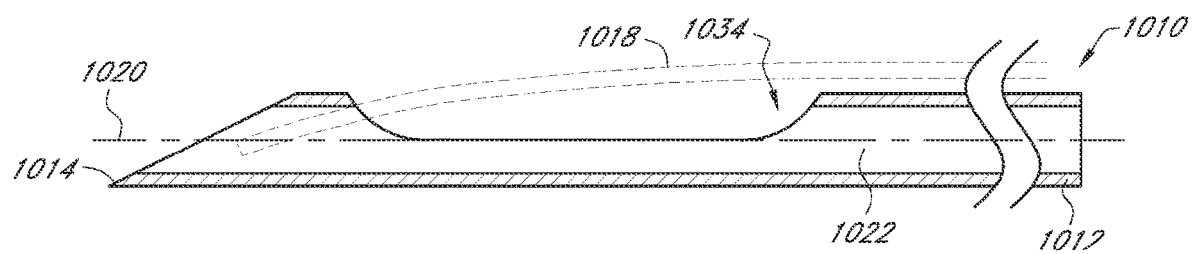
FIG. 115 is cross-sectional view of the needle of FIG. 114.

In one embodiment, the bend 1030 advantageously repositions or offsets the leading point (and initial contacting cutting feature) of a conventional needle to the opposite side of the circular cross-section by 0.0112 inches, as shown by comparison of FIGS. 114 and 115. Thus, the offset of the point pushes it over (0.002 inches, as shown in FIG. 113) the central axis 1020. For example, the point is about 62% of the way across the diameter to the opposite side of the circumscribed circle. In this manner, the central axis 1020 (as it would for any offset of greater than 50% of the diameter or other relevant dimension associated with the position of the sensor) passes through the blunt contour 1016 rather than above the cutting edge 1014.

It should be noted, however, that an advantage of presenting a blunt contour 1016 starts with any sized bend 1030 (or other structure or modification) that moves the point and other cutting edges 1014 within the outermost periphery of the circumscribed wall structure 1012. Offsetting the cutting edge away from the outermost periphery and closer to (or past) the central axis than the adjacent outer edge by even 1% therefore results in some benefit of reduced invasiveness. Such positioning presents a blunt contour to the skin during insertion of the needle. Generally, the further the positioning across the dimension of the needle 1010, the larger the proportion of the area presented to the skin that is made up by a blunt contour (versus cutting edge). For example, in some embodiments, the cutting edge can be repositioned across the dimension from about 5% to about 65% of the dimension in intervals of 5%. At the same time, some amount of cutting edge must be presented or no initial opening in the skin will be formed large enough to be dilated without tearing by the blunt dissection—hence the concept of "balance" between cutting and blunt dissection described above.

Although sometimes referred to as a diameter for the purposes of the round tubing used for wall structure 1012 in the illustrated embodiments, the relevant "dimension" is any major dimension across the portion of the wall structure 1012—or "cross dimension"—configured to hold the sensor. Another metric that can be used to characterize the proportion of cutting edge 1014 to blunt contour 1016 is the projected area dedicated to blunt contours 1016 projected along from a perspective viewed along the central axis 1020. For example, as shown in a view along the central axis in FIG. 113, about ⅔ of the area of the circle circumscribing the outer edge of the rounded wall structure 1012 is dedicated to blunt contour 1016.

Figure 127:
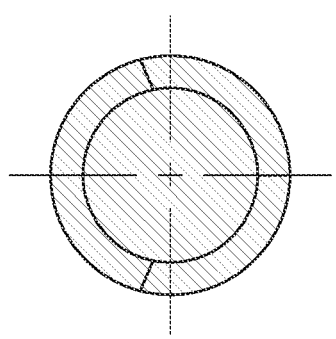
Figure 124:
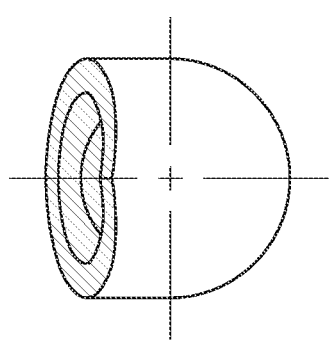

The various degrees of bend and bevel angles disclosed herein are not arbitrary. Rather, they impact wound size (and consequently dip-and-recover and other foreign body responses) and sensor deployment amongst other things. For example, FIGS. 118-126 and Table 1 below show variations in the bend angle and bevel angles and the impact on the ratio of blunt area (in grey) to cutting area (cross-hatched). Ratios run from as low as 0.85 for FIG. 120—where the blunt area is smaller than the cutting area—to as high as 2.74 times as much blunt area as cutting area for FIG. 124. Notably, there is an interplay between the bend angle and the bevel angles that determines the ultimate proportion. If a lower bend angle is used, then it restricts the amount of primary bevel angle before the blunt area drops dramatically and may not reduce wound formation. Eventually, the blunt area is so small as to approach that of the conventional needle shown in FIG. 127. Similarly, if a high bend angle is used, the cutting edge may not be sufficient to pierce the dermis layer during the initial cutting phase. The bend in the needle can also be limited by other constraints. If the bend is too severe, then the sensor could get stuck in the lumen of the needle and may not deploy. Or, the sensor may be damaged when it is deployed.

TABLE 1

| FIG. | Bend Angle (°) | Primary Bevel (°) | Secondary Bevel (°) | Cutting Surface Area (In^2) | Blunt Surface Area (In^2) | Ratio (Blunt SA/Cutting SA) |
|---|---|---|---|---|---|---|
| 118 | 10 | 5 | 12 | 0.000096 | 0.000188 | 1.96 |
| 119 | 10 | 7 | 12 | 0.000122 | 0.000151 | 1.24 |
| 120 | 10 | 9 | 12 | 0.000143 | 0.000121 | 0.85 |
| 121 | 17 | 5 | 12 | 0.000079 | 0.000206 | 2.61 |
| 122 | 17 | 7 | 12 | 0.000104 | 0.000168 | 1.62 |
| 123 | 17 | 9 | 12 | 0.000126 | 0.000136 | 1.08 |
| 124 | 20 | 5 | 12 | 0.000076 | 0.000208 | 2.74 |
| 125 | 20 | 7 | 12 | 0.000101 | 0.000171 | 1.69 |
| 126 | 20 | 9 | 12 | 0.000124 | 0.000138 | 1.11 |

The relationship of the ratio (blunt surface area/cutting surface area) versus needle bend and primary bevel angle can be defined by an equation: Ratio (BSA/CSA)=0.1895+0.2266*(Bend Angle)−0.004952*(Bend Angle)$^2$ for a primary bevel angle of 5 degrees. The constants change with each of the primary bevel angle changes. Ratio=0.171+0.1379*Bend Angle)−0.003095*(Bend Angle)$^2$ for a primary bevel angle of 7 degrees. Ratio=0.1329+0.09457*Bend Angle)−0.002286*(Bend Angle)$^2$ for a primary bevel angle of 9 degrees. The changing constants can be determined via curve fit to the data above in Table 1 for different bevel angles.

Figure 111:
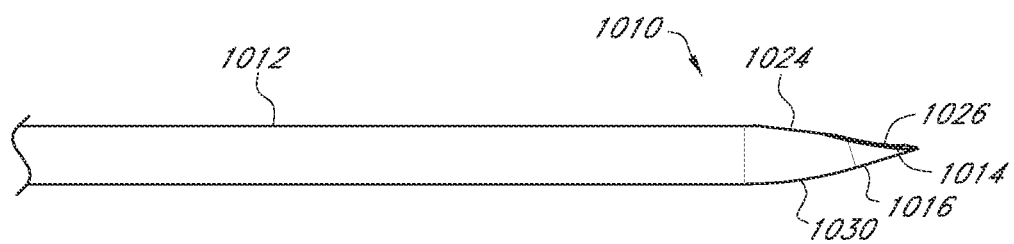
FIG. 111 shows an elevation view of the tubing of FIG. 110 with a secondary bevel formed thereon.

FIGS. 109-111 illustrate in part how the needle 1010 is manufactured. Stock tubing is first bent to a predetermined angle (e.g., about 10 or 17 degrees) to form the bend 1030 in wall structure 1012. The primary bevel 1024 is then ground or machined to the first desired angle. Then, the secondary bevels 1026 are ground to the second desired angle. Non-cutting edges are blasted with material to round them out and remove burrs. The cutting edges 1014, if necessary, are either present from the grinding or generated by further sharpening on the axially directed bevel edges.

Referring now to FIGS. 114 and 115, the needle 1010 may be designed with slot 1034 (or slots). These slots may facilitate delivery or removal of the sensor 1018, or aid in reducing wound trauma. FIGS. 114 and 115, for example, illustrate slot 1034 formed as a window near the distal end of the wall structure 1012 of the needle 1010. The slot 1034 is formed by cutting a portion (e.g., about half of the circumference of the tubular wall structure) away and having ramped or rounded (radius about 0.5 to about 1 inches) walls near the proximal and distal ends for a smooth transition. In the particular embodiment shown, the distal edge of the slot 1034 is about 0.8 mm from the end of the wall structure 1012 beginning at the primary bevel 1024. The slot 1034 is about 3 mm long. Advantageously, the sensor (shown in dashed lines) can be inserted through the slot 1034 into the distal-most, closed section of the wall structure 1012, allowing it to be more easily freed for delivery. It is contemplated that the dimensions corresponding to the embodiment illustrated in FIGS. 114 and 115 can be different depending at least in part on the dimensions of the sensor to be inserted.

Figure 116:
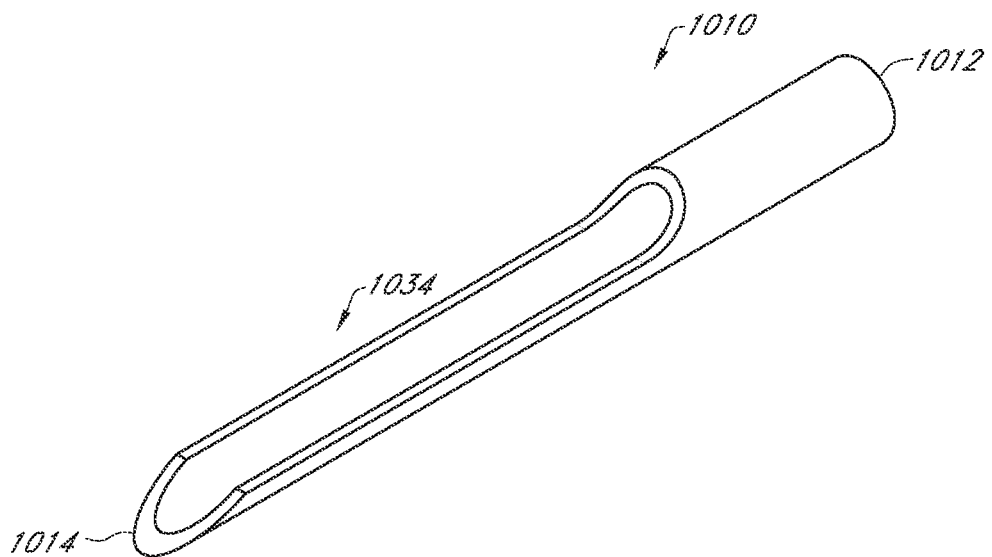
FIG. 116 is a perspective view of another needle with a slot extending through the distal end of the needle.
Figure 117:
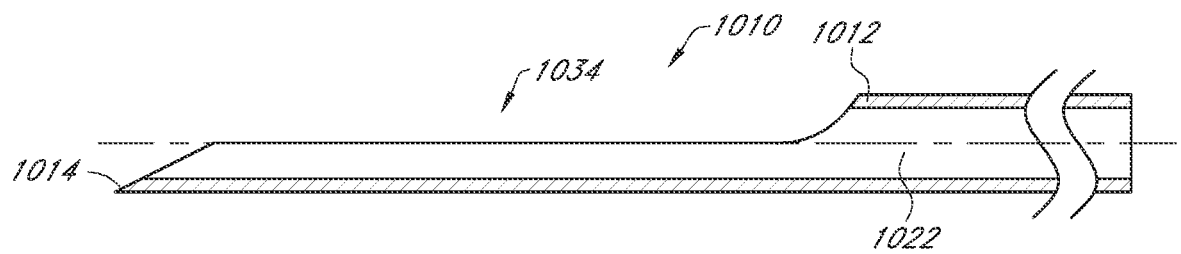
Figure 126:
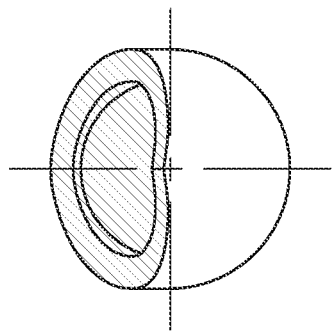
Figure 125:
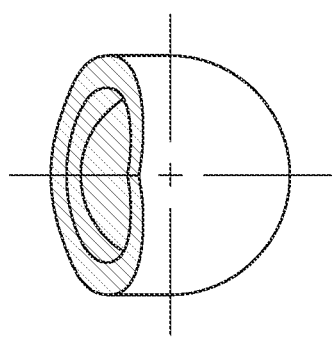

FIGS. 116 and 117 illustrate a needle with a slot 1034 that extends to the distal end of the needle 1010. In one embodiment, the proximal closed portion of the needle wall structure 1012 is about 8 mm and the slot extends along 6 mm of the end of the wall structure. Viewed along the central axis, the slot 1034 forms a C-shape at the distal end of the needle.

Sensor delivery systems that employ a needle without a slot are typically unable to deliver a pre-connected sensor (i.e., a sensor connected to sensor electronics prior to sensor insertion). With these systems, electrical connection between the sensor and the sensor electronics occurs after the sensor has been inserted and often after the needle has been retracted. In some embodiments, such as the embodiment illustrated in FIGS. 116 and 117, a slot 1034 facilitates removal of the needle from a pre-connected sensor which may be designed to connect to sensor electronics through an electrical wire that extends through the slot prior to and during sensor insertion. After sensor insertion, the slot 1034 allows for removal of the needle from the sensor 1018 without disturbing the electrical connection which was already established prior to insertion.

In short, the C-shape or V-shape or other shape formed by a slot 1034 extending through the distal end of the needle 1010 may provide for delivery of pre-connected sensors 1018. The wires from the sensor can extend through the slot 1034 while the rest of the sensor is held within the opening 1022. More than one slot could be used, such as for several electrical connectors. In addition, the slots may vary in size, shape and positioning depending upon the desired use and/or reduction of invasiveness.

The windows and slots may be combined with the bend and other characteristics of the needles illustrated in FIGS. 107-113.

FIGS. 130 and 131 show another embodiment of the needle 1010. The needle 1010 includes a single primary bevel 1024 having a 13 degree angle for the bend 1030 from the lower horizontal wall line of the wall structure 1012. The point is elevated 0.152 (plus/minus 0.051) mm from the bottom wall line of the wall structure. The needle 1010 has an inner diameter of 0.343 (plus 0.025/minus 0.013) mm and an outer diameter of 0.457 (plus 0.025/minus 0.013) mm. The primary bevel has a gentle curvature extending from its tip to the proximal edge. FIG. 131 shows a bevel length of 1.270 (plus/minus 0.152) mm. Shown in cross-hatch is a bead blasted (for burr removal and anti-coring) proximal length of 0.762 (plus/minus 0.152) mm. Advantageously, reducing the bend angle from 17 to 13 degrees reduced the chances of sensor damage during deployment.

FIG. 132 shows another embodiment of the single-bevel needle 1010 with a 13 degree bend 1030, but with no gentle curve in its bevel 1024. Instead, the primary bevel is straight and at about a 13.5 degree angle with respect to the top outer edge of the wall structure 1012.

FIG. 133 shows another embodiment of the needle 1010 with a single bevel 1024, including a 17 degree bend angle with a 7 degree bevel angle. The point is elevated 0.012 inches from the bottom edge of the wall structure 1012.

FIG. 134 shows another embodiment of the needle 1010 wherein the wall structure defines a proximal slot 1040. The proximal slot is scalloped into a portion of the needle on the side of the needle 1010 having the point. The sensor 1018 includes a kink 1042 configured to seat into the proximal slot 1040 so as to maintain the orientation of the sensor. In particular, the proximal portion of the sensor dips down into—and optionally somewhat extending out of—the proximal slot 1040, reverses direction and continues distally into alignment with the needle central opening 1022, opposite the proximal slot. Advantages of the proximal slot 1040 include holding the sensor 1018 in a specified position until a pushrod moves it out of position. Also, needle assembly would be facilitated by holding the sensor 1018 in a desired or predictable positon. Another advantage is the bend 1030 of the needle 1010 can be cleared by biasing the sensor 1018's distal end to the opposite side of the wall structure 1012. The sensor 1018 would be less likely to run into the bend in the central opening 1022 during deployment.

Embodiments can incorporate various additional or alternative features to avoid or limit tissue trauma. For example, some embodiments can be configured to reduce vibration and/or lateral motion of the needle tip during the insertion and retraction phases of sensor deployment by de-coupling at least a portion of the device from the needle. For example, some embodiments can include additional bearing features operatively coupled to the inner needle hub, so as to decouple the inner needle hub from the outer needle hub or other portions of the device and minimize transfer of any vibrational forces to the needle. Additionally or in the alternative, some embodiments can include features configured to counteract any moments placed on the needle during the insertion or retraction phases, or to otherwise limit or constrain the path of the needle during the insertion and retraction phases to a straight line and thereby avoid or reduce the likelihood of tissue trauma. In some embodiments, the needle hub itself can comprise a semi-rigid or somewhat compliant material, to provide damping of high frequency vibrations and/or lateral movement during actuation and ensure that the needle follows the prescribed path. In some embodiments, the needle itself can comprise a relatively low temper (e.g. less than full hard stainless steel), to allow the needle shaft to flex during the insertion and retraction phases.

Figure 39:
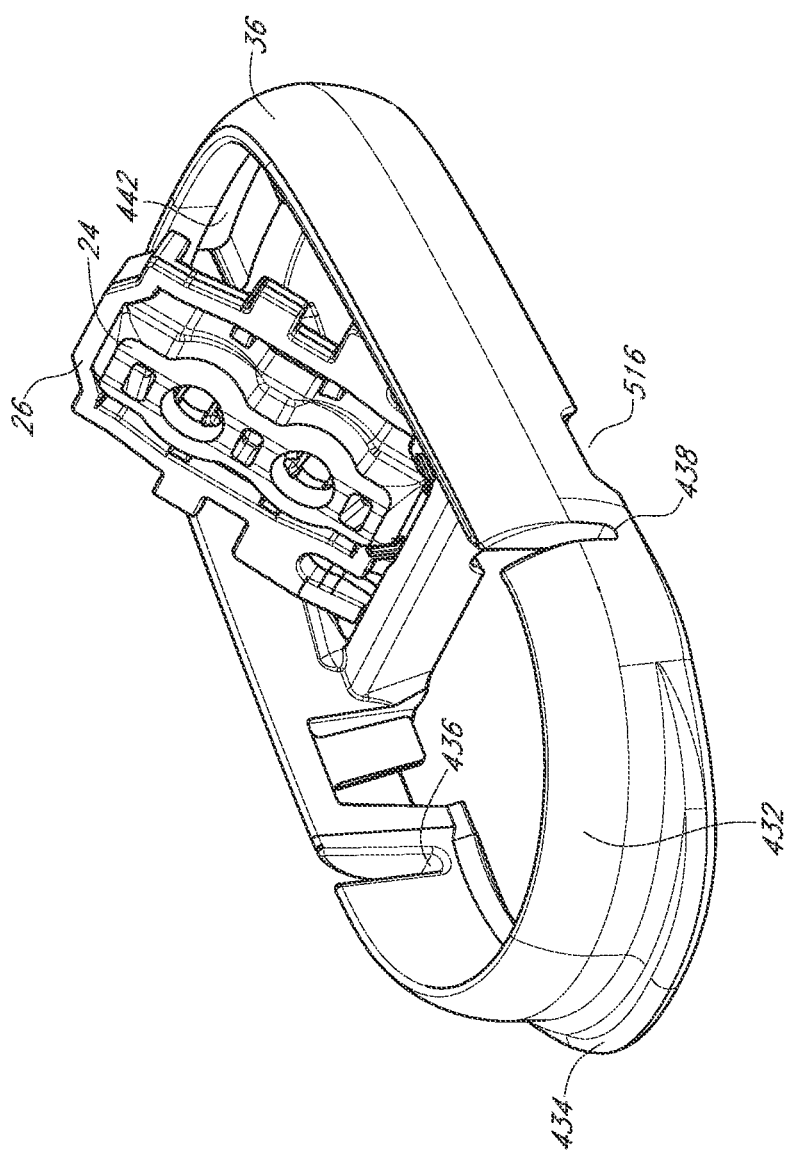
FIG. 39 illustrates a perspective view of a disposable housing and seal carrier, configured in accordance with an embodiment.
Figure 40:
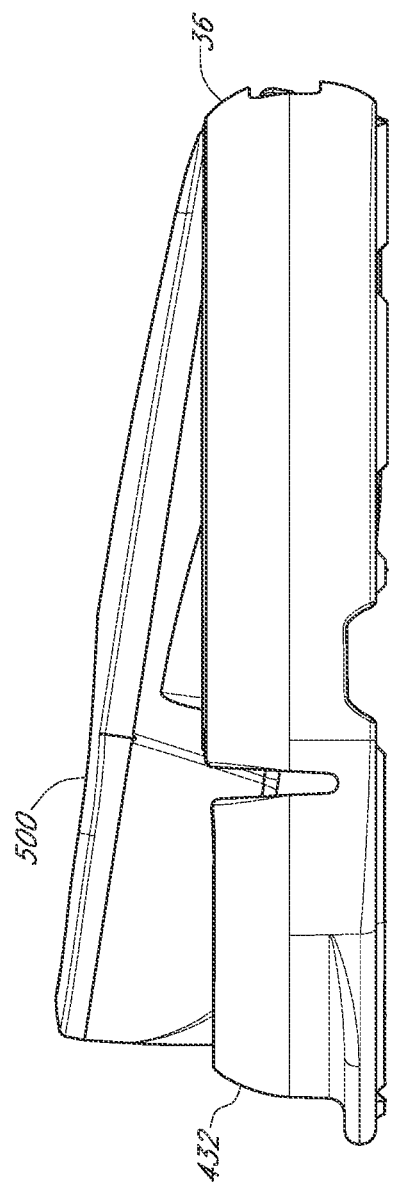
FIG. 40 illustrates a side view of a transmitter being inserted into a disposable housing, in accordance with an embodiment.
Figure 41:
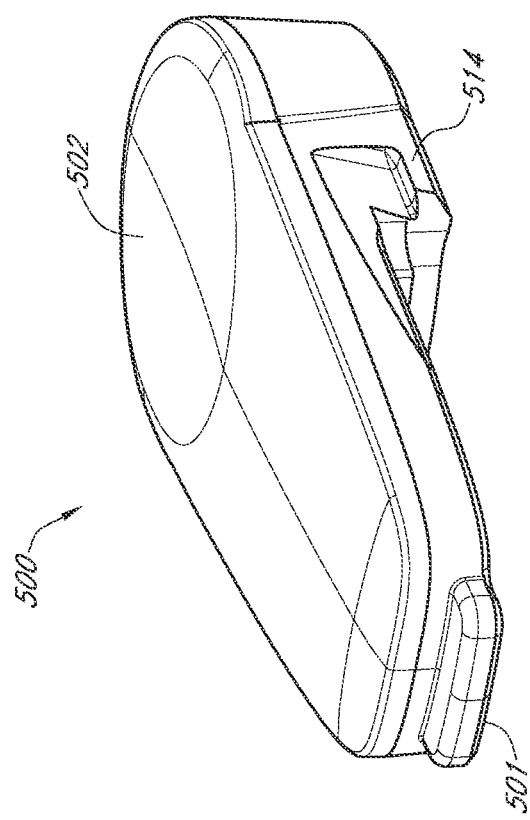
FIG. 41 illustrates a perspective view of a transmitter configured in accordance with an embodiment.

Other aspects of systems and methods according to present principles are now described. FIGS. 39-48 illustrates steps of transmitter insertion into a sensor housing according to variations of present principles. Referring to FIG. 39, a disposable housing 36 is illustrated with various components as described above, including a seal carrier 26 and a seal 24. In the figure, the seal carrier 26 is illustrated in the position in which it would be just subsequent to removal of the cannula hub as part of the retraction step. In particular, the seal carrier 26 is at an approximately 45° angle to the plane of the disposable housing 36. In many cases, the influence of gravity would overcome the frictional resistance of the hinge axis, causing the seal carrier 26 to rotate generally towards the disposable housing 36. However, in some cases it fails to do so, and as a consequence the seal carrier is left at the 45° angle. This is generally a minor inconvenience as the user can easily push the seal carrier down into the disposable housing prior to attachment of a transmitter. See, e.g., FIG. 40 for a depiction of a transmitter 500 being inserted into the disposable housing 36, and in particular where a tab 501 (FIG. 41) is inserted into a corresponding slot 442 (FIG. 40) in the disposable housing 36. The transmitter 500 is then snapped into place by user depression of the transmitter thumb pad 502 (FIG. 41). In some embodiments, the snap fit between the transmitter 500 and the disposable housing 36 can be configured such that a force of greater than about 2 pounds, greater than about 5 pounds, greater than about 10 pounds, or greater than about 20 pounds is required to remove the transmitter from the disposable housing 36, so as to prevent unwanted (or premature, in the case of reusable transmitters) separation of the transmitter from the disposable housing.

If the seal carrier 26 falls into place in the disposable housing 36 upon removal of the cannula hub, it is generally apparent to users how the transmitter 500 is to be snapped into the disposable housing. However, when the seal carrier 26 is left at a significant angle with respect to the disposable housing 36, it may not be apparent to all users how the transmitter is to be snapped into the disposable housing, particularly where the angled position of the seal carrier obscures the user view of the slot 442. Accordingly, it is desirable to have a component that serves to exert a force to rotate (or otherwise push) the seal carrier 26 down into place in the disposable housing 36.

Figure 102:
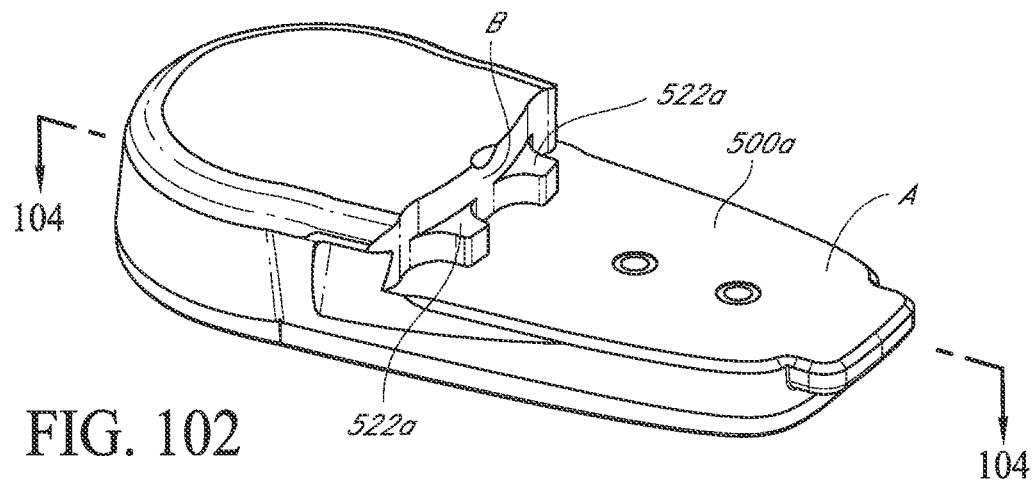
FIG. 102 illustrates a bottom perspective view of a transmitter configured in accordance with an embodiment.
Figure 103:
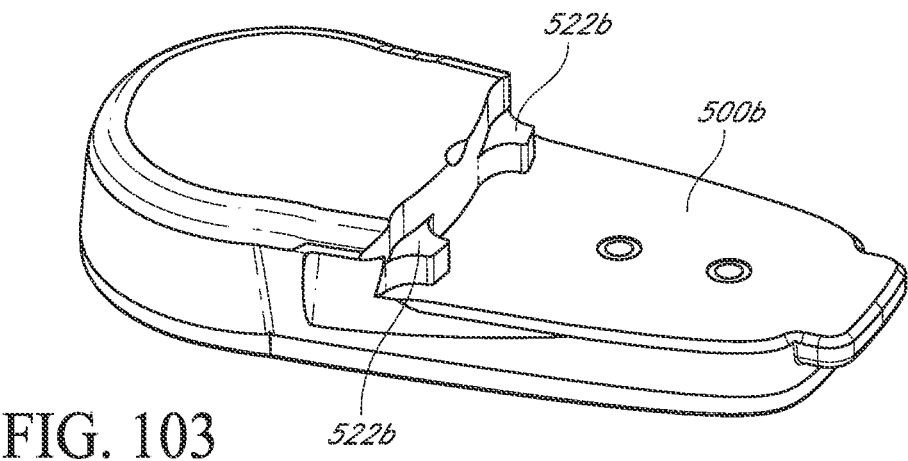
FIG. 103 illustrates a bottom perspective view of a transmitter configured in accordance with another embodiment.
Figure 104:
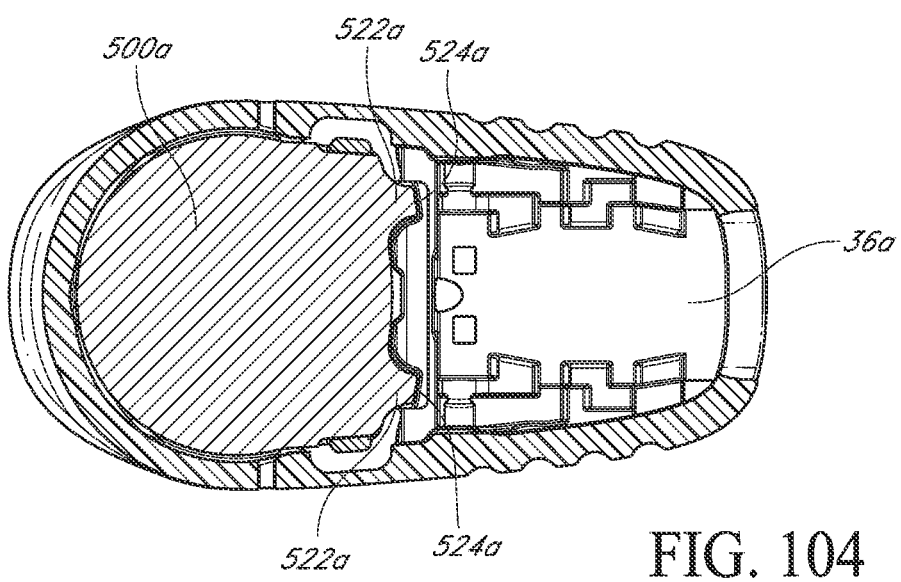
FIG. 104 illustrates a cross-sectional top plan view of the transmitter of FIG. 102, taken along line 104-104 of FIG. 102, with the transmitter shown installed in a disposable housing in accordance with an embodiment.

In some embodiments, as illustrated in FIGS. 102 and 104, a transmitter 500*a* can include one or more keys 522*a* configured to engage with corresponding seats 524*a* in a corresponding disposable housing 36*a*. FIG. 103 illustrates another transmitter 500*b* having keys 522*b* having a different configuration than keys 522*a*. The configuration of the keys 522*b* prevents seating of the transmitter 500*b* in the disposable housing 36*a*, such that the transmitter 500*b* cannot be pressed in, snapped in, or otherwise installed in the disposable housing 36*a* (for example as illustrated in FIG. 40). Similarly, the seats in a disposable housing (not shown) which is configured to receive the transmitter 500*b* can be configured to prevent seating of the transmitter 500*a* in that disposable housing. FIG. 104*a* shows a cross-sectional view of the transmitter 500*a* installed in a compatible disposable housing 36*a*, the cross section being taken along the surface A of the transmitter 500*a* (see FIG. 102). By providing corresponding transmitter/disposable housing combinations with corresponding keys and seats which are incompatible with the keys and seats of other combinations, users can be prevented from installing the wrong transmitter (e.g., an incompatible transmitter) in a disposable housing. As shown in FIG. 102, the keys 522*a* comprise a pair of protrusions extending from a lower surface B of the transmitter 500*a*. In other embodiments, a single protrusion or more than two protrusions are possible. Further, although the keys 522*a* have a tapering configuration as they extend in the direction of surface A, other configurations of keys are also possible; e.g. the keys can taper in the opposite direction, or can have any other regular or irregular shape. In embodiments, one or more keys can extend from the surface A in a direction normal to the surface A.

Figure 42:
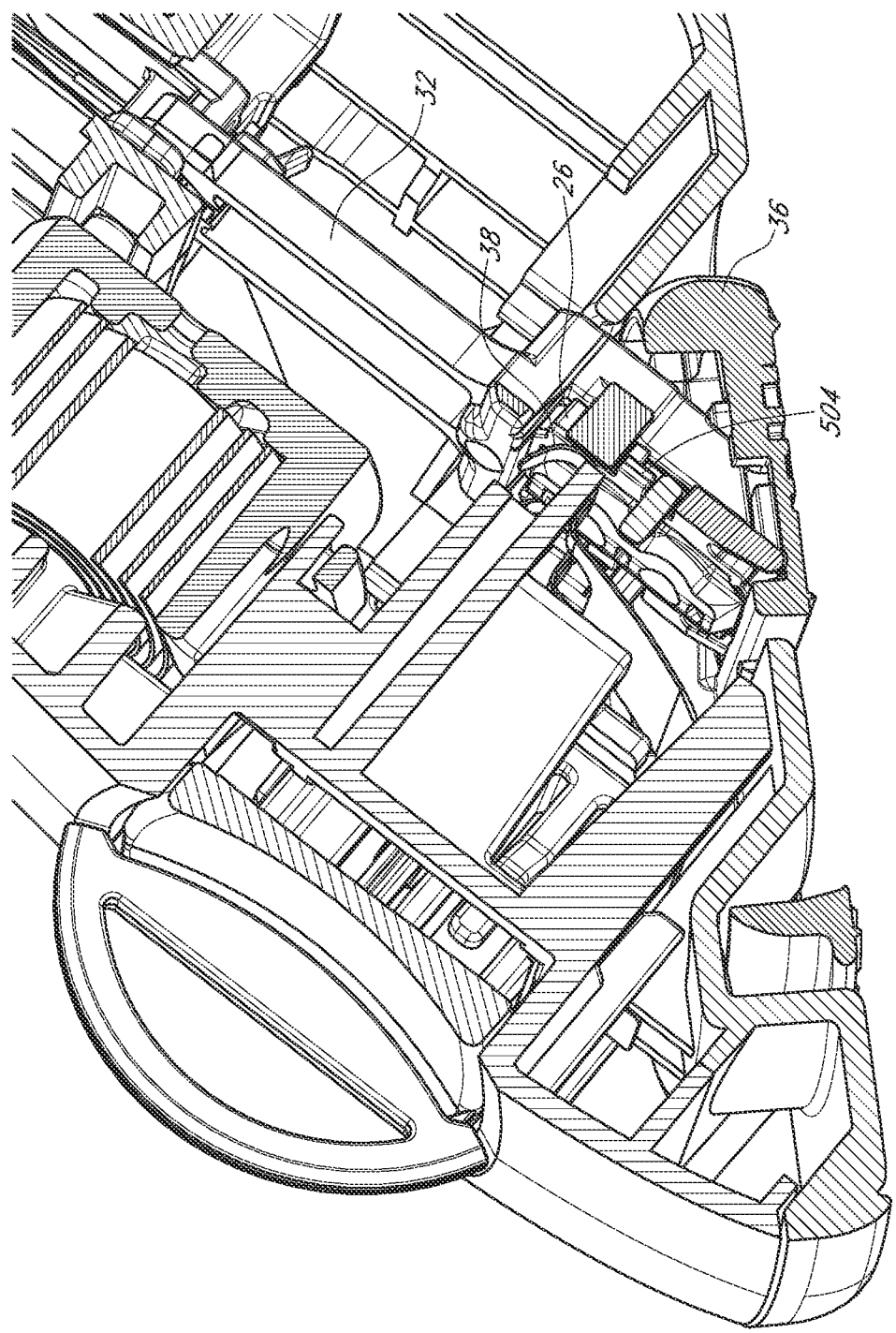
FIG. 42 illustrates a partial cross-sectional side view of an applicator configured in accordance with an embodiment, with the cannula hub in a distal position.
Figure 43:
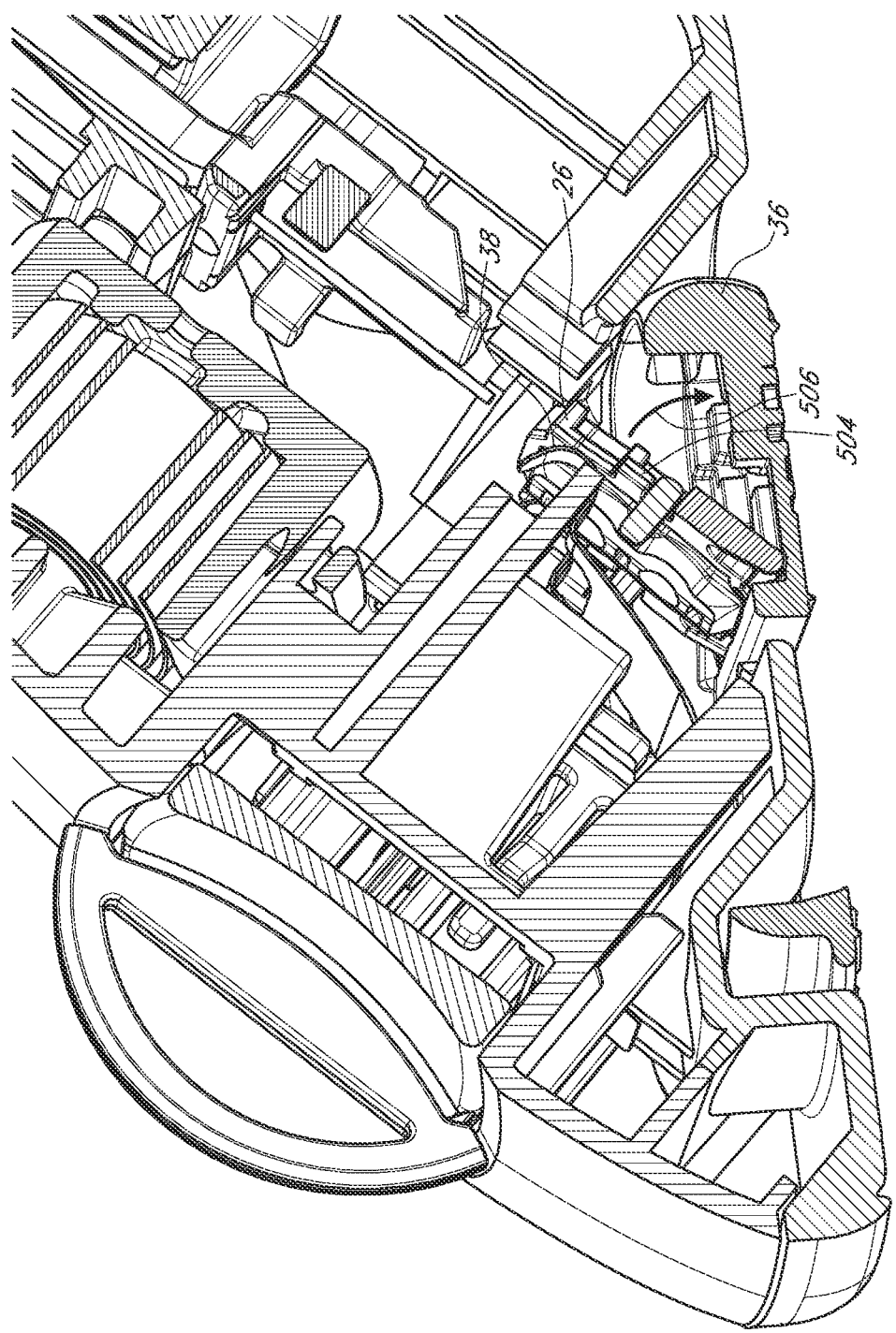
FIG. 43 illustrates a partial cross-sectional side view of the applicator of FIG. 42, with the cannula hub in a retracted position.
Figure 44:
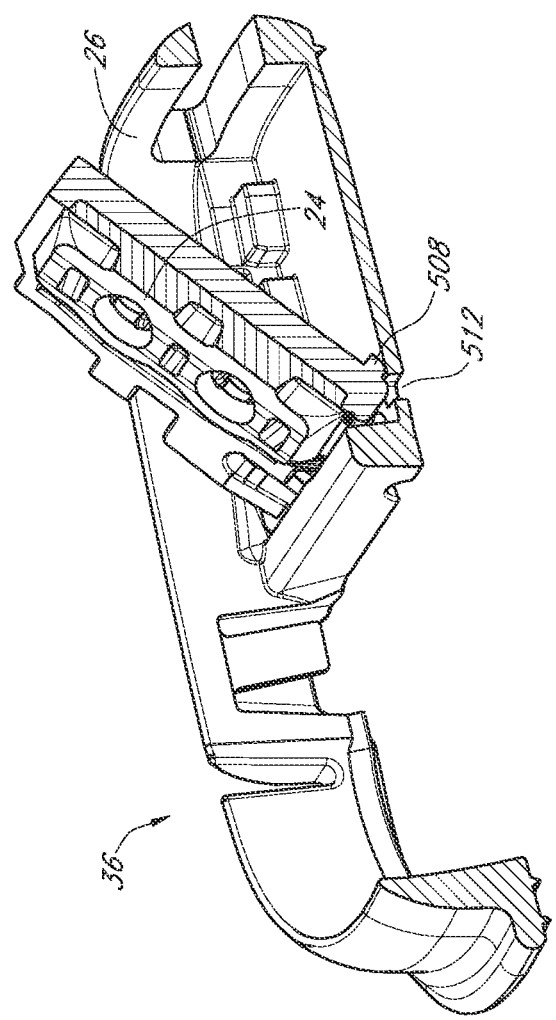
FIG. 44 illustrates a cross-sectional perspective view of the disposable housing of FIG. 40, with the seal carrier in a first orientation.
Figure 45:
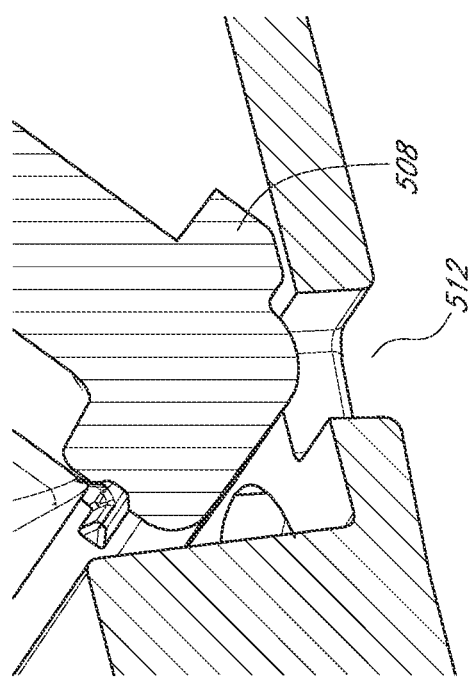
FIG. 45 illustrates a detail view of a portion of FIG. 44.
Figure 46:
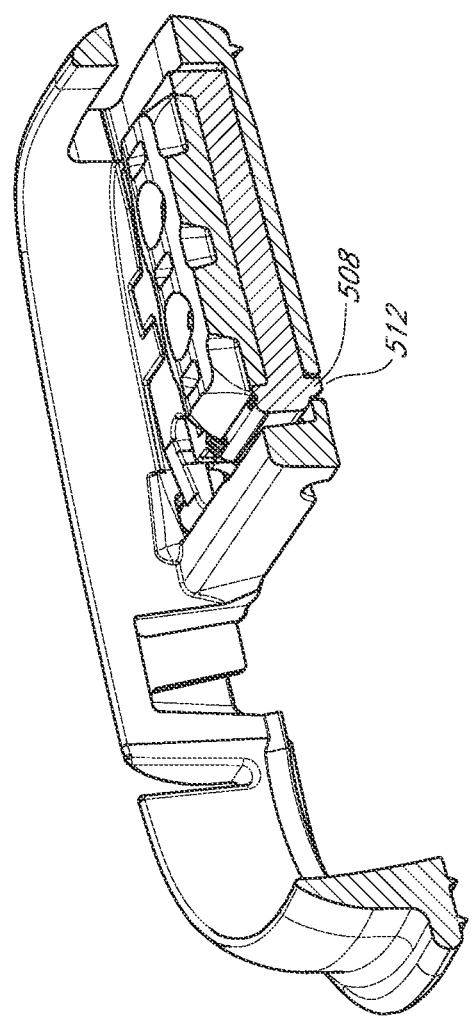
FIG. 46 illustrates a cross-sectional perspective view of the disposable housing of FIG. 40, with the seal carrier in a second orientation.

Referring now to FIGS. 44 and 45, a spring 38 may be coupled to the upper applicator housing 30 which is preloaded and biased against a tab 504 on the seal carrier 26. It will be understood that in alternative implementations, the spring 38 may be replaced with other types of drive components, and the same may be coupled to other features of the applicator, so long as the feature remains stationary relative to the seal carrier 26. Moreover, the spring 38 may be biased against other portions of the seal carrier, or even biased against the seals. FIG. 42 indicates the arrangement of the components when the cannula hub 32 is in place, and FIG. 43 indicates the arrangement of the components upon retraction of the cannula hub 32. In the latter figure, the spring 38 is exerting a force in the direction of arrow 506, and as there is no longer a cannula hub situated to oppose this force, the seal carrier 26 is about to be forced down by the spring 38 into the disposable housing 36.

Referring to FIGS. 44 and 45, the seal carrier 26 may further be provided with a tab 508 which engages and locks into a corresponding slot 512 in the disposable housing 36 via a snap fit connection, disallowing the seal carrier from moving from the desired down/flat position. FIG. 45 shows a more detailed view of how this connection is made.

Referring back to FIG. 40, the disposable housing 36 is further configured to provide a one-time-use feature. This one-time-use feature prevents multiple re-insertions of the transmitter to protect the integrity of the seal, seal grease, and conductive pucks, as well as sensor location. It further prevents sensor restart sessions, i.e., reuse of a sensor in a second session, such being generally deleterious and inconsistent with labeling. In addition, the one-time-use feature may ensure that a transmitter 500 remains in place in the disposable housing 36 during removal of the combination transmitter/disposable housing/sensor (the "wearable") from the body of the patient.

In more detail, the disposable housing 36 includes a breakaway section 432 which is attached to a remainder of the disposable housing 36 via frangible portions 436 and 438. An access strip 434 may be employed in some implementations to further ease the removal of the breakaway section 432 from the remainder of the disposable housing 36. For example, a user may grab, push, or pull on the access strip 434 and twist or pull so as to remove the breakaway section 432 from the remainder. That is, the breakaway section 432 can be used to bend or break out of the way in order to remove the transmitter from the disposable housing once the same has been removed from the body. In some embodiments, a breakaway section can be configured to break away from the remainder of the disposable housing 36 under a force of between about 2-4 pounds. Also in some embodiments, a breakaway section can be configured to break away from the remainder of the disposable housing 36 at a break angle of between about 30-60 degrees.

Figure 47:
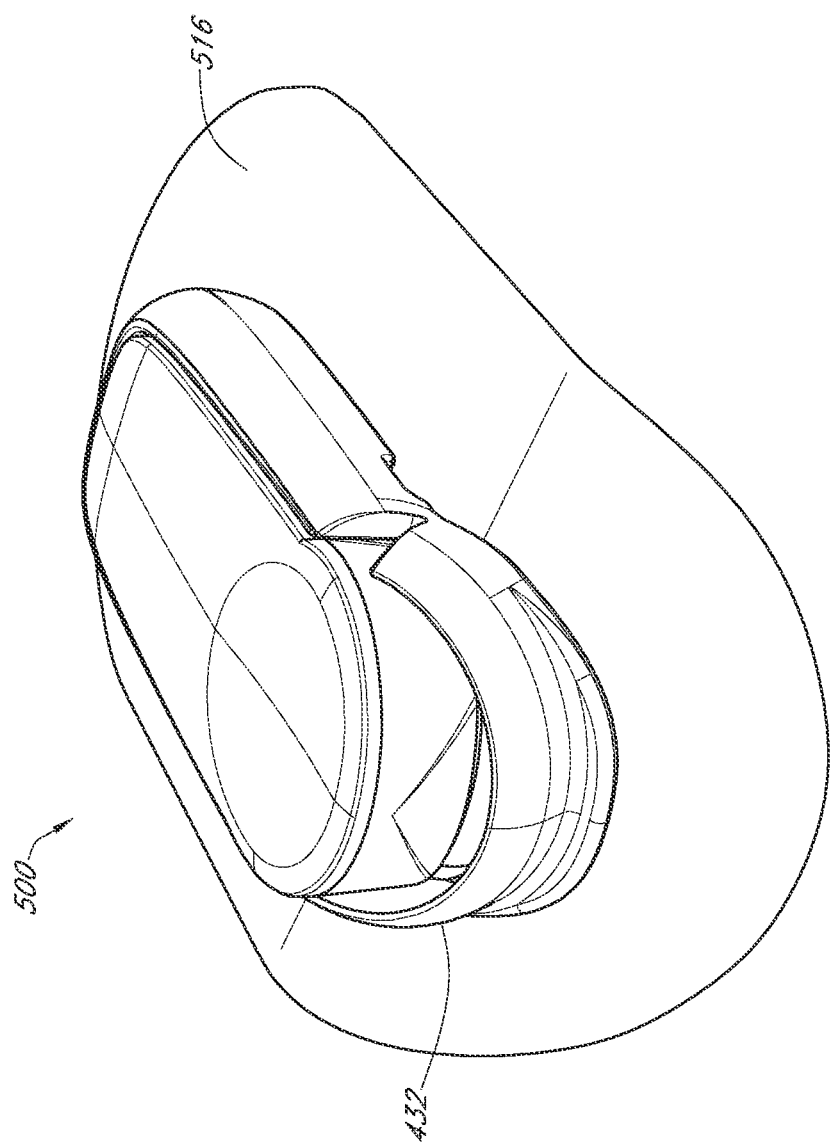
FIG. 47 illustrates a perspective view of the disposable housing of FIG. 40, with a breakaway section being removed so as to facilitate removal of the transmitter.
Figure 48:
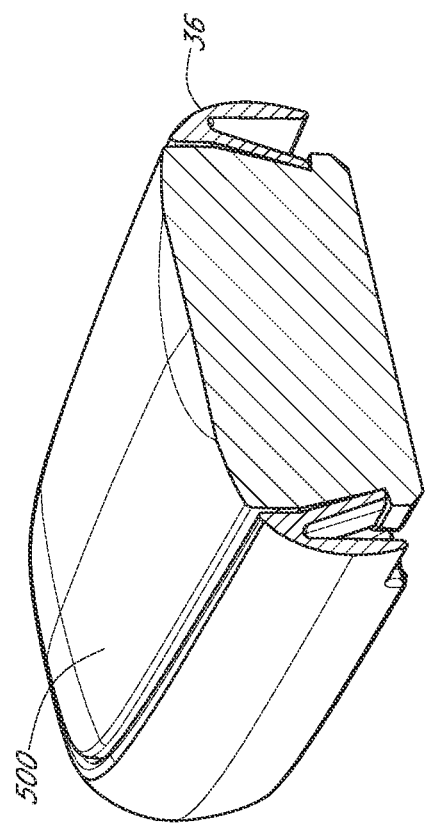
FIG. 48 illustrates a cross-sectional perspective view of the disposable housing and transmitter of FIG. 40, further illustrating the breakaway feature of the disposable housing.

FIG. 47 illustrates a system in which the breakaway section is being twisted as part of the removal process of the same, subsequent to which the transmitter 500 can be removed and reused. FIG. 47 also illustrates an adhesive portion 516 which adheres the wearable to the skin of the user.

Additional advantages ensue to the disposable housing 36 including a breakaway section 432. The same allows a minimization of insertion forces required to latch the transmitter onto the disposable housing. This system minimizes deflection of the disposable housing due to compression of the seal. The system maintains compression of the seal over time and temperature, acting against deleterious consequences including creep. The same provides a user-friendly removal process to separate the transmitter from the disposable housing after the wearable has been removed from the body.

Referring back to FIGS. 39 and 41, the system may include a one-way double snap feature configured such that it is generally impossible to remove the transmitter while on the body. (This aspect is also detailed in FIG. 48 in which the flush nature of the transmitter 500 with respect to the disposable housing 36 is made evident.) The double snaps may be located on the sidewalls of the disposable housing and in part are embodied by voids 516 defined in the disposable housing 36 and cooperating tabs 514 on the transmitter 500. In particular, the tabs 514 snap into voids 516 during transmitter insertion. The sidewall snaps also help to minimize deflection and maintain seal compression.

As noted above, many of the implementations described provide ways to make available additional power and force to perform the steps of insertion or retraction. In some cases, the additional force does not result in an increase of overall force, but a better distribution of force, so that force is available when needed to perform the desired steps. In some cases, and as described below, systems and methods according to present principles relate to ways to decrease the force required, e.g., to lower the force required in a given force profile. Many systems and methods as described below achieve this effect by modification of the seal component 24 discussed generally above, as well as modifications to its associated seal carrier 26. In addition, besides easing force requirements on insertion and retraction components, systems and methods according to present principles also relate to reducing the effect of seal slingshotting as described above, again by modification of the seal 24 and/or by other means of arresting movement of the sensor wire.

In particular, FIGS. 49 and 51-56 describe ways to reduce slingshotting, FIGS. 73-77 describe ways to hold sensors, e.g., sensor wires, more stably or in a stronger fashion, which also combats slingshotting, and FIGS. 50, 57-72, and 78-83 describe ways of separating the seal from an insertion component, e.g., from the cannula, so as to reduce the force required to remove the cannula.

Figure 49A:
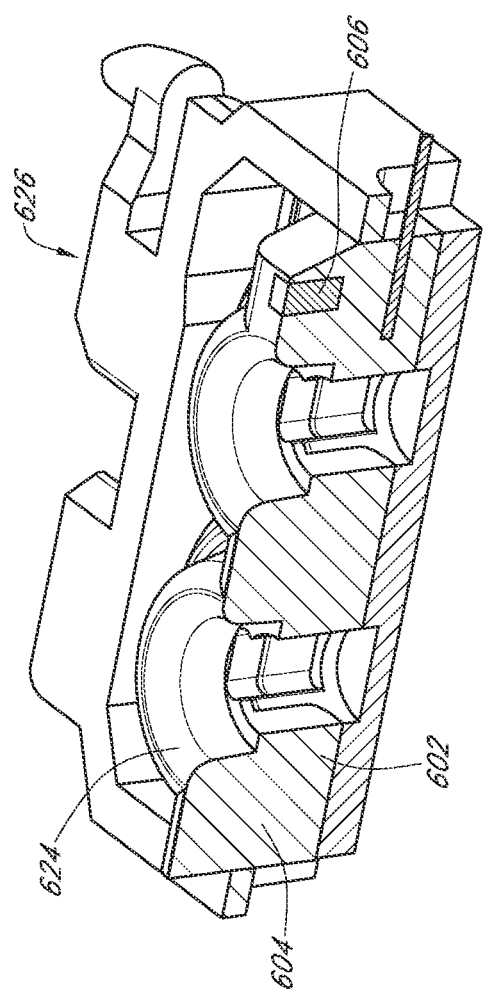
FIG. 49A illustrates a cross-sectional perspective view of a seal configured in accordance with an embodiment.
Figure 49B:
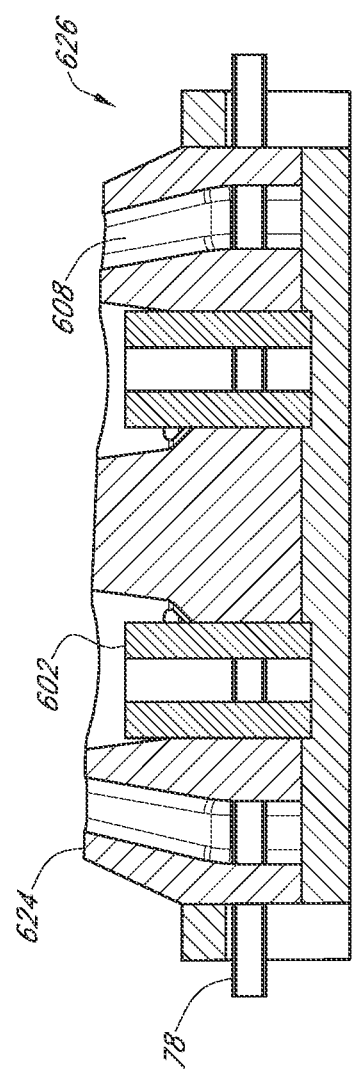
FIG. 49B illustrates a cross-sectional side view of the seal of FIG. 49A.
Figure 49C:
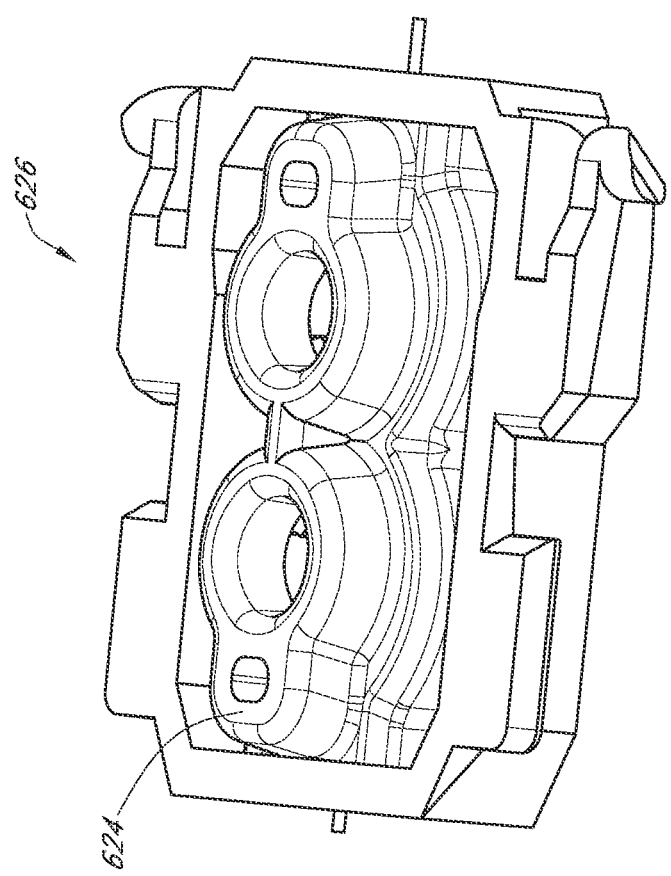
FIG. 49C illustrates a perspective view of the seal of FIG. 49A.
Figure 51:
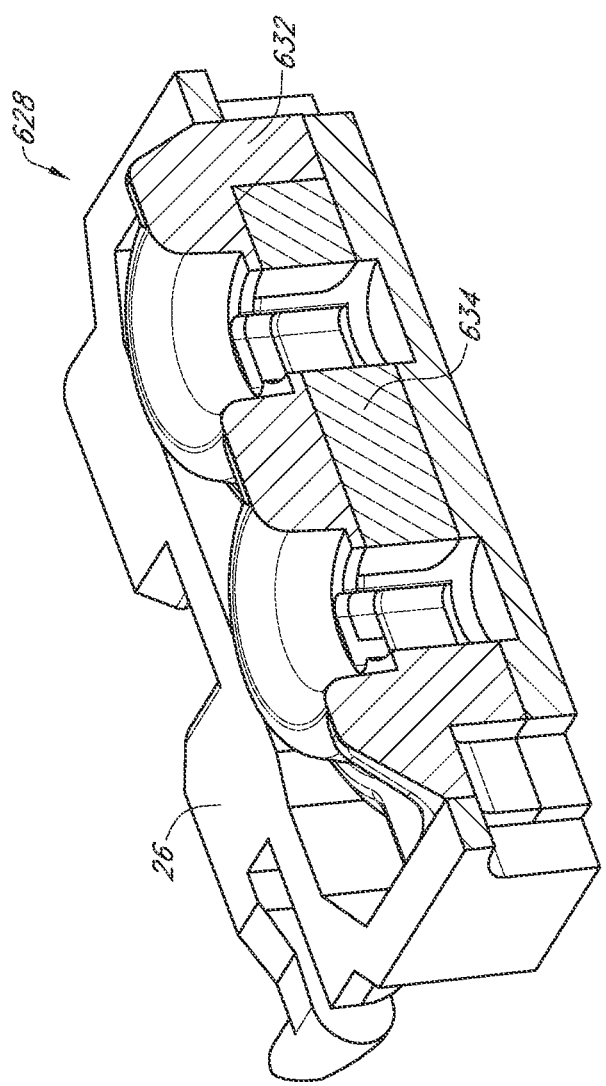
FIG. 51 illustrates a cross-sectional perspective view of a hybrid seal configured in accordance with an embodiment.
Figure 52:
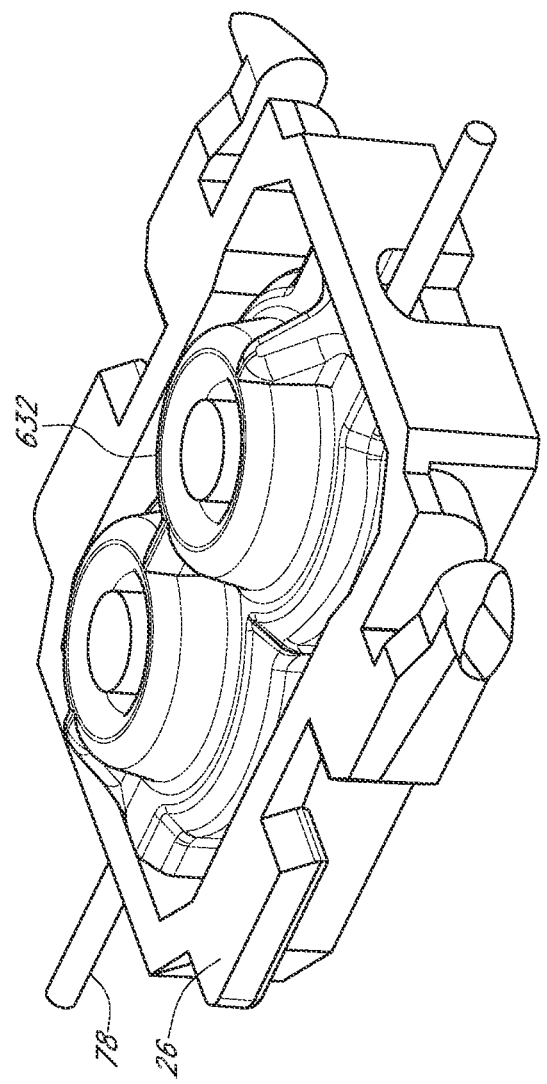
FIG. 52 illustrates another perspective view of the hybrid seal of FIG. 51.
Figure 53:
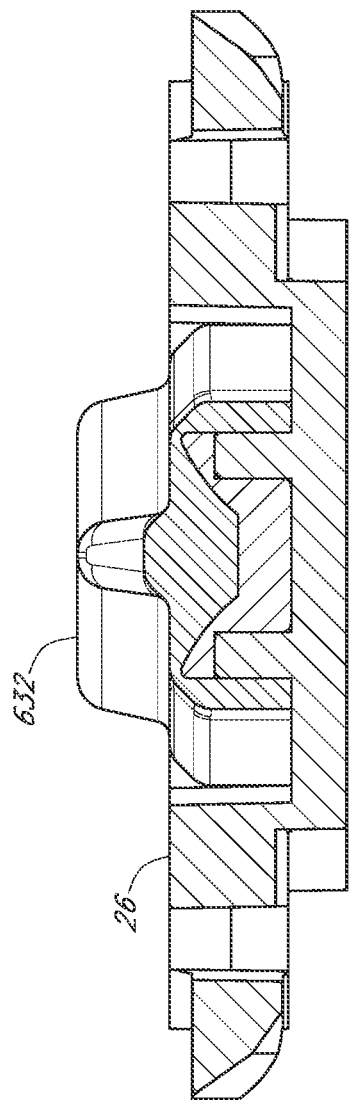
FIG. 53 illustrates a cross-sectional end view of the hybrid seal of FIG. 51.
Figure 54:
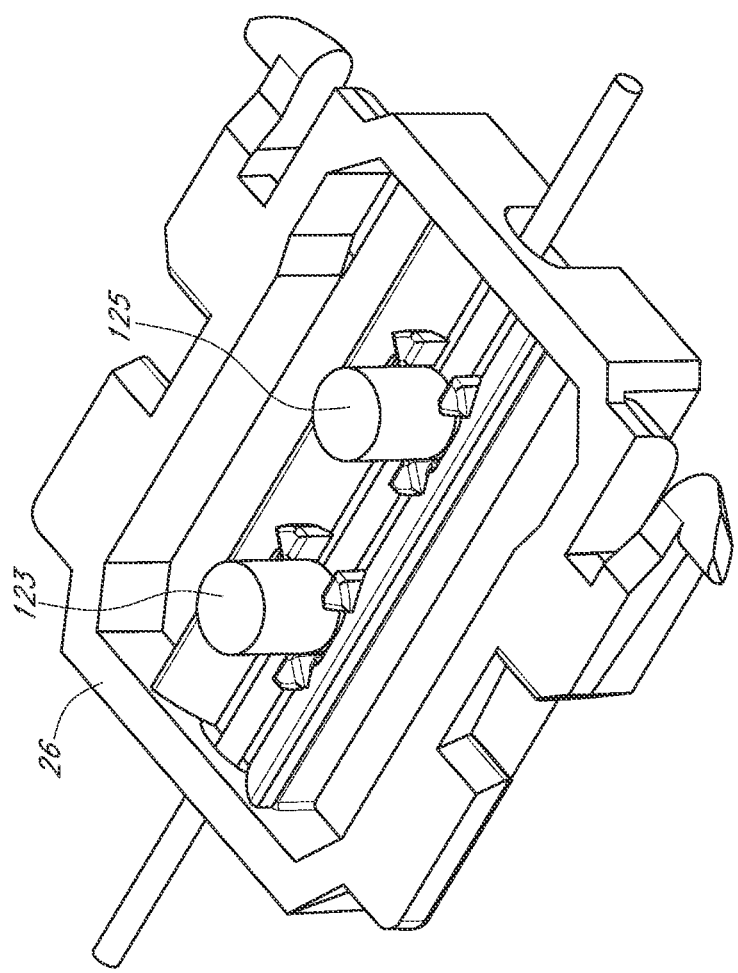
FIG. 54 illustrates a bottom perspective view of the hybrid seal of FIG. 51.
Figure 55:
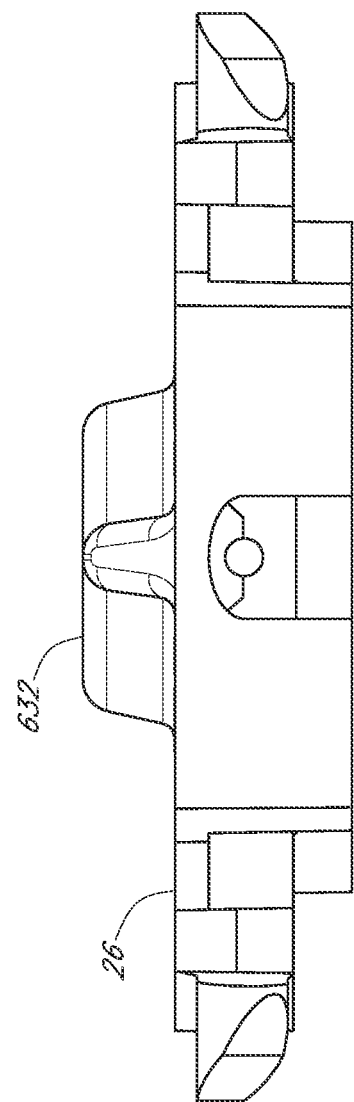
FIG. 55 illustrates an end view of the hybrid seal of FIG. 51.
Figure 56:
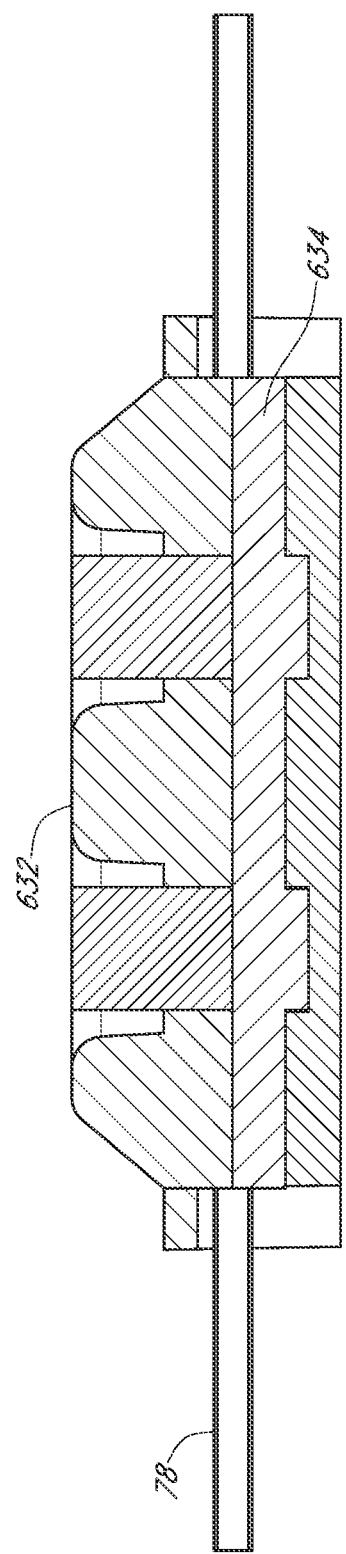
FIG. 56 illustrates a cross-sectional side view of the hybrid seal of FIG. 51.

In more detail, FIGS. 49A-C describe one way of modifying the seal so as to reduce or eliminate seal slingshotting. In this figure, a seal 624, e.g., an elastomer seal such as a silicone seal, is overmolded onto a seal carrier 626, where the overmold includes adhesion between the elastomeric seal 624 and the seal carrier 626, which may be constituted of, e.g., a hard rigid poly carbonate material. While overmolding is discussed here, it will be understood that other means of adhering may also be employed, including by the use of glue.

In this implementation, various ribs may be provided to reduce seal deformation during cannula removal. The ribs may be adhered to the seal during the overmolding process to even more fully situate the seal in place. One or more pillar ribs 602 at least partially surround the conductive pucks (not shown). The pillar ribs 602 may completely surround the pucks or may only partially surround the pucks. Sidewall ribs may also be provided in some configurations to reduce seal deformation during cannula removal. A continuous wall rib 604 is illustrated which extends from one side of the seal carrier to the other, e.g., along the distal/proximal axis. The ribs as described may be formed of materials similar or the same as the seal carrier 626, and may moreover be integral therewith. The ribs may also be formed of a different material, but in general the material should be of higher durometer than that of the seal 624. An additional rib 606 is illustrated, and the same may either be a "floating" rib, situated within the seal 624 but not directly connected to the seal carrier 626, or the additional rib 606 may be directly connected to the seal carrier 626.

Variations of these configurations of ribs will also be understood to help reduce seal slingshotting, e.g., by prohibiting motion of the seal in and along the distal/proximal axis. Certain of these configurations are described below. For example, to even further lessen the effect or possibility of seal slingshotting, voids 608 may be defined in the seal 624 to reduce the amount of seal material in contact with the cannula, thus reducing the effect of seal slingshotting.

Another way of easing force requirements on insertion and retraction is described with respect to FIG. 50, in which a system is illustrated which is intended to reduce the force required to remove an insertion component such as a cannula. In the figure, a conductive puck 123' is illustrated with a cored-out section 518, cored out in the same fashion as a pineapple is cored out before slicing. A cannula 78 is also illustrated, but the remainder of the seal and seal carrier components, which surround the conductive puck 123', are omitted for clarity. By coring out the conductive pucks, frictional resistance is reduced when the cannula is retracted out of the pucks. Resistance may still be present from the seals, but the same may also be reduced in ways as described below. The coring may be such that a minimum wall thickness still remains in the cylinder wall, e.g., at least about 0.030", so as to allow compression on the puck and prevent buckling. The shape may generally be a cylinder to prevent the need to key the puck during assembly, but other shapes are also possible. For example, square, hexagonal, or hourglass, but these may be less preferable due to added difficulty in assembly.

FIGS. 51-56 illustrate another implementation 628 of a seal for use in a seal carrier, this implementation termed a hybrid seal. Hybrid seal implementations may employ different materials having different durometers. A rigid or high durometer material may be employed for sensor placement, thus reducing slingshotting, and a softer or lower durometer seal material may be employed for increased sealing ability. In the implementation of FIGS. 51-56, the hybrid dual material design is employed which provides the properties of a high durometer material such as silicone, desired for sensor placement, but with a different softer material placed in strategic locations for sensor wire sealing. This implementation addresses certain problems that arise when a seal material is of a single unitary type, particularly a material like silicone. Silicone has properties which are advantageous and which result in accurate sensor placement relative to pucks in an applicator device. As noted, however, the same properties which help place the sensor accurately sometimes makes sealing around the sensor wire more difficult.

In more detail, a first material 634, which may be a high durometer material such as an elastomer, e.g., silicone, may be disposed in locations in which significant contact is made with a cannula, needle, and sensor wire. A second lower durometer material 632 may then be placed to constitute the rest of the seal 628, and in particular in locations where a sealing function is desired. The second material 632 may be, e.g., a thermoplastic elastomer (TPE). As noted the second material 632 typically has a lower durometer than that of the silicone, allowing the same to achieve a better seal.

The implementation of FIGS. 51-56 provides a unique solution for at least the reason of sterilization. TPE is typically more robust to sterilization effects than silicone (e.g., for gamma and e-beam), and thus the hybrid seal 628 provides significant advantages over nonhybrid seals.

Figure 57A:
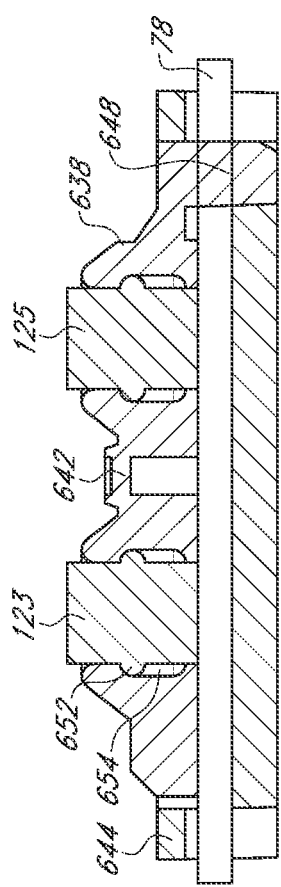
FIGS. 57A-C illustrate cross-sectional side views of a flow seal configured in accordance with an embodiment, at various stages of needle and grease insertion.
Figure 57B:
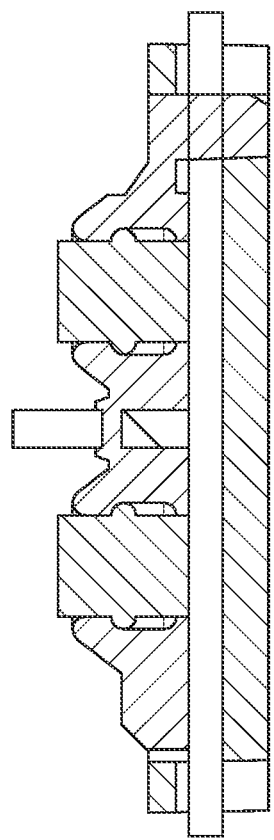
Figure 57C:
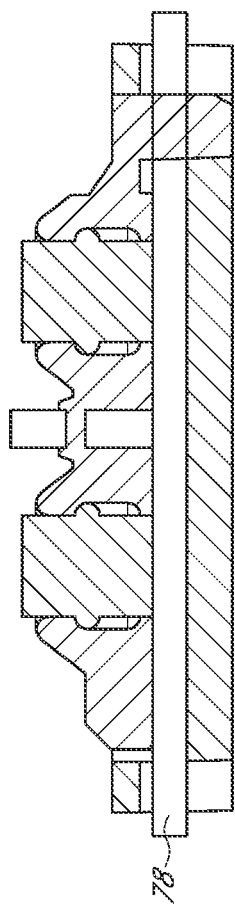
Figure 58:
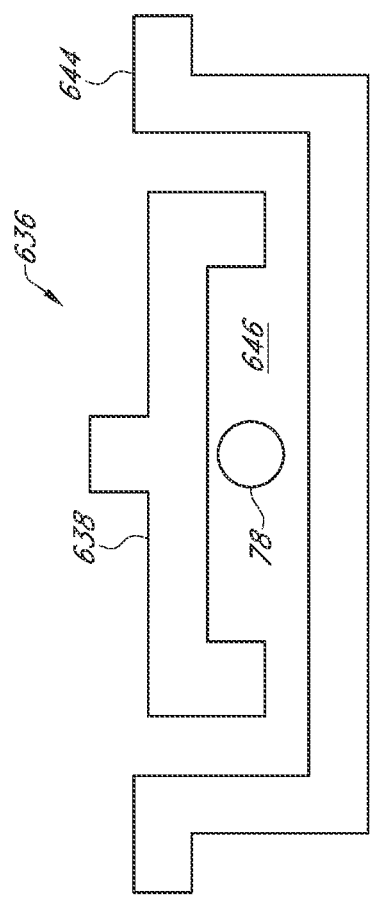
FIG. 58 illustrates a schematic end view of the flow seal of FIG. 57, installed within a seal carrier.
Figure 59:
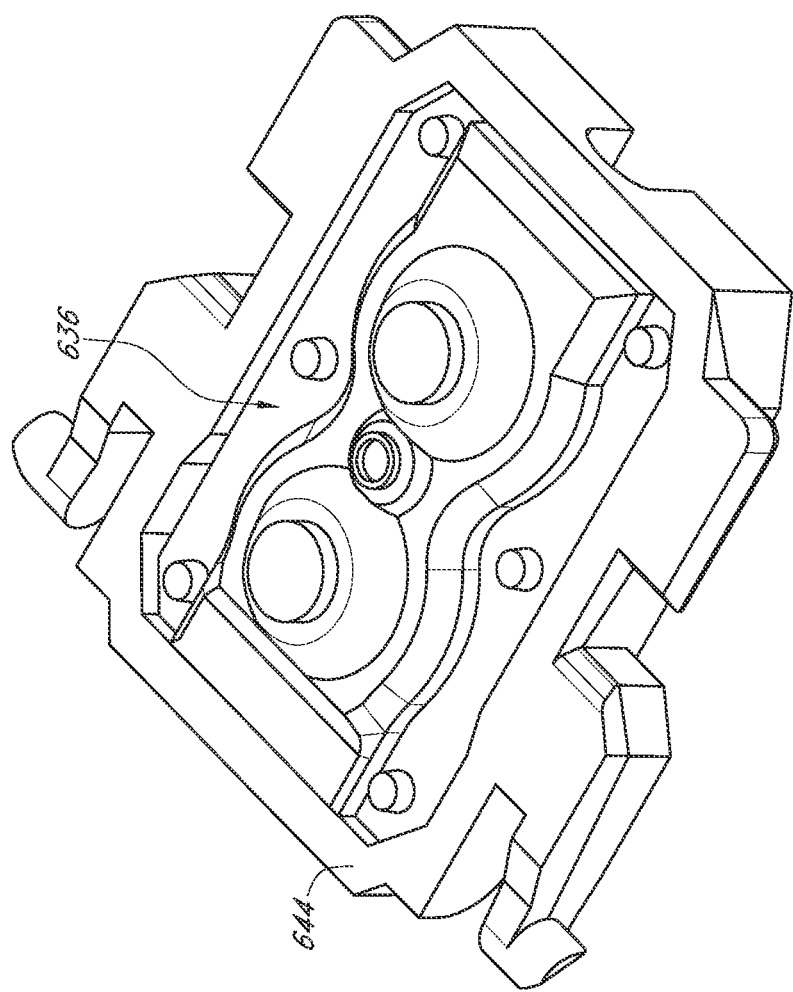
FIG. 59 illustrates a perspective view of the flow seal of FIG. 57, installed within a seal carrier.

FIGS. 57-59 illustrate another implementation of the seal 636 according to present principles, such termed a flow seal 636. In particular, as noted above during application deployment the force required to remove the cannula from the seal causes stress within the components and adds risk because of preloaded and stressed components, particularly in situations of long shelf life. The implementation of FIGS. 57-59 solves this problem by significantly reducing the force required to remove the cannula from the seal. It does so by removing a significant portion of the seal from the seal carrier, and replacing the same with a flowable material.

In particular, the cannula 78 passes through a channel 646 formed between a seal portion 638 and the seal carrier 644. During manufacture, a fluid such as grease, e.g., petroleum jelly, is injected into the channel 646. Following injection, it need not occupy the entirety of the channel. However, when the transmitter is placed on top of the seal and forced onto the seal and seal carrier, making contact with the pucks 123 and 125, the seal portion 638 will be significantly compressed, forcing the grease throughout the channel. The grease provides a moisture barrier and significantly reduces the retraction force required for the cannula, consequently reducing slingshotting.

The grease may be inserted through a septum 642, e.g., with a needle. A front septum 648 may be provided, and the same may advantageously be employed to help retain the sensor wire in place via friction. The septum 648 (and septum 642) may be made of seal material, e.g., an elastomer, and the same generally is pre-stressed to "close up" when the cannula or needle is removed. In some implementations, the septum may be made of a more rigid elastomer, to allow a more rigid hold on the wire. Because of this there may still be an increase in force required when the cannula begins to be retracted from the septum, but in many of the applicator implementations, the beginning of cannula retraction is at a point when the retraction drive, e.g., spring, has considerable energy with which to exert a force, e.g., the spring is not at the end of its movement, and thus such retraction is easily performed.

The pucks 123 and 125 may be "floating", in the sense that they are held by the seal 638 and are not penetrated by the cannula (nor is the seal 638), except at the septum 648. However, the pucks 123 and 125 may be held within the seal 638 by the use of annular tabs 652 moving within cylindrical channels 654.

FIGS. 57A-57C illustrate the seal 638 before needle and grease insertion (FIG. 57A), with needle insertion but before grease is injected (FIG. 57B), and finally after grease injection (FIG. 57C). FIG. 59 indicates a perspective view of the flow seal 636 in place within a seal carrier 644.

Various advantages inure to the implementation of FIGS. 57-59. For example, when the transmitter is forced onto the disposable housing and seal/seal carrier, the grease flows throughout the interior of the seal carrier, significantly protecting the wire from moisture. Another significant advantage results in the implementation of FIGS. 57-59 particularly as compared to where an entire solid seal is employed. In particular, elastomer seals can become "set" during the process of sterilization. Thus, when the seal is manufactured and is sterilized with the cannula in place, removal of the cannula sometimes may leave a void. In the present system, the grease or petroleum jelly could provide a gap filling function. Another significant advantage inures in the effect of the flow seal on applicator mechanisms. For example, the flow seal may reduce the force of seal retraction such that a booster spring or other "extra" retraction force mechanism is not required.

Alternatives of the system of FIGS. 57-59 will also be understood. For example, while just a single wire-holding septum is shown in FIG. 57, septum 648, another septum may be placed on the other side of the seal, creating a dual septum system, which would serve to trap the grease between the two septa. In addition, the septa serve an additional purpose of removing grease from the cannula, so that the same stays within a sealed zone.

In another alternative, rather than piercing the septum, the cannula could be held just proximal to it. During deployment, i.e., needle insertion, the needle pierces the septum and performs sensor insertion. The cannula still serves the purpose of preventing needle contact with the grease inside the flow seal. This implementation has the benefit that the septum remains in an unstressed state during sterilization and storage. This aspect eliminates the compression set that would otherwise reduce sensor retention by the septum post sterilization and after storage.

Figure 60:
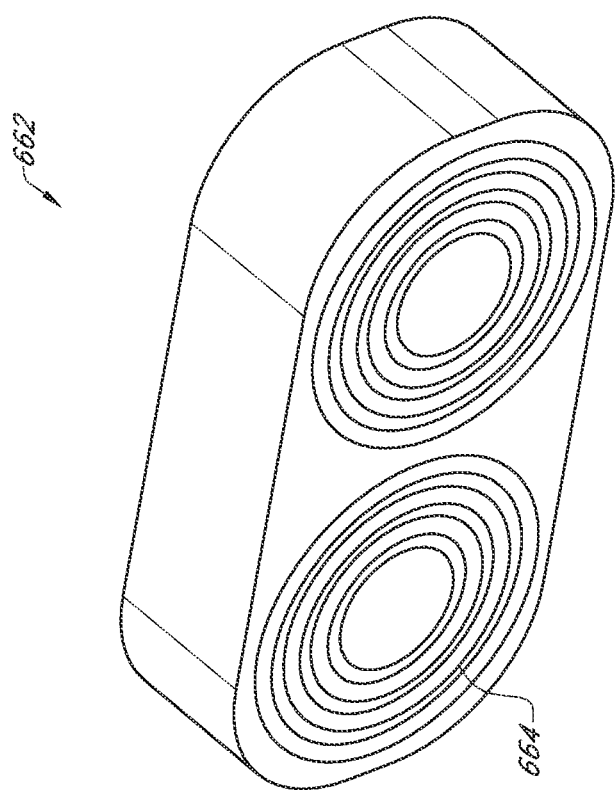
FIG. 60 illustrates a perspective view of a ringed seal configured in accordance with an embodiment.
Figure 61:
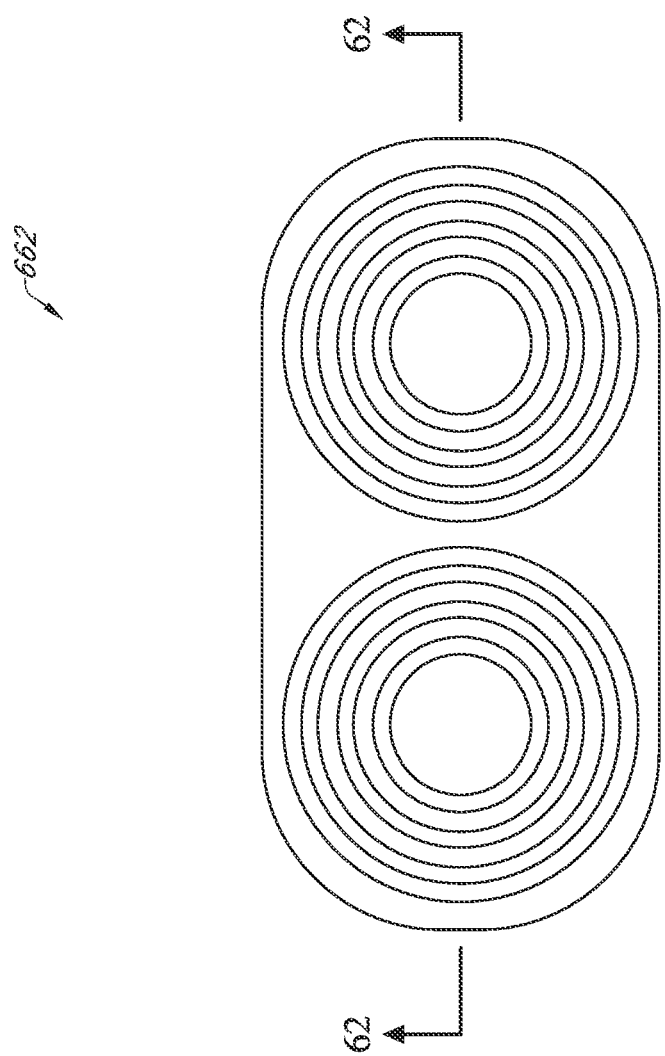
FIG. 61 illustrates a top view of the ringed seal of FIG. 60.
Figure 62:
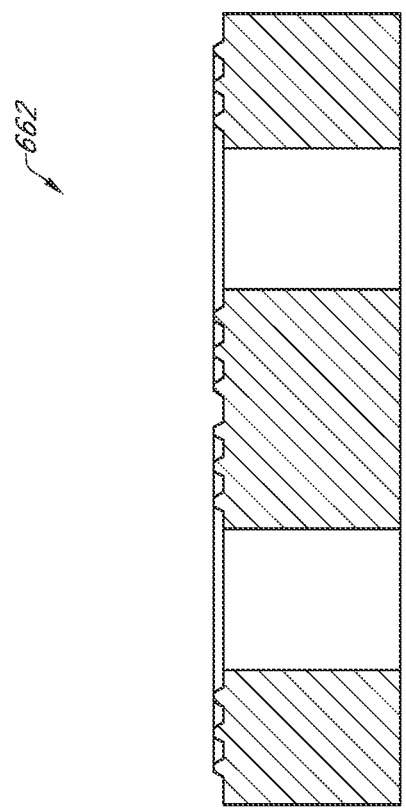
FIG. 62 illustrates a cross-sectional side view of the ringed seal of FIG. 60, taken along line 62-62 of FIG. 61.

In yet another implementation, as shown in FIGS. 60-62, a seal 662 may be constructed with a number of annular or ringed seals 664, e.g., a face seal with one or more concentric annular ringed protrusions or ridges on the sealing face. Embodiments employing multiple rings can provide multiple sealing barriers to ingress, and can also concentrate the sealing force to the more critical areas of the seal. In some embodiments, one or more O-rings can be disposed near one or more of the annular protrusions (e.g., in the groove between two of the ridges) to create an additional seal. As with prior implementations, the top of the ringed seals contacts the transmitter and the bottom contacts the seal carrier.

This implementation may reduce the amount of force needed to remove the cannula from the seal. In addition, the same allow for seal breaches to occur, e.g., in one ring, without affecting the seal integrity of the other ring(s). (Seal breaches may occur due to surface defects, tolerances, and the like.) In variations of the implementation of FIGS. 60-62, the number of rings can be varied, their cross-sectional shape can be varied, and the shape of the ring itself can vary, e.g., in some implementations noncircular rings may be employed.

Another implementation which may be employed to reduce the normal force on the cannula by the seal, and thus to make the cannula easier to remove, is by use of the sandwich seal. Such a sandwich seal is illustrated by FIGS. 63-69.

In particular, as noted the force required to remove the cannula from the seal typically stresses the components of the seal and applicator system. Efforts have been attempted at reducing the required force to remove the cannula by slitting the seals, but such seal slitting operations are typically undesirable and deleterious.

A sandwich seal employs a two-part design in which the cannula is sandwiched between the two parts. This results in a generally much lower cannula pull force requirement because along the length of the cannula the frictional force of the seal thereon is less. Other advantages include that no grease is required for sealing, and sensor retention is decoupled from the seal and can be made much more robust. Ideal sealing materials, such as low durometer elastomers, can be employed because the sealing function is decoupled from other functions such as sensor placement.

In more detail, a sandwich seal may be employed which increases the gap spacing between the seal and the cannula. Instead of a single block of elastomeric material, two blocks may be employed and the cannula can pass through in-between the blocks. The cannula thus has a larger opening through which to pass, minimizing resistance and slingshotting.

Figure 63:
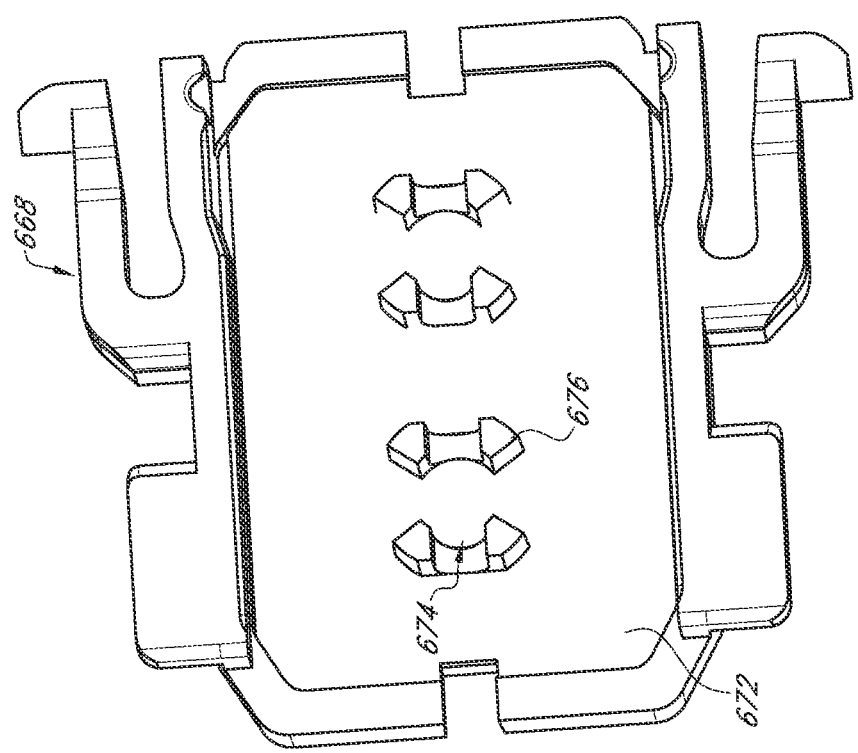
FIG. 63 illustrates a bottom perspective view of a seal carrier configured in accordance with an embodiment.

Referring first to FIG. 63, a seal carrier 668 is illustrated with a bottom sandwich seal component 672. A passage 674 is seen with a general "U"-shape through pillar columns 676. Between each set of pillar columns a puck may be placed (not shown). The seal carrier 668 may be made of a rigid material such as a polycarbonate, and the bottom sandwich seal component 672 may be made of, e.g., an elastomer or other material such as silicone, or any material allowing for sensor retention.

A top sandwich component 678 is illustrated, having a top frame 682 and a top seal 684. The top sandwich component 678 may be hinged to the bottom component 672 (see hinge 692 in FIG. 64), and the top sandwich component may then be held fast to the bottom component 672 by a latch tab 686 which may pass and hold fast to a tab 688 in the bottom component.

Figure 64:
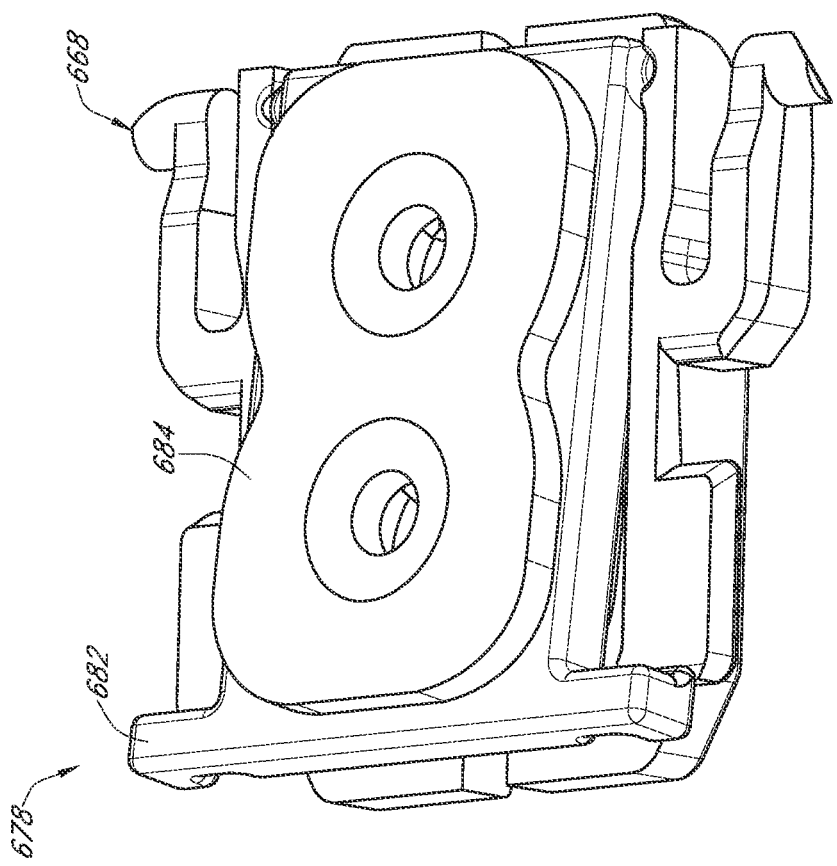
FIG. 64 illustrates a top perspective view of the seal carrier of FIG. 63, with a sandwich seal being installed in the seal carrier.

In use, and during insertion, the system may be in the unlatched position, as illustrated in FIG. 64. Any of the applicators described above may be employed to deploy the sensor wire between the top seal 684 and the bottom seal 672. The top seal and bottom seal (and top frame and seal carrier) may then be snapped together using the latch 686 and the tabs 688. The top seal and bottom seal may be snapped together when the transmitter is inserted, providing the seal and sensor retention needed. The pucks may be contained in the top seal, and may snap down on top of the sensor wire, again when the transmitter is inserted.

In one implementation, the bottom seal material 672 may have a higher durometer than the seal material 684. In another implementation, the opposite may be true. Having a higher durometer bottom seal material 672 allows support of the sensor wire in a way so as to produce a reliable connection to the pucks but which also allows good sealing when sandwiched to the lower durometer material snapping down from above it. In some cases, the frame 682 and the top seal 684 may both be made of an overmolded low durometer seal material.

Figure 65:
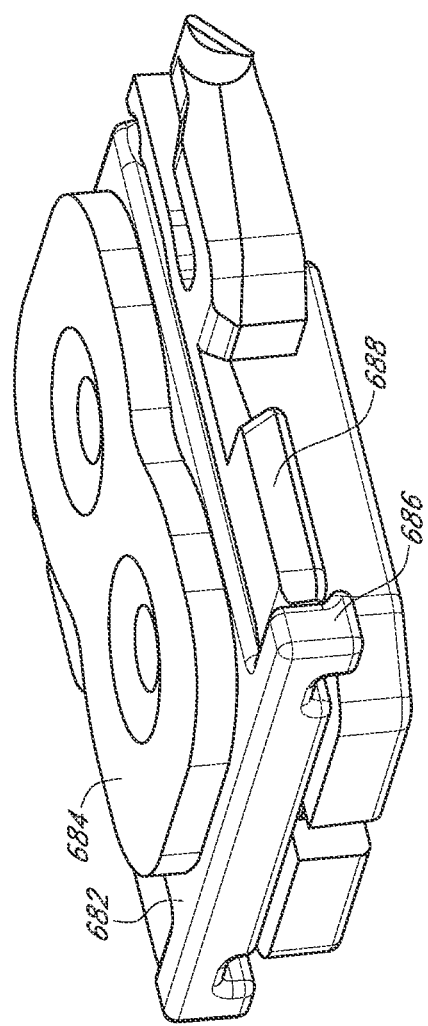
FIG. 65 illustrates another perspective view of the seal carrier and sandwich seal of FIG. 64.

Variations of the implementation of FIGS. 63-65 may include one or more of the following. A septum may be placed at the distal end of the seal, e.g., within the top frame 682, and the same may be pre-pierced by the needle. Upon deployment, the sensor wire may be held by the septum. In another variation, the bottom housing may include puck retaining features which keep the wire from moving out of the path of puck conduction, as well as providing added stability to the pucks.

In yet another variation, the top portion of the seal (frame 682 and seal 684) may be held above the needle, and the septum (described above) is not pierced in its manufactured state. Rather, the needle pierces the septum upon activation of the applicator. In this variation, the cannula can be eliminated, reducing parts and increasing manufacturability. The septum beneficially remains in an unstressed state during sterilization and storage. This aspect has the advantage of a limited compression set that would otherwise reduce sensor retention by the septum post sterilization and after storage. In this variation, the top portion of the seal may be held out of the way of the needle before and during deployment as well as during storage, which may be accomplished by putting snaps on the top seal component or incorporating features into the carrier that hold the seal in the applicator and prevent the top seal from compressing on the needle.

Figure 66:
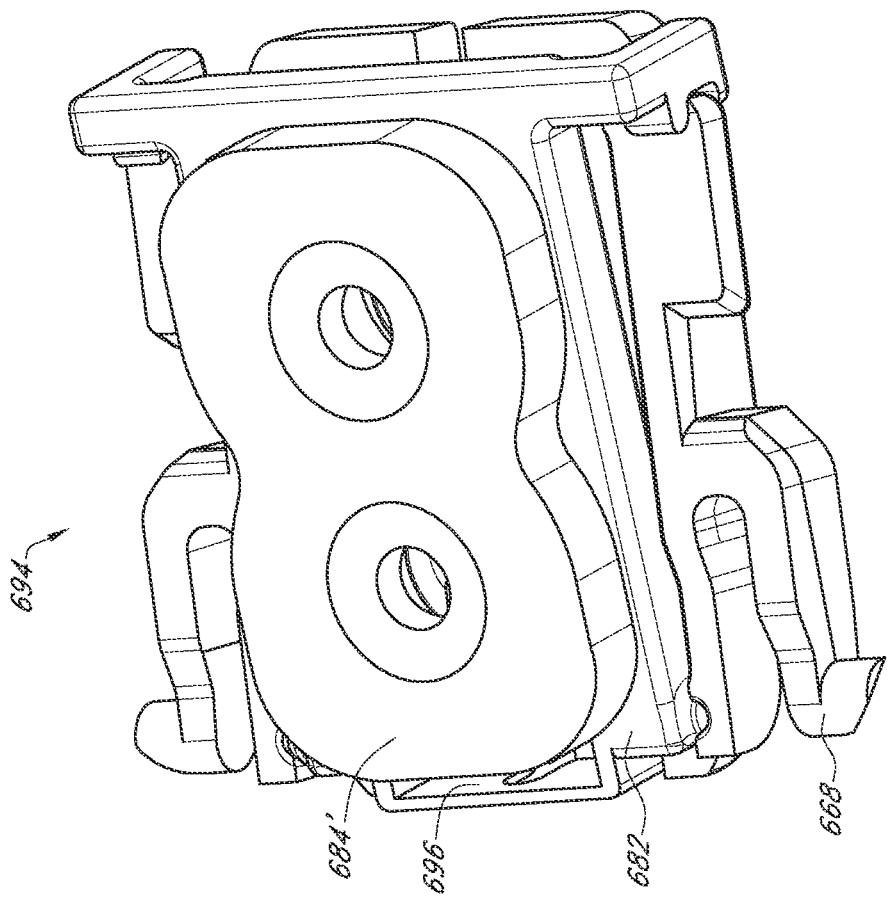
FIG. 66 illustrates a perspective view of a seal carrier and sandwich seal configured in accordance with another embodiment.

FIG. 66 shows a particular implementation of a sandwich seal 694, showing a low durometer seal material 684' held in the top frame 682, which is hingedly attached to the seal carrier 668. In this implementation, a septum 696 is disposed, where the septum material has a relatively high durometer, e.g., silicone with a durometer of 50-70 shore A, e.g., with an exemplary thickness of, e.g., 0.062". Unlike the implementations of FIGS. 63-65, in the implementation of FIG. 66, there is no lower durometer seal material from the top seal 684 in the path of the cannula. Rather, the high durometer silicone of the septum provides the retention force for the sensor wire to keep the same from being removed before the seal is completely snapped down. As before, the seal may be snapped down to a final configuration upon the insertion of the transmitter. Even before this final configuration is attained, the sensor wire is still held firmly in place by the septum, to reduce the chance of accidental removal of the sensor wire prior to the transmitter being snapped down.

Figure 67:
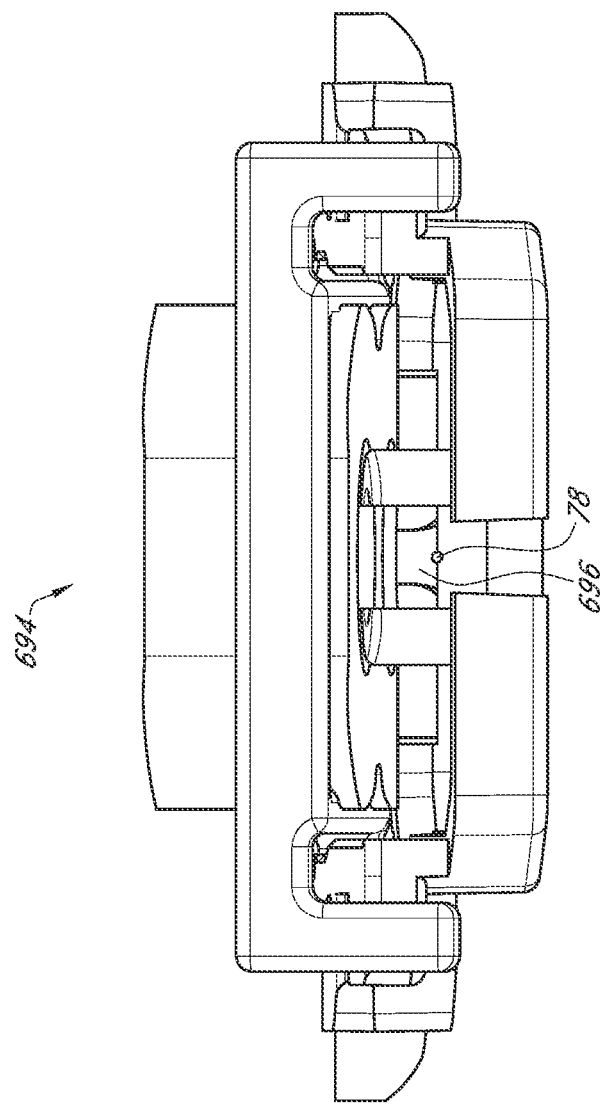
FIG. 67 illustrates an end view of the seal carrier and sandwich seal of FIG. 66.
Figure 68:
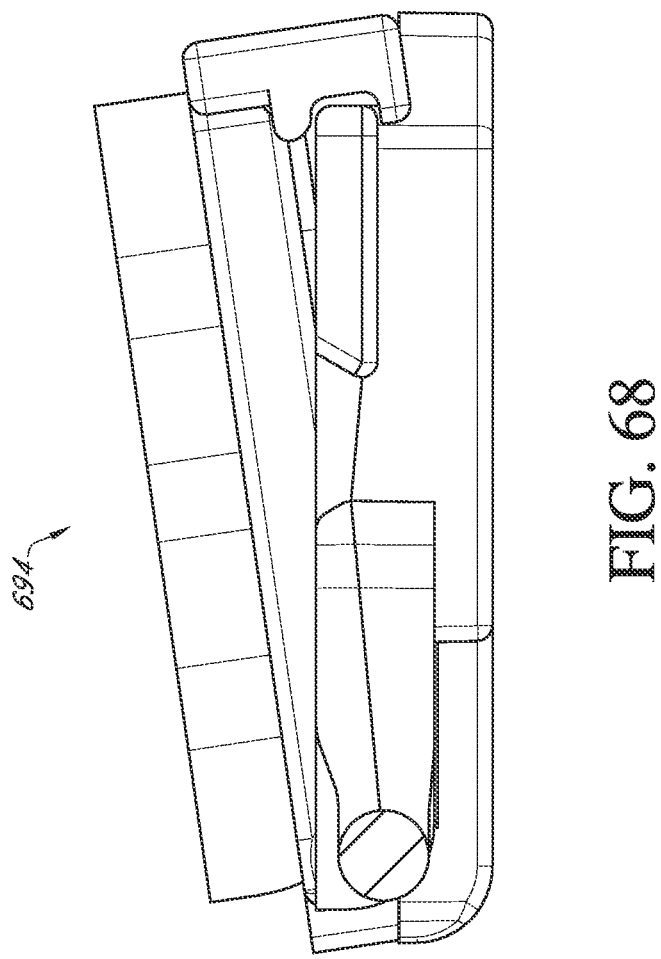
FIG. 68 illustrates a side view of the seal carrier and sandwich seal of FIG. 66, with the sandwich seal being installed in the seal carrier.
Figure 69:
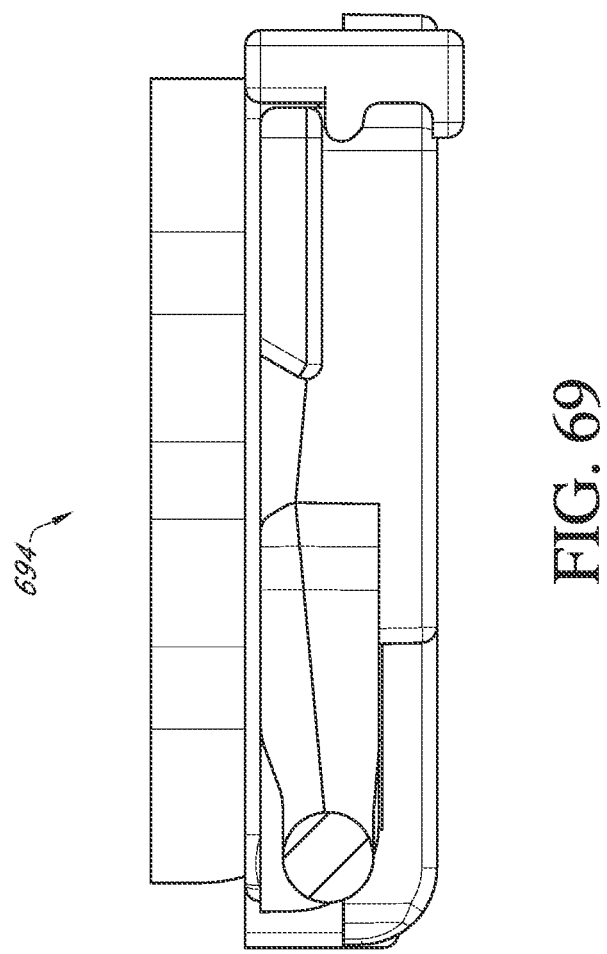
FIG. 69 illustrates another side view of the seal carrier and sandwich seal of FIG. 66, with the sandwich seal installed in the seal carrier.

FIGS. 67-69 illustrate progressive steps of the use of a sandwich seal with septum 694. FIG. 67 illustrates a profile view of the sandwich seal in an open position, and FIG. 68 illustrates a side view. FIG. 67 illustrates a side view in a closed position.

Advantages of the implementation of FIGS. 63-69 may include one or more of the following. In some implementations, the cannula may be removable from the design. The implementation may significantly reduce or eliminate slingshotting effects of retraction. Either the top or the bottom portions of the seal design, or both, may be overmolded. The implementations allow improved product manufacturability and reliability. For example, slitting and exchange processes required in single piece seals may be eliminated in these implementations. In some implementations, additional force devices such as booster springs may be eliminated, because the cannula or needle has force for retraction has been reduced.

Figure 70:
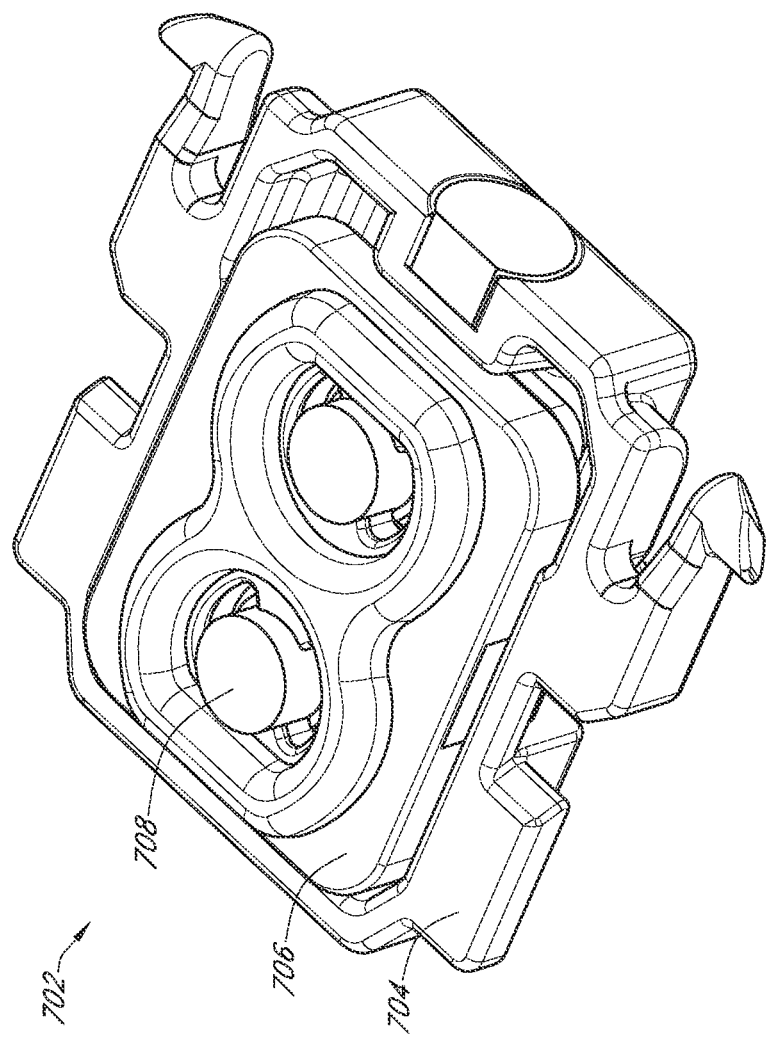
FIG. 70 illustrates a perspective view of a stack seal configured in accordance with an embodiment.
Figure 71:
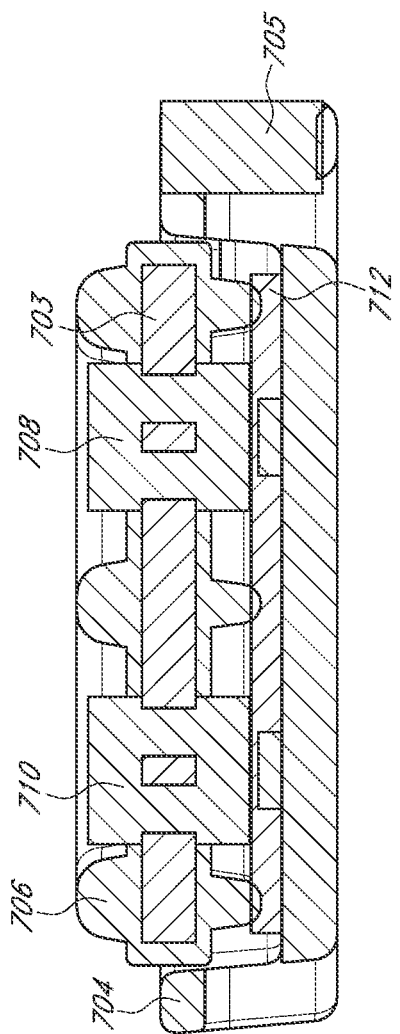
FIG. 71 illustrates a cross-sectional end view of the stack seal of FIG. 70.
Figure 72:
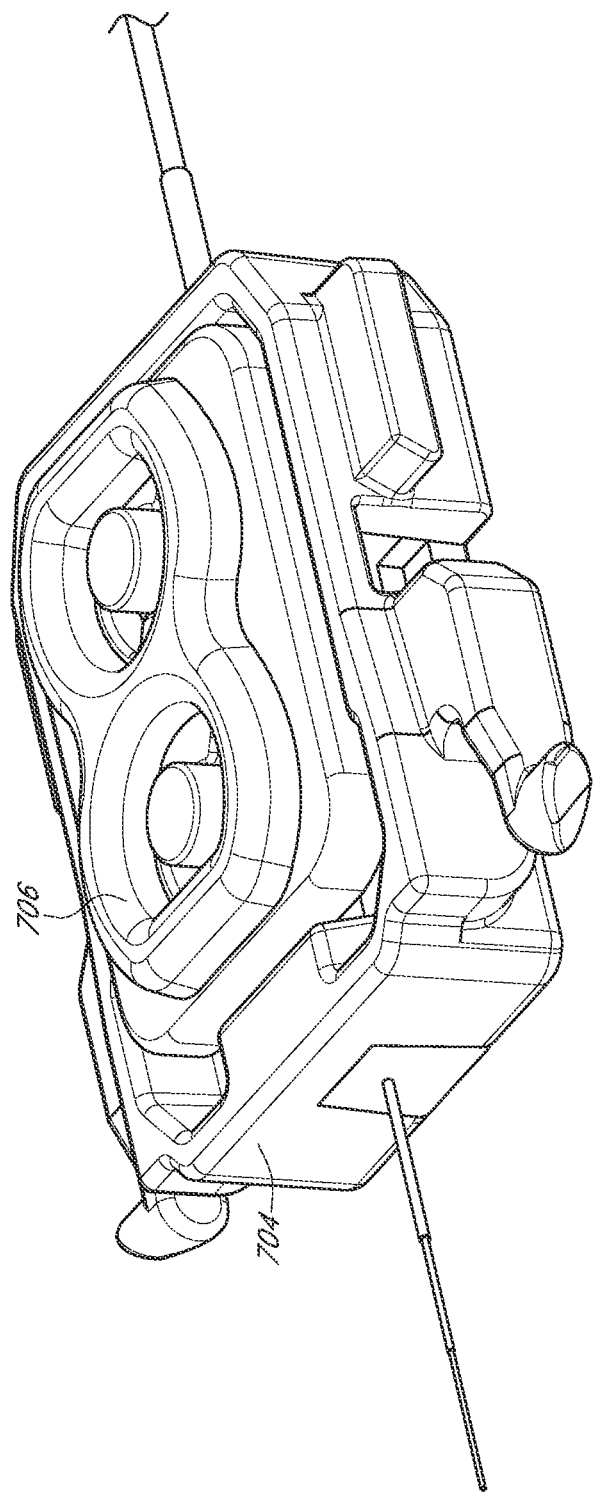
FIG. 72 illustrates another perspective view of the stack seal of FIG. 70, shown coupled to a cannula.

FIGS. 70-72 illustrate another implementation 702 of a seal design, in particular showing a "stack" seal. This implementation, like the sandwich seal, places less normal force on the cannula, resulting in a lower cannula retraction force requirement. Sensor retention is decoupled and can be much more robust, as the same can be accomplished by a septum. The implementation of FIG. 70 requires no grease for sealing, and ideal sealing materials, e.g., low durometer TPE, can be employed, as the sealing function is decoupled from other functions, e.g., sensor placement. In addition, seal slitting process, which is undesired, is no longer required.

In implementations according to these principles, a seal housing 704 includes a septum 705 for use in holding a sensor wire as described above, the septum 705 located at a distal portion of the seal subassembly. A material 706 is illustrated, which is overmolded onto a rigid plastic component 703. The material 706 may be a low durometer component, e.g., TPE or silicone or other sealing material. The material 706 also contacts a bottom portion of the rigid plastic component 703, as shown in FIG. 71. The pucks 708 and 710 are shown in the figures, along with the cannula 712. The implementation of FIG. 70 bears certain similarities with the sandwich seal of FIG. 63, one difference being that the implementation of FIG. 70 includes an overmolded top sealing material, rather than one which is mechanically inserted into a frame.

Figure 73:
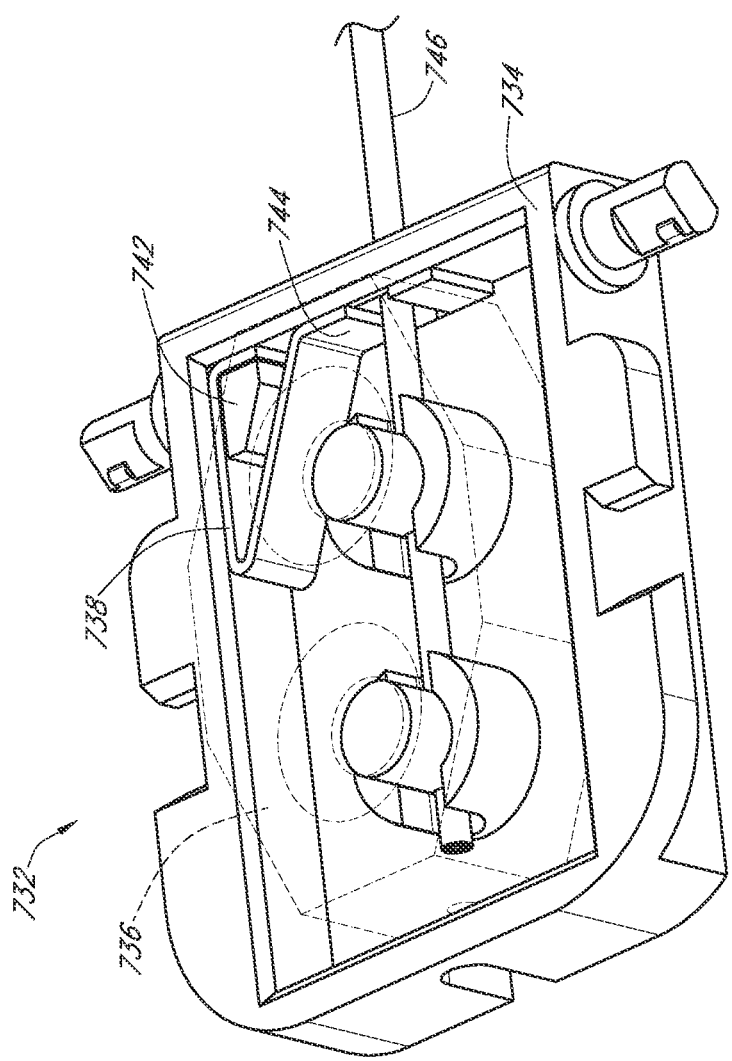
FIG. 73 illustrates one method of performing sensor wire capture in a seal carrier, in accordance with an embodiment.
Figure 74:
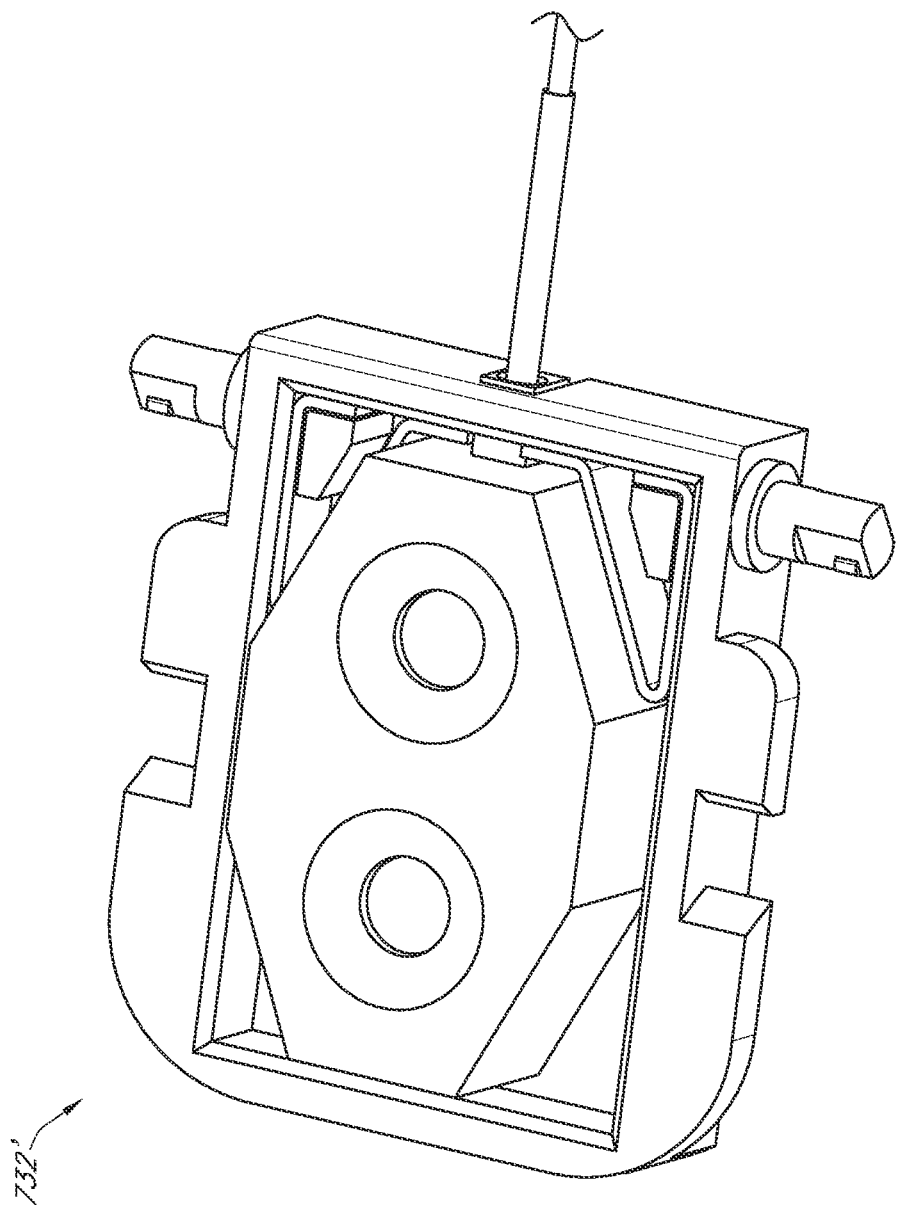
FIG. 74 illustrates another method of performing sensor wire capture in a seal carrier, in accordance with another embodiment.

FIGS. 73-77 illustrate other ways to combat slingshotting and to ensure accurate sensor placement. In particular, and referring to FIGS. 73 and 74, a seal carrier 732 may have a base 734 and a top portion 736, which base and top portions may be according to any of the implementations described. Either or both (the base portion is shown in the figures) may incorporate a spring element 738 which, e.g., abuts and is held in place by an element 742 integral with the base 734. The spring element 738 includes a contact element 744 which abuts and provides pressure against a cannula 746 prior to removal of the cannula. FIG. 73 illustrates a seal carrier with one spring element 738. FIG. 74 illustrates a seal carrier 732' incorporating two spring elements. The operations are the same whether one or two spring elements are used.

When the cannula is removed during retraction, the spring element 738, and in particular the contact element 744, no longer abuts the cannula but rather it abuts the sensor wire, providing additional force against sensor wire movement. In one variation, spring element 738 may be configured to provide a greater force when contacting the sensor wire then when contacting the cannula. In another variation, the spring element 738 may be arrested from movements such that the contact element 744 does not even abut the cannula until such time as the cannula is removed, and then the arresting of movement may be removed and the spring element caused to contact and provide a force against the sensor wire.

Figure 75:
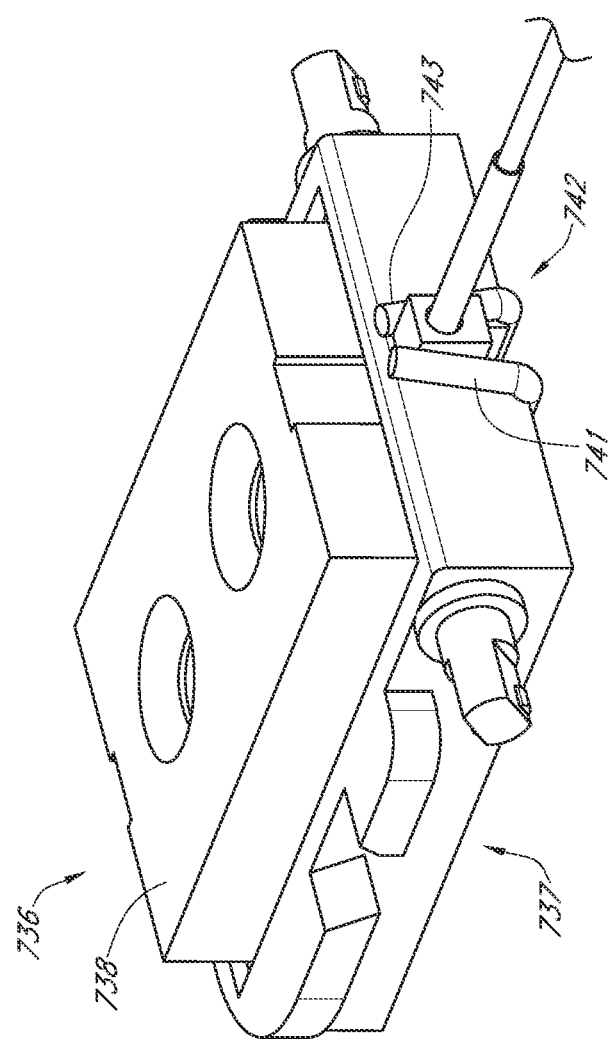
FIG. 75 illustrates another method of performing sensor wire capture in a seal carrier, in accordance with another embodiment.

FIG. 75 illustrates another implementation of a spring element system, in which a spring element 736 has a first portion 738 and a second portion 742, and the same are configured on opposite sides of the seal carrier 737. By being on opposite sides of the seal carrier 737, the spring element 736 may be both frictionally and by virtue of a spring force in solid engagement with the seal carrier 737. The spring element 742 may include, e.g., two fingers 741 and 743, which are kept apart by the cannula, or by an element the cannula passes through. Upon removal of the cannula, or upon removal of the element the cannula passes through, the two fingers 741 and 743 closed down upon the sensor wire, and hold the same in a secure fashion.

Figure 76:
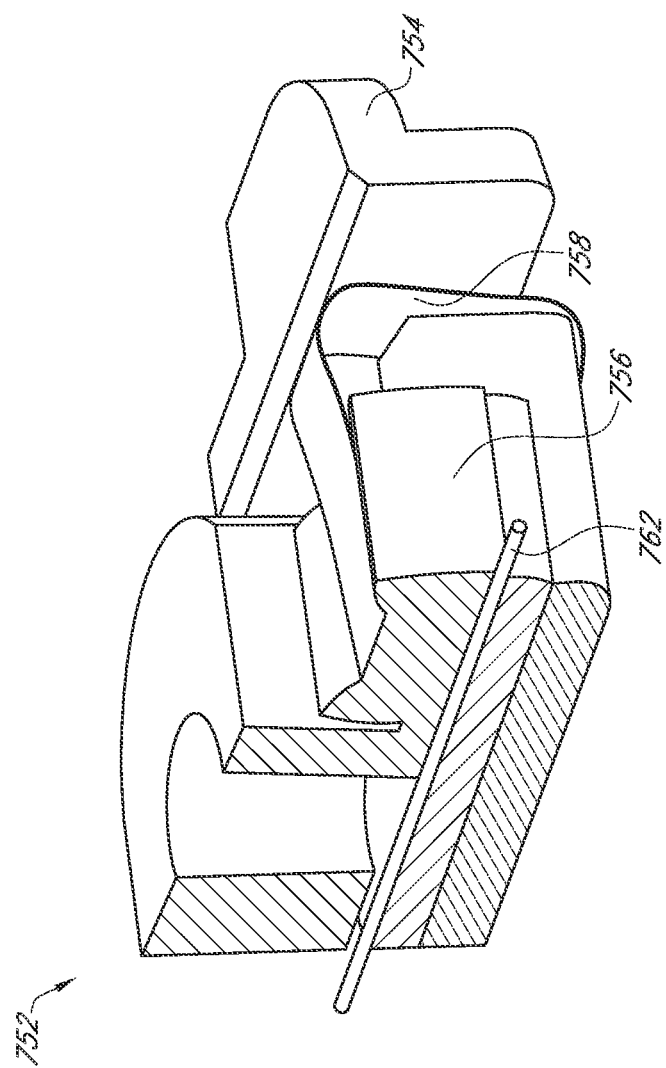
FIG. 76 illustrates another method of performing sensor wire capture in a seal carrier, in accordance with another embodiment.

FIG. 76 illustrates an alternative implementation, in which instead of the cannula or sensor wire being held securely by the spring element, the seal is held by a spring element against slingshotting. In particular, a seal carrier 754 is illustrated having a seal 756, shown in cross-section in FIG. 76. A cannula 762 is illustrated, through which a needle and sensor wire may be delivered as described above. A spring element 754 is employed to hold the seal 756 securely, and in particular against movement such as slingshotting. In this way, the seal is prohibited from movements during cannula removal, reducing the effects of slingshotting on the sensor wire.

Figure 77:
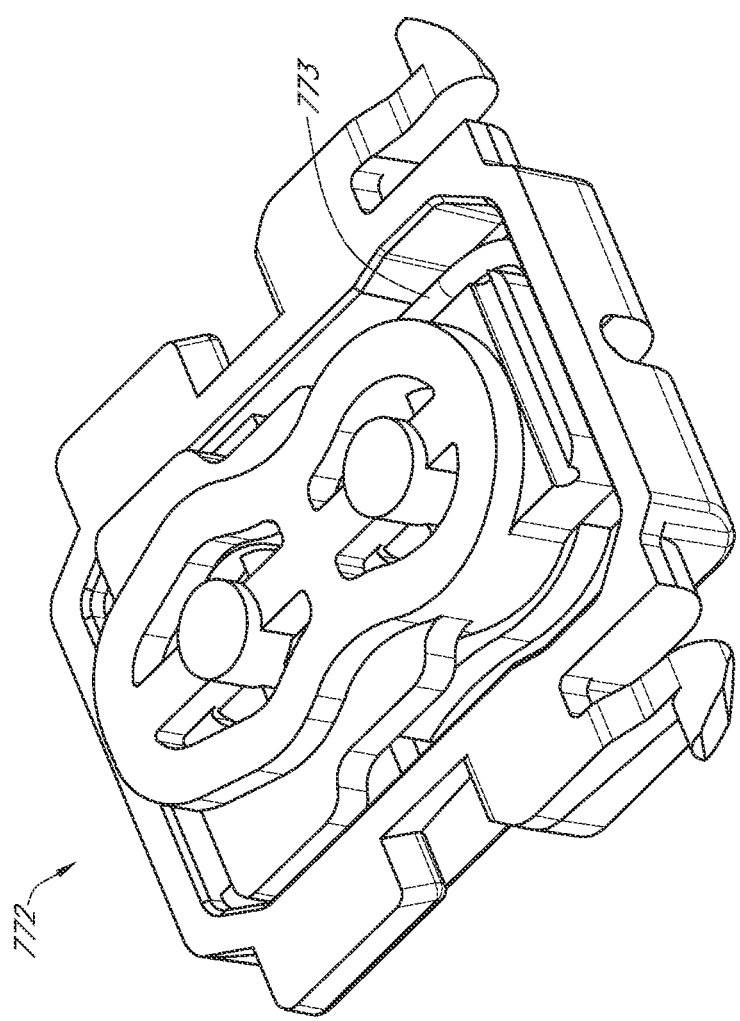
FIG. 77 illustrates another method of performing sensor wire capture in a seal carrier, in accordance with another embodiment.

FIG. 77 illustrates an assembly 772 that operates in a way similar to a mouse trap. In this implementation, a spring element 773 provides a force generally perpendicular to the cannula retraction direction on the distal side of the seal.

FIGS. 78-83 further illustrate ways according to present principles to withdraw the cannula and deposit a sensor wire within an elastomeric seal. As noted, friction between the seal and the cannula can cause the elastomeric seal to move, and such movement may cause unwanted side effects such as sensor placement error due to slingshotting.

Figure 78:
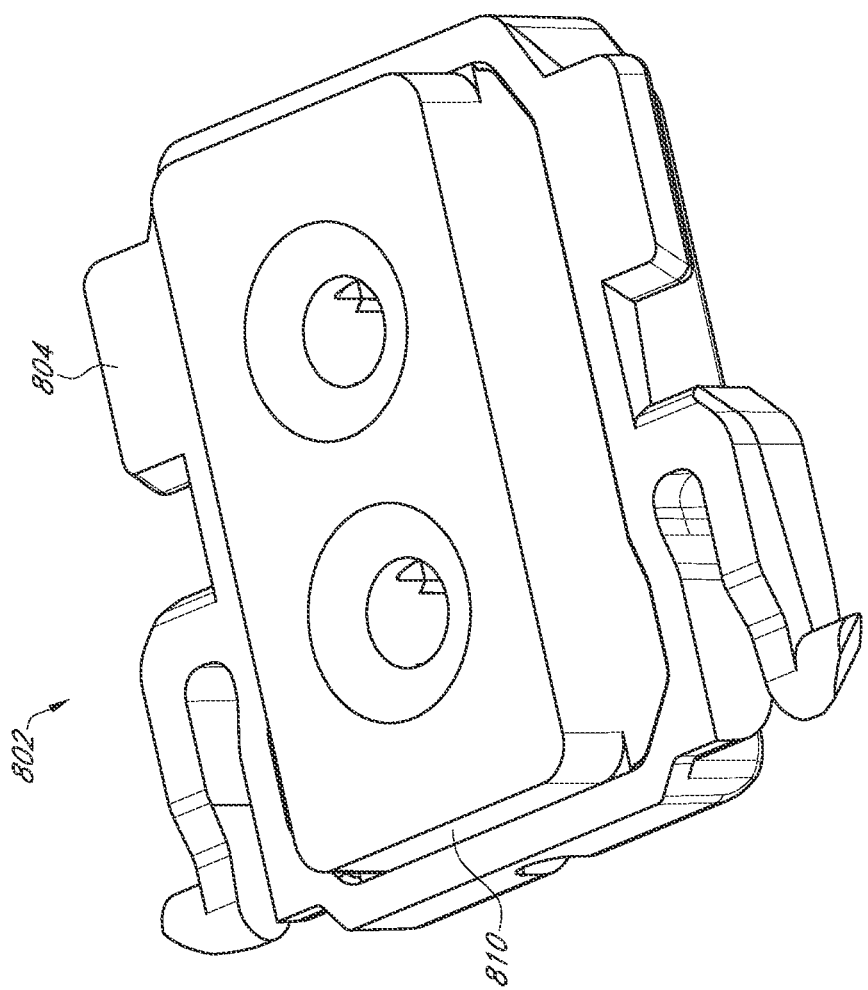
FIG. 78 illustrates a perspective view of one example of a seal, configured in accordance with an embodiment.

The implementations of FIG. 78 et seq. provide ways to reduce the amount of seal interaction with the sensor wire by creating voids along the sensor path. In addition, anchoring features are provided to limit the amount the seal can move. For example, physical walls may be employed within the sensor housing to limit the amount the sensor can move, and/or a glue may be employed to further limit seal movement. In addition, certain of the implementations described provide a reduction in force required to remove the cannula.

Figure 79:
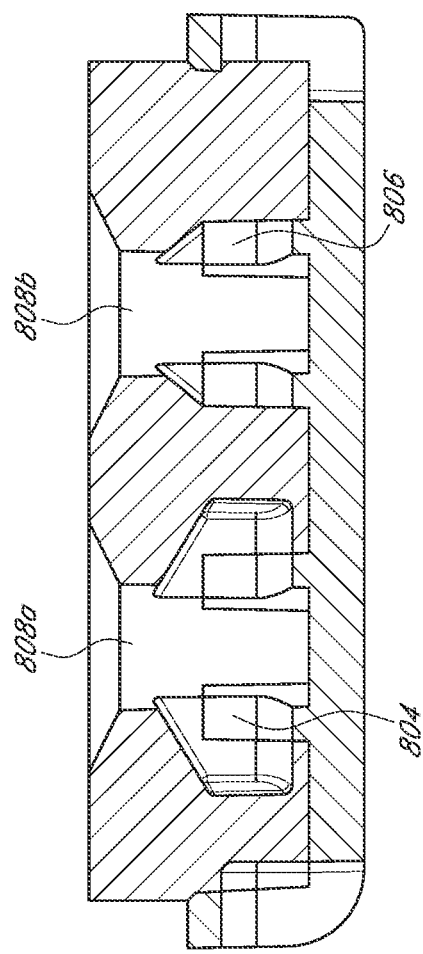
FIG. 79 illustrates a cross-sectional side view of the seal of FIG. 78.

In more detail, and referring first to FIG. 78-79, a design is shown for a seal assembly 802 having a seal housing 804 in which undercuts are created through the puck holes to create voids in the cannula/wire pathway. A void 804 is illustrated adjacent puck hole 808*a* (which is the distal puck hole) and a void 806 is illustrated adjacent puck hole 808*b* (which is the proximal puck hole). In both cases undercuts below the top of the puck hole are disposed to create the void. In the implementation shown, material is removed around both sides of the distal puck, while for the proximal puck, material is removed only up to the puck support walls. An inset 810 is illustrated for the distal portion of the seal, such that the same is inset from the front of the seal carrier. The inset 810 serves the purpose of exposing the tip of the cannula (such that there is no seal piercing by the moving needle) and limiting the wall thickness of the seal material between void 804 and 810.

Figure 80:
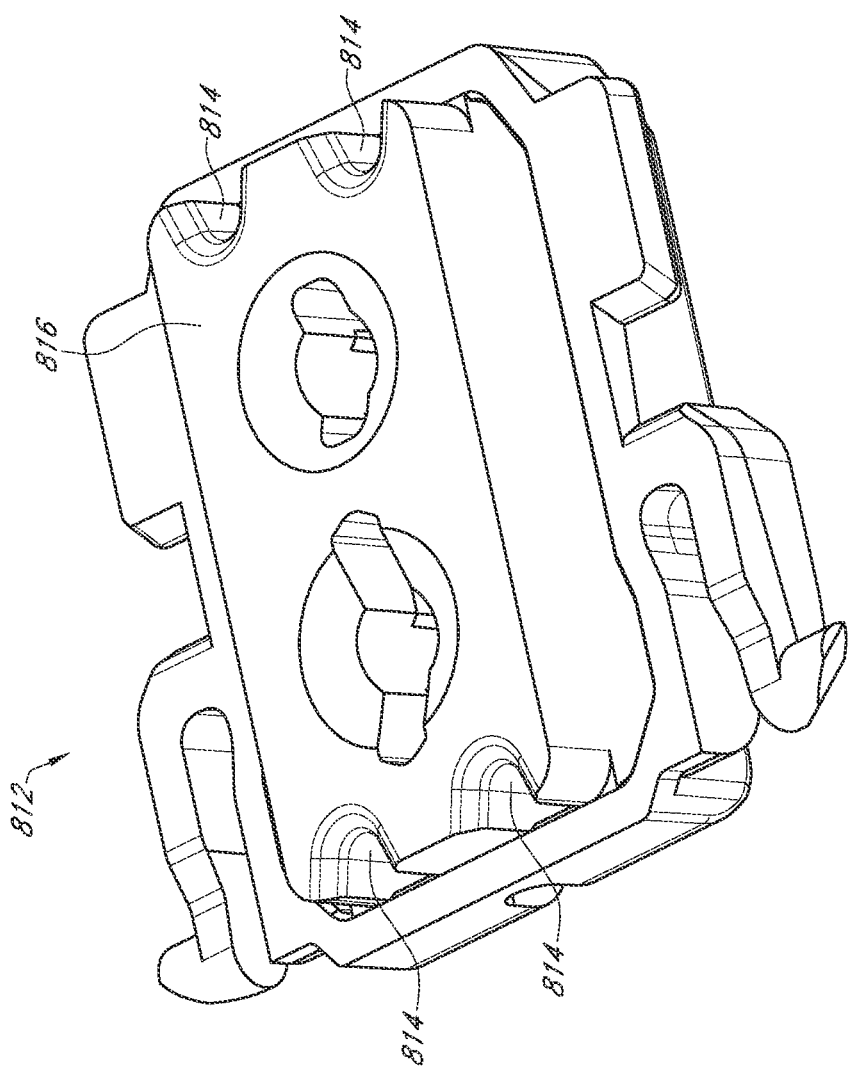
FIG. 80 illustrates a perspective view of one example of a seal, configured in accordance with an embodiment.
Figure 81:
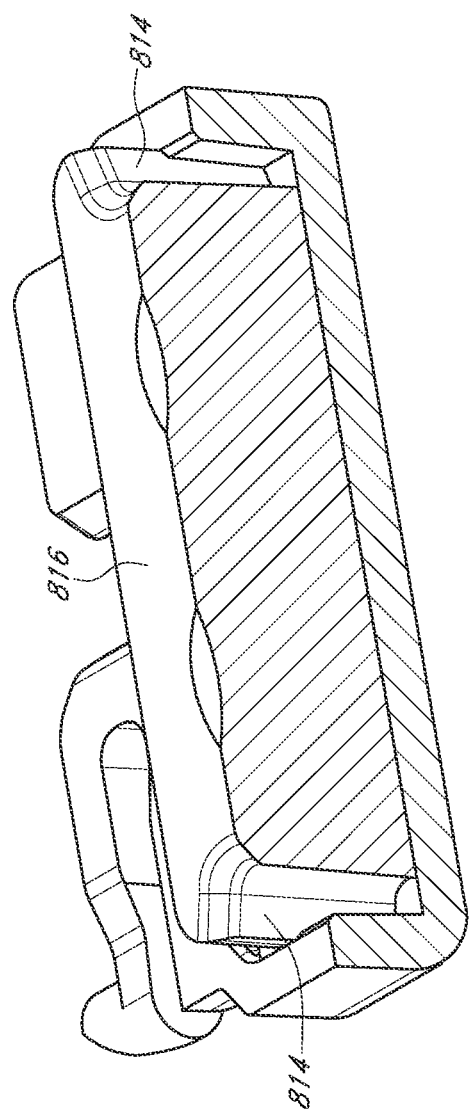
FIG. 81 illustrates a cross-sectional perspective view of the seal of FIG. 80.

FIG. 80-81 illustrate another implementation, in which glue wells are added in the front and back. Adding glue through an opening serves to adhere the elastomer to the rigid seal carrier. This embodiment further illustrates the same voids and inset as shown in FIGS. 78-79.

In more detail, the seal housing 812 includes one or more glue wells 814. In FIG. 80, four glue wells 814 are illustrated, two in the front of the seal assembly and two in the back. A seal 816 is also shown, and referring further to FIG. 81 it may be seen how the glue wells 814 are formed in the seal 816. The glue wells may be chamfered and rounded. The glue wells may run to the floor of the seal carrier, and once glue has been disposed in the glue wells, the seal is adhesively coupled to the seal housing, reducing seal movement and subsequent slingshotting.

Figure 82:
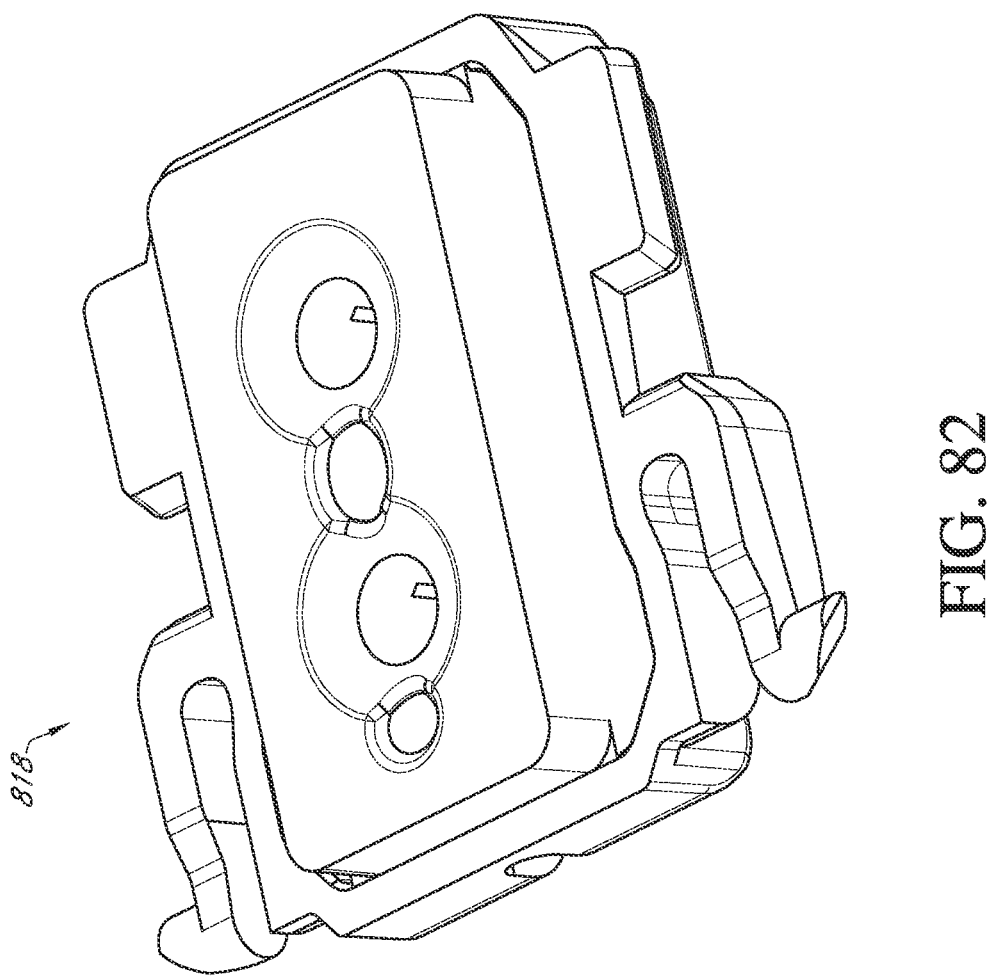
FIG. 82 illustrates a perspective view of one example of a seal, configured in accordance with an embodiment.
Figure 83:
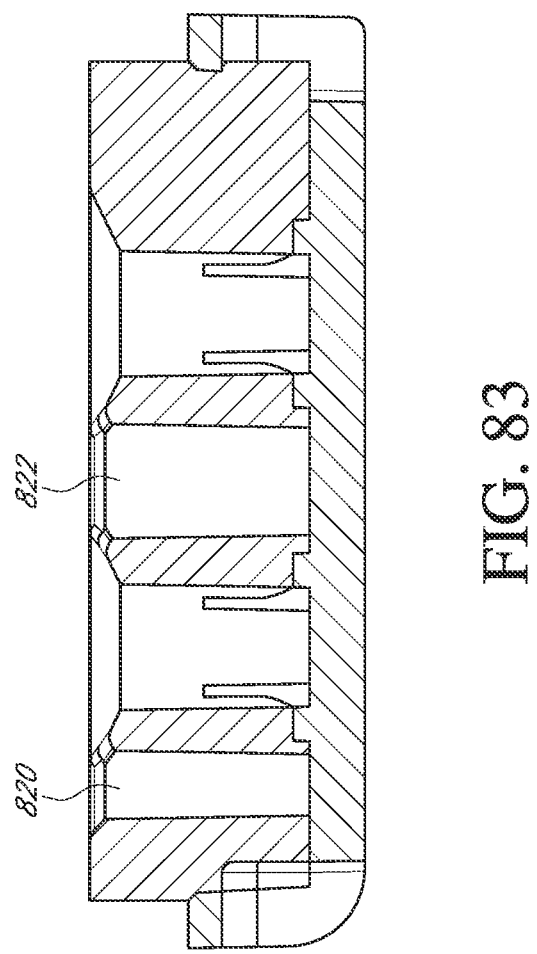
FIG. 83 illustrates a cross-sectional side view of the seal of FIG. 82.

FIG. 82-83 illustrate another implementation, in which again material is removed along the sensor wire and cannula path by creating shaped voids formed from the top surface. In the implementation 818, a front seal void 820 is formed or defined which may have, e.g., an oval shape of seal material removed. Puck support is still maintained. This void has no undercut, and thus simplifies the corresponding manufacturing tool. A mid-seal void 822 is also shown, which again may have an oval shape of material removed, although in this and the front seal void, non-oval shapes may also be removed. Again puck support is maintained, and the mid-seal void, like the front seal void, has no undercut, simplifying the manufacturing tool. As with the implementation of FIGS. 78-79, the distal seal may be inset from the front of the seal carrier.

It will be understood that in any of the implementations of FIG. 78 et seq., variations in the placement and shape of voids and glue wells are possible, and depend on the particular seal assembly design, as well as on the sensor wire and/or cannula placement and removal force profile required.

Figure 84:
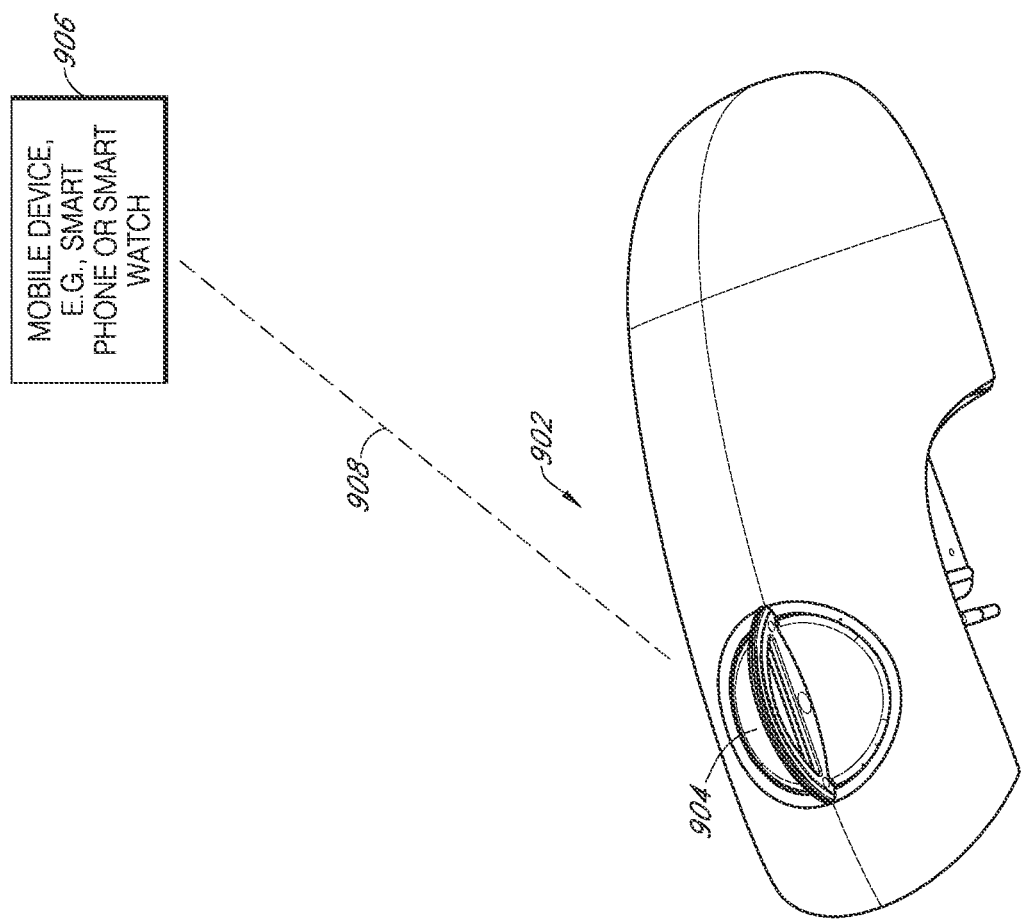
FIG. 84 illustrates one method of triggering a device for performing automatic insertion in accordance with an embodiment.

Variations of the above will also be understood. For example, in some cases users may find it difficult or inconvenient to hold the applicator flat on their skin and push the activation button at the same time. Such may be particularly true if the user is inserting the sensor on their side or back. For these reasons, and referring to FIG. 84, an applicator 902 may be automatically triggered by a remote device 906 by having an electromechanical device 904 activate the trigger. While the receiver 904 is shown in the figure as occupying the location of the button, it will be understood that the same may be entirely internal to the applicator 902.

The activating device 906 and the activated device 902, i.e., the applicator, may be communicatively coupled in a number of ways, including wirelessly or via a wired link. Wireless communication schemes may include RF links such as may be enabled by Bluetooth protocols, WiFi, or the like. Other communication schemes will also be understood. Advantages of such systems and methods according to present principles are described above, but also include that the user may situate the applicator on their body in a more stable fashion, rather than having to use one of their fingers to also push the activation button (or manipulate another activator, such as a slider or the like disclosed here).

The activating device 906 may be, e.g., a smart phone, a smart watch, a computing device, a dedicated receiver or transmitter, e.g., similar to a garage door opener or other remote control, or the like. The same may incorporate timers or other time delay devices, as well. In alternative implementations, a button on the applicator may be employed, as in FIGS. 3-16, but the same may employ a time delay.

Figure 85:
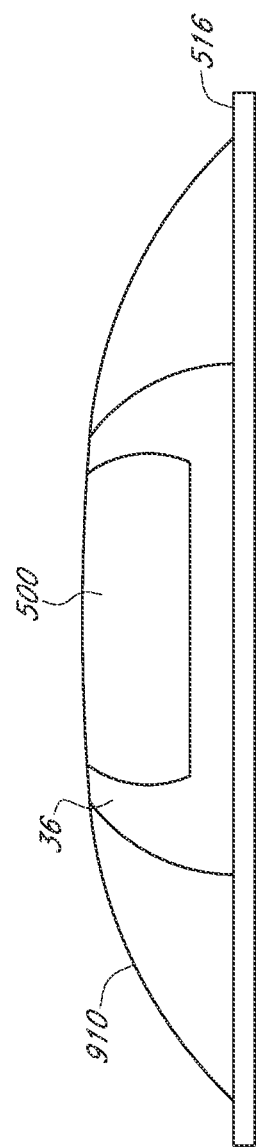
FIG. 85 illustrates a transmitter within a housing configured in accordance with an embodiment.

In another variation, and referring to FIG. 85, an implementation is shown in which a transition region is provided at the intersection of the adhesive 516 and the disposable housing 36. In particular, a transition region comprising a volumetric solid 910 is provided to ease the transition between the adhesive 516 and the disposable 36. The transition region may include a material such as silicone which can be formed and which can provide a profile transition between the adhesive patch and the transmitter housing on the wearable. The transition region limits the occurrence of features on the wearable that can snag on elements, e.g., the user's clothes, and tear the wearable off. The material may be flexible for patient comfort.

In another embodiment, and referring to FIGS. 105 and 106, an applicator device (only a lower housing 40*d* is illustrated in FIG. 105) can be adapted for use in applying a disposable housing 36*d* to the skin of a patient. The disposable housing 36*d* can be disposed on an adhesive patch 90*d*. The disposable housing 36*d* can be configured to receive a transmitter 500*d* (see FIG. 106) which is adapted for one time use. The disposable housing 36*d* can include a slot 442*d* configured to receive a corresponding tab (not shown in FIG. 106, but similar to the tab 501 illustrated in FIG. 41) on the transmitter 500*d*, so as to help position the transmitter 500*d* as it is installed in the disposable housing 36*d*, in a similar fashion as the transmitter 500 and disposable housing 36 illustrated in FIG. 40.

In contrast to the transmitter 500 and disposable housing 36 illustrated in FIG. 40, however, the disposable housing 36*d* and the transmitter 500*d* can be configured without any breakaway features, release tabs or snaps, or other release features designed to facilitate removal of the transmitter 500*d* after installation in the disposable housing 36*d*. Thus, some embodiments can include single-use disposable housings which are configured for use with single-use transmitters. In some embodiments, such a disposable housing can be configured with a smaller footprint than a disposable housing configured with a breakaway portion or other release features designed to facilitate the removal of a reusable transmitter.

In embodiments, a sensor insertion device can generally include an upper housing, a lower housing, a protective tab (e.g., a safety frangible), a trigger button, a torsion spring housing or wheel cam, a torsion spring, an outer needle hub, an inner needle hub, a needle, a sensor, a push rod hub, a push rod, a cannula hub, a cannula, a compression spring, a seal carrier, a seal, a disposable housing, and an adhesive patch, for example as described herein. In some embodiments, a sensor insertion device can be configured to deploy generally as follows. In an initial configuration, for example as manufactured and provided to the consumer, the upper housing and lower housing are coupled together to house the inner components of the device. The torsion spring and the compression spring are pre-energized or pre-loaded. The outer needle hub, inner needle hub, cannula hub, and push rod hub are fixedly coupled to one another in an initial, pre-deployed configuration, with the needle and push rod in an initial proximal position. The cannula is in an initial distal position, and is operatively coupled to the disposable housing via the seal. In some embodiments, the cannula extends through the elastomeric seal in frictional engagement with the elastomeric seal. The seal carrier is hingedly coupled to the disposable housing, but disposed at an angle with respect to the disposable housing, in line with an angle of insertion. In the initial configuration, the cannula hub cooperates with ribs of the lower housing to secure the seal carrier in this angled position. Also in the initial configuration, a tab or other protrusion of the trigger is disposed so as to block or prevent rotation of the torsion spring housing, and thereby prevent activation of the torsion spring. The sensor is disposed fully within the lumen of the needle, distal of the push rod. The push rod, needle, and cannula are arranged telescopically along the axis of insertion of the sensor.

In order to enable deployment of the device, the user first decouples or otherwise removes the protective tab, which is initially coupled to the trigger to prevent unintentional deployment of the device. The user then presses down on the trigger. The trigger slides through a track in the upper housing, and the tab is displaced from its blocking engagement with the torsion spring housing, thereby releasing or activating the torsion spring and causing the torsion spring housing to rotate about its center axis.

The torsion spring housing includes a pin configured to engage with a slot or yoke in the outer needle hub. As the torsion spring housing begins to rotate (under the force of the activated torsion spring), the pin pushes the slot and, thus, the outer needle hub, in a distal direction. Since the inner needle hub and push rod hub are both fixed to the outer needle hub at this stage, but the cannula hub is fixed in the distal direction (e.g., prevented from moving distally by the positioning of the seal carrier and disposable housing), the inner needle hub and push rod hub both move distally with respect to the cannula hub. With this movement, the inner needle hub moves from a first engagement position with the cannula hub, travelling to a second engagement position with the cannula hub. The needle, sensor, and push rod travel together to their most distal positions, and the needle and sensor are inserted into the skin.

After (or at the same time as) the outer needle hub, the inner needle hub, and the push rod hub reach their most distal position, arms or other features of the push rod hub engage with corresponding tabs or other positional engagement features of the lower housing to lock the push rod hub in its distal position (e.g. to prevent proximal movement of the push rod hub). Backspring features forming part of (or coupled to) the push rod hub deform as the push rod hub reaches its distal position to bias the push rod hub against the positional engagement features of the lower housing, thereby fixing the position of the push rod hub (and the push rod) in the axial direction.

As the torsion spring housing continues to rotate (still under the force of the activated torsion spring), the drive mechanism self-reverses, and the engagement of the pin with the slot begins to move the outer needle hub back in a proximal direction, initiating retraction of the needle. Since the push rod hub is fixed in a distal position at this stage (e.g., prevented from moving proximally by its engagement with the lower housing), the push rod provides a backstop to the sensor in the distal position and prevents proximal movement of the sensor as the needle moves in the proximal direction.

The movement of the outer needle hub in the proximal direction causes the outer needle hub to decouple from the push rod hub (e.g., by causing the disengagement or interengaging features of the outer needle hub and the push rod hub). As the outer needle hub continues to move proximally with respect to the push rod hub, tabs or protrusions of the push rod hub engage with tabs or protrusions of the inner needle hub, to release the inner needle hub from engagement with the outer needle hub. At or about the same time, the torsion spring housing rotates into a section of the upper housing containing one or more ratchet engagement teeth and a hard stop. This structure engages the ratchet arm of the torsion spring housing and arrests rotational movement of the torsion spring housing, as well as and linear movement of the outer needle hub. The decoupling of the inner needle hub from the outer needle hub serves to release or otherwise activate the compression spring, which drives the inner needle hub further in the proximal direction. As the inner needle hub is driven proximally, it couples with second engagement feature of the cannula hub. The movement of the inner needle hub pulls the needle, the cannula hub, and the cannula in the proximal direction. This drives the cannula out of the seal and the cannula and needle to the fully retracted proximal position.

Once the cannula hub is moved out from under the seal carrier to a proximal position, the seal carrier is free to rotate about its hinged coupling with the disposable housing, from its initial angled orientation to a flat or other final orientation within the disposable housing, in which the disposable housing can receive a transmitter. In some embodiments, this rotation is assisted with the addition of, for example, a spring-like arm biased against the seal carrier. At this stage, the disposable housing is also decoupled from the remainder of the device, such that the device need only be lifted away by the user to leave the disposable housing applied to the skin and ready to receive the transmitter.

It should be appreciated that all methods and processes disclosed herein may be used in any glucose monitoring system, continuous or intermittent. It should further be appreciated that the implementation and/or execution of all methods and processes may be performed by any suitable devices or systems, whether local or remote. Further, any combination of devices or systems may be used to implement the present methods and processes.

Methods and devices that are suitable for use in conjunction with aspects of the preferred embodiments are disclosed in U.S. Pat. Nos. 4,757,022; 4,994,167; 6,001,067; 6,558, 321; 6,702,857; 6,741,877; 6,862,465; 6,931,327; 7,074, 307; 7,081,195; 7,108,778; 7,110,803; 7,134,999; 7,136, 689; 7,192,450; 7,226,978; 7,276,029; 7,310,544; 7,364, 592; 7,366,556; 7,379,765; 7,424,318; 7,460,898; 7,467, 003; 7,471,972; 7,494,465; 7,497,827; 7,519,408; 7,583, 990; 7,591,801; 7,599,726; 7,613,491; 7,615,007; 7,632, 228; 7,637,868; 7,640,048; 7,651,596; 7,654,956; 7,657, 297; 7,711,402; 7,713,574; 7,715,893; 7,761,130; 7,771, 352; 7,774,145; 7,775,975; 7,778,680; 7,783,333; 7,792, 562; 7,797,028; 7,826,981; 7,828,728; 7,831,287; 7,835, 777; 7,857,760; 7,860,545; 7,875,293; 7,881,763; 7,885, 697; 7,896,809; 7,899,511; 7,901,354; 7,905,833; 7,914, 450; 7,917,186; 7,920,906; 7,925,321; 7,927,274; 7,933, 639; 7,935,057; 7,946,984; 7,949,381; 7,955,261; 7,959, 569; 7,970,448; 7,974,672; 7,976,492; 7,979,104; 7,986, 986; 7,998,071; 8,000,901; 8,005,524; 8,005,525; 8,010, 174; 8,027,708; 8,050,731; 8,052,601; 8,053,018; 8,060, 173; 8,060,174; 8,064,977; 8,073,519; 8,073,520; 8,118, 877; 8,128,562; 8,133,178; 8,150,488; 8,155,723; 8,160, 669; 8,160,671; 8,167,801; 8,170,803; 8,195,265; 8,206, 297; 8,216,139; 8,229,534; 8,229,535; 8,229,536; 8,231, 531; 8,233,958; 8,233,959; 8,249,684; 8,251,906; 8,255, 030; 8,255,032; 8,255,033; 8,257,259; 8,260,393; 8,265, 725; 8,275,437; 8,275,438; 8,277,713; 8,280,475; 8,282, 549; 8,282,550; 8,285,354; 8,287,453; 8,290,559; 8,290, 560; 8,290,561; 8,290,562; 8,292,810; 8,298,142; 8,311, 749; 8,313,434; 8,321,149; 8,332,008; 8,346,338; 8,364, 229; 8,369,919; 8,374,667; 8,386,004; 8,394,021; 8,527, 025; 7,896,809; 9,119,528; and 9,119,529.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196 Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-

A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-

0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013-0536650-A1; U.S. Patent Publication No. 2013-0053666-A1; U.S. Patent Publication No. 2010-0331644-A1; U.S. Patent Publication No. 2013-0053665-A1; U.S. Patent Publication No. 2013-0053666-A1; U.S. Patent Publication No. 2013-0060112-A1; U.S. Patent Publication No. 2013-0078912-A1; U.S. Patent Publication No. 2013-0076531-A1; U.S. Patent Publication No. 2013-0076532-A1; U.S. Patent Publication No. 2013-0131478-A1; U.S. Patent Publication No. 2014-0182350-A1; U.S. Patent Publication No. 2014-0188402-A1; U.S. Patent Publication No. 2013-0150692-A1; U.S. Patent Publication No. 2014-0005508-A1; U.S. Patent Publication No. 2014-0094671-A1; U.S. Patent Publication No. 2014-0107450-A1; U.S. Patent Publication No. 2013-0245412-A1; U.S. Patent Publication No. 2014-0088389-A1; U.S. Patent Publication No. 2014-0005505-A1; U.S. Patent Publication No. 2013-0325504-A1; U.S. Patent Publication No. 2013-0321425-A1; and U.S. Patent Publication No. 2014-0129151-A1.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' 'or' 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An applicator for applying an on-skin sensor assembly to skin of a host, the applicator including an insertion assembly comprising:
    an insertion member configured to insert a sensor into the skin of the host;
    a first drive assembly having a first amount of stored energy; and
    a second drive assembly having a second amount of stored energy,
    wherein the first amount of stored energy is wound in a rotational direction about an axis, and wherein the first drive assembly is configured to convert a portion of the first amount of stored energy to a first linear force to drive the insertion member and the second drive assembly in a distal direction to an inserted position, and wherein the first drive assembly is configured to convert another portion of the first amount of stored energy to a second linear force to drive the insertion member and the second drive assembly in a proximal direction from the inserted position,
    wherein the second drive assembly is configured to supplement the second linear force in driving the insertion member in the proximal direction from the inserted position, and
    wherein the first drive assembly is configured to activate the second drive assembly while driving the insertion member in the proximal direction.

2. The applicator of claim 1, wherein the first amount of stored energy is a wound torsional spring.

3. The applicator of claim 1, wherein the second amount of stored energy is a compressed helical spring.

4. The applicator of claim 1, wherein the insertion assembly further comprises a yoke configured to convert the portion of the first amount of stored energy to the first linear force and the second linear force.

5. The applicator of claim 1, wherein the insertion assembly further comprises a yoke configured to activate the second amount of stored energy of the second drive assembly.

6. The applicator of claim 1, wherein the insertion assembly is disposed in an applicator housing operatively coupled to a housing, the housing being configured to receive an electronics unit, and the electronics unit being configured to generate analyte information based on a signal from a sensor.

7. The applicator of claim 4, wherein the yoke is movable in the distal direction and the proximal direction and movement of the yoke in the proximal direction activates the second amount of stored energy in the second drive assembly driving the insertion member in the proximal direction from the inserted position.

8. The applicator of claim 4, wherein the yoke is disposed in a scotch yoke mechanism, wherein the scotch yoke mechanism is configured to convert the portion of the first amount of stored energy into the first linear force for driving the insertion member in the distal direction to the inserted position.

9. The applicator of claim 2,
    wherein the insertion assembly further comprises a yoke disposed in a scotch yoke mechanism configured to convert the portion of the first amount of stored energy to the first linear force and the second linear force, and
    wherein the first drive assembly comprises a torsional spring housing enclosing the wound torsional spring and moveable therewith, wherein the torsional spring housing is configured to move the yoke under the first amount of stored energy.

10. The applicator of claim 9, wherein the torsional spring housing comprises a tab movable within the yoke of the scotch yoke mechanism.

11. The applicator of claim 1, wherein the insertion assembly comprises a push rod hub and a yoke, wherein the push rod hub is operatively coupled to the insertion member and the yoke, the push rod hub configured for movement in the distal direction to the inserted position and in the proximal direction from the inserted position, and wherein the push rod hub is configured to activate the second amount of stored energy which drives the insertion member in the proximal direction from the inserted position.

12. An applicator for applying an on-skin sensor assembly to skin of a host, the applicator including:
   an applicator housing operatively coupled to a housing, the housing being configured to receive an electronics unit, and the electronics unit being configured to generate analyte information based on a signal from a sensor; and
   an insertion assembly comprising:
      an insertion member configured to insert a sensor into the skin of the host;
      a first drive assembly having a first amount of stored energy; and
      a second drive assembly having a second amount of stored energy,
      wherein the first amount of stored energy is wound in a rotational direction about an axis, and wherein the first drive assembly is configured to convert a portion of the first amount of stored energy to a first linear force to drive the insertion member and the second drive assembly in a distal direction to an inserted position, and wherein the first drive assembly is configured to convert another portion of the first amount of stored energy to a second linear force to drive the insertion member and the second drive assembly in a proximal direction from the inserted position,
      wherein the second drive assembly is configured to supplement the second linear force in driving the insertion member in the proximal direction from the inserted position, and
      wherein a ratchet member is configured to prevent the first drive assembly from driving the insertion member back in the distal direction.

13. The applicator of claim 12, wherein the first amount of stored energy is a wound torsional spring.

14. The applicator of claim 12, wherein the second amount of stored energy is a compressed helical spring.

15. The applicator of claim 12, wherein the insertion assembly further comprises a yoke configured to convert the portion of the first amount of stored energy to the first linear force and the second linear force.

16. The applicator of claim 12, wherein the insertion assembly further comprises a yoke configured to activate the second amount of stored energy of the second drive assembly.

17. The applicator of claim 12, wherein the insertion assembly is disposed in the applicator housing operatively coupled to the housing.

18. The applicator of claim 15, wherein the yoke is movable in the distal direction and the proximal direction and movement of the yoke in the proximal direction activates the second amount of stored energy in the second drive assembly driving the insertion member in the proximal direction from the inserted position.

19. The applicator of claim 15, wherein the yoke is disposed in a scotch yoke mechanism, wherein the scotch yoke mechanism is configured to convert the portion of the first amount of stored energy into the first linear force for driving the insertion member in the distal direction to the inserted position.

20. The applicator of claim 13,
   wherein the insertion assembly further comprises a yoke disposed in a scotch yoke mechanism configured to convert the portion of the first amount of stored energy to the first linear force and the second linear force, and
   wherein the first drive assembly comprises a torsional spring housing enclosing the wound torsional spring and moveable therewith, wherein the torsional spring housing is configured to move the yoke.

21. The applicator of claim 20, wherein the torsional spring housing comprises a tab movable within the yoke of the scotch yoke mechanism.

22. The applicator of claim 12, wherein the insertion assembly comprises a push rod hub and a yoke, wherein the push rod hub is operatively coupled to the insertion member and the yoke, the push rod hub configured for movement in the distal direction to the inserted position and in the proximal direction from the inserted position, and wherein the push rod hub is configured to activate the second amount of stored energy which drives the insertion member in the proximal direction from the inserted position.

* * * * *